US012721852B2

(12) United States Patent
Proia et al.

(10) Patent No.: US 12,721,852 B2
(45) **Date of Patent: *Sep. 1, 2026**

(54) ADVANTAGEOUS THERAPIES FOR DISORDERS MEDIATED BY IKAROS OR AIOLOS

(71) Applicant: C4 Therapeutics, Inc., Watertown, MA (US)

(72) Inventors: David Proia, Newton, MA (US); James A. Henderson, Weston, MA (US); Minsheng He, Andover, MA (US); Andrew Charles Good, Watertown, MA (US); Andrew J. Phillips, Littleton, CO (US)

(73) Assignee: C4 Therapeutics, Inc., Watertown, MA (US)

( * ) Notice: Subject to any disclaimer, the term of this patent is extended or adjusted under 35 U.S.C. 154(b) by 731 days.

This patent is subject to a terminal disclaimer.

(21) Appl. No.: 18/106,893

(22) Filed: Feb. 7, 2023

(65) Prior Publication Data

US 2023/0190760 A1 Jun. 22, 2023

Related U.S. Application Data

(63) Continuation of application No. PCT/US2021/045000, filed on Aug. 6, 2021.

(60) Provisional application No. 63/212,463, filed on Jun. 18, 2021, provisional application No. 63/173,160, filed on Apr. 9, 2021, provisional application No. 63/063,011, filed on Aug. 7, 2020.

(51) Int. Cl.

| | |
|---|---|
| ***A61K 31/5377*** | (2006.01) |
| ***A61K 39/00*** | (2006.01) |
| ***A61P 35/00*** | (2006.01) |

(52) U.S. Cl.

CPC .......... *A61K 31/5377* (2013.01); *A61P 35/00* (2018.01); *A61K 39/00* (2013.01)

(58) Field of Classification Search

None

See application file for complete search history.

(56) References Cited

U.S. PATENT DOCUMENTS

| | | | |
|---|---|---|---|
| 5,635,517 | A | 6/1997 | Muller et al. |
| 8,648,096 | B2 | 2/2014 | Muller et al. |
| 9,732,064 | B2 | 8/2017 | Muller et al. |
| 9,796,698 | B2 | 10/2017 | Muller et al. |
| 9,801,868 | B2 | 10/2017 | Muller et al. |
| 9,834,538 | B2 | 12/2017 | Muller et al. |
| 9,920,027 | B2 | 3/2018 | Ruchelman et al. |
| 10,125,114 | B2 | 11/2018 | Bradner et al. |
| 10,183,010 | B2 | 1/2019 | Xu et al. |
| 11,185,543 | B2 | 11/2021 | Alexander et al. |
| 2002/0147343 | A1 | 10/2002 | Chen et al. |
| 2009/0298882 | A1 | 12/2009 | Muller et al. |
| 2014/0356322 | A1 | 12/2014 | Crews et al. |
| 2014/0377293 | A1 | 12/2014 | Zeldis |
| 2016/0272639 | A1 | 9/2016 | Crew et al. |
| 2018/0008574 | A1 | 1/2018 | Xu et al. |
| 2019/0119285 | A1 | 4/2019 | Ndubaku et al. |
| 2019/0233433 | A1 | 8/2019 | Crews et al. |
| 2019/0328722 | A1 | 10/2019 | Ge et al. |
| 2020/0000776 | A1 | 1/2020 | Ge et al. |
| 2020/0061033 | A1 | 2/2020 | Lee et al. |
| 2020/0140456 | A1 | 5/2020 | Phillips et al. |
| 2021/0206743 | A1 | 7/2021 | Lee et al. |
| 2022/0213115 | A1 | 7/2022 | Baculi et al. |
| 2023/0322803 | A1 | 10/2023 | Degnan et al. |
| 2024/0360150 | A1 | 10/2024 | Fu et al. |
| 2024/0383886 | A1 | 11/2024 | Veits et al. |

FOREIGN PATENT DOCUMENTS

| | | | | |
|---|---|---|---|---|
| CN | 107739389 | A * | 2/2018 | .......... C07D 401/14 |
| WO | WO-2002/059109 | A2 | 8/2002 | |
| WO | WO-2005/030132 | A2 | 4/2005 | |
| WO | WO 2008/027542 | A2 | 3/2008 | |
| WO | WO 2008/033567 | A1 | 3/2008 | |
| WO | WO 2008/039489 | A2 | 4/2008 | |
| WO | WO 2008/115516 | A2 | 9/2008 | |
| WO | WO 2009/042177 | A1 | 4/2009 | |
| WO | WO 2009/139880 | A1 | 11/2009 | |
| WO | WO 2009/145899 | A1 | 12/2009 | |
| WO | WO 2010/053732 | A1 | 5/2010 | |
| WO | WO 2012/175481 | A1 | 12/2012 | |
| WO | WO 2015/085172 | A2 | 6/2015 | |
| WO | WO-2015/160845 | A2 | 10/2015 | |
| WO | WO 2017/197056 | A1 | 11/2017 | |
| WO | WO 2017/201069 | A1 | 11/2017 | |

(Continued)

OTHER PUBLICATIONS

Chen, Qiuni, et al. "Multiple Functions of Ikaros in Hematological Malignancies, Solid Tumor and Autoimmune Diseases." Gene, vol. 684, Feb. 2019, pp. 47-52. ScienceDirect, https://doi.org/10.1016/j.gene.2018.10.045. (Year: 2019).*

Duque Suárez, Leydy Katherin, et al. "Ikaros Expression Profiles Characterize Different Autoimmune Diseases." Translational Medicine Communications, vol. 3, No. 1, Dec. 2018, p. 11. BioMed Central, https://doi.org/10.1186/s41231-018-0030-3. (Year: 2018 ).*

U.S. Pat. No. 10,646,575, U.S. Appl. No. 16/186,339, Phillips et al., May 12, 2020.

U.S. Pat. No. 10,660,968, U.S. Appl. No. 16/186,334, Phillips et al., May 26, 2020.

U.S. Pat. No. 10,849,982, U.S. Appl. No. 16/186,341, Phillips et al., Dec. 1, 2020.

U.S. Pat. No. 10,905,768, U.S. Appl. No. 16/872,225, Phillips et al., Feb. 2, 2021.

U.S. Pat. No. 11,185,592, U.S. Appl. No. 16/882,236, Phillips et al., Nov. 30, 2021.

(Continued)

*Primary Examiner* — Clinton A Brooks

*Assistant Examiner* — Kyle Nottingham

(74) *Attorney, Agent, or Firm* — Knowles Intellectual Property Strategies, LLC

(57) ABSTRACT

New treatments for Ikaros and/or Aiolos mediated disorders are provided that comprise administering an effective amount of a cereblon binder that degrades Ikaros or Aiolos by the ubiquitin proteasome pathway.

19 Claims, 59 Drawing Sheets

(56) References Cited

FOREIGN PATENT DOCUMENTS

| | | | |
|---|---|---|---|
| WO | WO-2018/144649 | A1 | 8/2018 |
| WO | WO 2019/038717 | A1 | 2/2019 |
| WO | WO 2019/148055 | A1 | 8/2019 |
| WO | WO 2019/191112 | A1 | 10/2019 |
| WO | WO 2019/241274 | A1 | 12/2019 |
| WO | WO 2020/006233 | A1 | 1/2020 |
| WO | WO 2020/006262 | A1 | 1/2020 |
| WO | WO 2020/006265 | A1 | 1/2020 |
| WO | WO 2020/010177 | A1 | 1/2020 |
| WO | WO 2020/010227 | A1 | 1/2020 |
| WO | WO 2020/012334 | A1 | 1/2020 |
| WO | WO-2020/12337 | A1 | 1/2020 |
| WO | WO-2020/128972 | A1 | 6/2020 |
| WO | WO-2020/165833 | A1 | 8/2020 |
| WO | WO-2020/165834 | A1 | 8/2020 |
| WO | WO 2020/210630 | A1 | 10/2020 |
| WO | WO 2021/041664 | A1 | 3/2021 |
| WO | WO-2021/127586 | A1 | 6/2021 |

OTHER PUBLICATIONS

U.S. Pat. No. 11,254,672, U.S. Appl. No. 16/809,325, Norcross et al., Feb. 22, 2022.
U.S. Pat. No. 11,401,256, U.S. Appl. No. 16/809,345, Norcross et al., Aug. 2, 2022.
U.S. Pat. No. 11,407,734, U.S. Appl. No. 17/498,617, Henderson et al., Aug. 9, 2022.
U.S. Pat. No. 11,459,335, U.S. Appl. No. 16/721,650, Phillips et al., Oct. 4, 2022.
U.S. Pat. No. 11,584,748, U.S. Appl. No. 17/072,896, Nasveschuk et al., Feb. 21, 2023.
U.S. Pat. No. 11,623,929, U.S. Appl. No. 17/103,621, Nasveschuk et al., Apr. 11, 2023.
2020/0207783, U.S. Appl. No. 16/809,336, Norcross et al., Jul. 2, 2020.
2020/0207733, U.S. Appl. No. 16/809,345, Norcross et al., Jul. 2, 2020.
2021/0009559, U.S. Appl. No. 17/031,550, Henderson et al., Jan. 14, 2021.
2021/0198256, U.S. Appl. No. 17/192,634, Nasveschuk et al., Jul. 1, 2021.
2022/0098194, U.S. Appl. No. 17/541,035, Nasveschuk et al., Mar. 31, 2022.
2022/0251061, U.S. Appl. No. 16/874,475, Phillips et al., Aug. 11, 2022.
2022/0289738, U.S. Appl. No. 17/576,582, Norcross et al., Sep. 15, 2022.
2022/0313826, U.S. Appl. No. 17/107,781, Phillips et al., Oct. 6, 2022.
2022/0313827, U.S. Appl. No. 17/121,389, Phillips et al., Oct. 6, 2022.
2022/0372016, U.S. Appl. No. 17/351,935, Phillips et al., Nov. 24, 2022.
2023/0014124, U.S. Appl. No. 17/164,446, Phillips et al., Jan. 19, 2023.
2023/0019060, U.S. Appl. No. 17/465,583, Nasveschuk et al., Jan. 19, 2023.
2023/0060334, U.S. Appl. No. 17/901,775, Nasveschuk et al., Mar. 2, 2023.
2023/0082430, U.S. Appl. No. 17/723,199, Henderson et al., Mar. 16, 2023.
2023/0095223, U.S. Appl. No. 17/524,558, Phillips et al., Mar. 30, 2023.
2023/0110648, U.S. Appl. No. 17/843,769, Nasveschuk et al., Apr. 13, 2023.
U.S. Appl. No. 18/100,992, Nasveschuk et al., Jan. 24, 2023.
U.S. Appl. No. 18/105,735, Henderson et al., Feb. 3, 2023.
U.S. Appl. No. 18/117,978, Nasveschuk et al., Mar. 6, 2023.
U.S. Appl. No. 18/134,971, Nasveschuk et al., Apr. 14, 2023.
U.S. Appl. No. 18/134,985, Nasveschuk et al., Apr. 14, 2023.
U.S. Appl. No. 18/134,990, Nasveschuk et al., Apr. 14, 2023.
U.S. Appl. No. 18/144,800, Nasveschuk et al., May 8, 2023.
U.S. Appl. No. 17/878,753, Norcross et al., Aug. 1, 2022.
U.S. Appl. No. 17/959,144, Phillips et al., Oct. 3, 2022.
U.S. Appl. No. 17/965,569, Nasveschuk et al., Oct. 13, 2022.
U.S. Appl. No. 18/079,815, Phillips et al., Dec. 12, 2022.
U.S. Pat. No. 11,524,949, U.S. Appl. No. 16/874,475, Phillips et al., Dec. 13, 2022.
U.S. Pat. No. 11,673,902, U.S. Appl. No. 17/843,769, Nasveschuk et al., Jun. 13, 2023.
U.S. Pat. No. 11,691,972, U.S. Appl. No. 17/541,035, Nasveschuk et al., Jul. 4, 2023.
U.S. Pat. No. 11,753,197, U.S. Appl. No. 17/031,551, Henderson et al., Sep. 12, 2023.
U.S. Pat. No. 11,802,131, U.S. Appl. No. 16/809,336, Norcross et al., Oct. 31, 2023.
U.S. Pat. No. 11,787,802, U.S. Appl. No. 17/576,582, Norcross et al., Oct. 17, 2023.
2023/0145336, U.S. Appl. No. 18/084,380, Nasveschuk et al., May 11, 2023.
2023/0192643, U.S. Appl. No. 17/878,753, Norcross et al., Jun. 22, 2023.
2023/0233692, U.S. Appl. No. 18/105,735, Henderson et al., Jul. 27, 2023.
2023/0279023, U.S. Appl. No. 17/959,144, Phillips et al., Sep. 7, 2023.
2023/0357180, U.S. Appl. No. 18/079,815, Phillips et al., Nov. 9, 2023.
2023/0372496, U.S. Appl. No. 18/134,971, Nasveschuk et al., Nov. 23, 2023.
U.S. Appl. No. 18/240,231, Henderson et al., Aug. 30, 2023.
U.S. Appl. No. 18/370,186, Norcross et al., Sep. 19, 2023.
U.S. Appl. No. 18/385,277, Norcross et al., Oct. 30, 2023.
U.S. Appl. No. 18/516,589, Nasveschuk et al., Nov. 21, 2023.
U.S. Appl. No. 18/534,395, Nasveschuk et al., Dec. 8, 2023.
Burslem, George M. et al. "Efficient synthesis of immunomodulatory drug analogues enables exploration of structure-degradation relationships" Chem Med Chem Comm, vol. 13, No. 15, pp. 1508-1512, Aug. 10, 2018.
Kim, Sung et al. "A novel cereblon modulator for targeted protein degradation" European Journal of Medicinal Chemistry; vol. 166, pp. 65-74, Mar. 15, 2019.
Agafonov, Roman et al.; "Quantitative and high throughput method for measuring complex formation between target proteins and E3 ubiquitin ligase," C4 Therapeutics Presentation (2017).
Bartlett, et al. "The evolution of thalidomide and its IMiD derivatives as anticancer agents." Nat Rev Cancer 2004, 4(4):312-322.
Berndsen et al. "New insights into ubiquitin E3 ligase mechanism" Nat. Struct. Mol. Biol. 2014, 21:301-307.
C4 Therapeutics Presentation—S. Fisher, "Degrader Drugs: From cellular activity to in vivo pharmacology Discovery on Target," 21 pages, Sep. 18, 2019.
C4 Therapeutics Presentation—Huang et al., "CAMD Methods Development in Protein Degrader Space," 41 pages; Sep. 17, 2019.
C4 Therapeutics Presentation—C. Nasveschuk, "Degrader Drug Space: What Rules?" HT-ADME Conference Cambridge, MA. Jun. 20, 2019.
Chamberlain et al. "Structure of the human cereblon-DDB1-lenalidomide complex reveals basis for responsiveness to thalidomide analogs" Nature Structural and Molecule Biology, 2014, 21(9):803-809.
Chang, X. and Stewart, K. A. "What is the functional role of the thalidomide binding protein cereblon?" Int J Biochem Mol Bio. 2011, 2(3):287-294.
Contino-Pepin, et al., "Preliminary biological evaluations of new thalidomide analogues for multiple sclerosis application", Bioorganic & Medicinal Chemistry Letters, 2009, 19(3), 878-881.
Deshaies et al. "Ring domain E3 ubiquitin ligases." Ann. Rev. Biochem. 2009, 78:399-434.
Fischer et al. "Structure of the DDB1-CRBN E3 ubiquitin ligase in complex with thalidomide" Nature 2014, 512:49-53.

(56) References Cited

OTHER PUBLICATIONS

Fischer et al. "The Molecular Basis of CRL4DDB2/CSA Ubiquitin Ligase Architecture, Targeting, and Activation," Cell 2011, 147:1024-1039.
Fisher, Stewart L., et al.; "Targeted protein degradation and the enzymology of degraders," Elsevier, Chemical Biology, 2018, 44:47-55.
Hansen, Joshua D., et al.; "Discovery of Crbn E3 Ligase Modulator CC-92480 for the Treatment of Relapsed and Refractory Multiple Myeloma," Journal of Medicinal Chemistry, J. Med. Chem. 2020, 63, 6648-6676, American Chemical Society, ACS Publications, 2020.
International Application No. PCT/US2021/045000, filed Aug. 6, 2021; International Search Report and Written Opinion, dated Dec. 14, 2021, pp. 13.
Ito et al., "Identification of a Primary Target of thalidomide teratogenicity", Science, 2010, 327(5971), 1345-1350, XP0055062167.
Jacques et al. "Differentiation of anti-inflammatory and antitumorigenic properties of stabilized enantiomers of thalidomide analogs" PNAS 2015, 112:E1471-E1479.
Kronke et al. "Lenalidomide Causes Selective Degradation of IKZF1 and IKZF3 in Multiple Myeloma Cells" Science 2014, 343(6168):301-305.
Kronke et al. "Lenalidomide induces ubiquitination and degradation of CDK1 [alpha] in del(5q) MDS" Nature 2015, 523(7559):183-188.
Lu et al. "The myeloma drug lenalidomide promotes the cereblon-dependent destruction of Ikaros proteins" Science 2014, 343:305-309.
Matyskiela, Mary E.; et al.; "A Cereblon Modulator (CC-220) with Improved Degradation of Ikaros and Aiolos," Journal of Medicinal Chemistry, DOI:10.1021/acs.jmedchem.6b01921, J. Med. Chem. 2018, 61, 535-542, ACS Publications, 2017.
Rok Frlan et al.; "Evaluation of US 2016/0115161A1: Isoindoline compounds and methods of their use," Expert Opinion on Therapeutic Patents, 27:6, 637-641, 2017.
Ruchelman et al. "Isosteric analogs of lenalidomide and pomalidomide: Synthesis and biological activity" Bioorganic and Medicinal Chemistry Letters 2012, 23:360-365.
Schneekloth et al. "Chemical approaches to controlling intracellular protein degradation" Chembiochem 2005, 6(1):40-46.
Schneekloth et al. "Chemical Genetic Control of Protein Levels: Selective in Vivo Targeted Degradation" Journal of the American Chemical Society 2004, 126(12):3748-3754.
Schneekloth et al. "Targeted Intracellular Protein Degradation Induced by a Small Molecule: En Route to Chemical Proteomics" Bioorganic and Medicinal Chemistry Letters 2008, 18:5904-5908.
C4 Therapeutics Presentation—Zeid, Rhamy; Targeted protein degradation as a novel therapeutic approach, High throughput chemistry & chemical biology Gordon Research Conference; pp. 40 (2017).
Zhou et al. "Harnessing the Ubiquitination Machinery to Target the Degradation of Specific Cellular Proteins" Molecular Cell 2000, 6:751-756.
Asatsuma-Okumura et al., "Molecular mechanisms of cereblon-based drugs". Pharmacol. Ther. 202, 132-139, Oct. 2019.
Bjorklund C., et al. "Rate of $CRL4^{CRBN}$ substrate Ikaros and Aiolos degradation underlies differential activity of lenalidomide and pomalidomide in multiple myeloma cells by regulation of c-Myc and IRF4" Blood Cancer Journal vol. 5, e354, Oct. 2, 2015.
Cippitelli et al., "Role of Aiolos and Ikaros in the antitumor and immunomodulatory activity of IMiDs in multiple myeloma: better to lose than to find them" Int. J. Mol. Sci. vol. 22(3), Issue 1103, Jan. 21, 2021.
Duan et al., "Targeting Brd4 for cancer therapy: inhibitors and degraders", Med. Chem. Comm. 2018. 9, pp. 1779-1802, XP055842447.
Hörig H. et al., "From bench to clinic and back: perspective on the 1st IQPC translational research conference" J. Translational Med. vol. 2, Article 44, 2004.
Liu Zhiqing, et al., "Drug Discovery Targeting Bromodomain-Containing Protein 4", J. Med. Chem., vol. 60, No. 11, 2017, pp. 4533-4558, XP055933167.
Pubchem, SID 434110878, Available Date: Sep. 28, 2020 [retrieved on Jan. 26, 2022]., Retrieved from the Internet <URL: https://pubchem.ncbi.nlm.nih.gov/substance/434110878>.
U.S. Pat. No. 11,992,531, May 28, 2024, Phillips et al., U.S. Appl. No. 17/107,781.
U.S. Pat. No. 12,048,757, Jul. 30, 2024, Phillips et al., U.S. Appl. No. 17/121,389.
U.S. Pat. No. 12,048,748, Jul. 30, 2024, Phillips et al., U.S. Appl. No. 17/524,558.
U.S. Pat. No. 12,049,464, Jul. 30, 2024, Nasveschuk et al., U.S. Appl. No. 17/901,775.
U.S. Pat. No. 12,076,405, Sep. 3, 2024, Phillips et al., U.S. Appl. No. 17/164,446.
U.S. Pat. No. 12,091,397, Sep. 17, 2024, Norcross et al., U.S. Appl. No. 17/878,753.
U.S. Pat. No. 12,157,735, Dec. 3, 2024, Nasveschuk et al., U.S. Appl. No. 17/965,569.
U.S. Pat. No. 12,180,225, Dec. 31, 2024, Phillips et al., U.S. Appl. No. 17/959,144.
U.S. Pat. No. 12,227,504, Feb. 18, 2025, Nasveschuk et al., U.S. Appl. No. 18/100,992.
U.S. Pat. No. 12,365,681, Jul. 22, 2025, Norcross et al., U.S. Appl. No. 18/370,186.
U.S. Pat. No. 12,371,442, Jul. 29, 2025, Nasveschuk et al., U.S. Appl. No. 18/144,800.
U.S. Pat. No. 12,421,220, Sep. 23, 2025, Nasveschuk et al., U.S. Appl. No. 18/972,557.
U.S. Pat. No. 12,441,740, Oct. 14, 2025, Phillips et al., U.S. Appl. No. 18/973,867.
U.S. Pat. No. 12,454,521, Oct. 28, 2025, Phillips et al., U.S. Appl. No. 17/351,935.
U.S. Pat. No. 12,486,253, Dec. 2, 2025, Nasveschuk et al., U.S. Appl. No. 18/980,700.
U.S. Pat. No. 12,486,290, Dec. 2, 2025, Nasveschuk et al., U.S. Appl. No. 19/205,510.
2023/0024096, Jan. 26, 2023, Duplessis et al., U.S. Appl. No. 17/771,204.
2023/0339902, Oct. 26, 2023, Nasveschuk et al., U.S. Appl. No. 18/134,985.
2024/0018118, Jan. 18, 2024, Nasveschuk et al., U.S. Appl. No. 18/134,990.
2024/0018156, Jan. 18, 2024, Nasveschuk et al., U.S. Appl. No. 18/117,978.
2024/0158418, May 16, 2024, Nasveschuk et al., U.S. Appl. No. 18/516,589.
2024/0199581, Jun. 2023, Nasveshuk et al., U.S. Appl. No. 18/534,395.
2024/0199638, Jun. 20, 2024, Norcross et al., U.S. Appl. No. 18/385,277.
2024/0245677, Jul. 25, 2024, Jackson et al. U.S. Appl. No. 18/600,097.
2024/0391912, Nov. 28, 2024, Henderson et al., U.S. Appl. No. 18/797,261.
2024/0398959, Dec. 5, 2024, Phillips et al., U.S. Appl. No. 18/642,602.
2025/0057957, Feb. 20, 2025, Phillips et al., U.S. Appl. No. 18/774,801.
2025/0084055, Mar. 13, 2025, Norcross et al., U.S. Appl. No. 18/806,363.
2025/0084081, Mar. 13, 2025, Nasveschuk et al., U.S. Appl. No. 18/945,284.
2025/0121069, Apr. 17, 2025, Phillips et al., U.S. Appl. No. 18/775,662.
2025/0121070, Apr. 17, 2025, Nasveschuk et al., U.S. Appl. No. 18/979,247.
2025/0127903, Apr. 24, 2025, Phillips et al., U.S. Appl. No. 18/774,794.
2025/0289827, Sep. 18, 2025, Yu et al. U.S. Appl. No. 19/224,081.
2025/0282780, Sep. 2025, Nasveschuk et al., U.S. Appl. No. 19/053,297.
2025/0368631, Dec. 2025, Nasveschuk et al., U.S. Appl. No. 19/303,022.
U.S. Appl. No. 19/255,607, filed Jun. 30, 2025, Norcross et al.

(56) References Cited

OTHER PUBLICATIONS

U.S. Appl. No. 19/303,091, filed Aug. 18, 2025, Nasveschuk et al.
U.S. Appl. No. 19/336,041, filed Sep. 22, 2025, Phillips et al.
U.S. Appl. No. 19/336,152, filed Sep. 22, 2025, Phillips et al.
U.S. Appl. No. 19/363,434, filed Oct. 20, 2025, Nasveschuk et al.
U.S. Appl. No. 19/384,750, filed Nov. 10, 2025, Nasveschuk et al.

* cited by examiner

*Open symbol indicates highest tested concentration at which growth was not inhibited by more than 50%

ADVANTAGEOUS THERAPIES FOR DISORDERS MEDIATED BY IKAROS OR AIOLOS

CROSS-REFERENCE TO RELATED APPLICATIONS

This application is a continuation of International Patent Application No. PCT/US2021/045000, filed in the U.S. Receiving Office on Aug. 6, 2021, which claims the benefit of U.S. Provisional Application No. 63/063,011 which was filed on Aug. 7, 2020; U.S. Provisional Application No. 63/173,160 which was filed on Apr. 9, 2021; and U.S. Provisional Application No. 63/212,463 which was filed on Jun. 18, 2021. The entirety of each of these applications is hereby incorporated by reference for all purposes.

FIELD OF THE INVENTION

The invention provides therapeutic compositions, combinations, and uses thereof to treat disorders mediated by transcriptional proteins Ikaros (IKZF1) and/or Aiolos (IKZF3) via degradation of these proteins through the ubiquitin proteasome pathway.

BACKGROUND

The Ikaros family is a series of zinc-finger protein transcription factors that are important for certain physiological processes, particularly hematopoietic cells, and lymphocyte development (see Fan, Y. and Lu, D. "The Ikaros family of zinc-finger proteins" Acta Pharmaceutica Sinica B, 2016, 6:513-521). Ikaros (IKZF1) was first discovered in 1992 (see Georgopoulos, K. et al. "Ikaros, an early lymphoid-specific transcription factor and a putative mediator for T cell commitment" Science, 1992, 258:802-812), and over the subsequent two decades four additional homologs have been identified: Helios (IKZF2), Aiolos (IKZF3), Eos (IKZF4), and Pegasus (IKZF5) (see John, L. B., and Ward, A. C. "The Ikaros gene family: transcriptional regulators of hematopoiesis and immunity" Mol Immunol, 2011, 48:1272-1278). The distribution of various members of the Ikaros protein family within the body varies significantly.

Ikaros, Helios, and Aiolos are primarily found in lymphoid cells and their corresponding progenitors, with Ikaros additionally detected in the brain, and Ikaros and Helios detected in erythroid cells. Eos and Pegasus are more wide spread, and found in skeletal muscle, the liver, the brain, and the heart (see Perdomo, J. et al. "Eos and Pegasus, two members of the Ikaros family of proteins with distinct DNA binding activities: J Biol Chem, 2000, 275:38347-38354; Schmitt, C. et al. "Aiolos and Ikaros: regulators of lymphocyte development, homeostasis and lymphoproliferation" Apoptosis, 2002, 7:277-284; Yoshida, T. and Georgopoulos, K. "Ikaros fingers on lymphocyte differentiation" Int J Hematol, 2014, 100:220-229).

Ikaros is important for proper lymphocyte development. Deletion of the exons encoding the first three N-terminal zinc fingers leads to mice lacking T-cells, B-cells, natural killer (NK) cells, and their progenitors. Genetic alterations in Ikaros are correlated with a poor outcome in the treatment of acute lymphoblastic leukemia (ALL). Ikaros and Aiolos are involved in the proliferation of multiple myeloma cells and lymphoma cells.

Multiple myeloma (MM) is a plasma cell malignancy typically characterized by the abnormal production of monoclonal immunoglobulin, bone marrow involvement, renal dysfunction, immune dysfunction, and skeletal damage. In the United States, MM represents nearly 1.8% of all new cancers. Although outcomes for subjects with MM have improved substantially over the past several decades, the disease remains incurable with a predicted five-year relative survival rate currently of 53.9%. As available therapies are not curative, almost all patients ultimately progress.

Management of MM historically included chemotherapy, including alkylating agents together with corticosteroids. Treatment was further advanced in the 1980's with autologous stem cell transplants. In the 1990's the discovery of thalidomide (first-in-class immunomodulatory imide drug, IMiD®) efficacy in myeloma led to large shifts in treatment regimens and improvements in patient outcomes. The follow-on approved IMiD®s, lenalidomide and pomalidomide, are now widely used to treat MM, as is the first-in-class agent thalidomide. This class of agents binds the E3 ligase substrate-recognition adapter protein cereblon (CRBN) and promote the degradation of Ikaros (IKZF1) and Aiolos (IKZF3), resulting in antitumor effects, effects on the tumor microenvironment and immune modulation resulting in T-cell priming and antitumor activity. Many patients with MM are treated with multiple regimens containing one of these IMiDs. These drugs are now considered standard of care for the treatment of MM in numerous lines of therapy, in combination with agents including dexamethasone, anti-cluster of differentiation 38 (CD38) antibodies, and proteasome inhibitors, such as bortezomib. Although these agents have been successful in prolonging the progression free survival of patients with MM, patients generally relapse with shorter periods of progression free survival after each relapse. Recent studies with novel agents, belantamab and selinexor displayed improved outcomes in multiclass refractory myeloma resulting in recent FDA accelerated approvals; however, response rates were low (26-31%) and progression free survival intervals short (3.7-4.9 months), thus underscoring the continued unmet medical need among these patients.

Non-Hodgkin's Lymphoma (NHL) is a heterogenous group of lymphoid malignancies originating from T, B or NK cells. It includes diffuse large B-cell lymphoma, anaplastic large-cell lymphoma, Burkitt lymphoma, lymphoblastic lymphoma, mantle cell lymphoma, peripheral T-cell lymphoma, follicular lymphoma, cutaneous T-cell lymphoma, lymphoplasmacytic lymphoma, marginal zone B-cell lymphoma, MALT lymphoma, and small-cell lymphocytic lymphoma. B-cell NHL predominates, while T-cell lymphomas are less common. Among new diagnosed patients with aggressive NHL, chemotherapy-based regimens including cyclophosphamide, vincristine, prednisone and daunorubicin (referred to as CHOP) remain the mainstay of therapy. In B-cell aggressive lymphomas, rituximab in combination with CHOP is the main therapy administered to new diagnosed patients. In some patients, particularly those with T-cell NHL, initial chemotherapy is followed by autologous stem cell rescue. In relapsed refractory populations, various targeted agents have been developed, thus improving treatment options in multiple subtypes of NHL, however these treatment options tend not to be curative. Additionally, the NHL subtypes are biologically heterogeneous limiting the development of therapeutic agents broadly across indications.

In new diagnosed patients with aggressive lymphoma, initial treatment is frequently intense and administered with curative intent. Other than the addition of rituximab to CHOP in B-cell NHL and brentuximab to CHOP in anaplastic large cell lymphoma (ALCL), no other novel targeted agent has demonstrated survival improvements and therefore no others have been approved in treatment of naïve patients. Recent therapeutic advances in relapsed NHL include Bruton Tyrosine Kinase (BTK) inhibitors, particularly for mantle cell lymphoma (MCL) and more indolent forms of NHL, chimeric antigen receptors T-cell (CAR-T) therapies which have been approved for diffuse large B-cell lymphoma (DBLCL) and MCL, and novel antibody drug conjugates like polatuzumab, belantamab, or tafasitamab which have been approved for DLBCL. Drugs recently approved for T-cell NHL include romidepsin, belinostat, and brentuximab. Relevant to the NHL population being studied in this protocol, lenalidomide has demonstrated clinical activity in both B-cell and T-cell NHL, including MCL, DLBCL and peripheral T-cell lymphoma (PTCL). Lenalidomide was studied in the relapsed/refractory (r/r) MCL population and was approved by the Food and Drug Administration (FDA) in June 2013 following results from the Phase II EMERGE study which examined the efficacy and safety of lenalidomide in r/r subjects with MCL following bortezomib (overall response rate [ORR] 28%; median duration of response [DOR] 16.6 months). Lenalidomide is also active in DLBCL and PTCL. While lenalidomide and other novel targeted therapies have a modest to good response rate, durability of responses tends to be short across most NHL subtypes. Once patients relapse following 1-2 treatment regimens, the median duration of response tends to be low, and is dependent on patients having sufficient performance status and organ function to tolerate these therapies. Therefore, there remains an unmet medical need among patients with r/r NHL.

Protein degradation is a highly regulated and essential process that maintains cellular homeostasis. The selective identification and removal of damaged, misfolded, or excess proteins is achieved via the ubiquitin-proteasome pathway (UPP). The UPP is central to the regulation of almost all cellular processes, including antigen processing, apoptosis, biogenesis of organelles, cell cycling, DNA transcription and repair, differentiation and development, immune response and inflammation, neural and muscular degeneration, morphogenesis of neural networks, modulation of cell surface receptors, ion channels and the secretory pathway, the response to stress and extracellular modulators, ribosome biogenesis and viral infection. Covalent attachment of multiple ubiquitin molecules by an E3 ubiquitin ligase to a terminal lysine residue marks the protein for proteasome degradation, where the protein is digested into small peptides and eventually into its constituent amino acids that serve as building blocks for new proteins. Defective proteasomal degradation has been linked to a variety of clinical disorders including Alzheimer's disease, Parkinson's disease, Huntington's disease, muscular dystrophies, cardiovascular disease, and cancer among others.

Patent applications that describe certain protein degraders include WO 2020/210630, WO 2020/006262, WO 2020/010227, and WO 2020/010177.

Patent applications filed by C4 Therapeutics, Inc., that describe compounds capable of binding to an E3 ubiquitin ligase and a target protein for degradation include: WO/2021/127561 titled "Isoindolinone And Indazole Compounds For The Degradation Of EGFR"; WO/2021/086785 titled "Bifunctional Compounds"; WO/2021/083949 titled "Bifunctional Compounds for the Treatment of Cancer"; WO/2020/210630 titled "Tricyclic Degraders of Ikaros and Aiolos"; WO/2020/181232 titled "Heterocyclic Compounds for Medical Treatment"; WO/2020/132561 titled "Targeted Protein Degradation"; WO/2019/236483 titled "Spirocyclic Compounds"; WO2020/051235 titled "Compounds for the degradation of BRD9 or MTH1"; WO/2019/191112 titled "Cereblon binders for the Degradation of Ikaros"; WO/2019/204354 titled "Spirocyclic Compounds"; WO/2019/099868 titled "Degraders and Degrons for Targeted Protein Degradation"; WO/2018/237026 titled "N/O-Linked Degrons and Degronimers for Protein Degradation"; WO 2017/197051 titled "Amine-Linked C3-Glutarimide Degronimers for Target Protein Degradation"; WO 2017/197055 titled "Heterocyclic Degronimers for Target Protein Degradation"; WO 2017/197036 titled "Spirocyclic Degronimers for Target Protein Degradation"; WO 2017/197046 titled "C3-Carbon Linked Glutarimide Degronimers for Target Protein Degradation"; and WO 2017/197056 titled "Bromodomain Targeting Degronimers for Target Protein Degradation."

It is an object of the present invention to provide new compositions of matter, combinations, formulations and uses thereof as well as processes of preparing compounds for the treatment of medical disorders mediated by Ikaros or Aiolos.

SUMMARY OF THE INVENTION

Compound 1 is a small molecule anti-cancer agent that binds with high affinity to the cereblon E3 ligase thereby creating a new surface on cereblon that interacts with IKZF1 and IKZF3 (see WO 2020/210630). As a result, IKZF1 and IKZF3 are efficiently ubiquitinated by the cereblon E3 ligase and degraded by the proteasome. The high cereblon binding affinity of Compound 1 enables rapid, deep, and durable degradation of IKZF1/3 resulting in potent activity in cancer cells, for example including but not limited to, hematopoietic cancers such as multiple myeloma and the multiple types of Non-Hodgkin's Lymphoma.

(Compound 1)

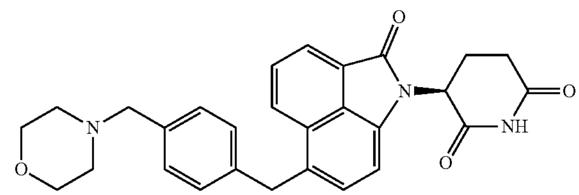

It has now been discovered that Compound 1, and other compounds described herein, can be administered to treat disorders mediated by Ikaros (IKZF1) and/or Aiolos (IKZF3) in a low dosage regimen once or twice a day, optionally with a drug holiday, in highly effective treatment regimens. For example, it has been discovered that anti-cancer treatment can be effective for a patient using one of the compounds described herein with a dosage of not more than about 500, 450, 400, 350, 325, 300, 275, 250, 225, 200, 175, 150, 125 or even 100, 75, 50, 45, 40, 35, 30, 25, 20, 15, 10, 5, or 1 micrograms (μg) once a day (QD) or twice a day (BID). In certain embodiments, the patient is an adult (typically a human of at least 100 pounds or more, and sometimes even 125 or 150 pounds (e.g., 70 kg or more and at least typically 18 years old or more). In an alternative embodiment, the patient is pediatric (and may be less than 100, 125 or 150 pounds and typically less than 18 years old). Not only has it been discovered that Compound 1 is effective as a low dose therapy, but it can also be delivered with a drug holiday which is advantageous to the patient. For example, Compound 1 can be delivered once or twice a day for 21 days followed by a drug holiday of 7 days. Alternative dosing regimens are also useful, for example, including but not limited to those that increase or decrease the drug holiday by 1, 2, 3, 4, 5, 6, or 7 days.

In certain embodiments Compound 1 or another compound described herein modulates the patient's immune activity. For example, it has been discovered that Compound 1 activates proliferation of cytotoxic T-cells, which can be critical to anti-cancer therapy.

Compound 1 or another compound described herein in a non-limiting embodiment can be administered daily or intermittently with dexamethasone. In certain embodiments, dexamethasone or another corticosteroid or another immunosuppressant or anti-inflammatory agent is administered every day without a drug holiday for the 28-day cycle. In other embodiments, the dexamethasone or another corticosteroid or another immunosuppressant or anti-inflammatory agent is administered with a drug holiday, which may be the same or different from that of Compound 1 or another compound described herein.

In one aspect of the present invention the low dose Ikaros (IKZF1) and/or Aiolos (IKZF3) degrading compound is Compound 1 or a pharmaceutically acceptable salt thereof.

Compound 1 has a high binding affinity to cereblon (dissociation constant $K_d$=0.9 nM). Compound 1 promotes the degradation of >75% of steady state IKZF1 in multiple myeloma cells within 1.5 hours at 0.3 nM. The high binding affinity and degradation catalysis of Compound 1 enables potent cell growth inhibition in both previously untreated NCIH929 multiple myeloma cell lines (96% maximal growth inhibition, mean half maximal inhibitory concentration $IC_{50}$ of 0.071 nM) and NCIH929 cells made resistant to both lenalidomide and pomalidomide (70% maximal growth inhibition, mean $IC_{50}$ of 2.3 nM).

The compounds described herein can be used to treat cancer cells that are resistant, refractive or unresponsive to standard of care therapies for cancers mediated by IKZF1 or IKZF3, including IMiDs including pomalidomide or any of those described in the Background or Detailed Description.

As shown in Examples 12, Compound 1 has demonstrated strong anti-cancer activity in a panel of multiple myeloma cell lines (eight of twelve were responsive, mean $IC_{50}$ of 0.3 nM among responsive lines). Anti-cancer activity with Compound 1 was also demonstrated in several cell line models of various Non-Hodgkin's Lymphoma subtypes, including mantel cell lymphoma (MCL) (four of six lines tested were responsive mean $IC_{50}$ of 13 nM among the responsive lines), diffuse large B-cell lymphoma (DLBCL) (six of eleven germinal center B-cell like DLBCL and three of six activated B-cell DLBCL lines were responsive, with mean $IC_{50}$ of 12 nM and 1.6 nM respectively, amongst the responsive lines), anaplastic large cell lymphoma (ALCL) (four out of six cell lines were responsive, mean $IC_{50}$ of 1.7 nM among the responsive lines) and cutaneous T-cell lymphoma (CTCL) (three of four cell lines tested were responsive, mean $IC_{50}$ of 30 nM among the responsive lines). In mouse xenograft tumor models, Compound 1 demonstrated dose dependent efficacy from 3 μg/kg/day to 100 μg/kg/day (see Example 13). In several tumor xenografts tested daily dosing of Compound 1 at dose of 30 μg/kg/day to 100 μg/kg/day led to durable tumor regression. As shown in FIG. 45A, FIG. 45B, FIG. 45C, FIG. 52, and others Compound 1 is more than 100-fold more potent than pomalidomide in a variety of cancer assays.

In a mouse xenograft model Compound 1 has measurable plasma and tumor concentrations for longer than CC-92480 (currently in human clinical trials by Celgene, a subsidiary of Bristol Myers Squibb) despite being dosed at a 10-fold lower dose. It also takes significantly longer for IKZF3 levels to recover after treatment with Compound 1 than pomalidomide or CC-92480. For example, in an NCI-H929 tumor model it takes more than 48 hours for the IKZF3 level to reach 50% of its pretreatment level after administration of Compound 1, whereas both CC-92480 (at a ×10 higher dose) and pomalidomide (at a ×30 higher dose) reach pretreatment levels of IKZF3 within 48 hours of treatment.

As a result of the remarkable efficacy of Compound 1 and other compounds described herein, new advantageous treatments of disorders mediated by Ikaros (IKZF1) and/or Aiolos (IKZF3) have been discovered. In non-limiting embodiments of the invention, the Ikaros (IKZF1) and/or Aiolos (IKZF3) degrading compounds described herein can be used, in non-limiting examples as follows:

1. The treatment of a disorder mediated by Ikaros (IKZF1) and/or Aiolos (IKZF3) wherein the compound is administered in a low dose. For example, a dosage is not more than about 500, 450, 400, 350, 325, 300, 275, 250, 225, 200, 175, 150, 125, 100, 95, 90, 85, 80, 75, 70, 65, 60, 55, 50, 45, 40, 35, 30, 25, 20, 15, 10, 5, or 1 micrograms (μg) once a day (QD) or twice a day (BID), optionally with a drug holiday.
2. The treatment of a disorder mediated by Ikaros (IKZF1) and/or Aiolos (IKZF3) wherein a compound described herein is administered in an effective amount in a dosage regimen that includes a drug holiday, for example a holiday of 1, 2, 3, 4, 5, 6, 7, 8, 9, 10, 11, 12, 13, or 14 days in a 28-day treatment cycle.
3. The treatment of a disorder mediated by Ikaros (IKZF1) and/or Aiolos (IKZF3) wherein a blood or tissue sample is first taken from the patient and the concentration of one or more biomarkers, for example a tumor immunity marker (e.g., a cytokine, tumor infiltrating lymphocyte, T-cell activation and/or proliferation, or a B-cell marker such as BCMA or M-protein, or a combination thereof); an apoptotic marker (e.g., total and/or cleaved caspase-1, caspase-3, caspase-7, PARP, BIM, or survivin, or a combination thereof); or a zinc finger protein (e.g., IKZF1, IKZF3, ZFP91, WIZ, or SALL4, or a combination thereof), is determined, and wherein if the patient has a statistically different concentration of the biomarker including but not limited to about 5, 10, 15 or 20% different than a healthy person then Compound 1 or a pharmaceutically acceptable salt thereof or another compound described herein is administered to the patient.
4. The treatment of a disorder mediated by Ikaros (IKZF1) and/or Aiolos (IKZF3) wherein a blood or tissue sample is first taken from the patient and the concentration of one or more biomarkers, for example IRF-1, caspase-3, IL-2, and/or IFN-γ, is determined, and wherein if the patient has a statistically lower concentration of the biomarker than a healthy person, including but not limited to up to about 5, 10, 15 or 20% lower, then Compound 1 or a pharmaceutically acceptable salt thereof or another compound described herein is administered to the patient.
5. The treatment of a disorder mediated by Ikaros (IKZF1) and/or Aiolos (IKZF3) wherein a blood or tissue sample is first taken from the patient and the concentration of one or more biomarkers, for example cyclin D1, E2F1, ZFP91, SALL4, IRF-4, BLIMP1, and/or MYC is determined, and wherein if the patient has a statistically higher concentration of biomarker including but not limited to up to about 5, 10, 15 or 20% higher than a healthy person then Compound 1 or a pharmaceutically acceptable salt thereof or another compound described herein is administered to the patient.

6. The treatment of a disorder mediated by Ikaros (IKZF1) and/or Aiolos (IKZF3) wherein the patient is administered Compound 1 or a pharmaceutically acceptable salt thereof or another compound described herein and then a blood or tissue sample is taken from the patient and the concentration of one or more biomarkers, for example IRF-1, caspase-3, IL-2, and/or IFN-γ, is determined, wherein if the concentration of the biomarker is not significantly increased, for example by at least about 1.25, 1.5, 1.75, or 2-fold, then the dose of the compound is increased. The treatment of a disorder mediated by Ikaros (IKZF1) and/or Aiolos (IKZF3) wherein the patient is administered Compound 1 or a pharmaceutically acceptable salt thereof or another compound described herein and then a blood or tissue sample is taken from the patient and the concentration of one or more biomarkers, for example cyclin D1, E2F1, ZFP91, SALL4, IRF-4, BLIMP1, and/or MYC is determined, wherein if the concentration of the biomarker is not significantly decreased, for example by about 1.25, 1.5, 1.75, or 2-fold, then the dose of the compound is increased.
7. The treatment of a disorder mediated by Ikaros (IKZF1) and/or Aiolos (IKZF3) wherein the patient is administered Compound 1 or a pharmaceutically acceptable salt thereof or another compound described herein and then a blood or tissue sample is taken from the patient and the concentration of one or more biomarkers, for example a tumor immunity marker (e.g., a cytokine, tumor infiltrating lymphocyte, T-cell activation and/or proliferation, and B-cell markers such as BCMA or M-protein, or a combination thereof); an apoptotic marker (e.g., total and/or cleaved caspase-1, caspase-3, caspase-7, PARP, BIM, or survivin, or a combination thereof); or a zinc finger protein (e.g., IKZF1, IKZF3, ZFP91, WIZ, or SALL4, or a combination thereof), is determined, wherein if the concentration of the biomarker has not changed significantly, for example by at least about 1.25, 1.5, 1.75, or 2-fold, then the dose of the compound is increased.
8. The treatment of an activated diffuse large B-cell lymphoma, germinal diffuse large B-cell lymphoma, extranodal natural killer (NK) cell lymphoma, or extranodal T-cell lymphoma, with an effective amount of a compound described herein or a pharmaceutically acceptable salt thereof.
9. The treatment of a disorder mediated by Ikaros (IKZF1) and/or Aiolos (IKZF3) wherein the compound is administered in a low dose. For example, a dosage is not more than about 500, 450, 400, 350, 325, 300, 275, 250, 225, 200, 175, 150, 125 or even 100, 75, 50 or 25 micrograms (μg) once a day (QD) or twice a day (BID), optionally with a drug holiday.
10. The treatment of a disorder mediated by Ikaros (IKZF1) and/or Aiolos (IKZF3) wherein a compound described herein is used in combination with a BTK inhibitor, for example a BTK inhibitor selected from acalabrutinib, spebrutinib, zanubrutinib, LOXO-305, evobrutinib, TG-1701, tolebrutinib, BhB091, DZD-9008, HZ-A-018, orelabrutinib, AC0058TA, SN1011, rilzabrutinib, ARQ 531, DTRMWXHS-12, JNJ-64264681, branebrutinib, ibrutinib, and fenebrutinib.
11. The treatment of a disorder mediated by Ikaros (IKZF1) and/or Aiolos (IKZF3) wherein a compound described herein is used in combination with a CD38 antibody, for example a CD38 antibody selected from felzarta.mab, daratumumab, GBR 1342, TAK-573, CID-103, OKT10, STI-6129, SGX301, TAK-079, and mezagitamab.
12. The treatment of a disorder mediated by Ikaros (IKZF1) and/or Aiolos (IKZF3) wherein a compound described herein is used in combination with a proteasome inhibitor, for example a proteasome inhibitor selected from bortezomib, carfilzomib, ixazomib citrate, oprozomib, delanzomib, lactacystin, epoxomicin, MG132, MG-262, CEP-18770, NEOSH101, TQB3602, and KZR-616.
13. The treatment of a disorder mediated by Ikaros (IKZF1) and/or Aiolos (IKZF3) wherein a compound described herein is used in combination with an IMiD for example an IMiD selected from thalidomide, pomalidomide, lenalidomide, ibertomide, C-92480, CC-90009, and CC-99282.
14. The treatment of a disorder mediated by Ikaros (IKZF1) and/or Aiolos (IKZF3) wherein a compound described herein is used in combination with an HDAC inhibitor, for example an HDAC inhibitor selected from trapoxin B, sodium phenylbutyrate, tacedinaline, mocetinostat, BRD73954, BG45, domatinostat, cay10603, HPOB, TMP269, nexturastat A, Santacruzamate A, splitomicin, LMK-235, sodium butyrate, pivaloyloxymethyl butyrate, pyroxamide, abexinostat, resminostat, givinostat, quisinostat, Psammaplin A, KD5170, 1-Alaninechlamydocin, depudecin, panobinostat, ricolinostat, vorinostat, and CUDC-101.
15. The treatment of a disorder mediated by Ikaros (IKZF1) and/or Aiolos (IKZF3) wherein a compound described herein is used in combination with another compound, for example a compound selected from selinexor, oxaphenamide, belantamab mafodotin, denosumab, zoledronic acid, plerixafor, eltrombopag, ipilumumab, palbociclib, ricolinostat, afuresertib, dinaciclib, filanesib, indatuximab ravtansine, masitinib, sonidegib, sotatercept, ulocuplumab, and urelumab.
16. A treatment of cancer mediated by Ikaros (IKZF1) and/or Aiolos (IKZF3) comprising administering an effective amount of Compound 1 to activate proliferation of T-cells.

These new treatments offer advantages over presently approved treatments of cancer. For example, a compound described herein can be administered at a lower dose than first generation IMiDs; can penetrate the blood brain barrier to treat a central nervous system (CNS) involved cancer, for example a CNS involved lymphoma; can treat a cancer that has relapsed or is refractory to a standard of care regimen, including a first generation IMiD treatment; and/or can provide a longer period of progression free survival to the patient than 1$^{st}$ generation IMiDs, for example thalidomide, pomalidomide, and lenalidomide. In certain embodiments a compound described herein is about 30, 40, 50, 60, 70, 80, 90, 100, 500, or even 1,000 times more potent in vivo than thalidomide, pomalidomide, lenalidomide, or CC-92480. In certain embodiments a compound described herein causes durable degradation of IKZF1 and/or IKZF3 (e.g. IKZF1 and/or IKZF3 levels take 12 hours, 18 hours, 24 hours, 36 hours, 48 hours, or longer to return to pretreatment levels). This durable degradation is a result of high in vivo efficacy, metabolic stability, and/or selectivity.

In one aspect, the compound used in the treatments described herein is selected from:

(Compound 1)

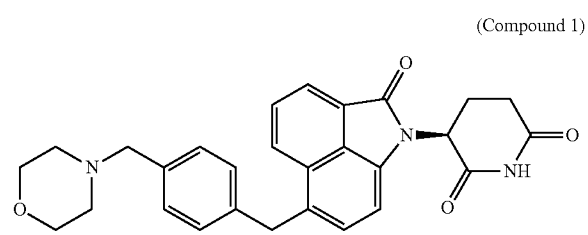

(Compound 2)

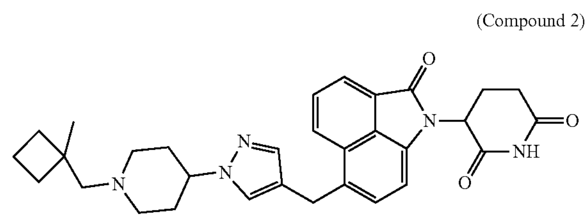

(Compound 3)

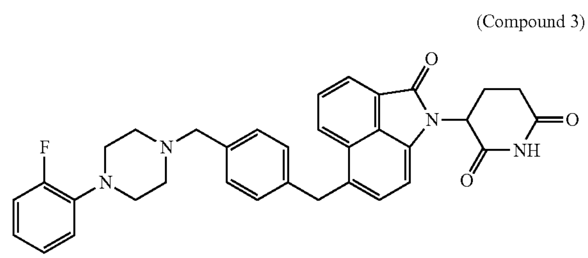

(Compound 4)

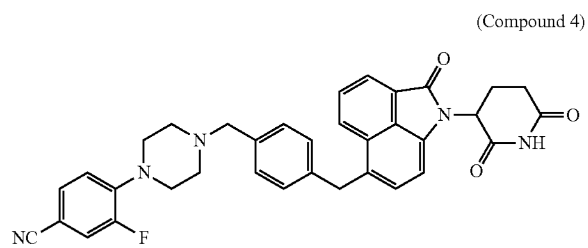

(Compound 5)

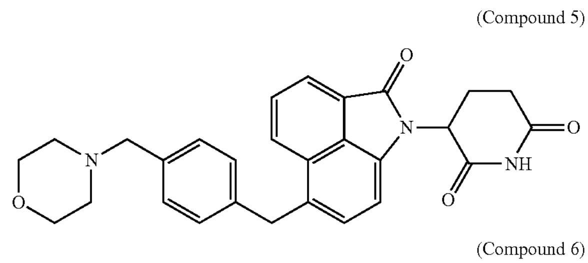

(Compound 6)

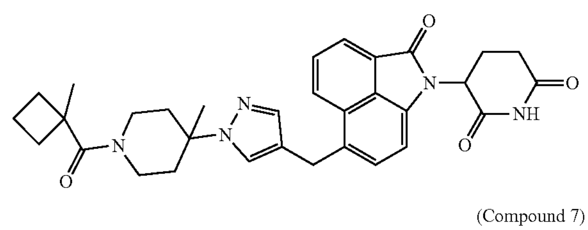

(Compound 7)

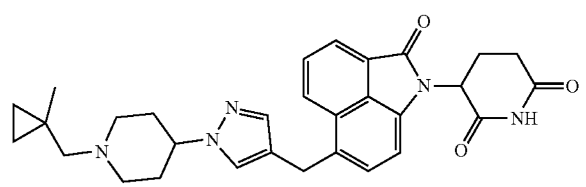

-continued (Compound 8)

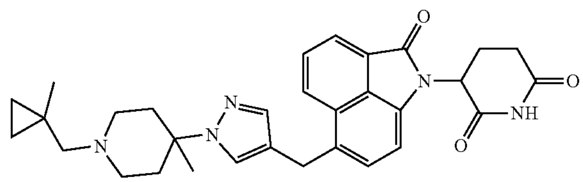

(Compound 9)

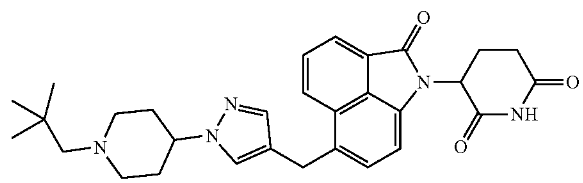

(Compound 10)

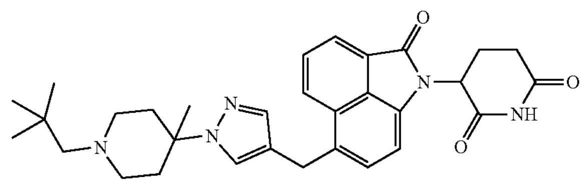

(Compound 11)

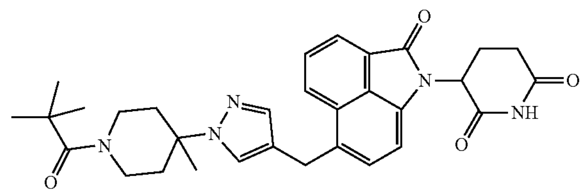

(Compound 12)

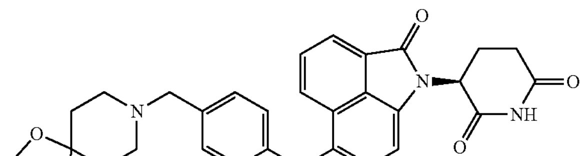

(Compound 13)

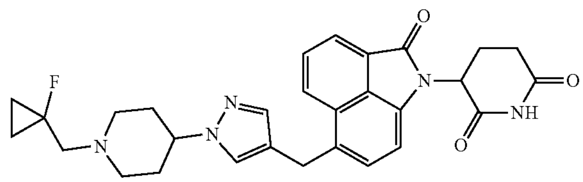

or a pharmaceutically acceptable salt thereof.

A compound described herein modulates immune system activity, for example activating IFN-alpha, IFN-beta, or IFN-gamma. By activating the immune system, the compound can more effectively treat cancer. This immunomodulatory activity increases the efficacy of a compound described herein with another anti-cancer agent such as daratumumab.

In certain embodiments the degradation of IKZF1 and IKZF3 from malignant B or T cells result in tumor cell death, and their depletion from the tumor microenvironment results in T-cell activation.

The compound may for example be provided for oral, parenteral or topical delivery. In certain embodiments, the compound is provided in a solid, gel or liquid dosage form for oral delivery, or may be provided intravenously. In some embodiments, the selected compound is provided as a softshell capsule or a solid dosage form tablet for oral administration. In certain embodiments, the dose strengths of the pharmaceutical composition is about 1 μg, 5 μg, 10 μg, 15 μg, 20 μg, 25 μg, 50 μg, 75 μg, 100 μg, 125 μg, 150 μg, 175 μg, 200 μg, 225 μg, 250 μg, 275 μg, 300 μg, 325 μg, 350 μg, 375 μg, 400 μg, 425 μg, 450 μg, 475 μg, 500 μg, 525 μg, 550 μg, 575 μg, 600 μg, 625 μg, 650 μg, 675 μg, 700 μg, 725 μg, 750 μg, 775 μg, or 800 μg, which may in one nonlimiting aspect be given once daily (QD) or twice a day (BID) on days 1-21 of a 28-day treatment cycle.

The compound may for example be provided for oral or parenteral delivery. In certain embodiments, the compound is provided in a solid, gel or liquid dosage form for oral delivery, or may be provided intravenously. In some embodiments, the selected compound is provided as a softshell capsule or tablet for oral administration. In certain embodiments, the dose strengths of the solid or gel dosage form is 25 μg, 50 μg, 100 μg, 200 μg, 300 μg or 400 μg, which may in one nonlimiting aspect be given once daily (QD) on days 1-21 of a 28-day cycle.

In a principal aspect the compound used in the treatments described herein is Compound 1 or a pharmaceutically acceptable salt thereof.

In certain embodiments, any of the compounds described herein have at least one desired isotopic substitution of an atom, at an amount about the natural abundance of the isotope, i.e., enriched. In certain embodiments, the compound includes a deuterium or multiple deuterium atoms.

Other features and advantages of the present invention will be apparent from the following detailed description and claims.

Both agents were administered orally (PO) every day (QD). The x-axis is the time measured in days and the y-axis is the tumor volume measured in $mm^3$.

Figure 11:
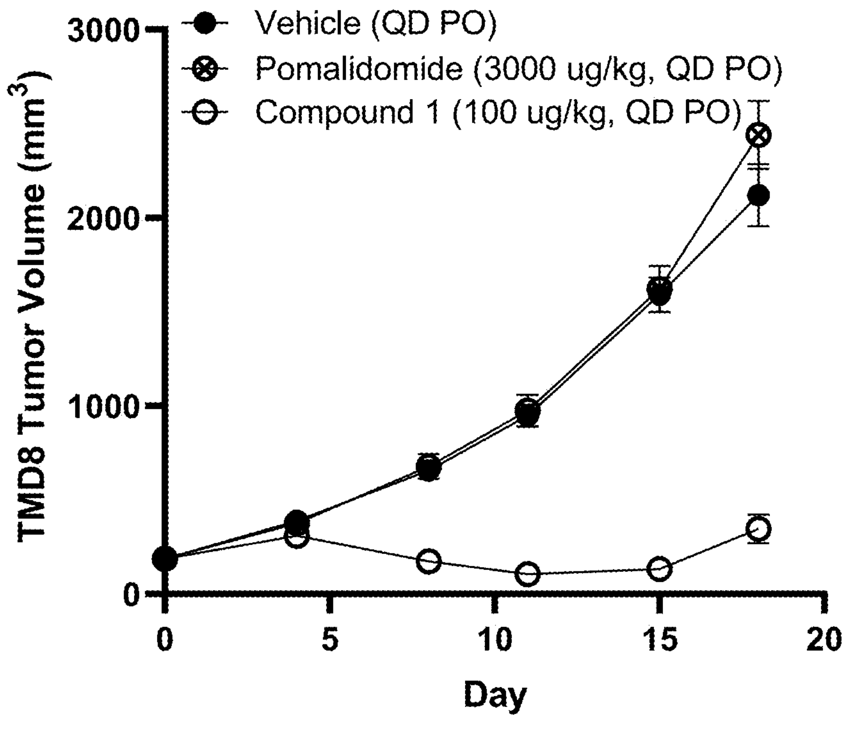

FIG. 11 is a graph of the tumor volume of mice injected with lymphoma TMD8 DLBCL and administered Compound 1 (100 μg/kg) or pomalidomide (3000 μg/kg) orally (PO) every day (QD) as described in Example 16. The x-axis is the time measured in days and the y-axis is the tumor volume measured in $mm^3$.

Figure 12:
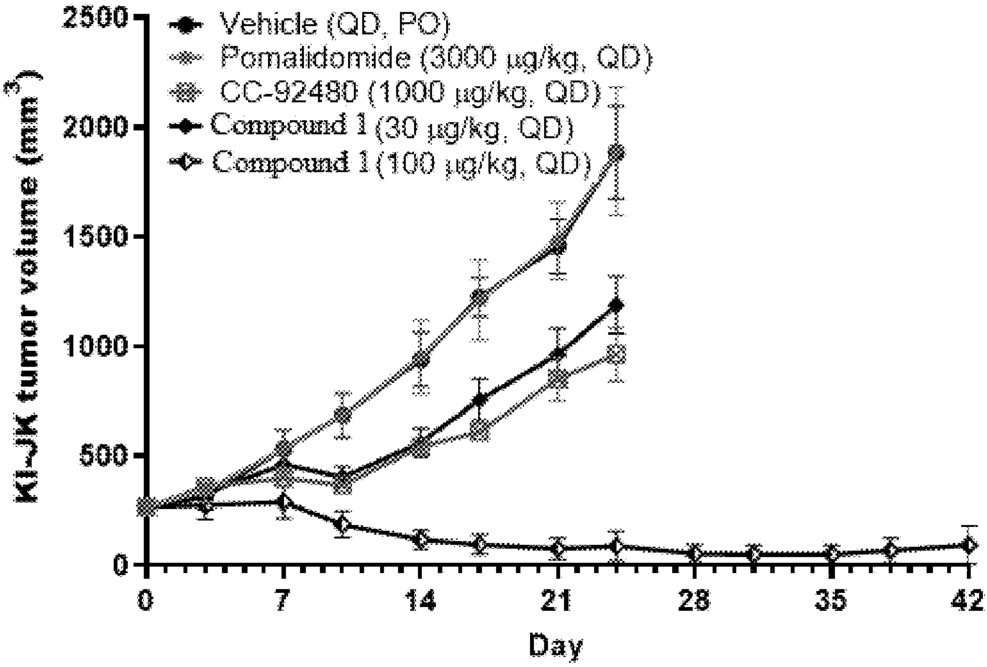

FIG. 12 is a graph of the tumor volume of mice injected with KI-JK ALCL tumors and administered Compound 1 at either 30 μg/kg or 100 μg/kg PO QD (orally every day) or pomalidomide (3000 μg/kg, QD PO) or CC-92480 (1000 μg/kg, QD PO) as described in Example 17. The mice were dosed for 21 days. The x-axis is the time measured in days and the y-axis is the tumor volume measured in $mm^3$.

Figure 13A:
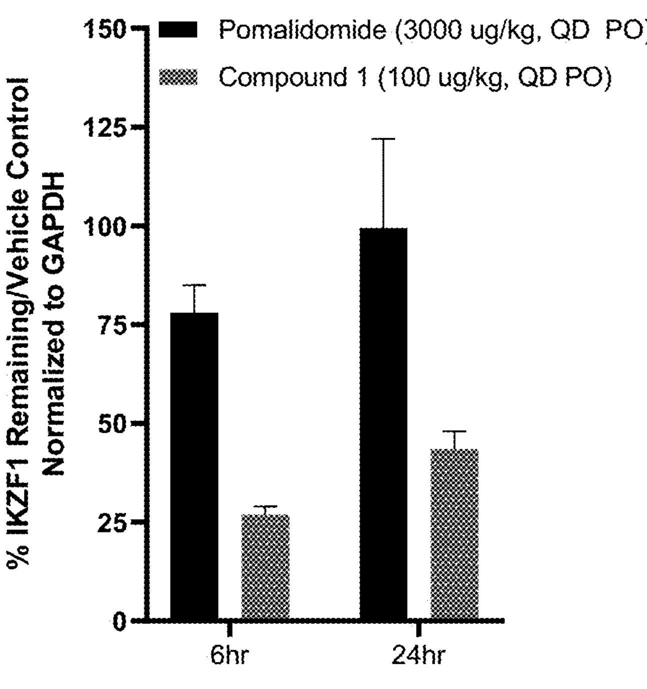

FIG. 13A is a bar graph of IKZF1 protein expression in mice injection with KI-JK ALCL tumors and administered Compound 1 or pomalidomide as described in Example 17. Mice were sacrificed and tumors harvested at 6 and 24 hours post single dose. The x-axis is labeled with the time post dose that the animal was sacrificed and the y-axis is the percent of IKZF1 protein compared to the vehicle control normalized to GAPDH.

Figure 13B:
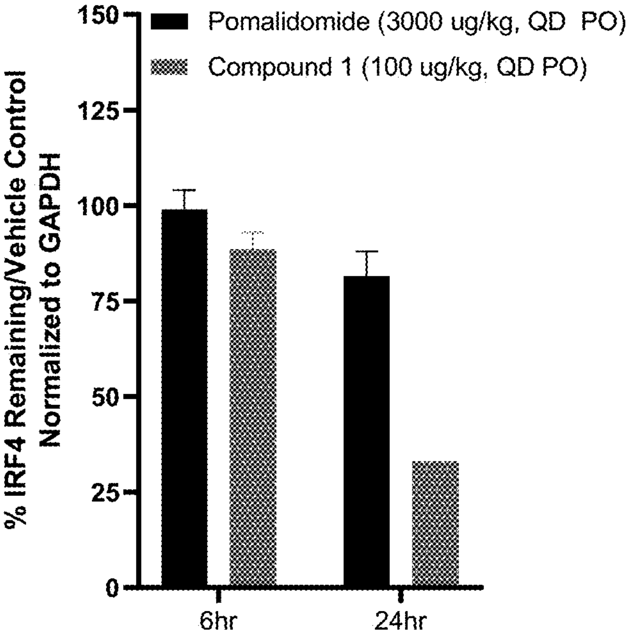

FIG. 13B is a bar graph of IRF4 protein expression in mice injection with KI-JK ALCL tumors and administered Compound 1 or pomalidomide as described in Example 17. Mice were sacrificed and tumors harvested at 6 and 24 hours post single dose. The x-axis is labeled with the time post dose that the animal was sacrificed and the y-axis is the percent of IRF4 protein compared to the vehicle control normalized to GAPDH.

Figure 14:
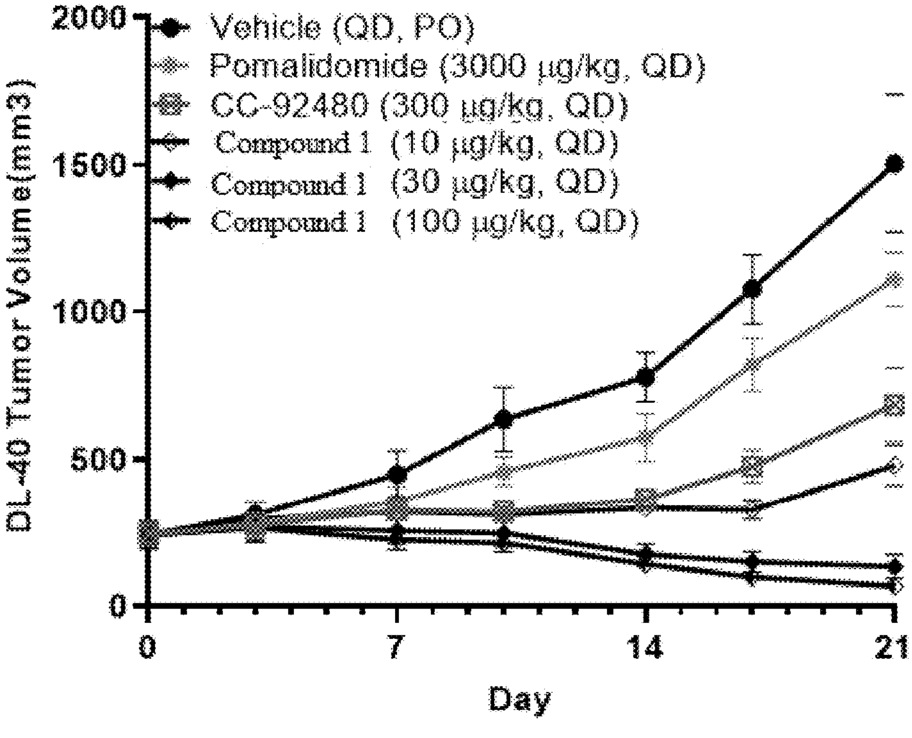

FIG. 14 is a graph of the tumor volume of mice injected with DL-40 ALCL tumors and administered Compound 1, pomalidomide, or CC-92480 as described in Example 18. Compound 1 was administered at three different concentrations (10 μg/kg, 30 μg/kg, or 100 μg/kg) orally (PO) every day (QD). Pomalidomide was administered at a dose of 3000 μg/kg orally every day. CC-92480 was administered at a dose of 300 μg/kg orally every day. The x-axis is the time measured in days and the y-axis is the tumor volume measured in $mm^3$.

Figure 15A:
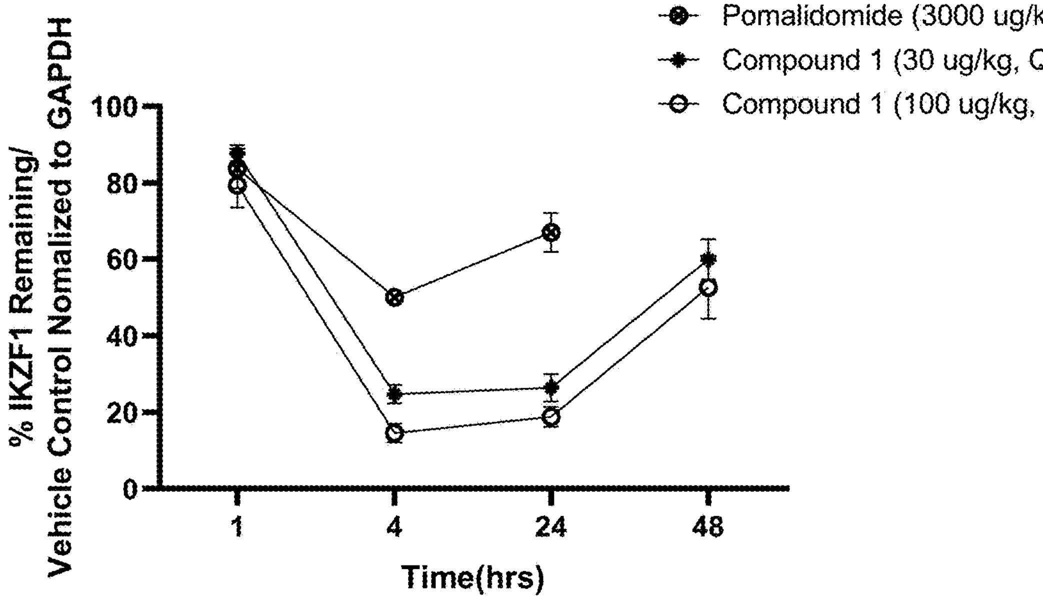

FIG. 15A is a graph of IKZF1 protein expression in mice injected with DL-40 ALCL tumors and administered Compound 1 or pomalidomide as described in Example 18. Mice were sacrificed and tumors harvested at 1, 4, and 24 hours post single dose. The x-axis is labeled with the time post dose that the animal was sacrificed and the y-axis is the percent of IKZF1 protein compared to the vehicle control normalized to GAPDH.

Figure 15B:
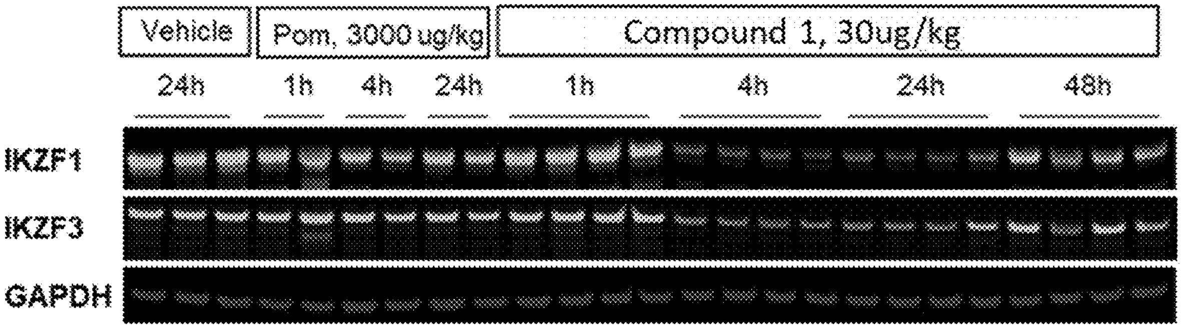
Figure 16:
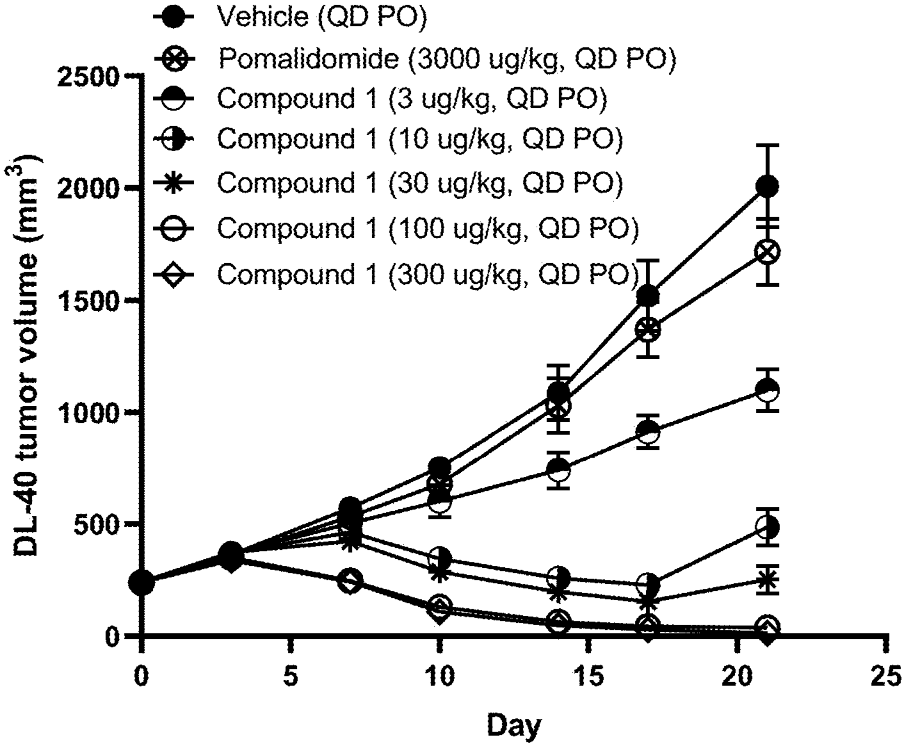

FIG. 15B is a western blot measuring the concentration of IKZF1 and IKZF3 in mice injected with DL-40 ALCL tumors and administered Compound 1 or pomalidomide as described in Example 18. The concentration was determined when mice were sacrificed at 1, 4, and 24 hours post single dose. DL-40 ALCL tumors FIG. 16 is a graph of the tumor volume of mice injected with DL-40 ALCL tumors and administered Compound 1 or pomalidomide as described in Example 19. Compound 1 was administered at five different concentrations (3 μg/kg, 10 μg/kg, 30 μg/kg, 100 μg/kg, or 300 g/kg) orally (PO) every day (QD). Pomalidomide was administered at a dose of 3000 μg/kg orally every day. The x-axis is the time measured in days and the y-axis is the tumor volume measured in $mm^3$.

Figure 17:
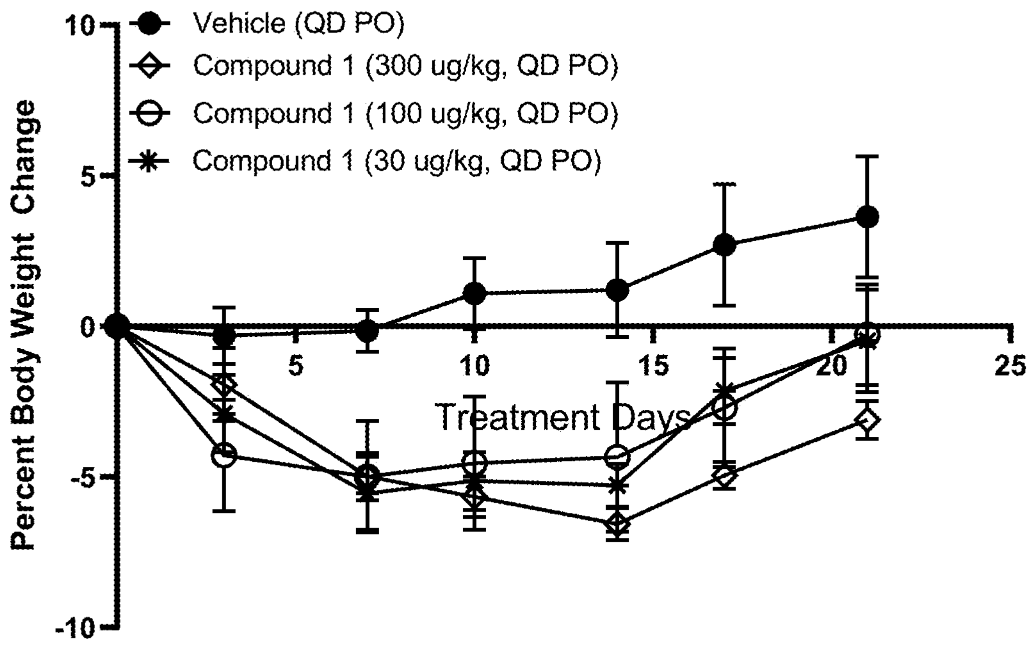

FIG. 17 is a graph of the tumor volume of mice injected with DL-40 ALCL tumors and administered Compound 1 as described in Example 19. Compound 1 was administered at three different concentrations (30 μg/kg, 100 μg/kg, or 300 μg/kg) orally (PO) every day (QD). The x-axis is the time measured in days and the y-axis is the body weight change measured in percent.

Figure 18:
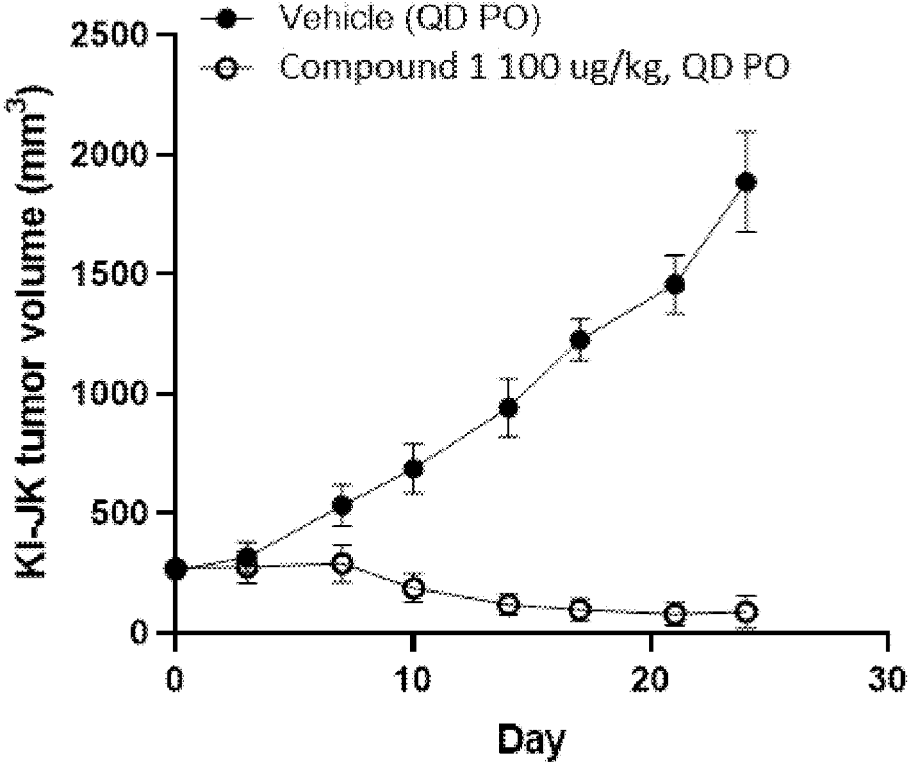

FIG. 18 is a graph of the tumor volume of mice injected with KI-JK ALCL tumors and administered Compound 1 (100 μg/kg orally (PO) every day (QD)) as described in Example 20. The x-axis is the time measured in days and the y-axis is the tumor volume measured in $mm^3$.

Figure 19:
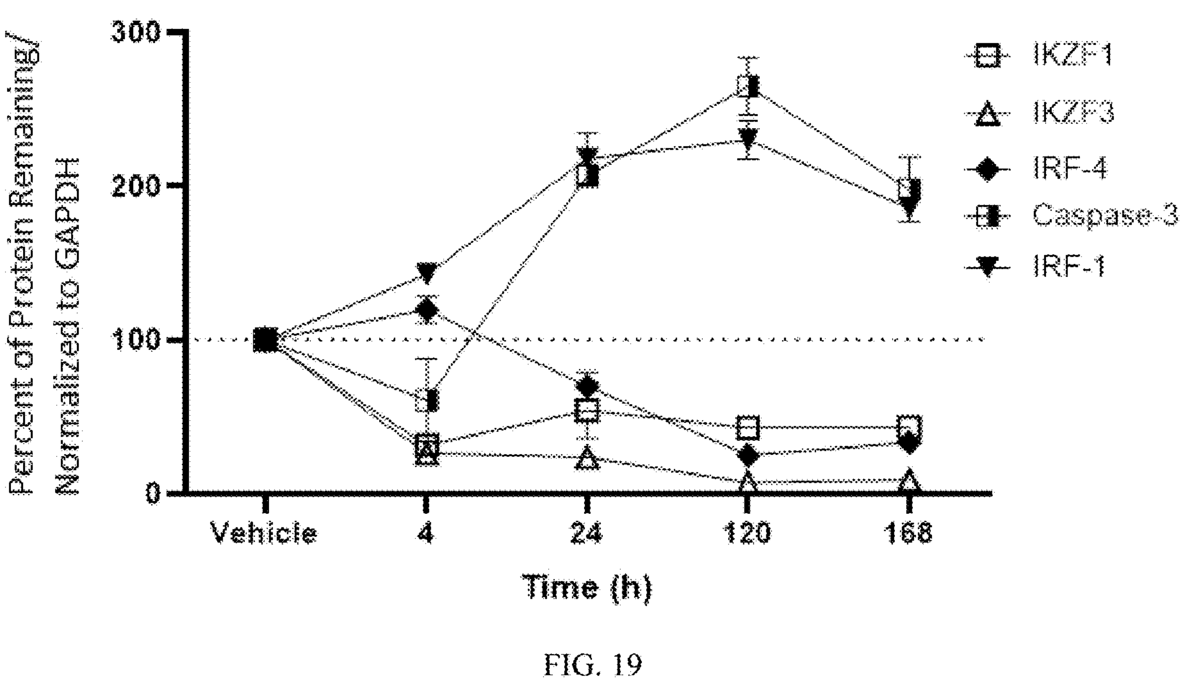

FIG. 19 is a graph of IKZF1, IKZF3, IRF-4, caspase-3, and IRF-1 protein expression in mice injected with KI-JK ALCL tumors and administered Compound 1 as described in Example 20. The x-axis is labeled with the time post dose that the animal was sacrificed and the y-axis is the percent of protein compared to the vehicle control normalized to GAPDH.

Figure 20:
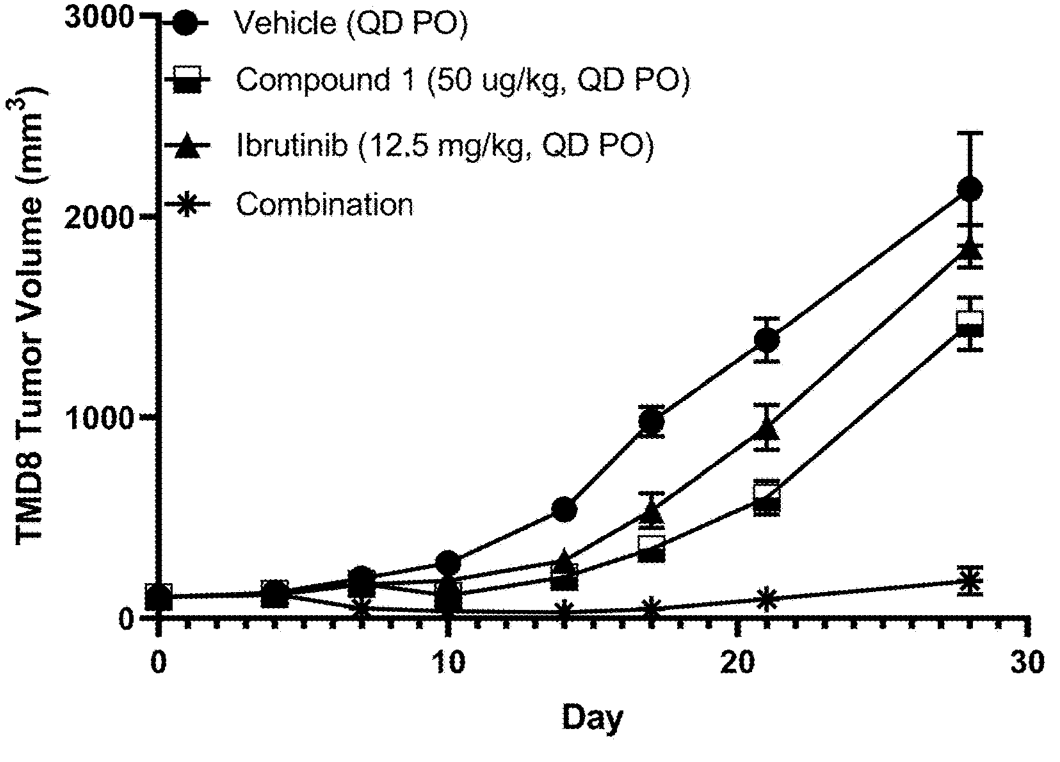

FIG. 20 is a graph comparing the effect of Compound 1, ibrutinib, and the combination of Compound 1 and ibrutinib on TMD8 tumor volume in mice as described in Example 13. Compound 1 was administered at a dose of 50 μg/kg orally every day and ibrutinib was administered at a dose of 12.5 mg/kg orally every day. The combination was dosed at each agent's respective dose. The x-axis is the time measured in days and the y-axis is the tumor volume measured in $mm^3$.

Figure 21:
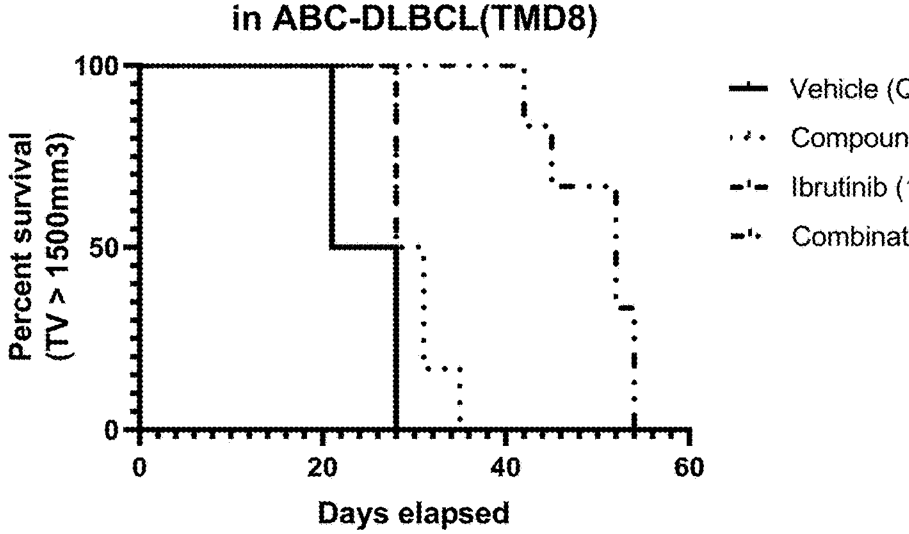

FIG. 21 is a graph of the percent survival of mice bearing TMD8 DLBCL administered Compound 1, ibrutinib, and the combination of Compound 1 and ibrutinib as described in Example 21. Compound 1 was administered at a dose of 50 μg/kg orally every day and ibrutinib was administered at a dose of 12.5 mg/kg orally every day. The combination was dosed at each agent's respective dose. The x-axis is days post-dose and the y-axis is the percent survival.

Figure 22:
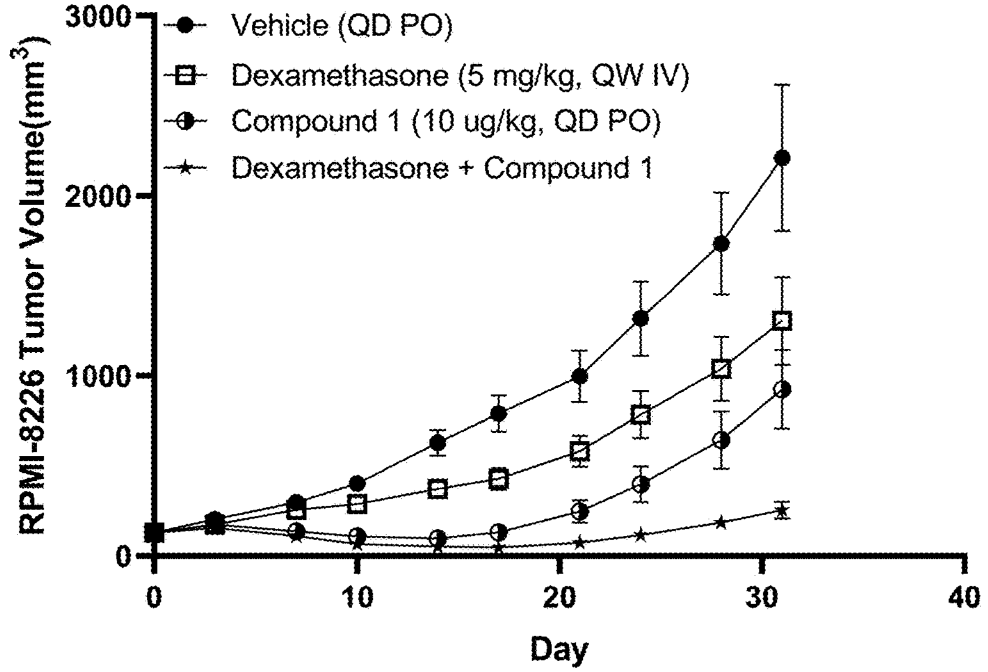

FIG. 22 is a graph comparing the effect of Compound 1, dexamethasone, and the combination of Compound 1 and dexamethasone on RPMI-8226 multiple myeloma tumor volume in mice as described in Example 22. Dexamethasone was administered at a dose of 5 mg/kg intravenously (IV) every week (QW) and Compound 1 was administered at a dose of 10 μg/kg orally every day. Compound 1 was dosed in combination with dexamethasone at each agent's respective dose levels and schedules. The x-axis is the time measured in days and the y-axis is the tumor volume measured in $mm^3$.

Figure 23:
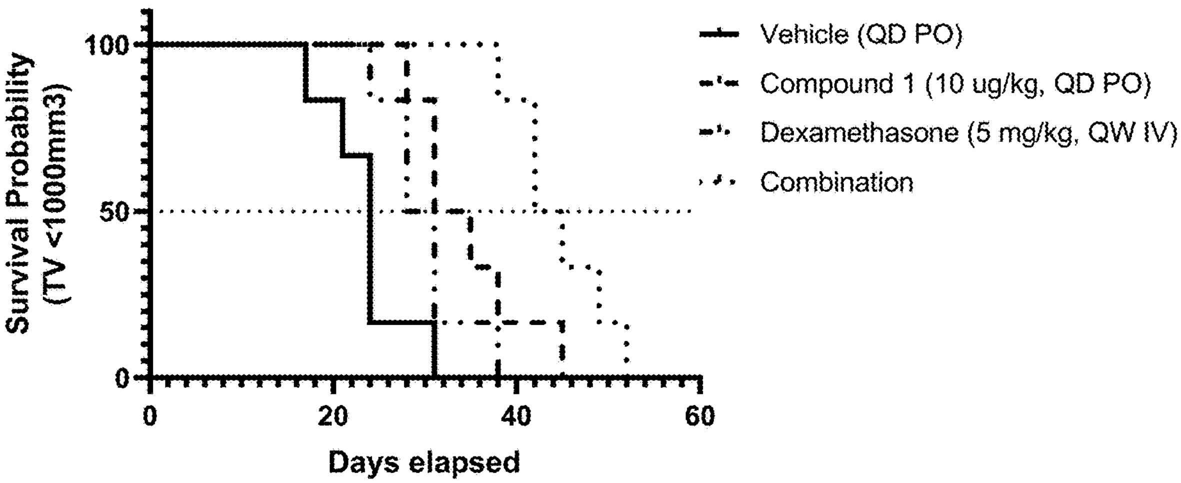

FIG. 23 is a graph of the percent survival of mice bearing RPMI-8226 multiple myeloma tumors administered Compound 1, dexamethasone, and the combination of Compound 1 and dexamethasone as described in Example 22. Dexamethasone was administered at a dose of 5 mg/kg intravenously (IV) every week (QW) and Compound 1 was administered at a dose of 10 g/kg orally every day. Compound 1 was dosed in combination with dexamethasone at each agent's respective dose levels and schedules. The x-axis is days post-dose and the y-axis is the percent survival.

Figure 24:
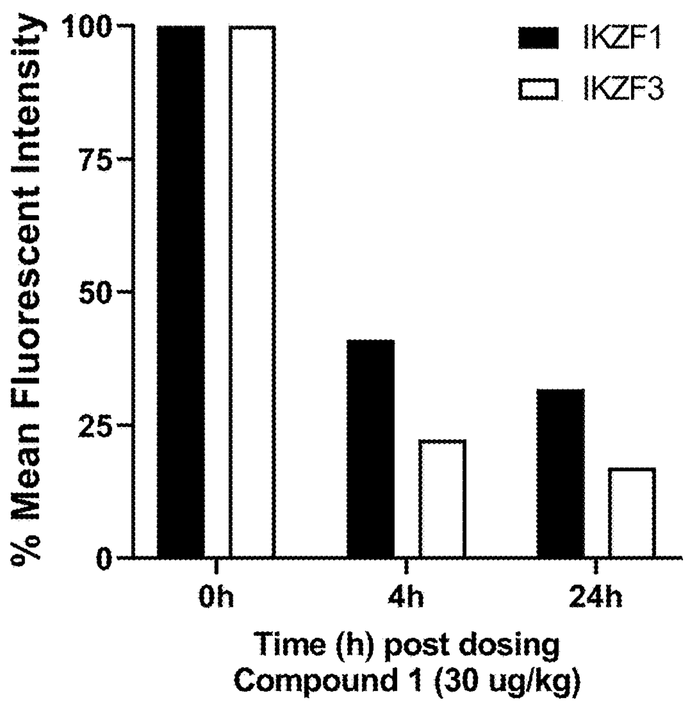

FIG. 24 is a graph measuring the concentration of IKZF1 and IKZF3 in a monkey administered Compound 1. As described in Example 23, one monkey was administered Compound 1 and blood was collected at 0, 4, and 24 hours post-dose to determine the concentration of IKZF1 and IKZF3. The x-axis is the time post-dosing measured in hours and the y-axis is the mean fluorescent intensity of IKZF1 and IKZF3.

Figure 25A:
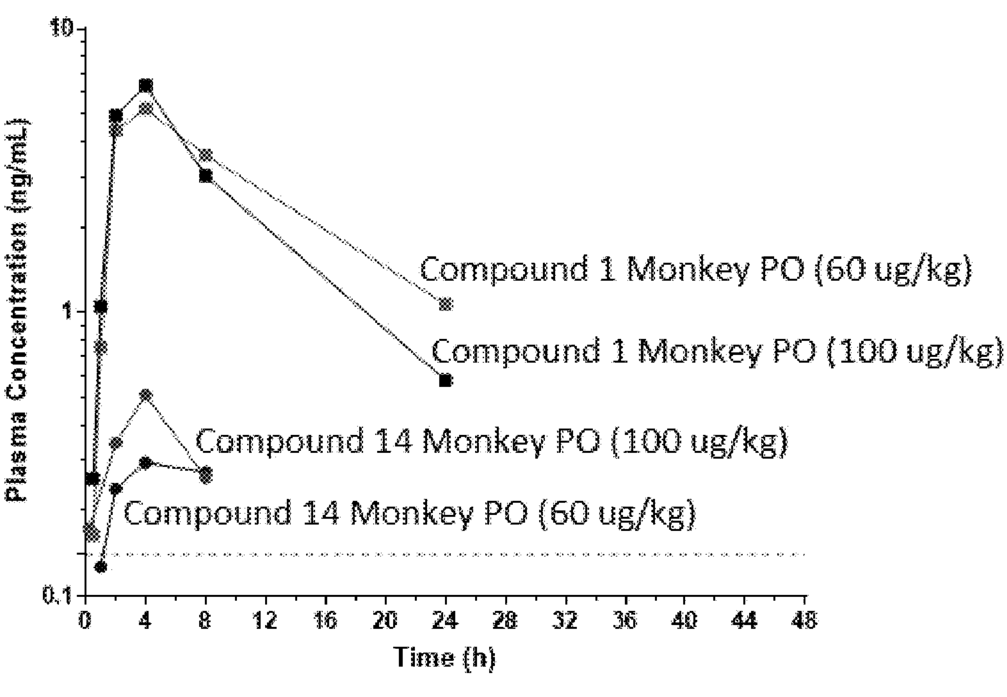

FIG. 25A is a graph measuring the plasma concentration of Compound 1 or Compound 14 following the administration of Compound 1 (60 μg/kg or 100 μg/kg) PO to monkeys as described in Example 24. The x-axis is time measured in hours and the y-axis is plasma concentration measured in ng/mL.

Figure 25B:
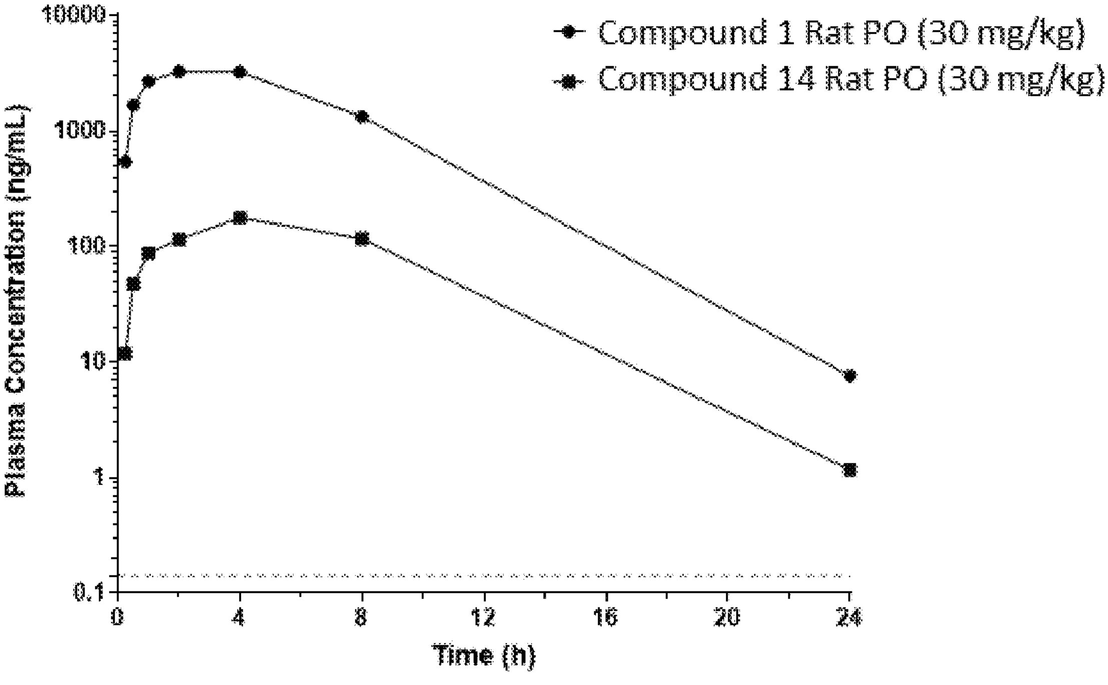

FIG. 25B is a graph measuring the plasma concentration of Compound 1 or Compound 14 following the administration of Compound 1 (30 mg/kg) PO to a rat as described in Example 24. The x-axis is time measured in hours and the y-axis is plasma concentration measured in ng/mL.

Figure 26A:
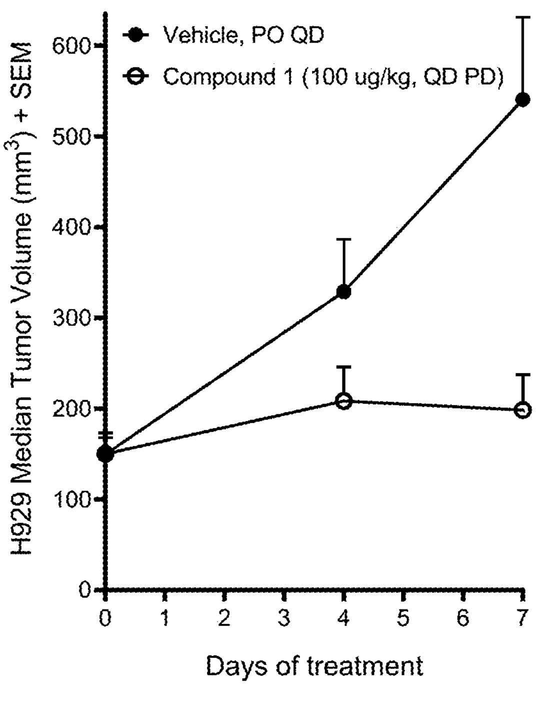

FIG. 26A is a graph measuring the effect of Compound 1 (100 μg/kg, QD PO) compared to vehicle on tumor volume in mice injected with H929 tumors as described in Example 25. The x-axis is treatment length measured in days and the y-axis is H929 tumor volume measured in $mm^3$.

Figure 26B:
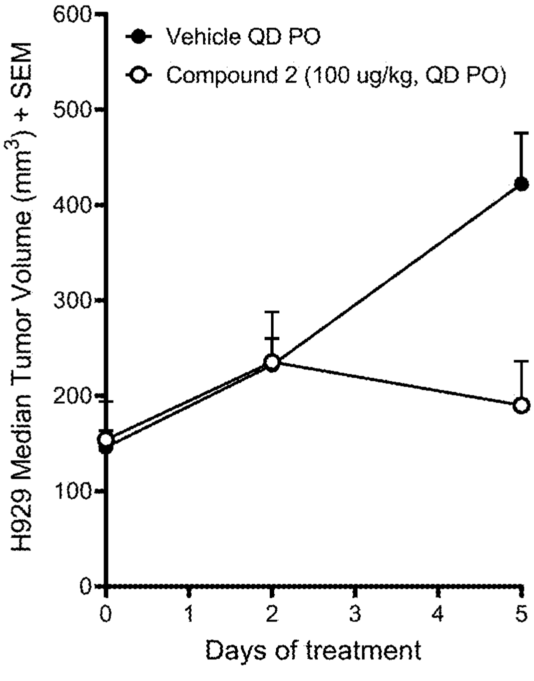

FIG. 26B is a graph measuring the effect of Compound 2 (100 μg/kg, QD PO) compared to vehicle on tumor volume in mice injected with H929 tumors as described in Example 25. The x-axis is treatment length measured in days and the y-axis is H929 tumor volume measured in $mm^3$.

Figure 26C:
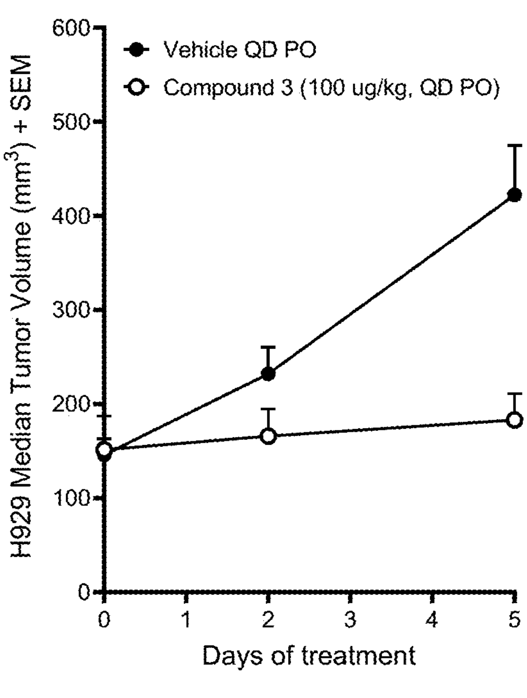

FIG. 26C is a graph measuring the effect of Compound 3 (100 μg/kg, QD PO) compared to vehicle on tumor volume in mice injected with H929 tumors as described in Example 25. The x-axis is treatment length measured in days and the y-axis is H929 tumor volume measured in $mm^3$.

Figure 26D:
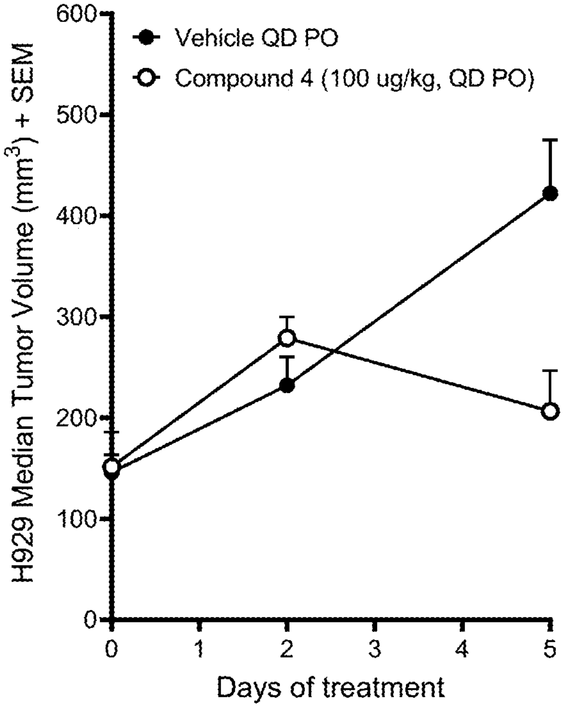

FIG. 26D is a graph measuring the effect of Compound 4 (100 μg/kg, QD PO) compared to vehicle on tumor volume in mice injected with H929 tumors as described in Example 25. The x-axis is treatment length measured in days and the y-axis is H929 tumor volume measured in $mm^3$.

Figure 26E:
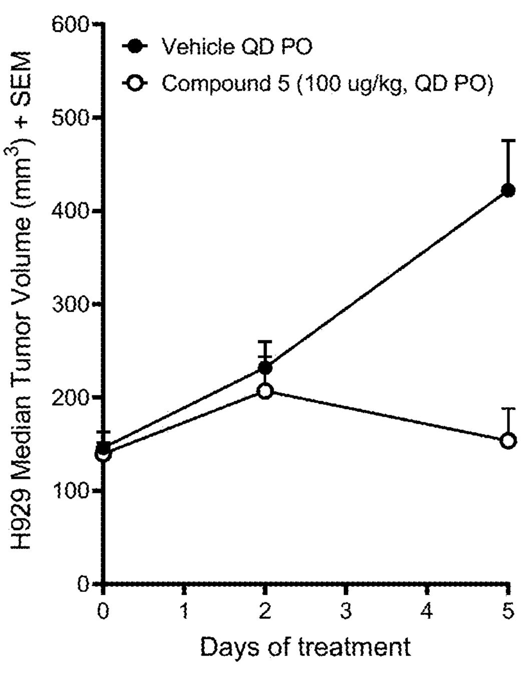

FIG. 26E is a graph measuring the effect of Compound 5 (100 μg/kg, QD PO) compared to vehicle on tumor volume in mice injected with H929 tumors as described in Example 25. The x-axis is treatment length measured in days and the y-axis is H929 tumor volume measured in $mm^3$.

Figure 26F:
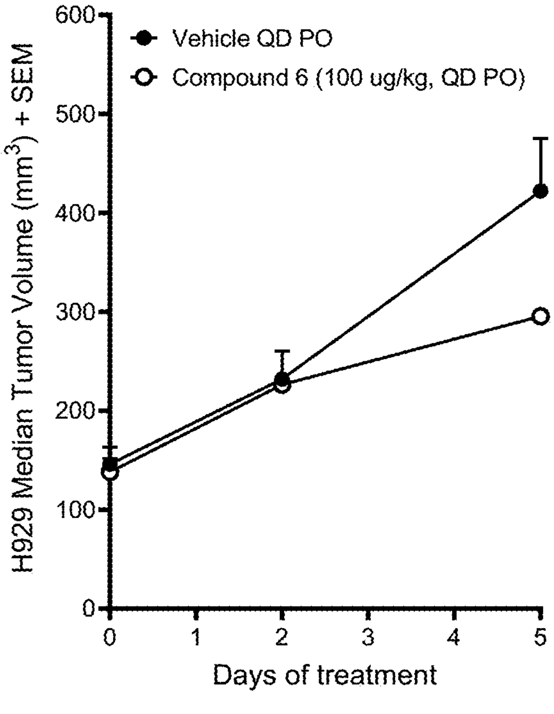

FIG. 26F is a graph measuring the effect of Compound 6 (100 μg/kg, QD PO) compared to vehicle on tumor volume in mice injected with H929 tumors as described in Example 25. The x-axis is treatment length measured in days and the y-axis is H929 tumor volume measured in $mm^3$.

Figure 26G:
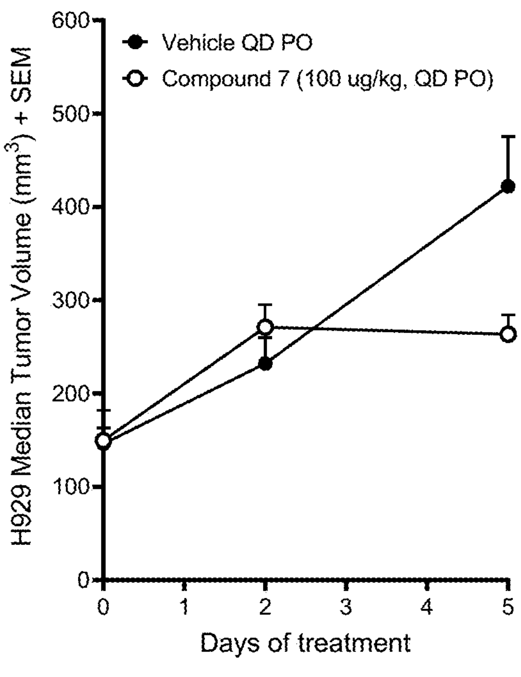

FIG. 26G is a graph measuring the effect of Compound 7 (100 μg/kg, QD PO) compared to vehicle on tumor volume in mice injected with H929 tumors as described in Example 25. The x-axis is treatment length measured in days and the y-axis is H929 tumor volume measured in $mm^3$.

Figure 26H:
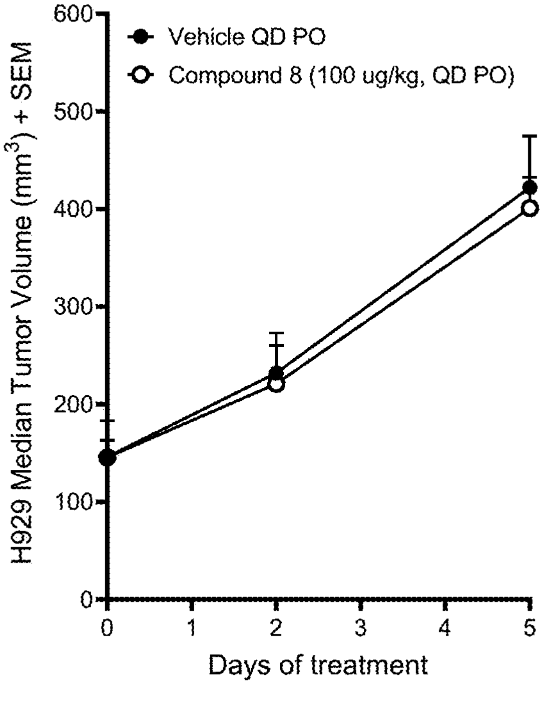

FIG. 26H is a graph measuring the effect of Compound 8 (100 μg/kg, QD PO) compared to vehicle on tumor volume in mice injected with H929 tumors as described in Example 25. The x-axis is treatment length measured in days and the y-axis is H929 tumor volume measured in $mm^3$.

Figure 26I:
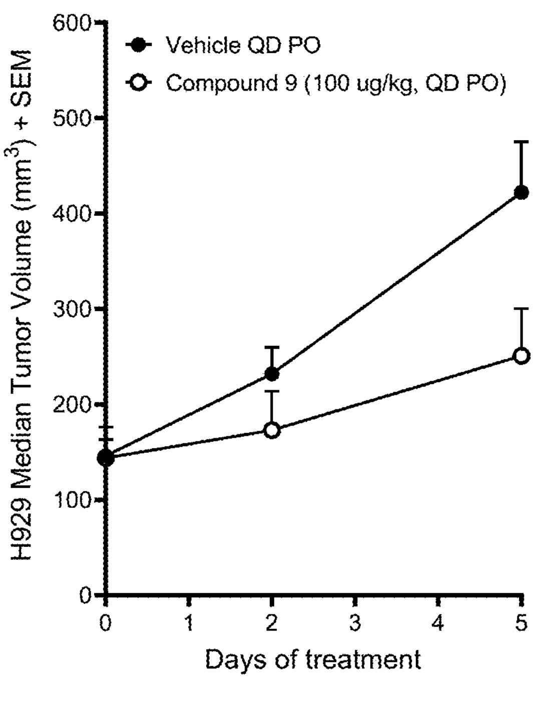

FIG. 26I is a graph measuring the effect of Compound 9 (100 μg/kg, QD PO) compared to vehicle on tumor volume in mice injected with H929 tumors as described in Example 25. The x-axis is treatment length measured in days and the y-axis is H929 tumor volume measured in $mm^3$.

Figure 26J:
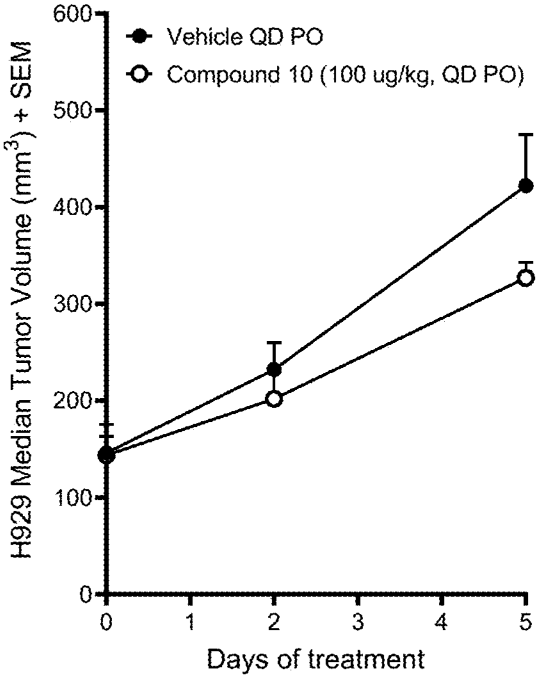

FIG. 26J is a graph measuring the effect of Compound 10 (100 μg/kg, QD PO) compared to vehicle on tumor volume in mice injected with H929 tumors as described in Example 25. The x-axis is treatment length measured in days and the y-axis is H929 tumor volume measured in $mm^3$.

Figure 26K:
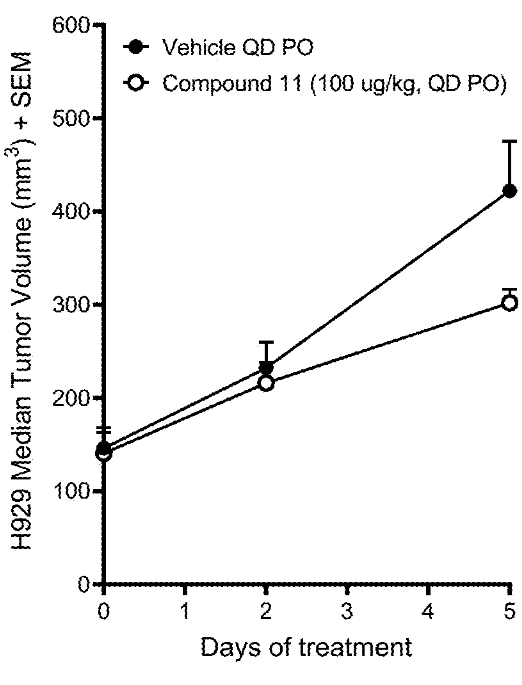

FIG. 26K is a graph measuring the effect of Compound 11 (100 μg/kg, QD PO) compared to vehicle on tumor volume in mice injected with H929 tumors as described in Example 25. The x-axis is treatment length measured in days and the y-axis is H929 tumor volume measured in $mm^3$.

Figure 26L:
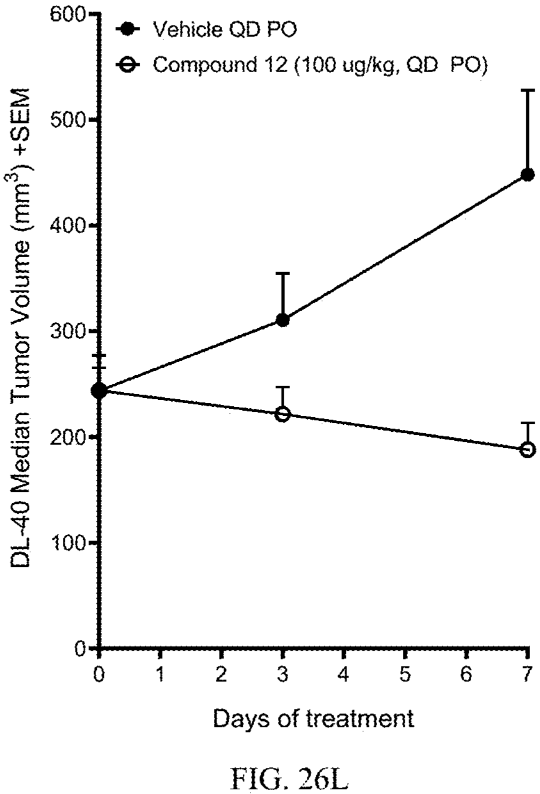

FIG. 26L is a graph measuring the effect of Compound 12 (100 μg/kg, QD PO) compared to vehicle on tumor volume in mice injected with DL-40 ALCL tumors as described in Example 25. The x-axis is treatment length measured in days and the y-axis is H929 tumor volume measured in $mm^3$.

Figure 26M:
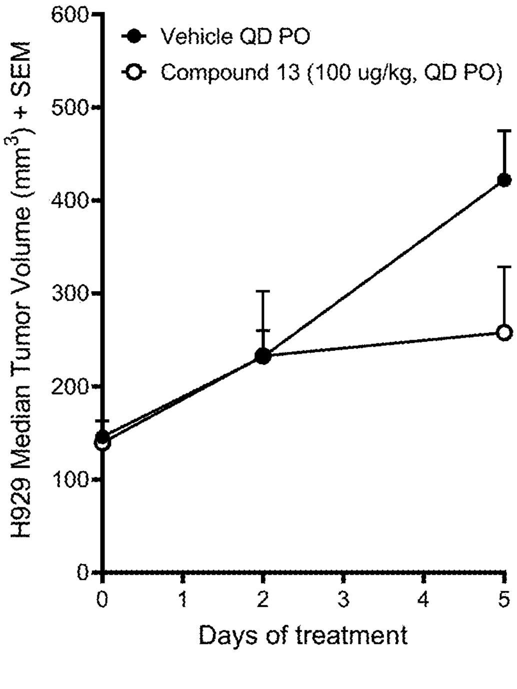

FIG. 26M is a graph measuring the effect of Compound 13 (100 μg/kg, QD PO) compared to vehicle on tumor volume in mice injected with H929 tumors as described in Example 25. The x-axis is treatment length measured in days and the y-axis is H929 tumor volume measured in $mm^3$.

Figure 27:
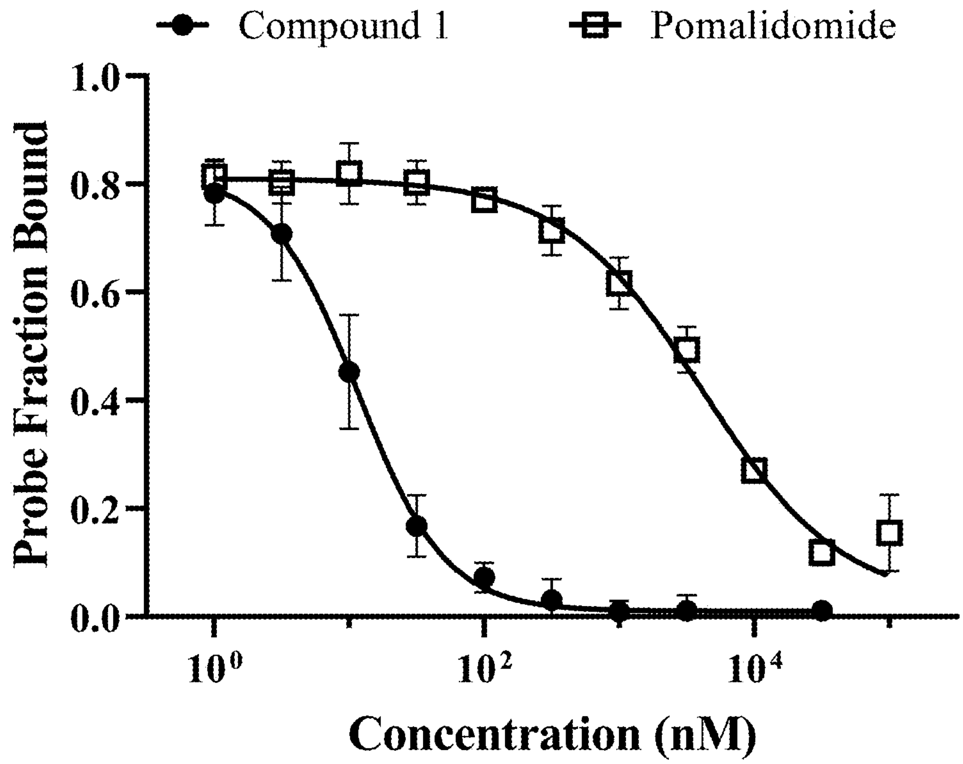

FIG. 27 is a graph demonstrating the in-vitro binding of Compound 1 to purified cereblon-DDB1 was measured via fluorescent polarization experiment. Compound 1 (circles) or reference compound (Pomalidomide) competes with Alexa-647 based fluorescence probe for binding to cereblon-DDB1. Probe displacement results in a decreased level of fluorescent polarization that is used to calculate the fraction of the bound probe using the signals from positive and negative controls. Error bars represent the standard deviation (SD). Measured Kd values are as follows: Compound 1: $K_d$=0.9±0.5 nM; Pomalidomide $K_d$=712±140 nM. The fluorescent polarization experiment is described in Example 26.

Figure 28:
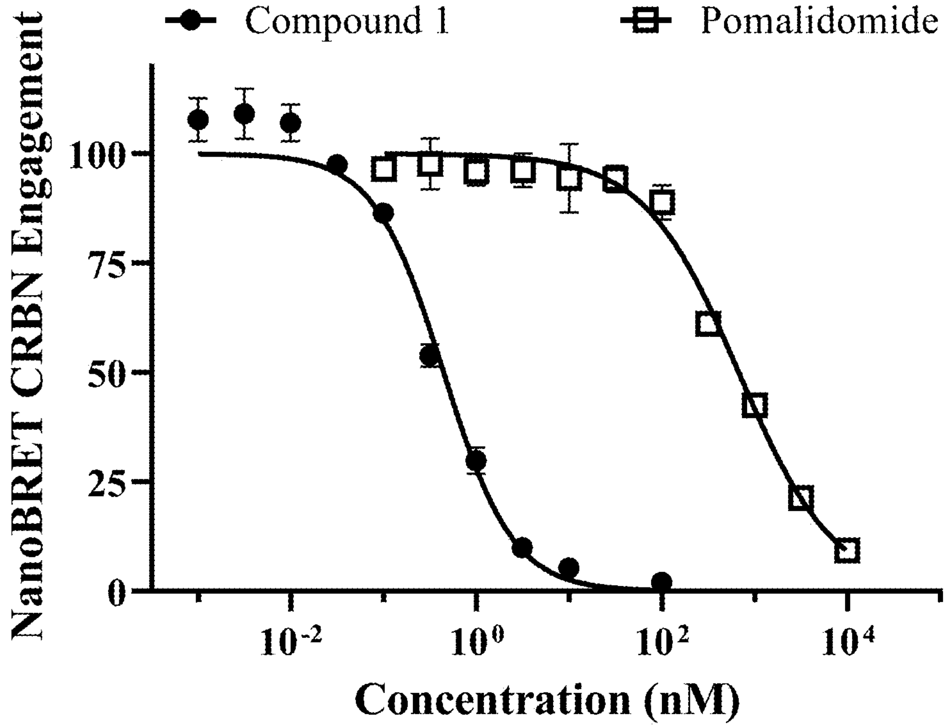

FIG. 28 is a dose-response curve describing the displacement of a cereblon binding tracer molecule by Compound 1 or pomalidomide in 293T cells expressing cereblon-NanoLuc fusion as described in Example 27. The x-axis is the concentration of Compound 1 or pomalidomide in nM and the y-axis is the % NanoBRET signal relative to cells treated with cereblon binding tracer only (100%) or without tracer (0%). 50% of the tracer was displaced by Compound 1 with $IC_{50}$=0.4 nM and by pomalidomide with $IC_{50}$=644 nM.

Figure 29:
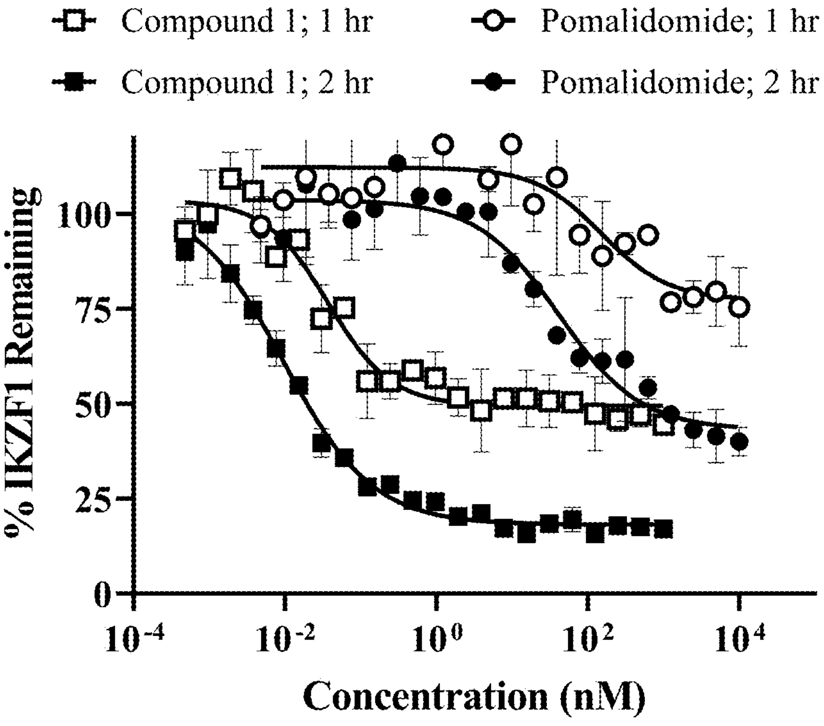

FIG. 29 is a dose-response curve describing the effect of Compound 1 on IKZF1 degradation compared to pomalidomide as described in Example 9. The x-axis is the concentration of Compound 1 or pomalidomide in nM and the y-axis is the % IKZF1 remaining after treatment with Compound 1 or pomalidomide for 1 or 2 hours.

Figure 30:
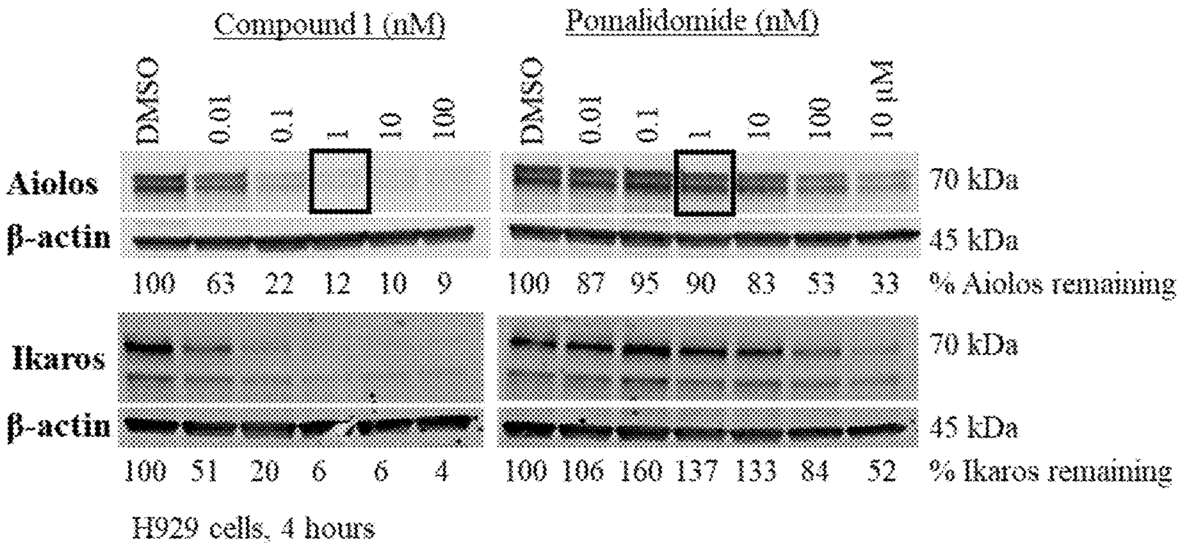

FIG. 30 is a western blot showing Aiolos and Ikaros levels remaining in H929 cells after 4 hours treatment with Compound 1 or pomalidomide in dose response. The method for this experiment is described in Example 28.

Figure 31:
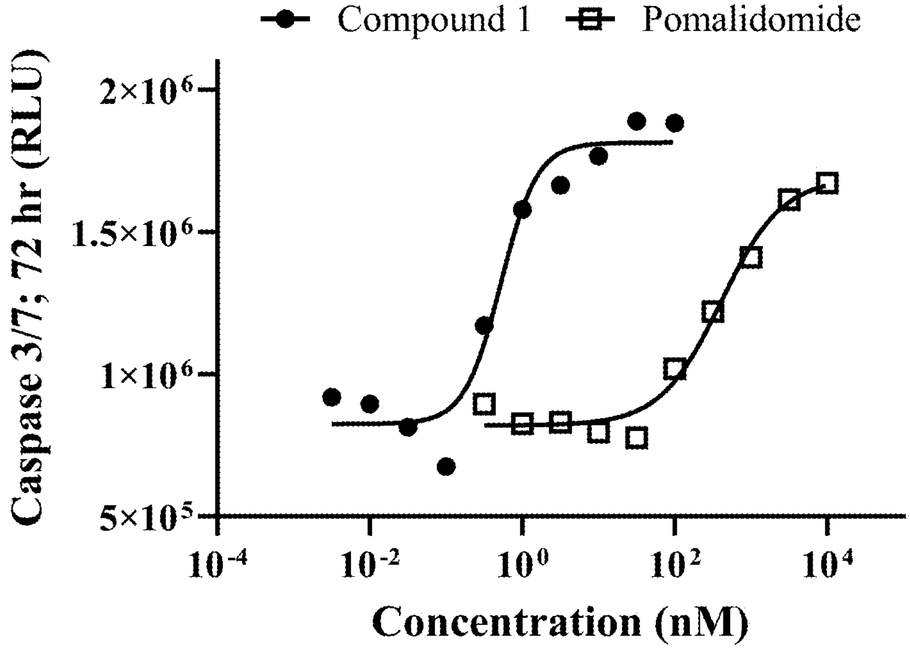

FIG. 31 is a dose-response curve describing the effect of Compound 1 on Caspase 3/7 activity in NCIH929 multiple myeloma cell line compared to pomalidomide after 72 hour treatment as described in Example 29. The x-axis is the concentration of Compound 1 or pomalidomide in nM and the y-axis is the luminescence signal (RLU) measured following addition of Caspase 3/7 substrate reagents. The method for this experiment is described in Example 29.

Figure 32:
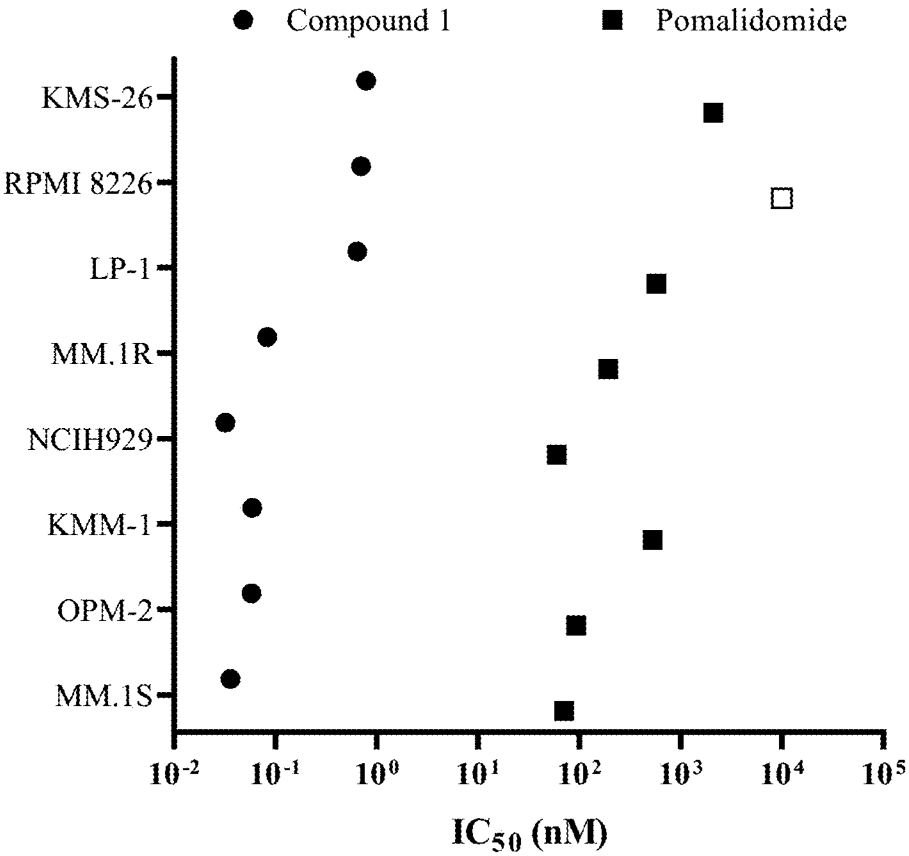

FIG. 32 is a plot showing the effect of Compound 1 on growth of eight multiple myeloma cell lines compared to pomalidomide as described in Example 30. The x-axis is the concentration of Compound 1 or pomalidomide in nM that inhibited cellular growth at 96 hours by 50% ($IC_{50}$) and the y-axis is the cell line tested.

Figure 33:
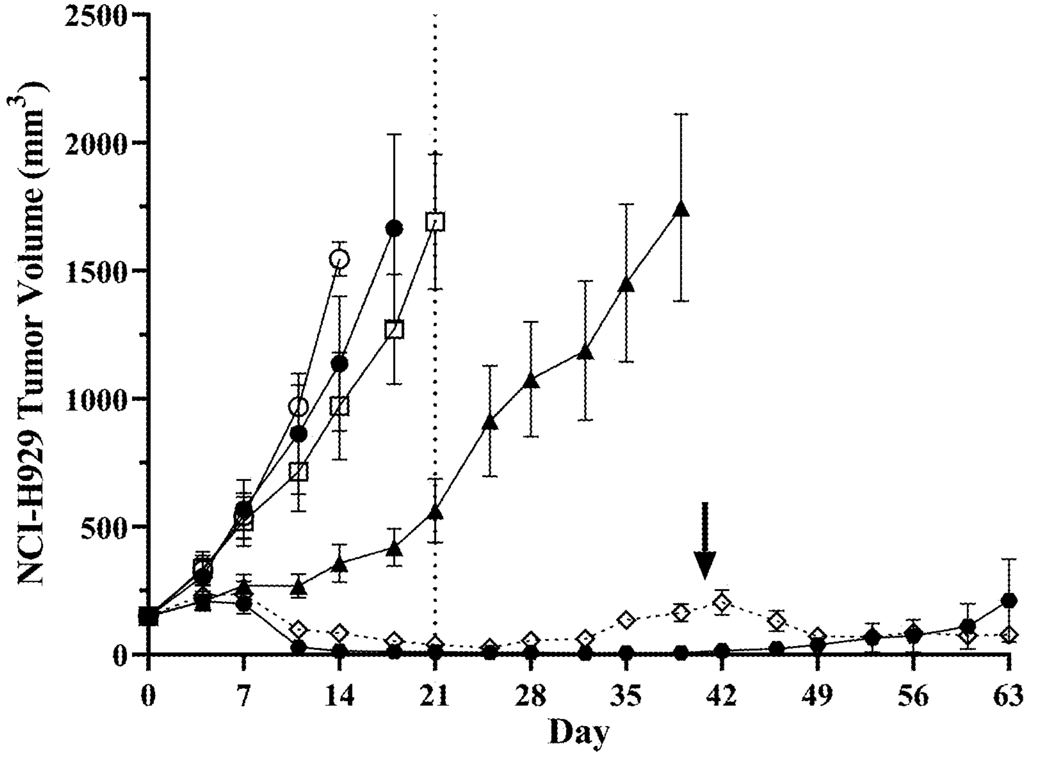

FIG. 33 is a graph showing the in vivo efficacy of Compound 1 and pomalidomide in the treatment of female NOD SCID mice bearing NCI-H929 multiple myeloma xenograft tumors. Mice we treated with the vehicle control, a dose response (3, 10, 30 and 100 μg/kg/day) of Compound 1, or 3000 μg/kg/day of pomalidomide for 21 days. All compounds were administered orally (PO) on a daily basis (QD) After 21 days of dosing tumors were monitored for regrowth. Arrow indicates rechallenging with 30 μg/kg/day of Compound 1 starting on Day 40. The x-axis is the time measured in days and the y-axis is NCI-H929 tumor volume measured in $mm^3$. This assay is described in Example 31.

Figure 34:
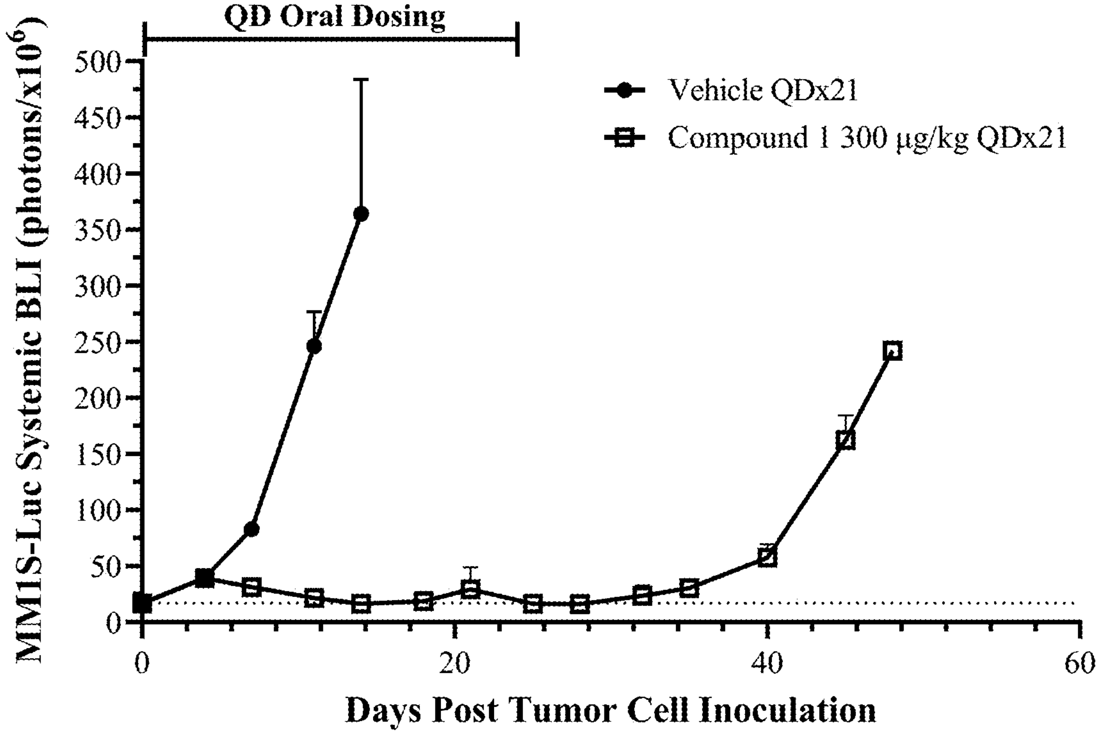

FIG. 34 is a graph of the bioluminescence signal of mice administered Compound 1 orally (PO) every day (QD) or vehicle and imaged using IVIS Lumina II as described in Example 14. The x-axis is time measured in days and the y-axis is the MM1S-Luc systemic BLI (total bioluminescence signal) measured in photons/106.

Figure 35:
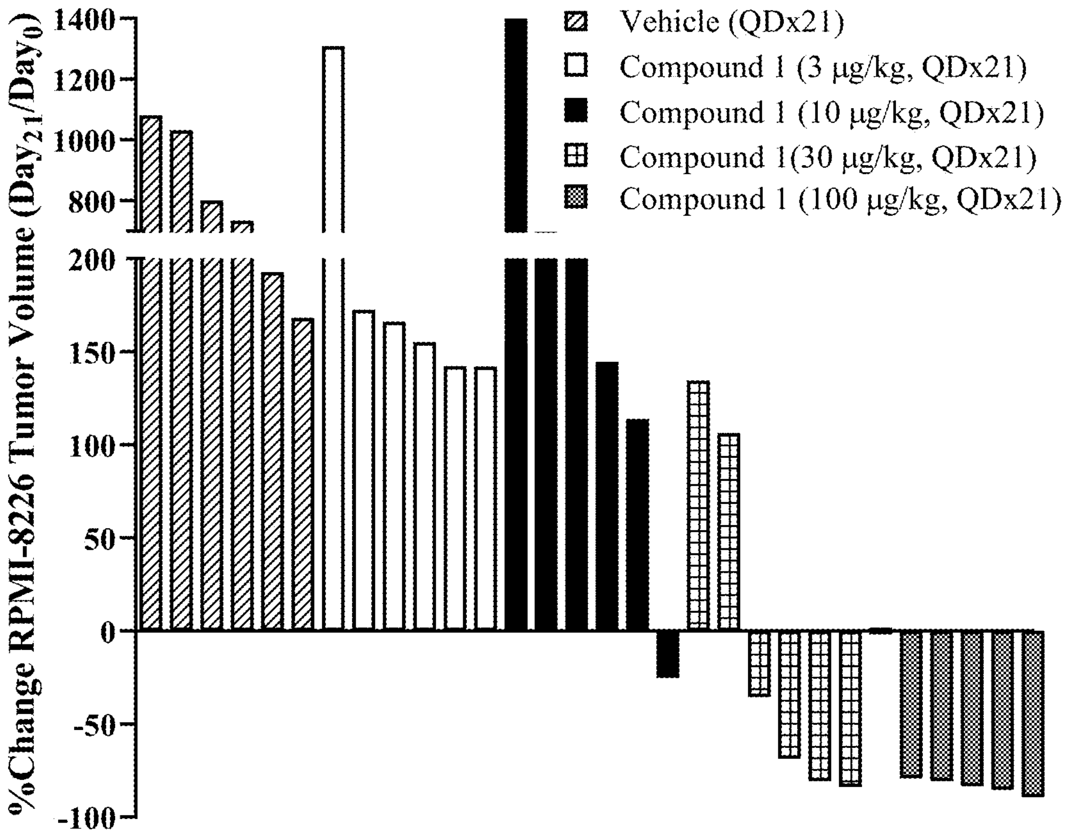

FIG. 35 is in vivo efficacy of Compound 1 and pomalidomide in the treatment of female CB17 SCID mice bearing RPM-8226 multiple myeloma xenograft tumors. Mice were treated with the vehicle control, a dose (3, 10, 30 and 100 μg/kg/day) of Compound 1, or 3000 μg/kg/day of pomalidomide for 21 days. All compounds were administered orally (PO) on a daily basis (QD). Tumors are graphed individually and represented as the percent of their original volume, as shown on the y-axis.

Figure 36:
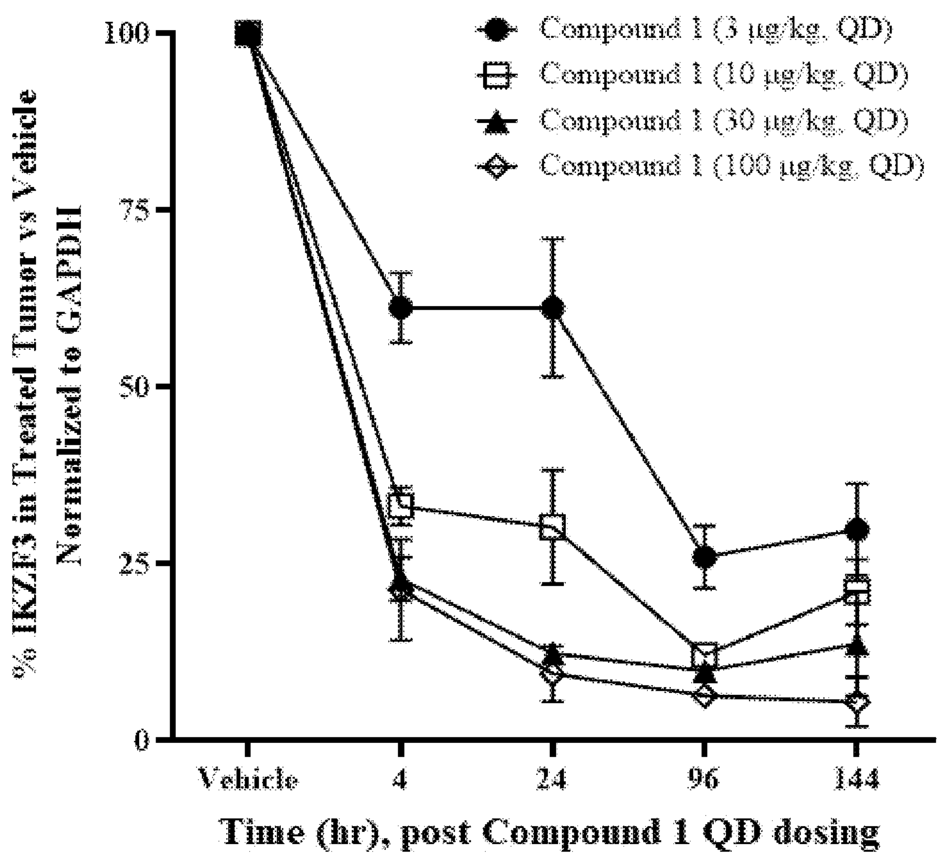

FIG. 36 is a graph of IKZF3 protein expression in mice injected with RPMI-8226 tumors and administered a dose response of Compound 1 as described in Example 32. The x-axis is labeled with the time post dose that the animal was sacrificed and the y-axis is the percent of protein compared to the vehicle control normalized to GAPDH.

Figure 37:
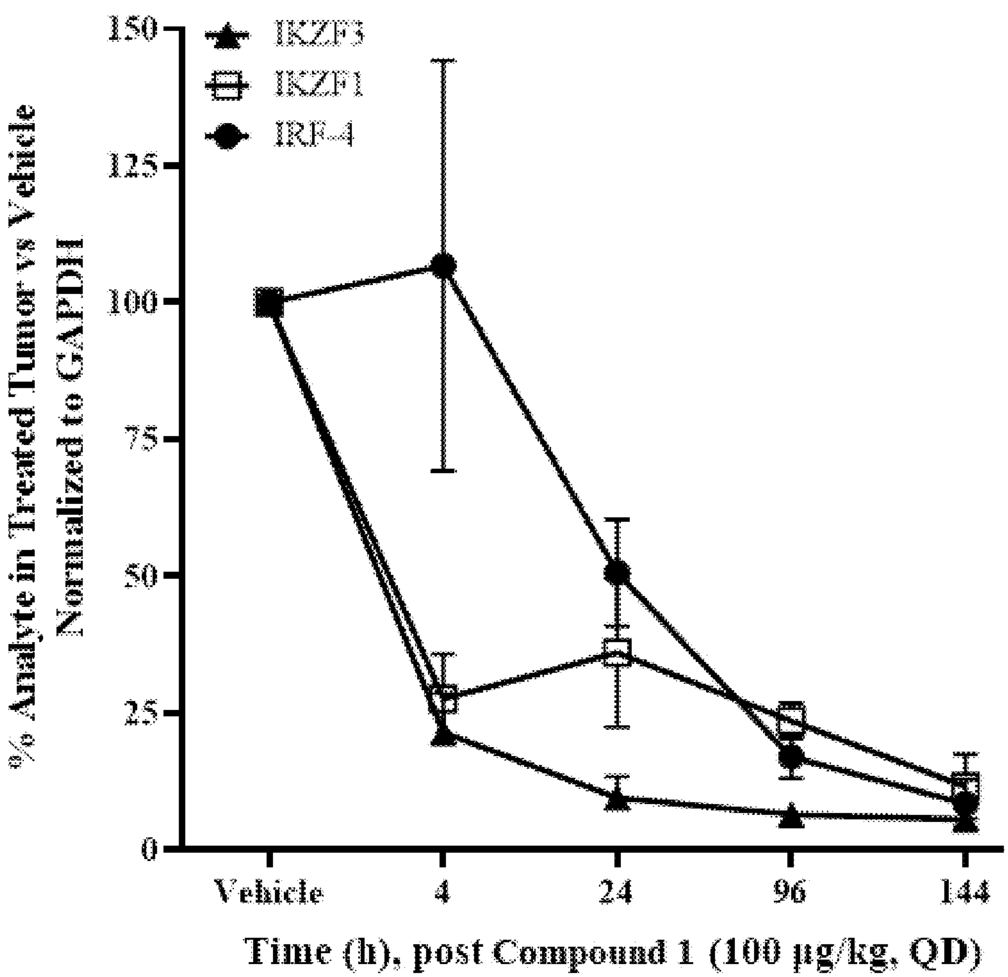

FIG. 37 is a graph of IKZF1, IKZF3 and IRF-4, tumor protein expression in mice injected with RPMI-8226 MM tumors and administered Compound 1 as described in Example 32. The x-axis is labeled with the time post dose that the animal was sacrificed and the y-axis is the percent of protein compared to the vehicle control normalized to GAPDH.

Figure 38:
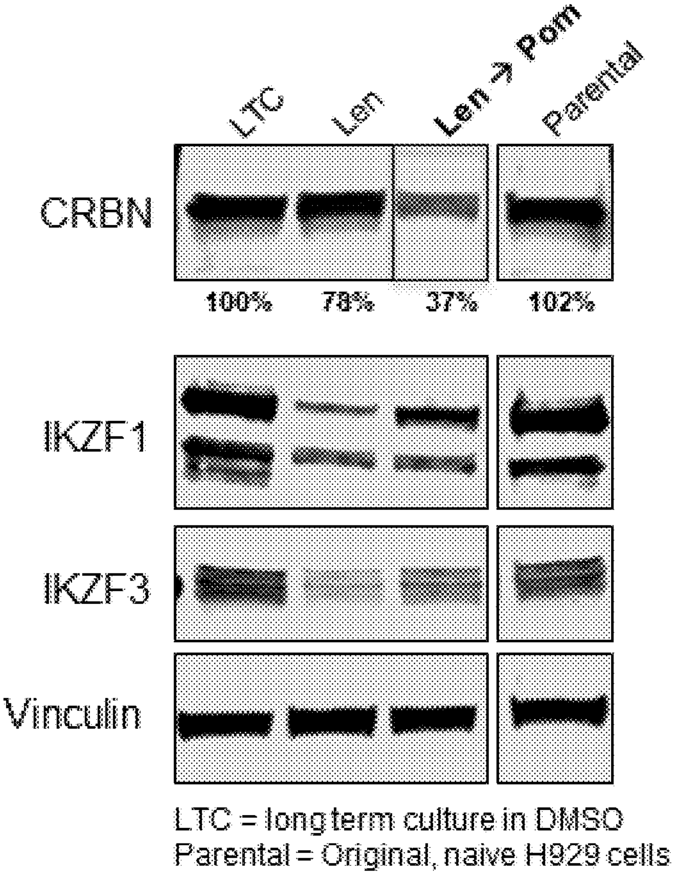

FIG. 38 is a western blot evaluating the levels of cereblon, IKZF1, and IKZF3 levels in H929 cells that were untreated (parental), treated with DMSO (LTC; long term culture), lenalidomide, or pomalidomide for four months. Vinculin was used as a loading control. The western blot was conducted using the method described in Example 33.

Figure 39:
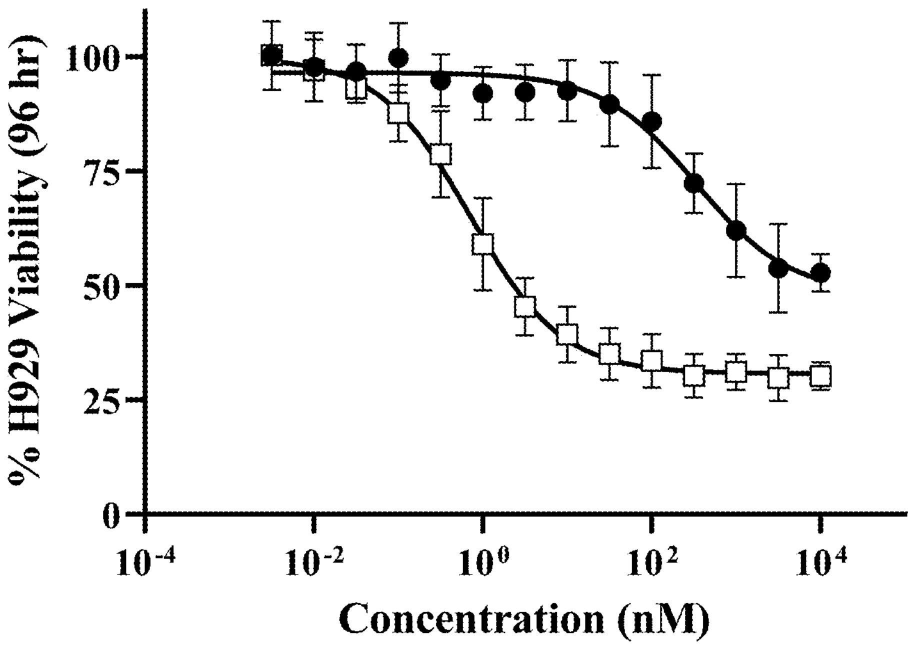

FIG. 39 describes the effect of Compound 1 on growth of IMiD-resistant NCIH929 multiple myeloma cells compared to pomalidomide as described in Example 34. The x-axis is the concentration of Compound 1 or pomalidomide in nM and the y-axis is the % viability of IMiD-resistant NCIH929 cells after 96 hours relative to untreated cells.

Figure 40:
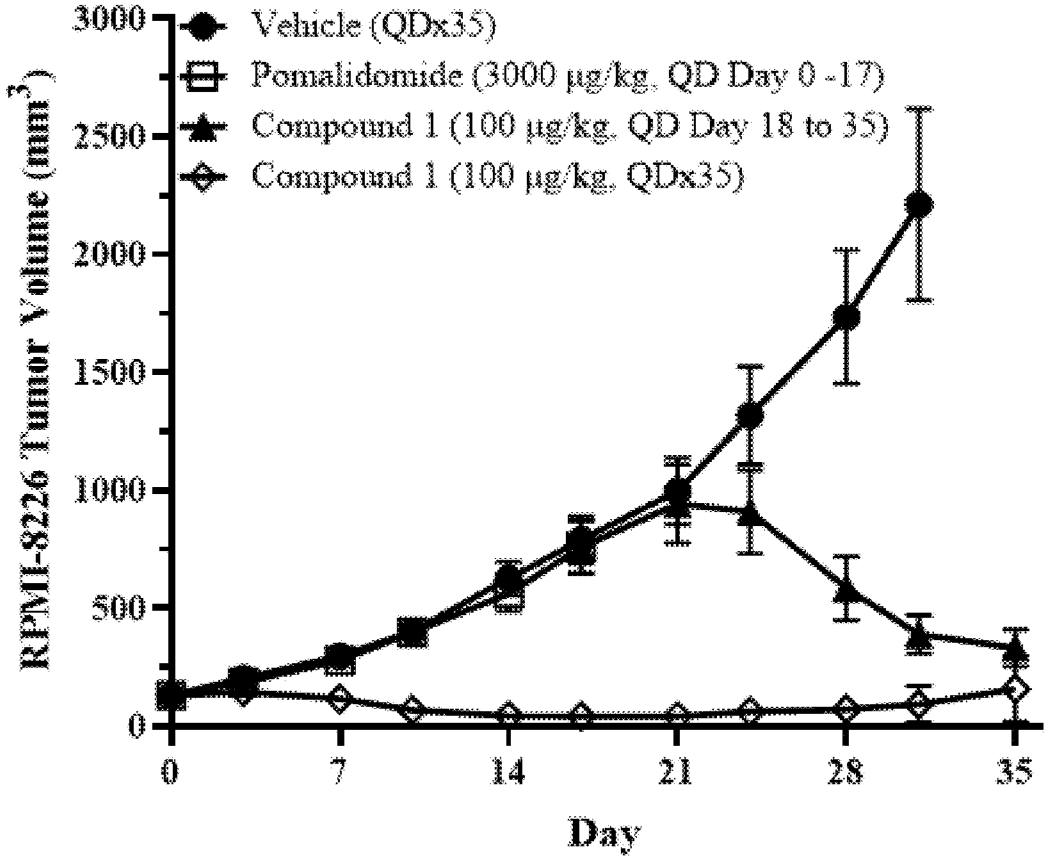

FIG. 40 is a graph of the tumor volume of mice injected with refractory multiple myeloma cell line RPMI-8226. Mice were dosed orally daily with the vehicle control, pomalidomide (3000 μg/kg/day) or Compound 1 (100 μg/kg/day) for 35 days, with the exception of the pomalidomide group. For this group pomalidomide dosing was stopped on Day 17 and replaced with Compound 1 dosing (100 μg/kg/day) for the remainder of the study. This experiment is described in more detail in Example 15.

Figure 41:
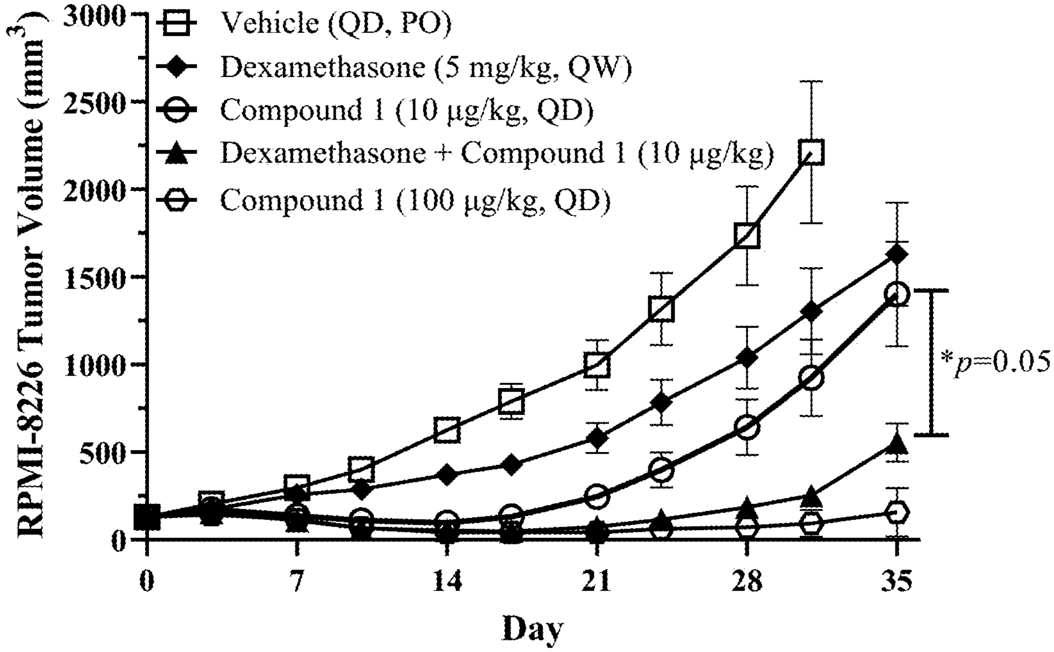

FIG. 41 is a graph comparing the effect of Compound 1, dexamethasone, and the combination of Compound 1 and dexamethasone on RPMI-8226 multiple myeloma tumor volume in mice as described in Example 22. Dexamethasone was administered at a dose of 5 mg/kg intravenously (IV) every week (QW) and Compound 1 was administered at a dose of 10 μg/kg or 100 μg/kg orally every day. Compound 1 at 10 μg/kg was dosed in combination with Dexamethasone at each agent's respective dose levels and schedules. The x-axis is the time measured in days and the y-axis is the tumor volume measured in $mm^3$.

Figure 42:
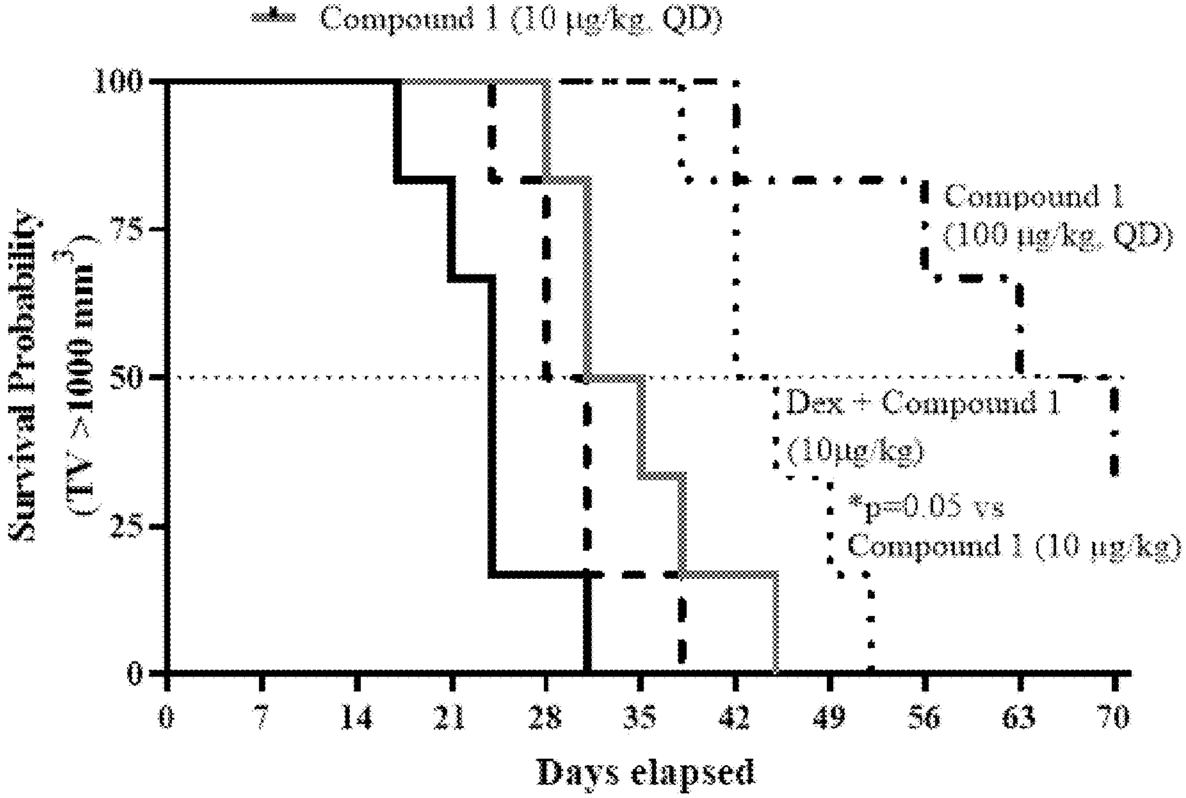

FIG. 42 is a graph comparing the effect of Compound 1, dexamethasone, and the combination of Compound 1 and dexamethasone on RPMI-8226 multiple myeloma tumor volume in mice as described in Example 22. Dexamethasone was administered at a dose of 5 mg/kg intravenously (IV) every week (QW) and Compound 1 was administered at a dose of 10 μg/kg orally every day. Compound 1 was dosed in combination with dexamethasone at each agent's respective dose levels and schedules. Once a tumor volume reached 1000 $mm^3$ the animal was removed from the study and recorded as a death. The y-axis is the probability of an animal's survival on a particular treatment and the x-axis is the numbers of days an animal has survived.

Figure 43:
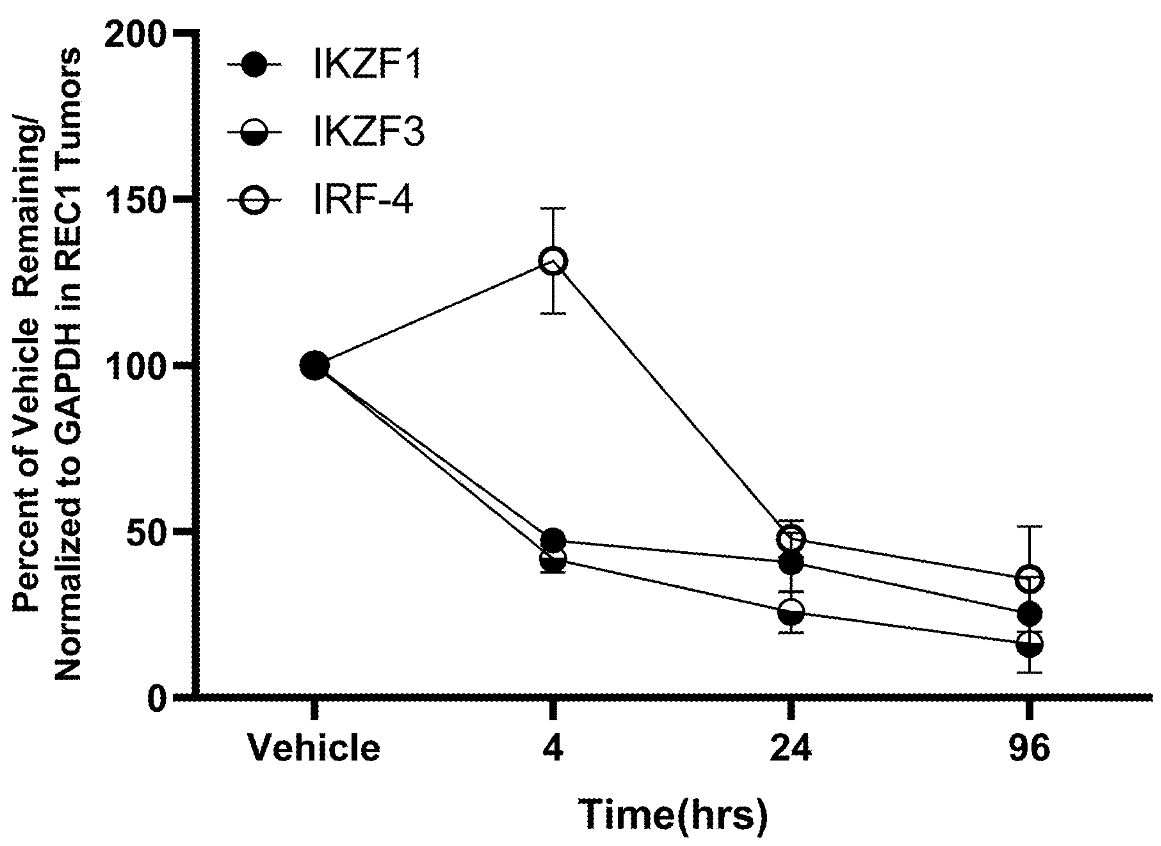

FIG. 43 is a graph of IKZF1, IKZF3 and IRF-4, tumor protein expression in mice injected with REC1 MCL tumors and administered Compound 1 as described in Example 35. The x-axis is labeled with the time post dose that the animal was sacrificed, and the y-axis is the percent of protein compared to the vehicle control normalized to GAPDH.

Figure 44:
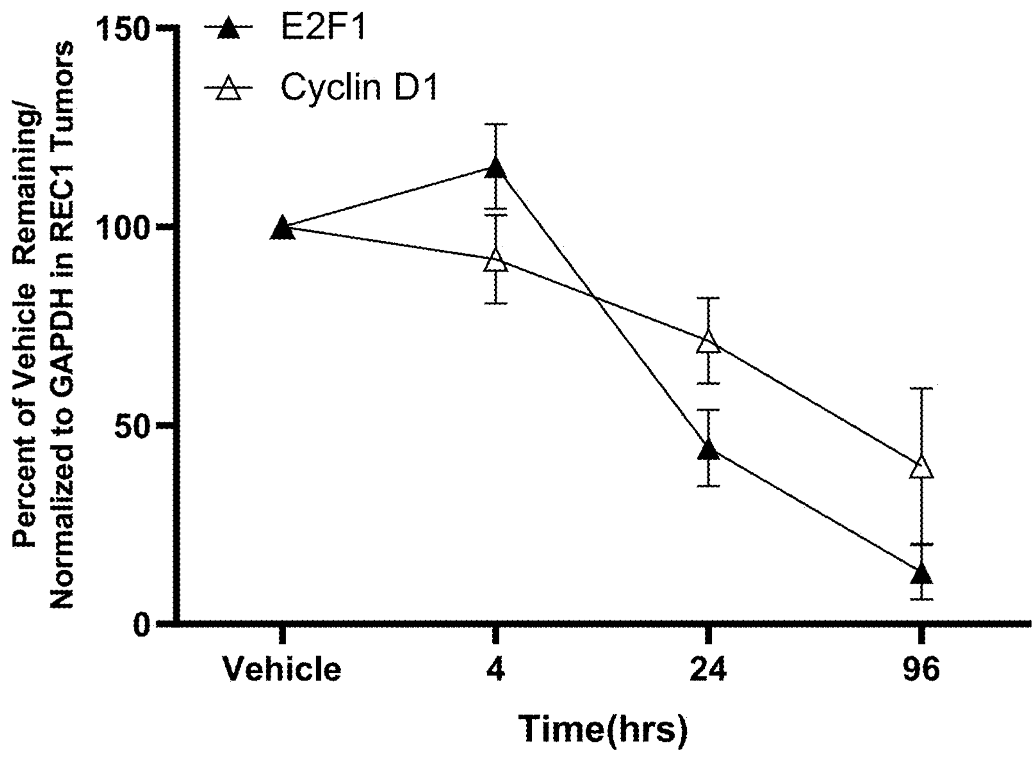

FIG. 44 is a graph of E2F1 and Cyclin D1, protein expression in mice injected with REC1 MCL tumors and administered Compound 1 as described in Example 35. The x-axis is labeled with the time post dose that the animal was sacrificed, and the y-axis is the percent of protein compared to the vehicle control normalized to GAPDH.

Figure 45A:
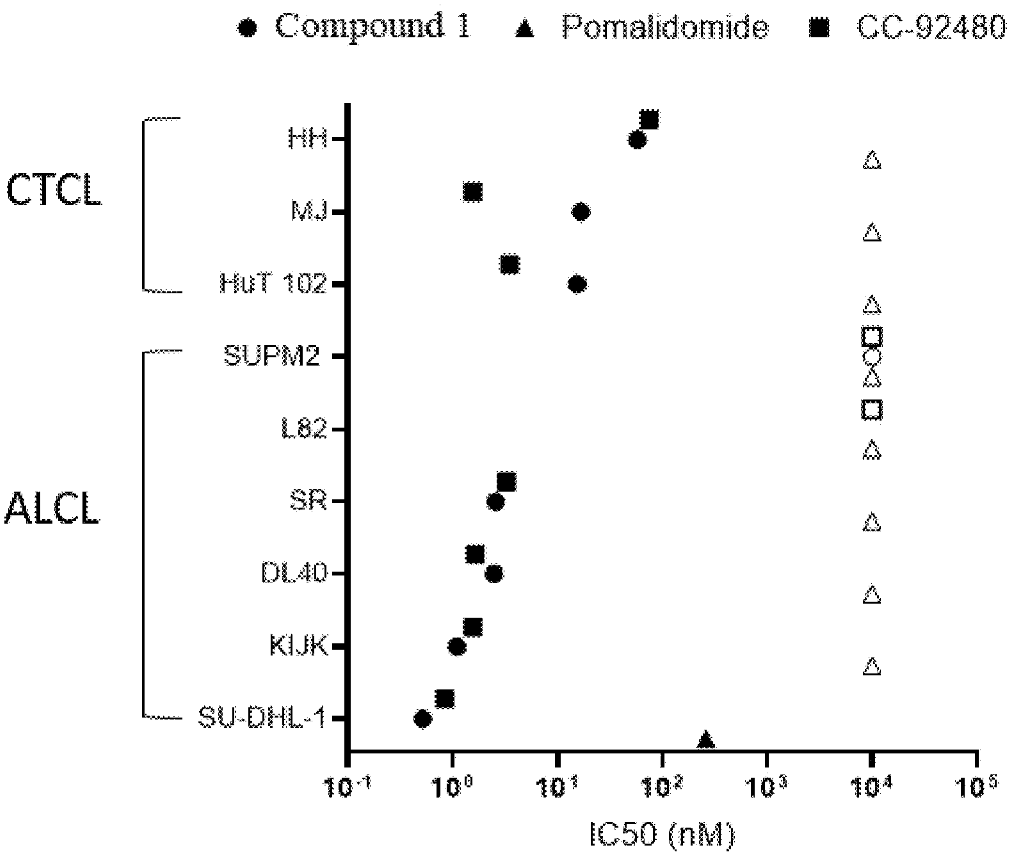
Figure 45B:
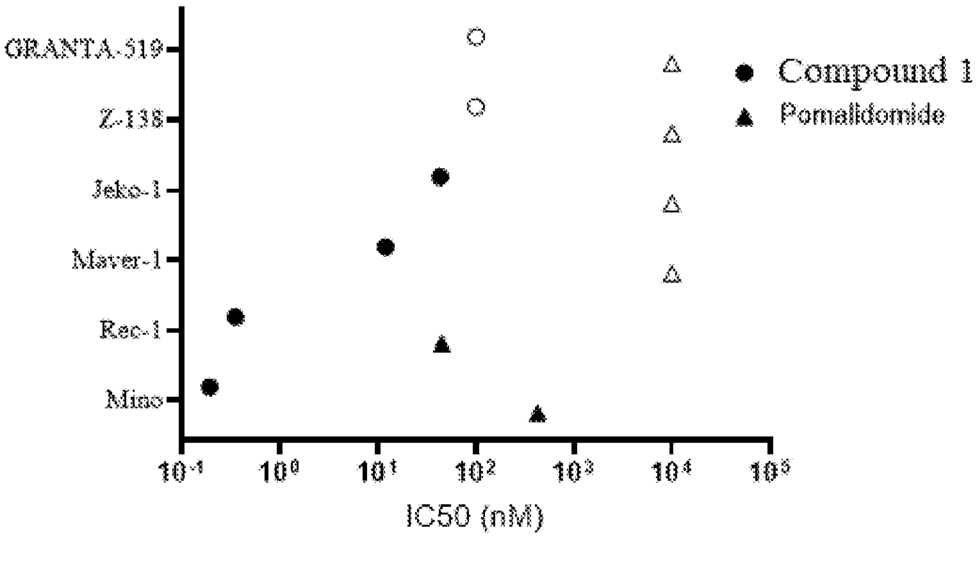
Figure 45C:
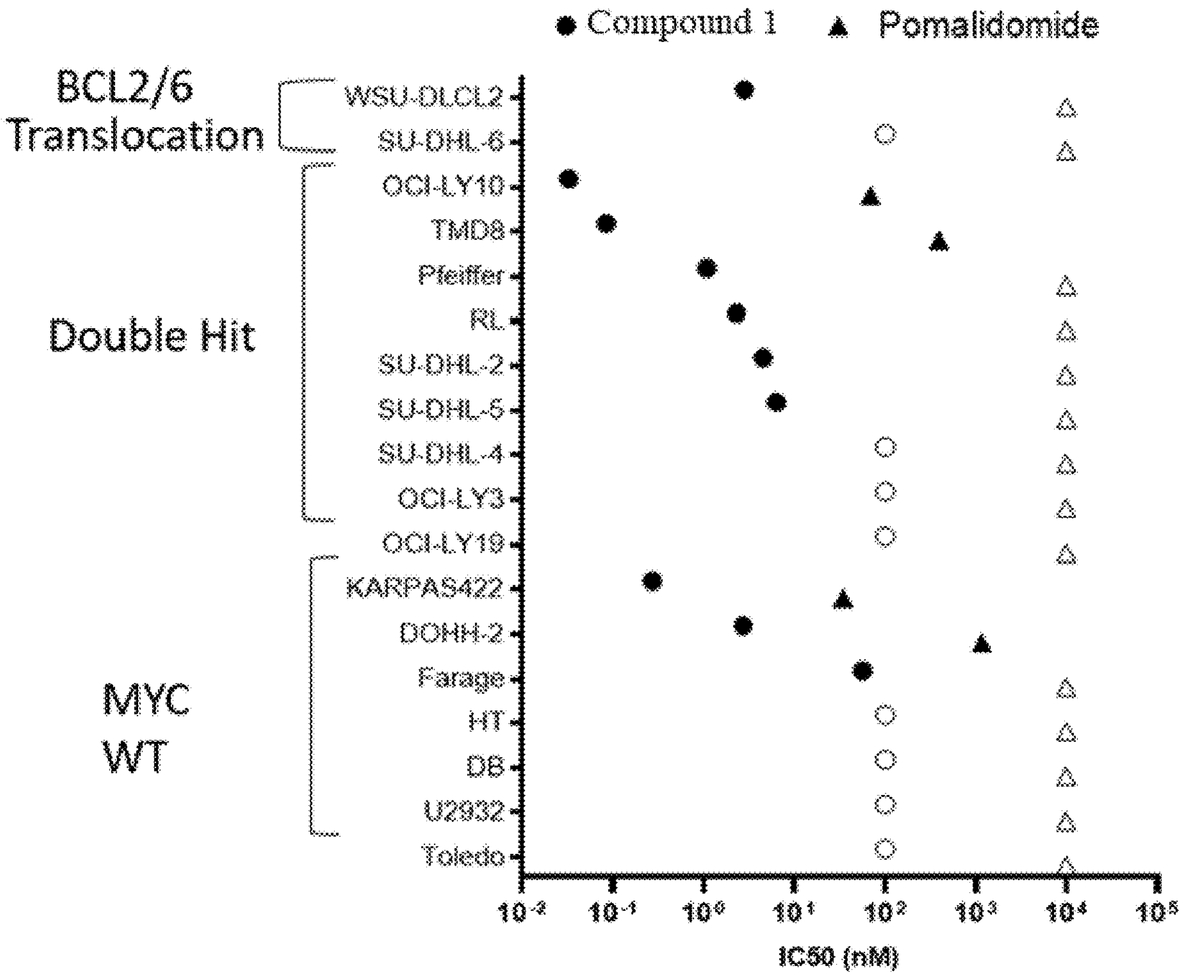

FIG. 45A, FIG. 45B, and FIG. 45C are dot bar graphs describing the effect of Compound 1 on growth of NHL cell lines compared to pomalidomide as described in Example 37. The x-axis is the concentration of Compound 1 or pomalidomide in nM that inhibited cellular growth at 96 hr by 50% ($IC_{50}$) and the y-axis is the cell line tested. Open symbols indicate that growth was not inhibited by more than 50% at the highest tested concentration (100 nM or 10 μM for Compound 1, 10 μM for pomalidomide, and 10 μM for CC-92480) and therefore $IC_{50}$ was not determined.

Figure 46:
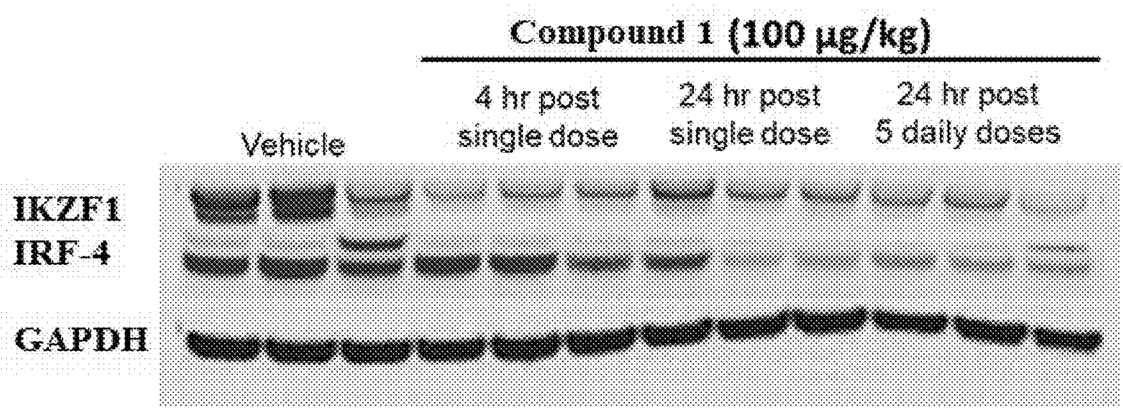

FIG. 46 is a western blot taken from mice bearing established KI-JK xenografts that were administered a single dose of Compound 1 (100 μg/kg) or daily for 5 days. Tumors were collected at 4 and 24 hours post single dose and 24 hours post 5 daily doses. Tumors were analyzed by western blot for IKZF1 and IRF-4 levels. The experimental procedure is described in Example 38.

Figure 47:
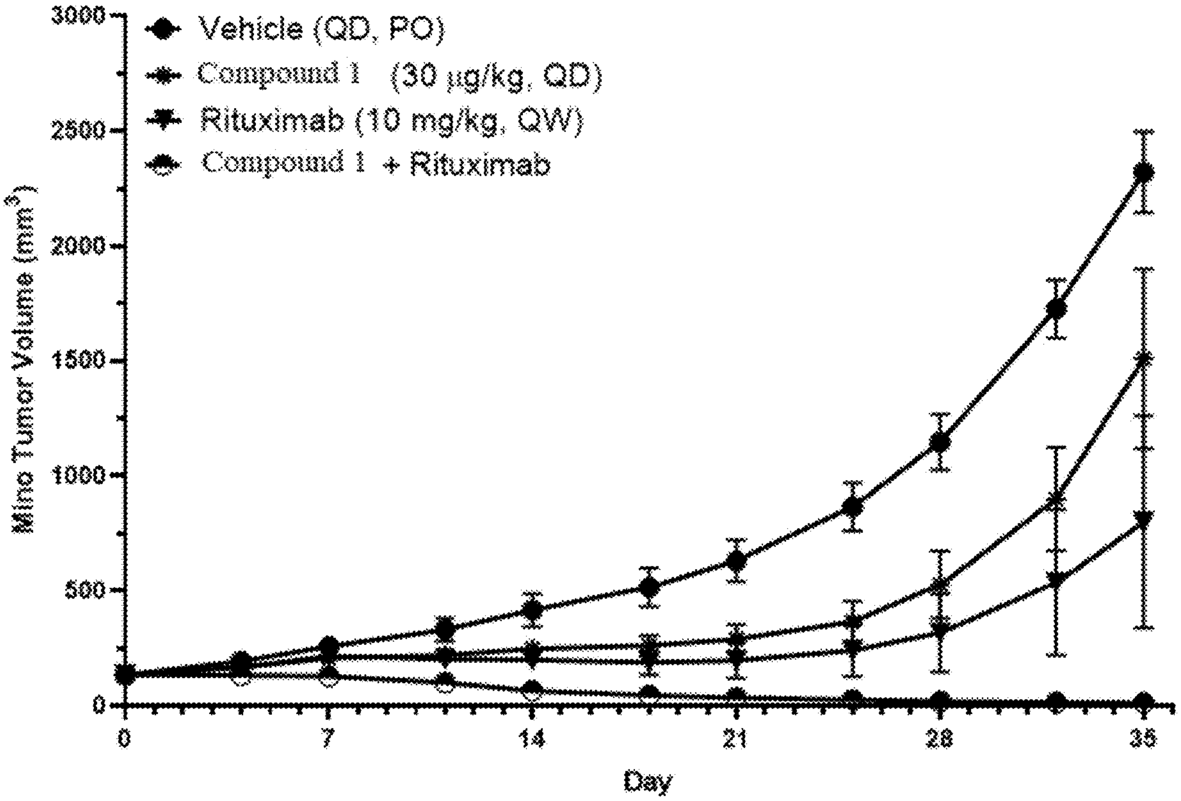

FIG. 47 is a line graph showing the change in tumor volume in mice bearing Mino xenograft tumors that were treated with Compound 1 (100 μg/kg) once a day orally, rituximab once a week IV (10 mg/kg), or the combination of the two at their respective doses. Data are expressed as mean tumor volumes±SEM values. The experimental procedure is described in Example 39.

Figure 48:
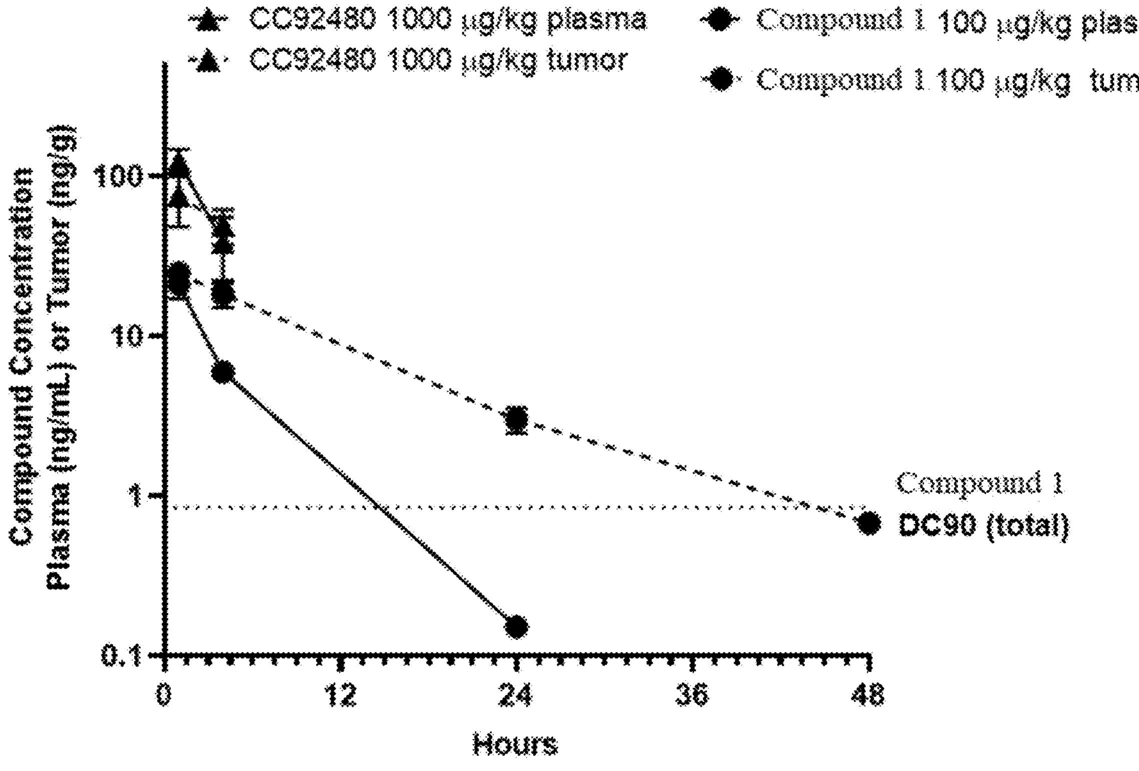

FIG. 48 is a line graph showing change in concentration over time after treating mice bearing established NCI-H929 xenograft tumors were treated with a single dose of Compound 1 (100 μg/kg) or CC-92480 (1000 μg/kg). Plasma and tumor samples were collected at 1, 4, 24, and 48 hours post single dose and analyzed by LC-MS/MS. Data are expressed total compound concentration±SEM values. The experimental procedure is provided in Example 40.

Figure 49:
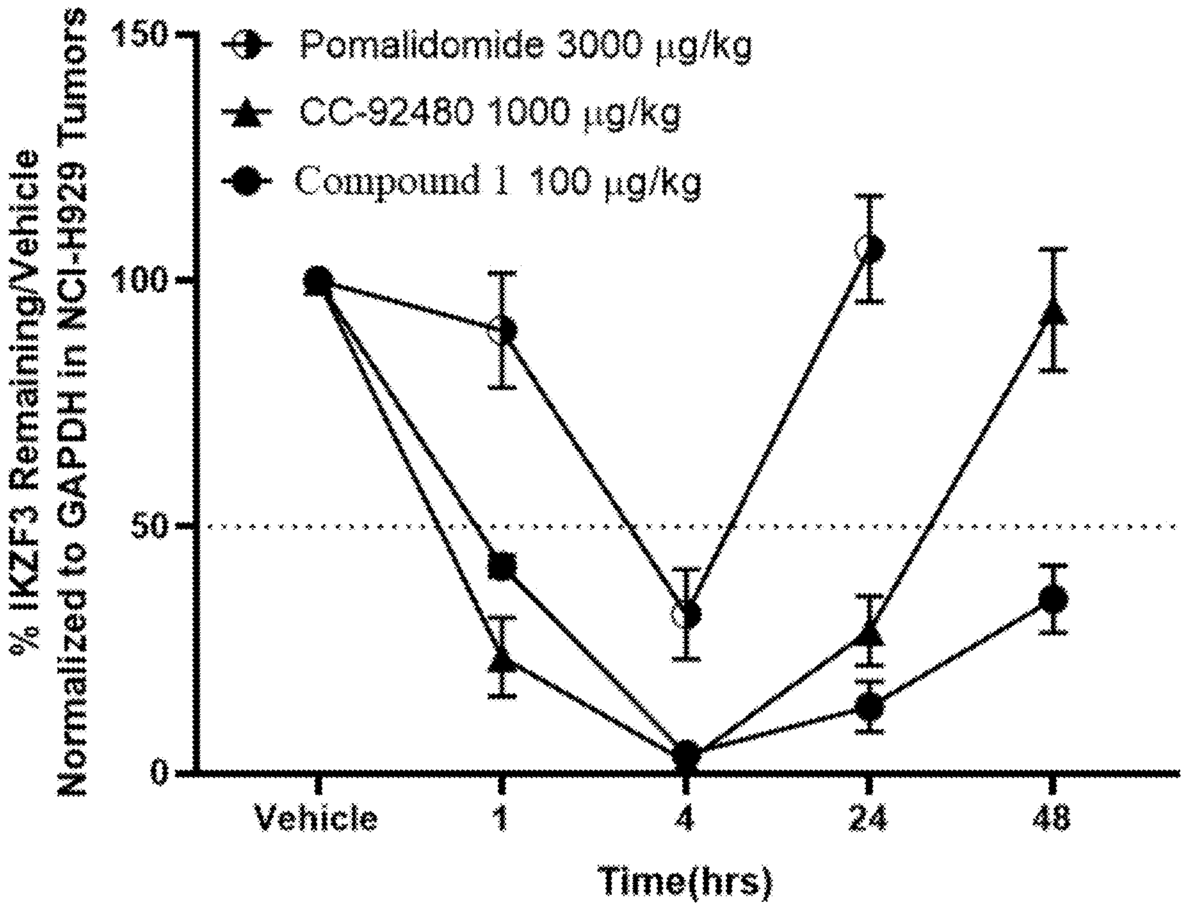

FIG. 49 is a line graph showing change in concentration over time after treating mice bearing established NCI-H929 xenograft tumors were treated with a single dose of Compound 1 (100 μg/kg), CC-92480 (1000 μg/kg), or pomalidomide (3000 μg/kg). Tumor samples were collected at 1, 4, 24, and 48 hours post single dose and analyzed by western blot for IKZF3 levels. Data are expressed as percent of IKZF3 remaining in comparison to the vehicle control and normalized to GAPDH±SEM values. The experimental procedure is provided in Example 40.

Figure 50:
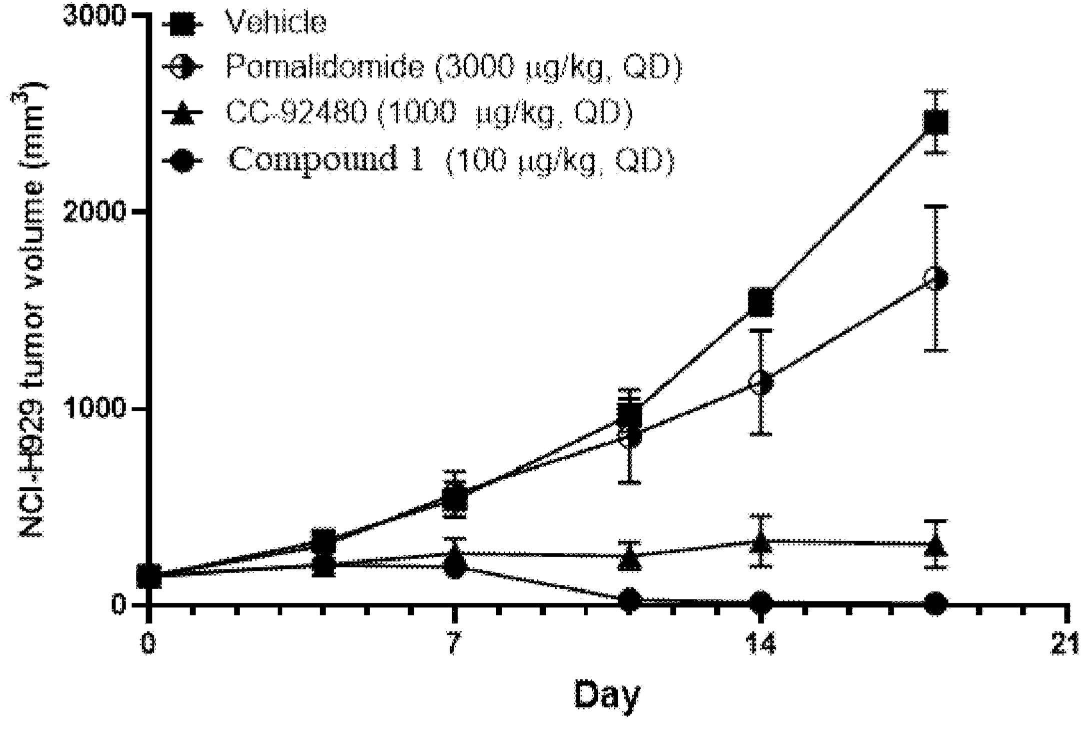

FIG. 50 is a line graph showing change in tumor volume over time after treating mice bearing established NCI-H929 xenograft tumors were treated with Compound 1 (100 μg/kg), CC-92480 (1000 μg/kg), or pomalidomide (3000 μg/kg) orally daily for 18 days. Tumor volume and body weights were measured twice a week. Data are expressed as mean tumor volumes±SEM values. The experimental procedure is provided in Example 40.

Figure 51:
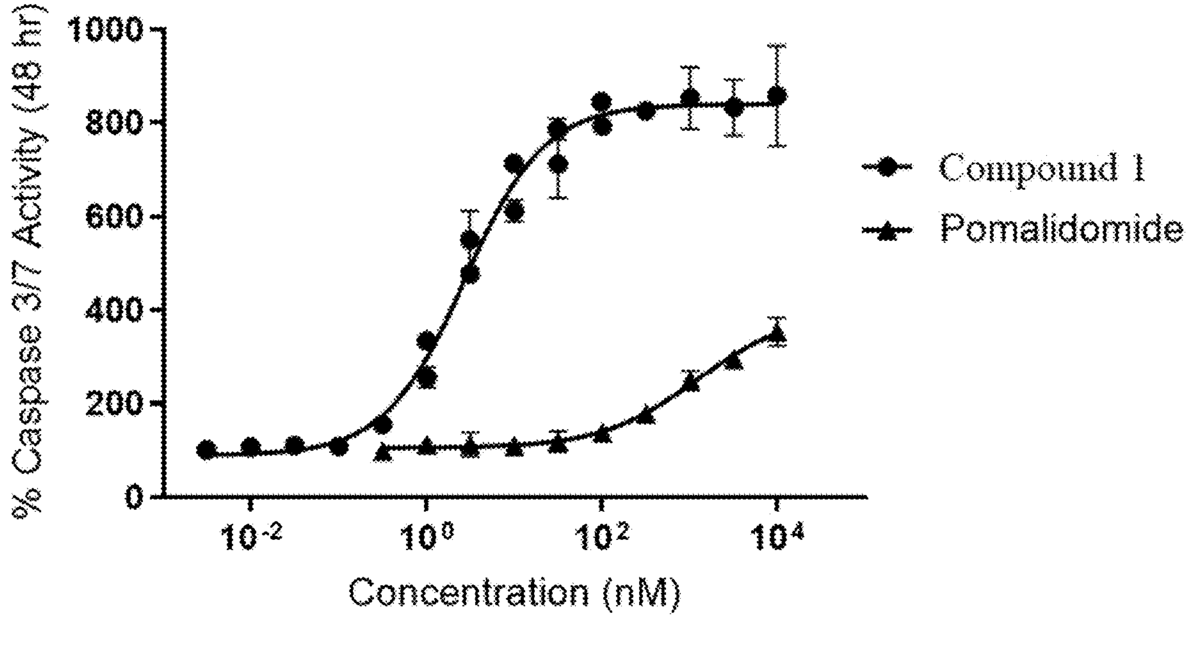

FIG. 51 is a dose-response curve describing the effect of Compound 1 on Caspase 3/7 activity in TMD8 cell line compared to pomalidomide after 48 hr treatment as described in Example 41. The x-axis is the concentration of Compound 1 or pomalidomide in nM and the y-axis is the luminescence signal (RLU) relative to DMSO-treated controls measured following addition of caspase 3/7 substrate reagents.

Figure 52:
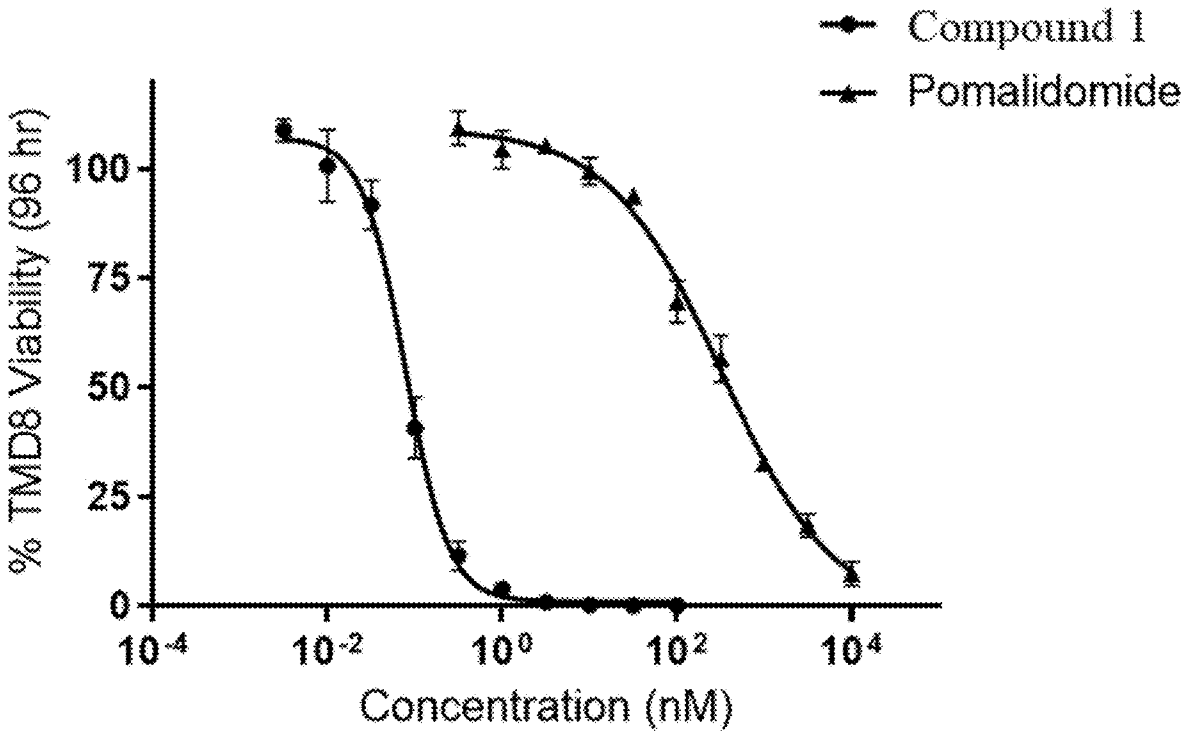

FIG. 52 is a dose-response curve describing the effect of Compound 1 on TMD8 cell viability compared to pomalidomide after 96-hour treatment as described in Example 42. The x-axis is the concentration of Compound 1 or pomalidomide in nM and the y-axis is the % cellular viability relative to DMSO-treated controls measured following addition of CellTiter Glo reagents.

Figure 53:
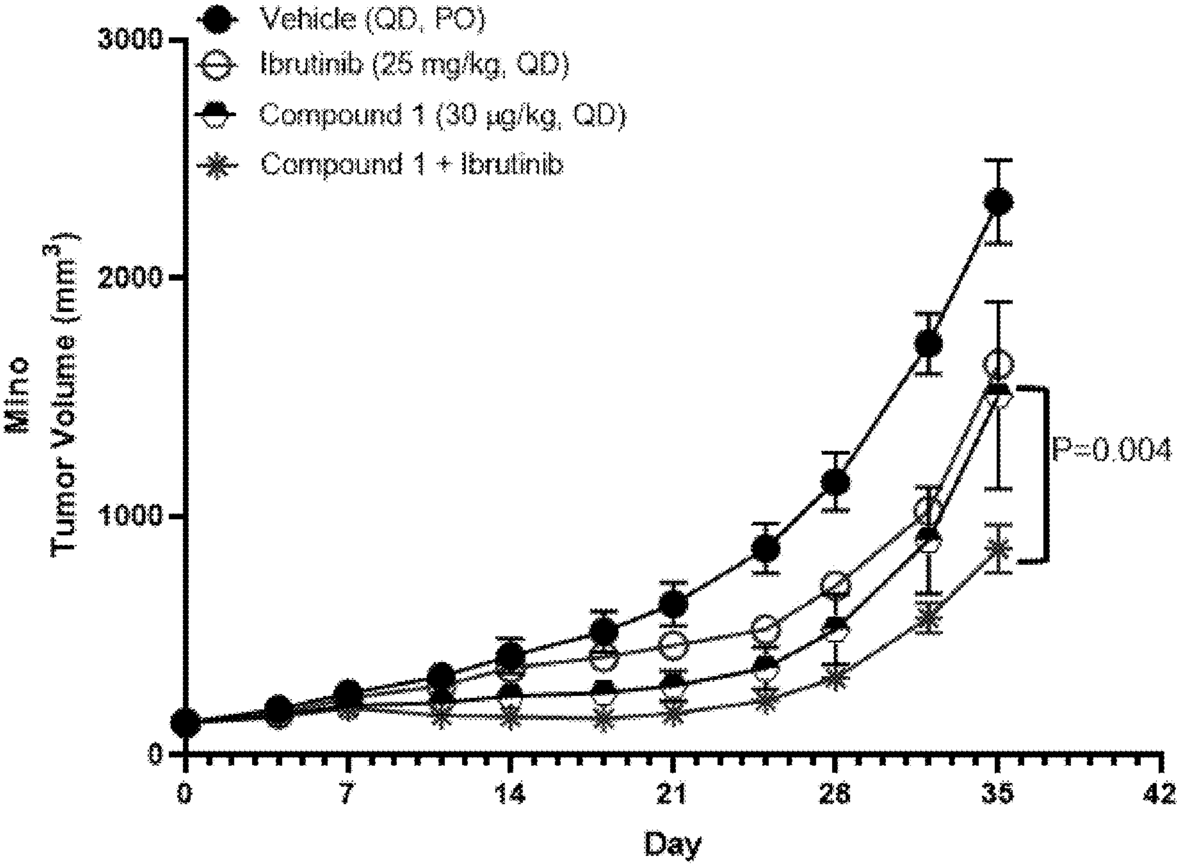

FIG. 53 is a line graph demonstrating the effect of Compound 1, ibrutinib, and the combination of Compound 1 and ibrutinib on Mino mantle cell lymphoma xenograft tumors. Mice were administered Compound 1 at a dose of 30 μg/kg/day, ibrutinib at a dose of 25 mg/kg, the combination of ibrutinib and Compound 1 at their respective dose levels, or the vehicle control orally daily for 34 days. The x-axis is the time measured in days and the y-axis is the tumor volume measured in $mm^3$. Statistics were done using a paired t test in GraphPad Prism software. The experimental procedure is provided in Example 44.

Figure 54:
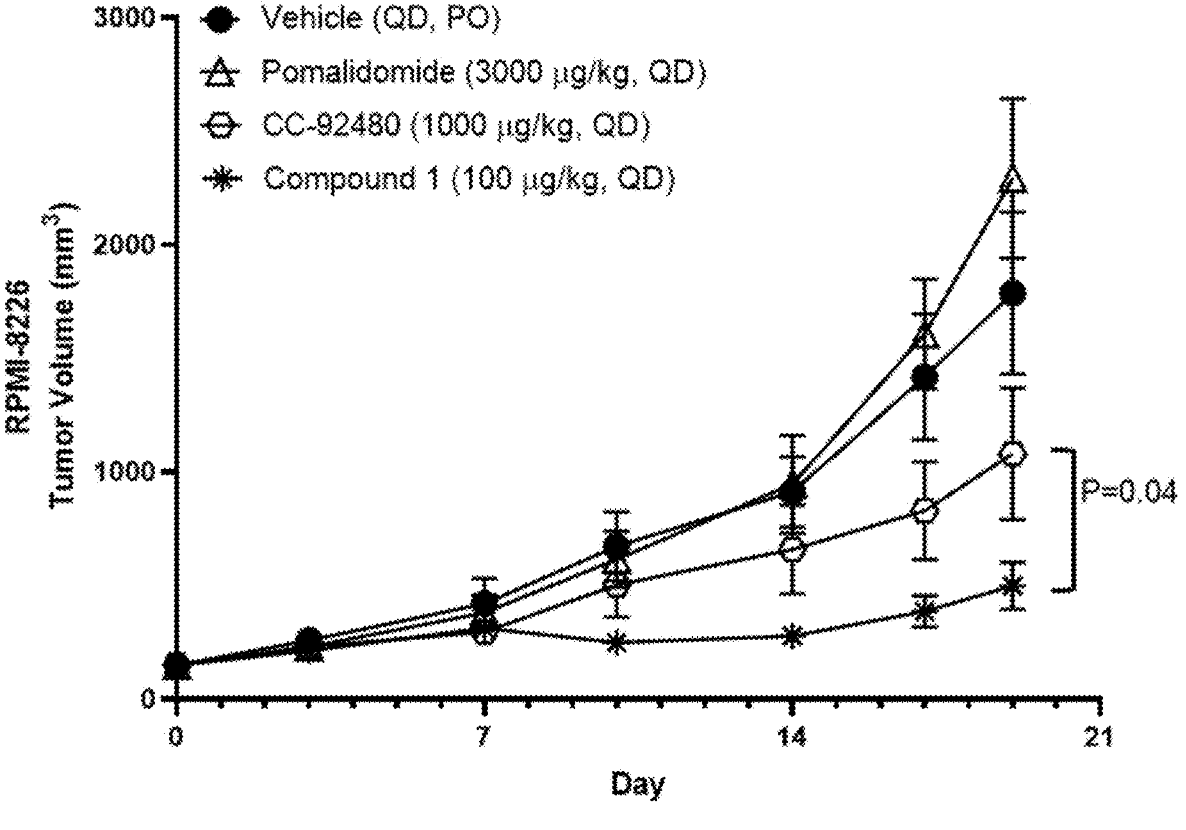

FIG. 54 is a line graph demonstrating the effect of Compound 1, CC-92480, pomalidomide, or the vehicle control on RPMI-8226 multiple myeloma xenograft tumors. Mice were administered Compound 1 at a dose of 100 μg/kg/day, CC-92480 at 1000 μg/kg/day, or pomalidomide at 3000 μg/kg/day orally daily for 19 days. The x-axis is the time measured in days and the y-axis is the tumor volume measured in $mm^3$. Statistics were done using a paired t test in GraphPad Prism software. The experimental procedure is provided in Example 45.

Figure 55:
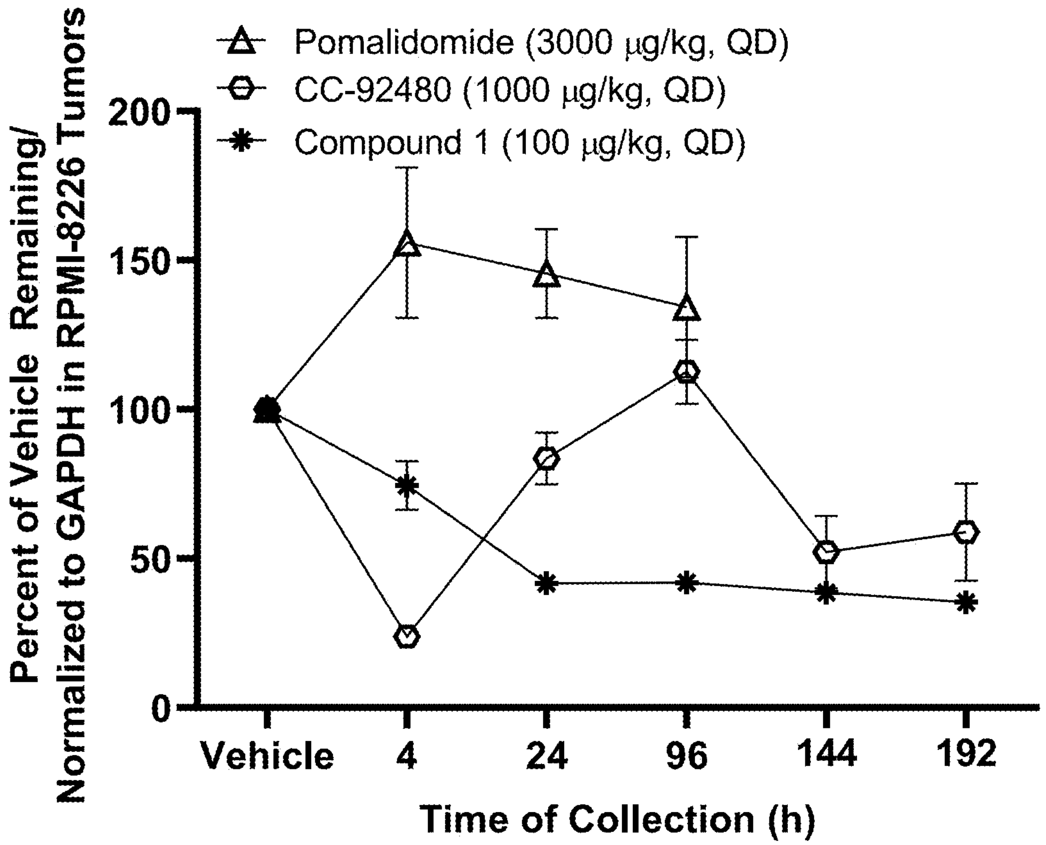

FIG. 55 is a line graph demonstrating the effect of Compound 1, CC-92480, pomalidomide, or the vehicle control on IKZF3 levels in RPMI-8226 multiple myeloma xenograft tumors. Mice were administered Compound 1 at a dose of 100 μg/kg/day, CC-92480 at 1000 μg/kg/day, or pomalidomide at 3000 μg/kg/day orally daily for 7 days. Tumors were sampled at 4 and 24 hours post single dose, and 24 hours post 3, 5, and 7 daily doses. Data is represented as percent of target present in the vehicle control and normalized for total protein. Error bars represent±SEM values. The experimental procedure is provided in Example 45.

Figure 56:
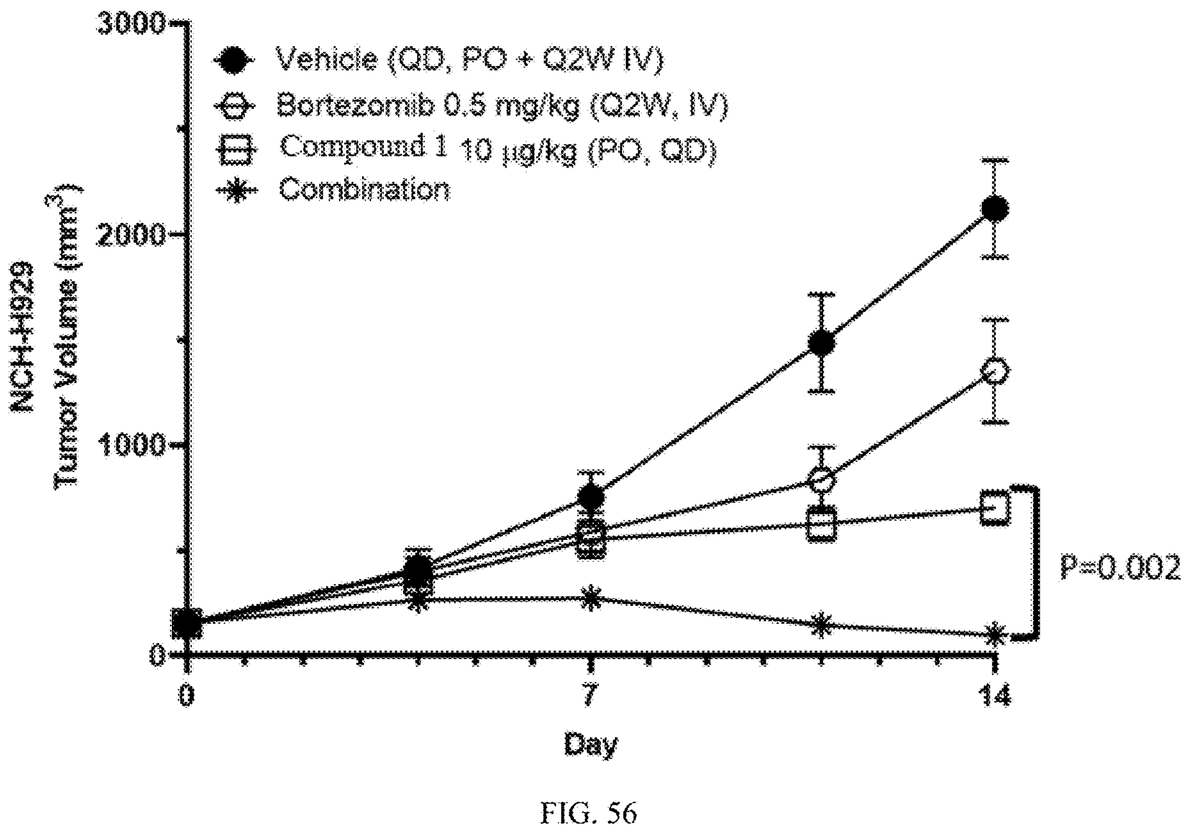

FIG. 56 is a line graph demonstrating the effect of Compound 1, bortezomib, and the combination of Compound 1 and bortezomib in NCI-H929 xenografts. Mice bearing established NCI-H929 xenografts were administered doses of Compound 1 (10 μg/kg), bortezomib (0.5 mg/kg), the combination of Compound 1 and bortezomib, or the vehicle control for 14 days. Compound 1 was dosed orally daily while bortezomib was dosed on a every other week schedule intravenously. Statistical analysis was done on day 14, the last day all animals were on study, by two-way ANOVA using GraphPad Prism software. Data are expressed as mean tumor volumes SEM.

Figure 57:
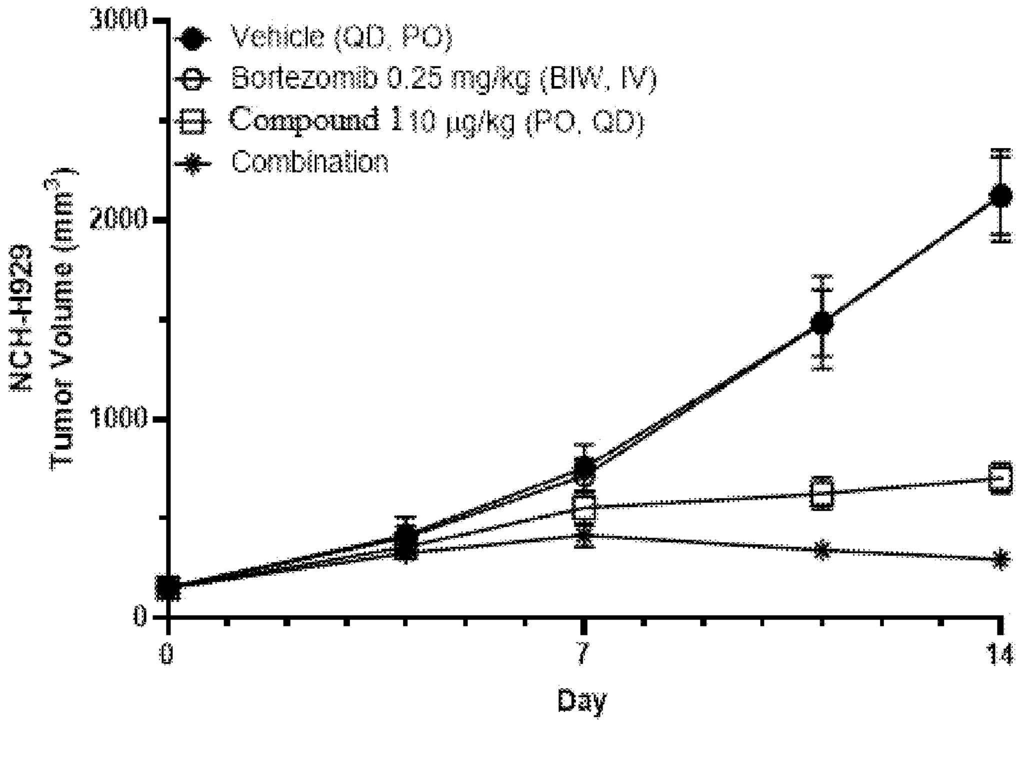

FIG. 57 is a line graph demonstrating the effect of Compound 1, bortezomib, and the combination of Compound 1 and bortezomib in NCI-H929 xenografts. Mice bearing established NCI-H929 xenografts were administered doses of Compound 1 (10 μg/kg), bortezomib (0.25 mg/kg), the combination of Compound 1 and bortezomib, or the vehicle control for 14 days. Compound 1 was dosed orally daily while bortezomib was dosed twice a week intravenously. Statistical analysis was done on day 14, the last day all animals were on study, by two-way ANOVA using GraphPad Prism software. Data are expressed as mean tumor volumes±SEM.

Figure 58:
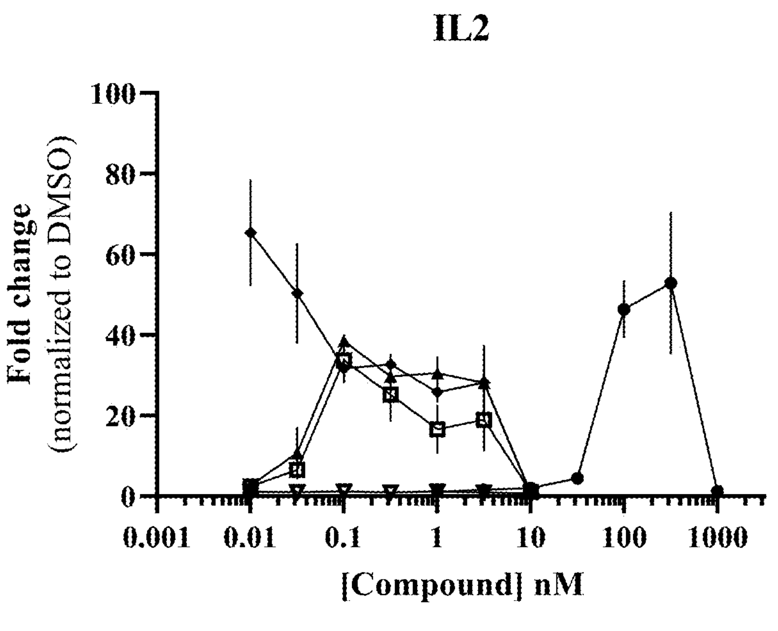

FIG. 58 is a line graph containing the effect of Compound 1, Compound 2, Compound 15, CC-92480, or Pomalidomide on the concentration of IL2 secreted from anti-CD3 stimulated T-cells after a six-day incubation. The x-axis is the concentration of compound in nM and the y-axis is the fold-change relative to DMSO treated control wells. The experimental procedure is provided in Example 46.

Figure 59:
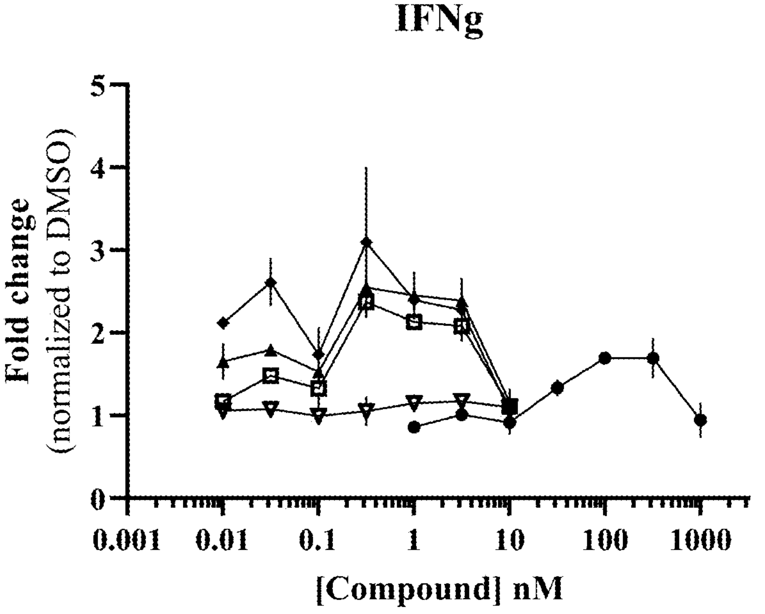

FIG. 59 is a line graph containing the effect of Compound 1, Compound 2, Compound 15, CC-92480, or Pomalidomide on the concentration of IFNg secreted from anti-CD3 stimulated T-cells after a six-day incubation. The x-axis is the concentration of compound in nM and the y-axis is the fold-change relative to DMSO treated control wells. The experimental procedure is provided in Example 46.

Figure 60:
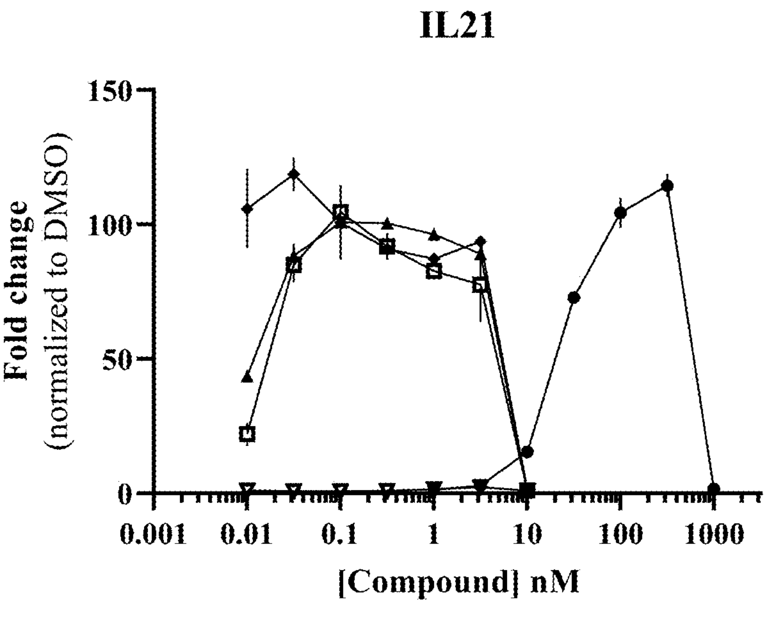

FIG. 60 is a line graph containing the effect of Compound 1, Compound 2, Compound 15, CC-92480, or Pomalidomide on the concentration of IL21 secreted from anti-CD3 stimulated T-cells after a six-day incubation. The x-axis is the concentration of compound in nM and the y-axis is the fold-change relative to DMSO treated control wells. The experimental procedure is provided in Example 46.

Figure 61:
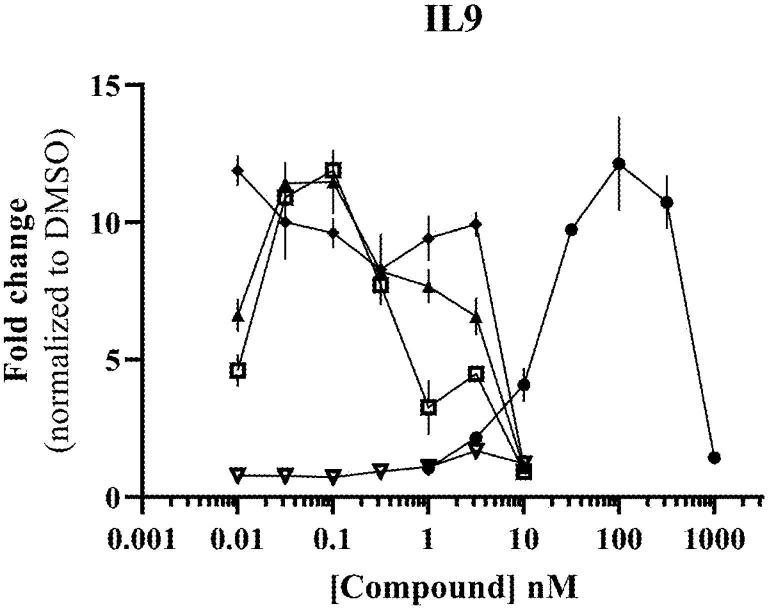

FIG. 61 is a line graph containing the effect of Compound 1, Compound 2, Compound 15, CC-92480, or Pomalidomide on the concentration of IL9 secreted from anti-CD3 stimulated T-cells after a six-day incubation. The x-axis is the concentration of compound in nM and the y-axis is the fold-change relative to DMSO treated control wells. The experimental procedure is provided in Example 46.

Figure 62:
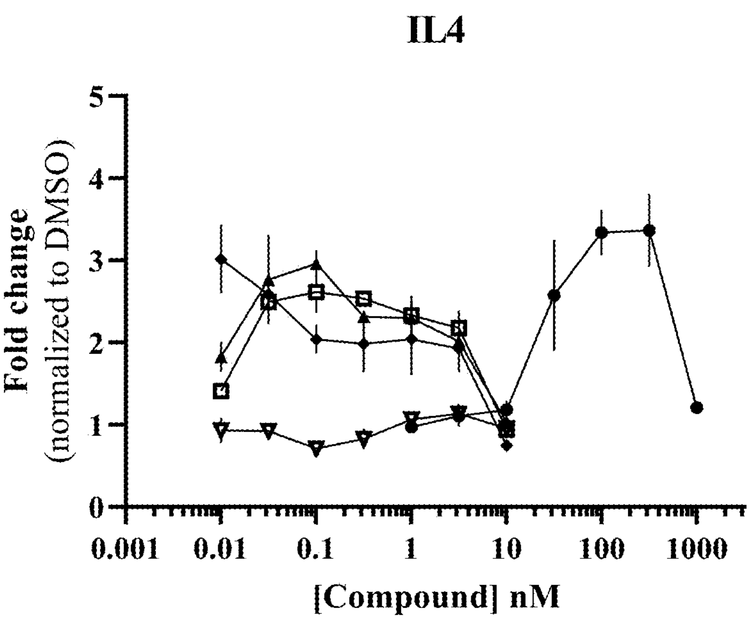

FIG. 62 is a line graph containing the effect of Compound 1, Compound 2, Compound 15, CC-92480, or Pomalidomide on the concentration of IL4 secreted from anti-CD3 stimulated T-cells after a six-day incubation. The x-axis is the concentration of compound in nM and the y-axis is the fold-change relative to DMSO treated control wells. The experimental procedure is provided in Example 46.

Figure 63:
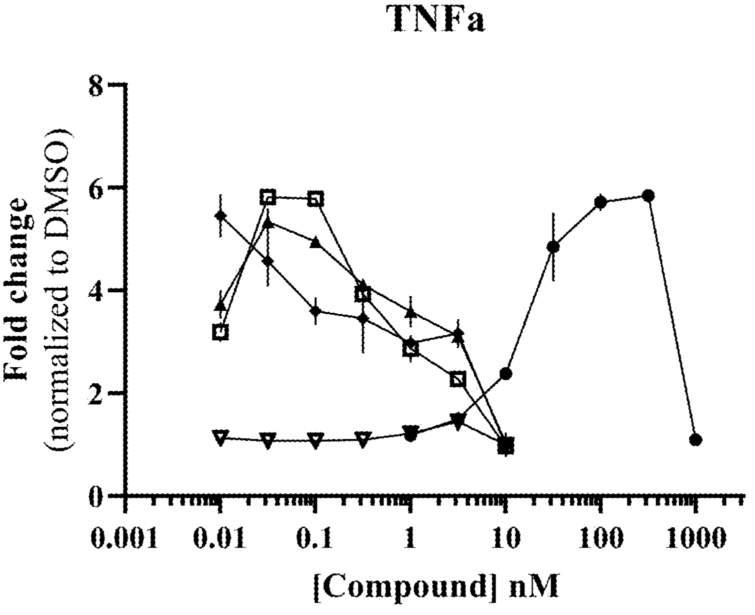

FIG. 63 is a line graph containing the effect of Compound 1, Compound 2, Compound 15, CC-92480, or Pomalidomide on the concentration of TNF-alpha secreted from anti-CD3 stimulated T-cells after a six-day incubation. The x-axis is the concentration of compound in nM and the y-axis is the fold-change relative to DMSO treated control wells. The experimental procedure is provided in Example 46.

Figure 64:
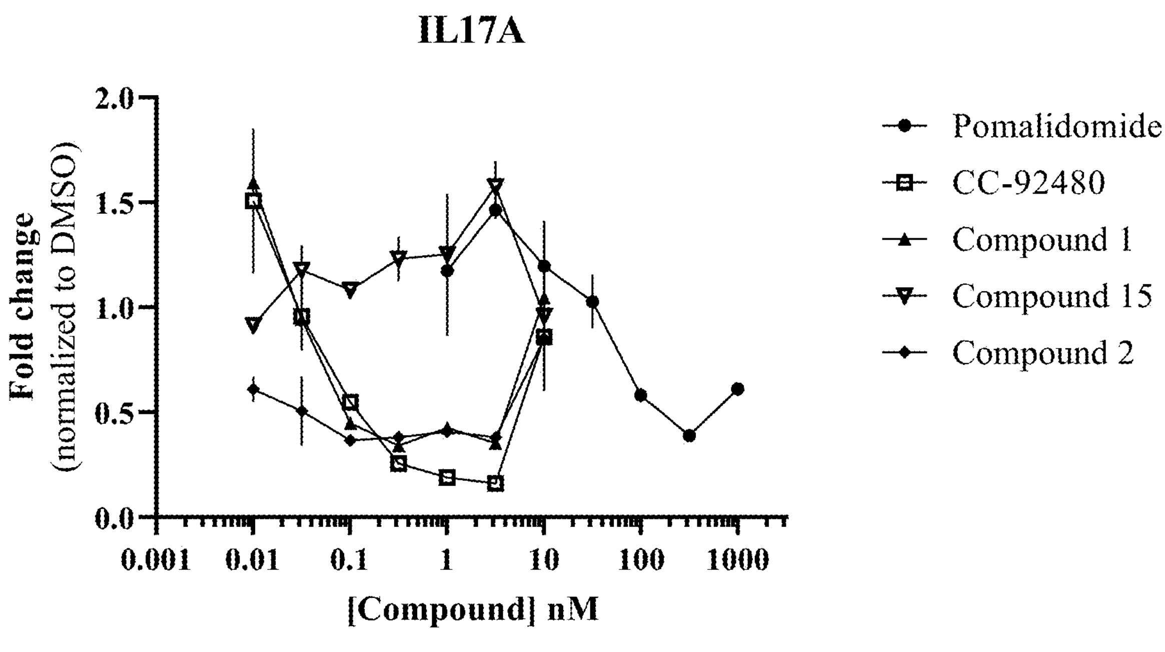

FIG. 64 is a line graph containing the effect of Compound 1, Compound 2, Compound 15, CC-92480, or Pomalidomide on the concentration of IL17A secreted from anti-CD3 stimulated T-cells after a six-day incubation. The x-axis is the concentration of compound in nM and the y-axis is the fold-change relative to DMSO treated control wells. The experimental procedure is provided in Example 46.

DETAILED DESCRIPTION OF THE INVENTION

The new treatments, for example low dosage regimens, described herein are based on the discovery that the described compounds are unusually highly active Ikaros and Aiolos degraders. It is thought that Compound 1 is the most potent IKZF1/3 degrader publicly disclosed to date. Data described herein and otherwise obtained establishes markedly improved antitumor effect of the combination of Compound 1 and dexamethasone. The Compounds described herein, and notably Compound 1, are significantly more efficacious than pomalidomide across NHL models, including PTCL and MCL, both in vitro and in vivo. Therefore, these compounds can be used in preference over thalidomide, lenalidomide, and pomalidomide, in NHL subtypes where classical IMiDs have demonstrated clinical activity but have not been widely adopted as standard of care (MCL, DLBCL, PTCL, etc.).

It has been discovered that the compounds described herein can be administered to treat disorders mediated by Ikaros (IKZF1) and/or Aiolos (IKZF3) in a low dosage regimen once or twice a day, optionally with a drug holiday, in highly effective treatment modalities. For example, it has been discovered that treatment can be effective for a patient using one of the compounds described herein with a dosage of not more than about 500, 450, 400, 350, 325, 300, 275, 250, 225, 200, 175, 150, 125 or even 100, 75, 50 or 25 micrograms (μg) once a day (QD) or twice a day (BID). In certain embodiments, the patient is an adult (typically a human of at least 100 pounds or more, and sometimes even 125 or 150 pounds (e.g., 70 kg or more and at least typically 18 years old or more). In an alternative embodiment, the patient is pediatric (and may be less than 100, 125 or 150 pounds and typically less than 18 years old).

In certain embodiments, the dosage includes a drug holiday. A drug holiday is a time period during which the patient is not administered the active compound. Treatment cycles, for the purposes of this disclosure are usually based on a 28 day cycle. For example, the patient may be administered the active compound or its pharmaceutically acceptable salt for 21 continuous days and not administered the chemotherapeutic for 7 days during the 28 day cycle, and then optionally the regimen is repeated once or several or more times. In certain examples, one of the compounds described herein may be administered once or twice a day for at least 13, 14 15, 16, 17, 18, 19, 20, 21, 22, 23, 24, 25, 26 or 27 continuous days, and then a holiday taken until the next 28 day cycle. In some embodiments, the compound is administered once or twice a day for at least 20, 21, 22, 23 or 24 continuous days followed by a drug holiday until the end of the 28 day cycle. In yet another embodiment, the drug is administered every day without a holiday to achieve continuous dosing during the dosing regimen period, which may be 1, 2, 3, or 4 weeks, or even 1, 2, 3, 4, 5 or 6 or more continual or periodic months. In another embodiment, the use of a compound described herein eliminates the need for an off-cycle period, drug holiday, or reduction in co-administered anti-neoplastic compound concentration during treatment. In yet another embodiment, the cycle period is greater than 28 days, such as greater than 30 or 35 days, and an appropriate on-cycle and off-cycle regimen determined by the patient's healthcare specialist.

In certain embodiments, the Ikaros (IKZF1) and/or Aiolos (IKZF3) degrader is administered in combination with one or more additional therapeutic agents. Non-limiting examples of therapeutic agents that can be used in combination with a degrader described herein include:

1. A BTK inhibitor selected from acalabrutinib, spebrutinib, zanubrutnib, LOXO-305, evobrutinib, TG-1701, tolebrutinib, BhB091, DZD-9008, HZ-A-018, orelabrutinib, AC0058TA, SN1011, rilzabrutinib, ARQ 531, DTRMWXHS-12, JN-64264681, branebrutinib, ibrutinib, and fenebrutinib.
2. A CD38 antibody selected from felzartamab, daratumumab, GBR 1342, TAK-573, CID-103, OKT10, STI-6129, SGX301, TAK-079, and mezagitamab.
3. A proteasome inhibitor selected from ixazomib citrate, oprozomib, delanzomib, lactacystin, bortezomib, carfilzomib, VLX1570, epoxomicin, MG132, MG-262, CEP-18770, NEOSH101, TQB3602, and KZR-616.
4. An IMiD selected from pomalidomide, lenalidomide, thalidomide, iberdomide CC-92480, CC-90009, and CC-99282.
5. An HDAC inhibitor selected from trapoxin B, sodium phenylbutyrate, tacedinaline, mocetinostat, BRD73954, BG45, domatinostat, cay10603, HPOB, TMP269, nexturastat A, Santacruzamate A, splitomicin, LMK-235, sodium butyrate, pivaloyloxymethyl butyrate, pyroxamide, abexinostat, resminostat, givinostat, quisinostat, Psammaplin A, KD5170, 1-Alaninechlamydocin, depudecin, and CUDC-101.
6. A compound selected from selinexor, oxaphenamide, belantamab mafodotin, denosumab, zoledronic acid, plerixafor, eltrombopag, ipilumumab, palbociclib, ricolinostat, afuresertib, dinaciclib, filanesib, indatuximab ravtansine, masitinib, sonidegib, sotatercept, ulocuplumab, and urelumab.

I. Definitions

Unless otherwise defined, all technical and scientific terms used herein have the same meaning as commonly understood by one of ordinary skill in the art to which this application belongs. In the specification, singular forms also include the plural unless the context clearly dictates otherwise. Although methods and materials similar or equivalent to those described herein can be used in the practice and testing of the present application, suitable methods and materials are described below. All publications, patent applications, patents, and other references mentioned herein are incorporated by reference. The references cited herein are not admitted to be prior art to the claimed application. In the case of conflict, the present specification, including definitions, will control. In addition, the materials, methods, and examples are illustrative only and are not intended to be limiting.

Compounds are described using standard nomenclature. Unless defined otherwise, all technical and scientific terms used herein have the same meaning as is commonly understood by one of skill in the art to which this invention belongs.

In certain embodiments, of each compound described herein, the compound may be in the form of a racemate, enantiomer, mixture of enantiomers, diastereomer, mixture of diastereomers, tautomer, N-oxide, or isomer, such as a rotamer, as if each is specifically described unless specifically excluded by context.

The terms "a" and "an" do not denote a limitation of quantity, but rather denote the presence of at least one of the referenced items. The term "or" means "and/or". Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods and treatments described herein can be performed in a suitable order unless otherwise indicated herein or otherwise clearly contradicted by context. The use of examples, or exemplary language (e.g., "such as"), is intended merely to better illustrate the invention and does not pose a limitation on the scope of the invention unless otherwise claimed.

The present invention includes compounds described herein with at least one desired isotopic substitution of an atom, at an amount above the natural abundance of the isotope, i.e., enriched. Isotopes are atoms having the same atomic number but different mass numbers, i.e., the same number of protons but a different number of neutrons. If isotopic substitutions are used, the common replacement is at least one deuterium for hydrogen.

More generally, examples of isotopes that can be incorporated into compounds of the invention include isotopes of hydrogen, carbon, nitrogen, oxygen, and fluorine such as $^{2}H$, $^{3}H$, $^{11}C$, $^{13}C$, $^{14}C$ $^{15}N$, $^{17}O$, $^{18}O$, and $^{18}F$, respectively. In one non-limiting embodiment, isotopically labelled compounds can be used in metabolic studies (with, for example $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. Additionally, any hydrogen atom present in the compound of the invention may be substituted with an $^{18}F$ atom, a substitution that may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

By way of general example and without limitation, isotopes of hydrogen, for example, deuterium ($^{2}H$) and tritium ($^{3}H$) may be used anywhere in described structures that achieves the desired result. Alternatively, or in addition, isotopes of carbon, e.g., $^{13}C$ and $^{14}C$, may be used.

Isotopic substitutions, for example deuterium substitutions, can be partial or complete. Partial deuterium substitution means that at least one hydrogen is substituted with deuterium. In certain embodiments, the isotope is 90, 95 or 99% or more enriched in an isotope at any location of interest. In one non-limiting embodiment, deuterium is 90, 95 or 99% enriched at a desired location.

In one non-limiting embodiment, the substitution of a hydrogen atom for a deuterium atom can be provided in any compound described herein. For example, when any of the groups are methyl or ethyl the alkyl residue may be deuterated (in non-limiting embodiments, $CDH_2$, $CD_2H$, $CD_3$, $CH_2CD_3$, $CD_2CD_3$, $CHDCH_2D$, $CH_2CD_3$, $CHDCHD_2$, etc.).

The compounds of the present invention may form a solvate with a solvent (including water). Therefore, in one non-limiting embodiment, the invention includes a solvated form of the compounds described herein. The term "solvate" refers to a molecular complex of a compound of the present invention (including a salt thereof) with one or more solvent molecules. Non-limiting examples of solvents are water, ethanol, isopropanol, dimethyl sulfoxide, acetone and other common organic solvents. The term "hydrate" refers to a molecular complex comprising a compound of the invention and water. Pharmaceutically acceptable solvates in accordance with the invention include those wherein the solvent may be isotopically substituted, e.g. $D_2O$, $d_6$-acetone, $d_6$-DMSO. A solvate can be in a liquid or solid form.

A "dosage form" means a unit of administration of an active agent. Examples of dosage forms include tablets, capsules, injections, suspensions, liquids, emulsions, implants, particles, spheres, creams, ointments, suppositories, inhalable forms, transdermal forms, buccal, sublingual, topical, gel, mucosal, and the like. A "dosage form" can also include an implant, for example an optical implant.

As used herein "endogenous" refers to any material from or produced inside an organism, cell, tissue or system.

As used herein, the term "exogenous" refers to any material introduced from or produced outside an organism, cell, tissue or system.

By the term "modulating," as used herein, is meant mediating a detectable increase or decrease in the level of a response in a patient compared with the level of a response in the patient in the absence of a treatment or compound, and/or compared with the level of a response in an otherwise identical but untreated patient. The term encompasses perturbing and/or affecting a native signal or response thereby mediating a beneficial therapeutic response in a patient, preferably, a human.

"Parenteral" administration of a compound includes, e.g., subcutaneous (s.c.), intravenous (i.v.), intramuscular (i.m.), or intrasternal injection, or infusion techniques.

As used herein, "pharmaceutical compositions" is a composition comprising at least one active agent such as a selected active compound described herein, and at least one other substance, such as a carrier. "Pharmaceutical combinations" are combinations of at least two active agents which may be combined in a single dosage form or provided together in separate dosage forms with instructions that the active agents are to be used together to treat any disorder described herein.

As used herein, a "pharmaceutically acceptable salt" is a derivative of the disclosed compound in which the parent compound is modified by making inorganic and organic, acid or base addition salts thereof with a biologically acceptable lack of toxicity. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are typical, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, $HOOC—(CH_2)_n—COOH$ where n is 0-4, and the like, or using a different acid that produces the same counterion. Lists of additional suitable salts may be found, e.g., in *Remington's Pharmaceutical Sciences*, 17th ed., Mack Publishing Company, Easton, Pa., p. 1418 (1985).

The term "carrier" means a diluent, excipient, or vehicle that an active agent is used or delivered in.

A "pharmaceutically acceptable excipient" means an excipient that is useful in preparing a pharmaceutical composition/combination that is generally safe, and neither biologically nor otherwise inappropriate for administration to a host, typically a human. In certain embodiments, an excipient is used that is acceptable for veterinary use.

A "patient" or "host" is a human or non-human animal in need of treatment, of any of the disorders as specifically described herein. Typically, the host is a human. A "host" may alternatively refer to for example, a mammal, primate (e.g., human), cow, sheep, goat, horse, dog, cat, rabbit, rat, mice, fish, bird and the like.

A "therapeutically effective amount" of a pharmaceutical composition/combination of this invention means an amount effective, when administered to a host, to provide a therapeutic benefit such as an amelioration of symptoms or reduction or diminution of the disease itself.

II. Compounds of the Present Invention

In certain embodiments, the compound used in the present invention is (Compound 1)

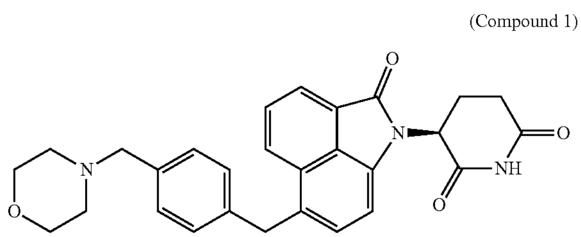 [SMILES: O=C1CC[C@H](N2C(=O)c3cccc4c(Cc5ccc(CN6CCOCC6)cc5)ccc2c34)C(=O)N1]

or a pharmaceutically acceptable salt thereof.

In certain embodiments, the compound used in the present invention is (Compound 2)

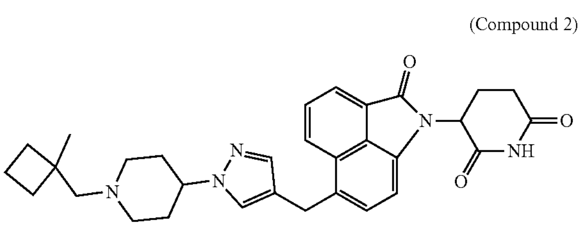 [SMILES: CC1(CN2CCC(n3cc(Cc4ccc5c6c(cccc46)C(=O)N5C4CCC(=O)NC4=O)cn3)CC2)CCC1]

or a pharmaceutically acceptable salt thereof.

In certain embodiments, the compound used in the present invention is (Compound 3)

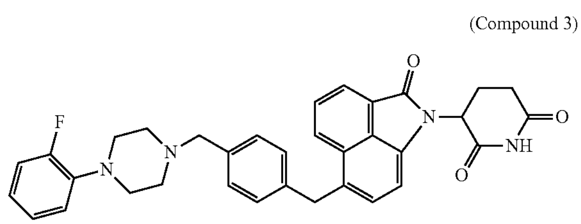 [SMILES: O=C1CCC(N2C(=O)c3cccc4c(Cc5ccc(CN6CCN(c7ccccc7F)CC6)cc5)ccc2c34)C(=O)N1]

or a pharmaceutically acceptable salt thereof.

In certain embodiments, the compound used in the present invention is (Compound 4)

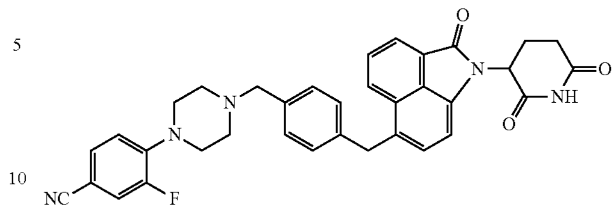

or a pharmaceutically acceptable salt thereof.

In certain embodiments, the compound used in the present invention is (Compound 5)

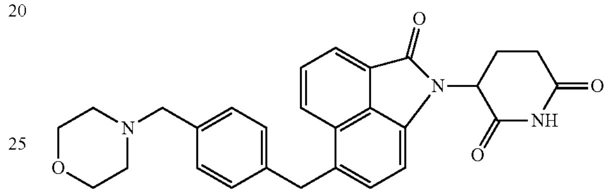

or a pharmaceutically acceptable salt thereof.

In certain embodiments, the compound used in the present invention is (Compound 6)

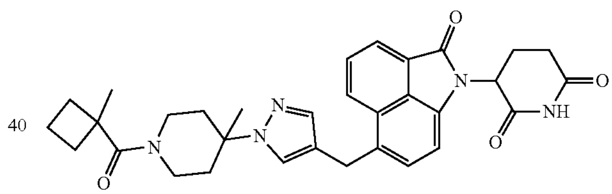

or a pharmaceutically acceptable salt thereof.

In certain embodiments, the compound used in the present invention is (Compound 7)

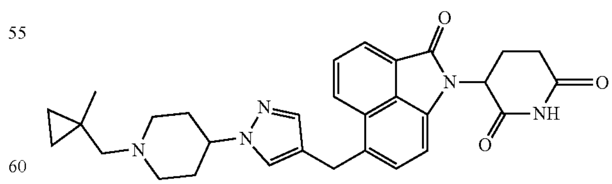

or a pharmaceutically acceptable salt thereof.

In certain embodiments, the compound used in the present invention is (Compound 8)

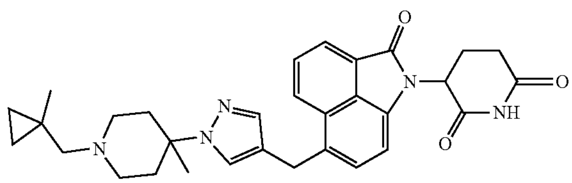

or a pharmaceutically acceptable salt thereof.

In certain embodiments, the compound used in the present invention is (Compound 9)

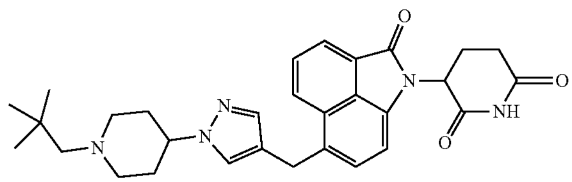

or a pharmaceutically acceptable salt thereof.

In certain embodiments, the compound used in the present invention is (Compound 10)

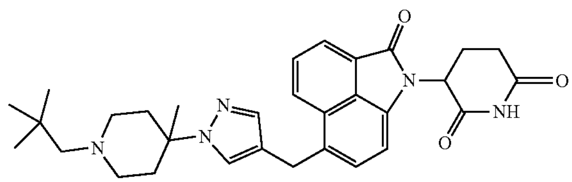

or a pharmaceutically acceptable salt thereof.

In certain embodiments, the compound used in the present invention is (Compound 11)

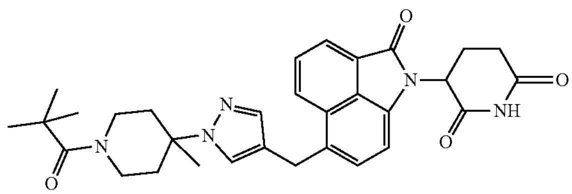

or a pharmaceutically acceptable salt thereof.

In certain embodiments, the compound used in the present invention is (Compound 12)

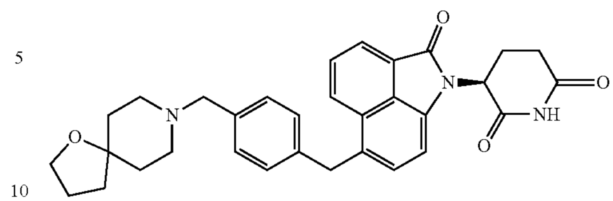

or a pharmaceutically acceptable salt thereof.

In certain embodiments, the compound used in the present invention is (Compound 13)

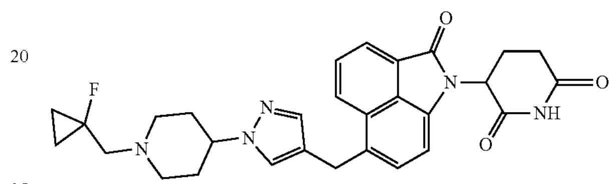

or a pharmaceutically acceptable salt thereof.

III. Embodiments of the Present Invention

1. In certain embodiments, the invention provides a treatment of an Ikaros or Aiolos mediated disorder comprising administering a low dose treatment regimen in a host in need thereof comprising administering a dose of not more than about 500, 450, 400, 350, 300, 250 200, 150 or even 100 micrograms (μg) once a day (QD) or twice a day (BID) of a compound selected from Compound 1, Compound 2, Compound 3, Compound 4, Compound 5, Compound 6, Compound 7, Compound 8, Compound 9, Compound 10, Compound 11, Compound 12, or Compound 13 or a pharmaceutically acceptable salt thereof.
2. The treatment of embodiment 1 wherein the treatment regimen includes a drug holiday.
3. The treatment of embodiment 2 wherein the drug holiday is accomplished with a regimen of therapy once or twice a day for at least 13, 14 15, 16, 17, 18, 19, 20, 21, 22, 23, 24, 25, 26 or 27 continuous days, and then a holiday taken until the next 28 day cycle.
4. The treatment of embodiment 3 wherein therapy is given once or twice a day for 21 days followed by a 7 day holiday.
5. The treatment of any one of embodiments 1-4, wherein the dose is less than about 400 μg.
6. The treatment of any one of embodiments 1-4, wherein the dose is less than about 300 μg.
7. The treatment of any one of embodiments 1-4, wherein the dose is less than about 200 μg.
8. The treatment of any one of embodiments 1-4, wherein the dose is less than about 100 μg.
9. The treatment of any one of embodiments 1-4, wherein the dose is less than about 50 or 25 μg.
10. The treatment of any one of embodiments 1-9, wherein the Ikaros or Aiolos mediated disorder is a diffuse large B-cell lymphoma.
11. The treatment of embodiment 10, wherein the diffuse large B-cell lymphoma is an activated B-cell lymphoma.

12. The treatment of embodiment 10, wherein the diffuse large B-cell lymphoma is a germinal center B-cell lymphoma.
13. The treatment of embodiment 1-9, wherein the Ikaros or Aiolos mediated disorder is a anaplastic large cell lymphoma.
14. The treatment of any one of embodiments 1-9, wherein the Ikaros or Aiolos mediated disorder is a cutaneous T-cell lymphoma.
15. The treatment of any one of embodiments 1-9, wherein the Ikaros or Aiolos mediated disorder is mantle cell lymphoma.
16. The treatment of any one of embodiments 1-9, wherein the Ikaros or Aiolos mediated disorder is a multiple myeloma.
17. The treatment of any one of embodiments 1-16, wherein the disorder is resistant to treatment with first generation IMiD drugs.
18. The treatment of embodiments 17, wherein the disorder is resistant to treatment with thalidomide.
19. The treatment of embodiment 17, wherein the disorder is resistant to treatment with pomalidomide.
20. The treatment of embodiment 17, wherein the disorder is resistant to treatment with lenalidomide.
21. The treatment of embodiment 17, wherein the disorder is resistant to treatment with iberdomide.
22. A treatment of a disorder mediated by Ikaros (IKZF1) and/or Aiolos (IKZF3) wherein a blood or tissue sample is taken from the patient and the concentration of one or more biomarkers, for example IRF-1, caspase-3, IL-2, and/or IFN-γ, is determined, wherein if the patient has a statistically lower concentration including but not limited to up to about 5, 10, 15 or 20% lower, of the biomarker than a healthy person then Compound 1 or a pharmaceutically acceptable salt thereof or another compound described herein is administered to the patient.
23. A treatment of a disorder mediated by Ikaros (IKZF1) and/or Aiolos (IKZF3) wherein a blood or tissue sample is taken from the patient and the concentration of one or more biomarkers, for example cyclin D1, E2F1, ZFP91, SALL4, IRF-4, BLIMP1, and/or MYC is determined, wherein if the patient has a statistically higher concentration including but not limited to up to about 5, 10, 15 or 20% higher of biomarker than a healthy person then Compound 1 or a pharmaceutically acceptable salt thereof or another compound described herein is administered to the patient.
24. A treatment of a disorder mediated by Ikaros (IKZF1) and/or Aiolos (IKZF3) wherein the patient is administered Compound 1 or a pharmaceutically acceptable salt thereof or another compound described herein and then a blood or tissue sample is taken from the patient and the concentration of one or more biomarkers, for example IRF-1, caspase-3, IL-2, and/or IFN-γ, is determined, wherein if the concentration of the biomarker is not significantly increased, for example by at least about 1.25, 1.5, 1.75, or 2-fold, then the dose of the compound is increased.
25. A treatment of a disorder mediated by Ikaros (IKZF1) and/or Aiolos (IKZF3) wherein the patient is administered Compound 1 or a pharmaceutically acceptable salt thereof or another compound described herein and then a blood or tissue sample is taken from the patient and the concentration of one or more biomarkers, for example cyclin D1, E2F1, ZFP91, SALL4, IRF-4, BLIMP1, and/or MYC is determined, wherein if the concentration of the biomarker is not significantly decreased, for example by at least about 1.25, 1.5, 1.75, or 2-fold, then the dose of the compound is increased.
26. The treatment of any one of embodiments 22-25, wherein the dose is increased if the concentration of biomarker is less than 150%.
27. The treatment of any one of embodiments 22-25, wherein the dose is increased if the concentration of biomarker is less than 160%.
28. The treatment of any one of embodiments 22-25, wherein the dose is increased if the concentration of biomarker is less than 170%.
29. The treatment of any one of embodiments 22-25, wherein the dose is increased if the concentration of biomarker is less than 180%.
30. A treatment of an Ikaros or Aiolos mediated disorder comprising administering an effective amount of a compound selected from Compound 1, Compound 2, Compound 3, Compound 4, Compound 5, Compound 6, Compound 7, Compound 8, Compound 9, Compound 10, Compound 11, Compound 12, and Compound 13 or a pharmaceutically acceptable salt thereof, to a patient in need thereof, wherein the Ikaros or Aiolos mediated disorder is an activated diffuse large B-cell lymphoma or germinal center large B-cell lymphoma.
31. A treatment of a disorder mediated by Ikaros (IKZF1) and/or Aiolos (IKZF3) wherein a compound selected from Compound 1, Compound 2, Compound 3, Compound 4, Compound 5, Compound 6, Compound 7, Compound 8, Compound 9, Compound 10, Compound 11, Compound 12, and Compound 13, or a pharmaceutically acceptable salt thereof, is used in combination with a BTK inhibitor selected from acalabrutinib, spebrutinib, zanubrutinib, LOXO-305, evobrutinib, TG-1701, tolebrutinib, BIIB091, DZD-9008, HZ-A-018, orelabrutinib, AC0058TA, SN1011, rilzabrutinib, ARQ 531, DTRMWXHS-12, JNJ-64264681, branebrutinib, and fenebrutinib.
32. A treatment of a disorder mediated by Ikaros (IKZF1) and/or Aiolos (IKZF3) wherein a compound selected from Compound 1, Compound 2, Compound 3, Compound 4, Compound 5, Compound 6, Compound 7, Compound 8, Compound 9, Compound 10, Compound 11, Compound 12, and Compound 13 or a pharmaceutically acceptable salt thereof, is used in combination with a CD38 antibody selected from feizartarmab, GBR 1342, TAK-573, CID-103, OKT10, STI-6129, SGX301, TAK-079, and mezagitamab.
33. A treatment of a disorder mediated by Ikaros (IKZF1) and/or Aiolos (IKZF3) wherein a compound selected from Compound 1, Compound 2, Compound 3, Compound 4, Compound 5, Compound 6, Compound 7, Compound 8, Compound 9, Compound 10, Compound 11, Compound 12, and Compound 13 or a pharmaceutically acceptable salt thereof, is used in combination with a proteasome inhibitor selected from ixazomib citrate, oprozomib, delanzomib, lactacystin, epoxomicin, MG132, MG-262, CEP-18770, NEOSH101, TQB3602, and KZR-616.
34. A treatment of a disorder mediated by Ikaros (IKZF1) and/or Aiolos (IKZF3) wherein a compound selected from Compound 1, Compound 2, Compound 3, Compound 4, Compound 5, Compound 6, Compound 7, Compound 8, Compound 9, Compound 10, Compound 11, Compound 12, and Compound 13 or a pharmaceutically acceptable salt thereof, is used in combination with an IMiD selected from CC-92480, CC-90009, and CC-99282.

35. A treatment of a disorder mediated by Ikaros (IKZF1) and/or Aiolos (IKZF3) wherein a compound selected from Compound 1, Compound 2, Compound 3, Compound 4, Compound 5, Compound 6, Compound 7, Compound 8, Compound 9, Compound 10, Compound 11, Compound 12, and Compound 13 or a pharmaceutically acceptable salt thereof, is used in combination with a HDAC inhibitor selected from trapoxin B, sodium phenylbutyrate, tacedinaline, mocetinostat, BRD73954, BG45, domatinostat, cay10603, HPOB, TMP269, nexturastat A, Santacruzamate A, splitomicin, LMK-235, sodium butyrate, pivaloyloxymethyl butyrate, pyroxamide, abexinostat, resminostat, givinostat, quisinostat, Psammaplin A, KD5170, 1-Alaninechlamydocin, depudecin, and CUDC-101.

36. A treatment of a disorder mediated by Ikaros (IKZF1) and/or Aiolos (IKZF3) wherein a compound selected from Compound 1, Compound 2, Compound 3, Compound 4, Compound 5, Compound 6, Compound 7, Compound 8, Compound 9, Compound 10, Compound 11, Compound 12, and Compound 13 or a pharmaceutically acceptable salt thereof, is used in combination with a compound selected from selinexor, oxaphenamide, belantamab mafodotin, denosumab, zoledronic acid, plerixafor, eltrombopag, ipilumumab, palbociclib, ricolinostat, afuresertib, dinaciclib, filanesib, indatuximab ravtansine, masitinib, sonidegib, sotatercept, ulocuplumab, and urelumab.

37. The treatment of any one of embodiments 1-36, wherein the compound is (Compound 1)

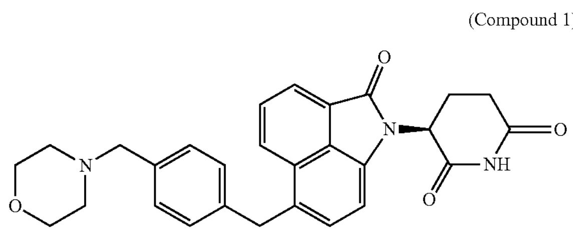

or a pharmaceutically acceptable salt thereof.

38. The treatment of any one of embodiments 1-36, wherein the compound is (Compound 2)

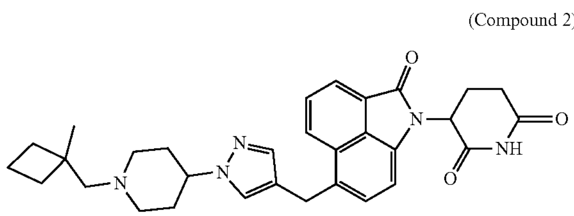 [SMILES: CC1(CN2CCC(n3cc(Cc4ccc5c6c(cccc46)C(=O)N5C4CCC(=O)NC4=O)cn3)CC2)CCC1]

or a pharmaceutically acceptable salt thereof.

39. The treatment of any one of embodiments 1-36, wherein the compound is (Compound 3)

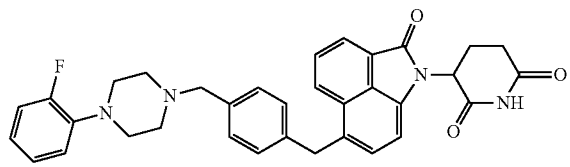

or a pharmaceutically acceptable salt thereof

40. The treatment of any one of embodiments 1-36, wherein the compound is (Compound 4)

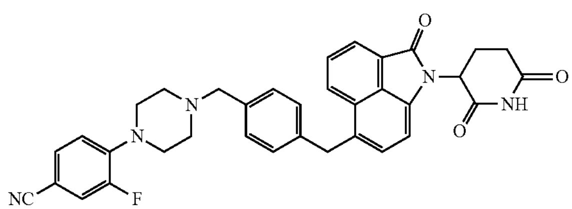

or a pharmaceutically acceptable salt thereof

41. The treatment of any one of embodiments 1-36, wherein the compound is (Compound 5)

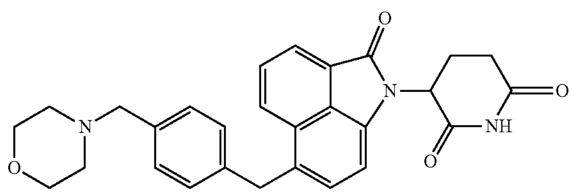

or a pharmaceutically acceptable salt thereof.

42. The treatment of any one of embodiments 1-36, wherein the compound is (Compound 6)

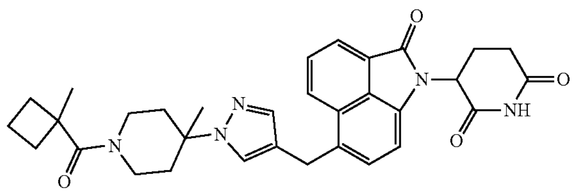

or a pharmaceutically acceptable salt thereof.

43. The treatment of any one of embodiments 1-36, wherein the compound is (Compound 7)

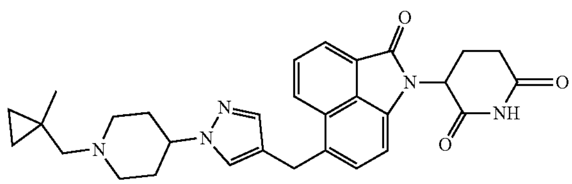

or a pharmaceutically acceptable salt thereof

44. The treatment of any one of embodiments 1-36, wherein the compound is (Compound 8)

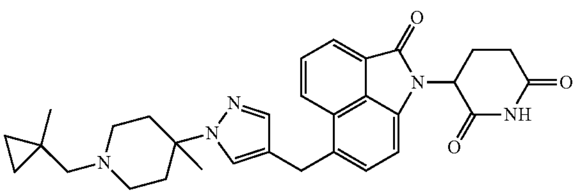

or a pharmaceutically acceptable salt thereof

45. The treatment of any one of embodiments 1-36, wherein the compound is (Compound 9)

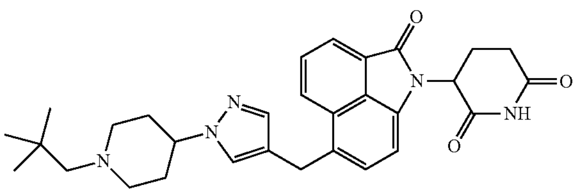

or a pharmaceutically acceptable salt thereof.

46. The treatment of any one of embodiments 1-36, wherein the compound is (Compound 10)

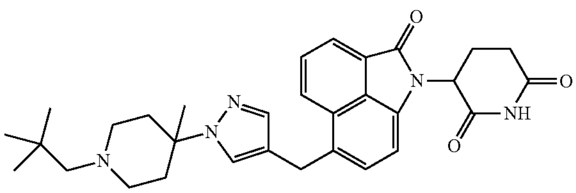

or a pharmaceutically acceptable salt thereof.

47. The treatment of any one of embodiments 1-36, wherein the compound is (Compound 11)

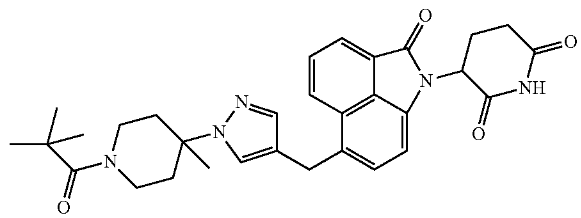

or a pharmaceutically acceptable salt thereof.

48. The treatment of any one of embodiments 1-36, wherein the compound is (Compound 12)

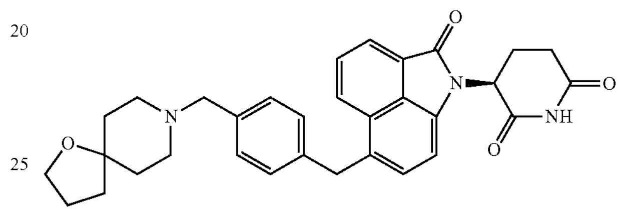

or a pharmaceutically acceptable salt thereof.

49. The treatment of any one of embodiments 1-36, wherein the compound is (Compound 13)

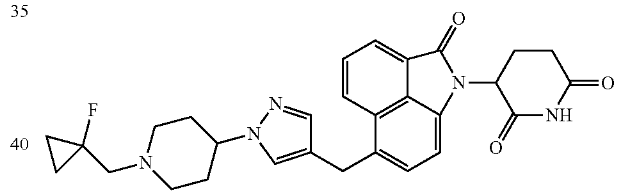

or a pharmaceutically acceptable salt thereof.

50. The treatment of any one of embodiments 1-49, wherein the compound is administered in combination with a Bruton tyrosine kinase inhibitor.

51. The treatment of embodiment 50, wherein the Bruton tyrosine kinase inhibitor is ibrutinib.

52. The treatment of any one of embodiments 1-49, wherein the compound is administered in combination with a corticosteroid.

53. The treatment of embodiment 52, wherein the corticosteroid is dexamethasone.

54. The treatment of any one of embodiments 1-49, wherein the compound is administered in conjunction with CAR T-cell therapy.

55. The treatment of any one of embodiments 1-49, wherein the compound is administered in conjunction with an antibody-drug conjugate.

56. The treatment of any one of embodiments 1-49, wherein the compound is administered in conjunction with BiTE therapy.

57. The treatment of any one of embodiments 1-49, wherein the compound is administered in conjunction with a bispecific antibody.

58. The treatment of any one of embodiments 1-49, wherein the compound is administered in conjunction with a monoclonal antibody.
59. The treatment of any one of embodiments 1-49, wherein the compound is administered in conjunction with a BTK inhibitor selected from acalabrutinib, spebrutinib, zanubrutinib, LOXO-305, evobrutinib, TG-1701, tolebrutinib, BIIB091, DZD-9008, IZ-A-018, orelabrutinib, AC0058TA, SN-1011, rilzabrutinib, ARQ 531, DTRMWXHS-12, JNJ-64264681, branebrutinib, ibrutinib, and fenebrutinib.
60. The treatment of any one of embodiments 1-49, wherein the compound is administered in conjunction with a CD38 antibody selected from felzartamab, daratumumab, GBR 1342, TAK-573, CID-103, OKT10, STI-6129, SGX301, TAK-079, and mezagitamab.
61. The treatment of any one of embodiments 1-49, wherein the compound is administered in conjunction with a proteasome inhibitor selected from ixazomib citrate, oprozomib, delanzomib, lactacystin, bortezomib, carfilzomib, VLX1570, epoxomicin, MG132, MG-262, CEP-18770, NEOSH101, TQB3602, and KZR-616.
62. The treatment of any one of embodiments 1-49, wherein the compound is administered in conjunction with an IMiD selected from pomalidomide, lenalidomide, thalidomide, iberdomide CC-92480. CC-90009, and CC-99282.
63. The treatment of any one of embodiments 1-49, wherein the compound is administered in conjunction with an HDAC inhibitor selected from trapoxin B, sodium phenylbutyrate, tacedinaline, mocetinostat, BRD73954, BG45, domatinostat, cay10603, HPOB, TMP269, nexturastat A, Santacruzamate A, splitomicin, LMK-235, sodium butyrate, pivaloyloxymethyl butyrate, pyroxamide, abexinostat, resminostat, givinostat, quisinostat, Psammaplin A, KD5170, 1-Alaninechlamydocin, depudecin, and CUDC-101.
64. The treatment of any one of embodiments 1-49, wherein the compound is administered in conjunction with a compound selected from selinexor, oxaphenamide, belantamab mafodotin, denosumab, zoledronic acid, plerixafor, eltrombopag, ipilumumab, palbociclib, ricolinostat, afuresertib, dinaciclib, filanesib, indatuximab ravtansine, masitinib, sonidegib, sotatercept, ulocuplumab, and urelumab.

In certain embodiments a treatment is provided as described above wherein the dose of Compound 1 is less than or equal to about 5 μg.

In certain embodiments a treatment is provided as described above wherein the dose of Compound 1 is less than or equal to about 10 μg.

Additional Embodiments

1. In certain embodiments a method of treating a disorder mediated by Ikaros and/or Aiolos comprising administering a dose of no more than about 500 micrograms (μg) once a day (QD) or twice a day (BID) of a compound selected from (Compound 1)

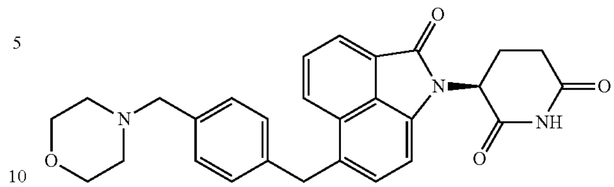

(Compound 2)

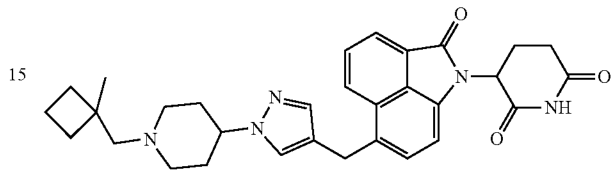

(Compound 3)

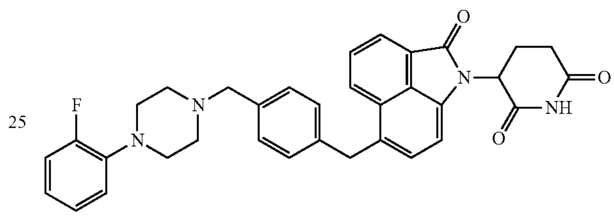

(Compound 4)

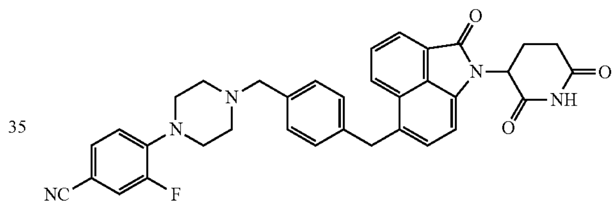

(Compound 5)

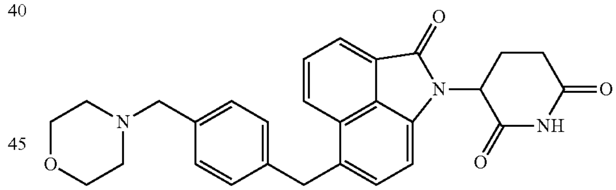

(Compound 6)

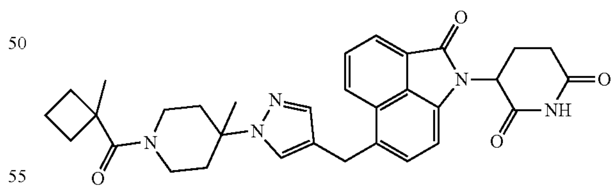

(Compound 7)

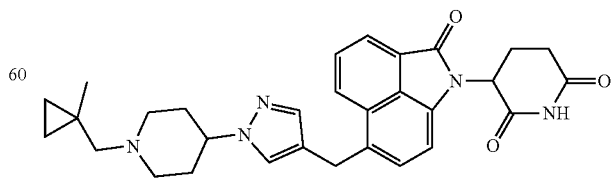

-continued (Compound 8)

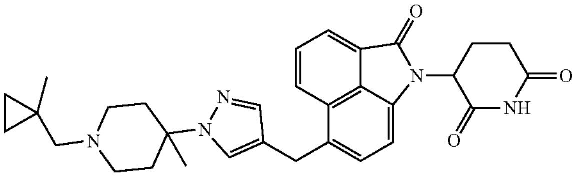

(Compound 9)

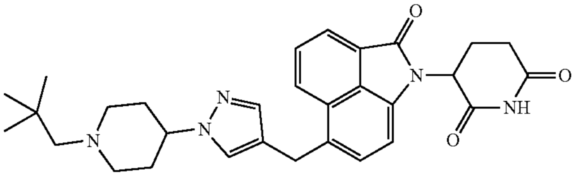

(Compound 10)

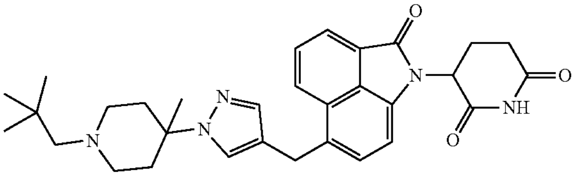

(Compound 11)

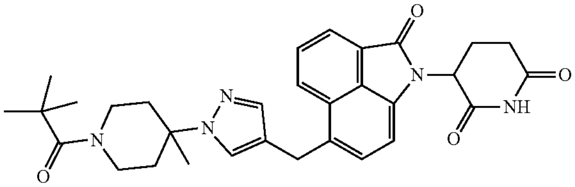

(Compound 12)

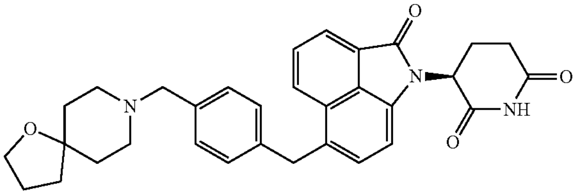

(Compound 13)

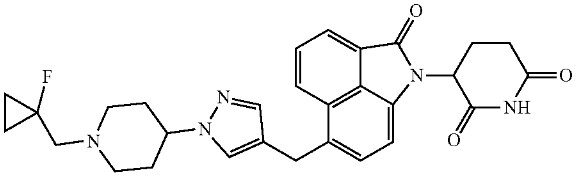

or a pharmaceutically acceptable salt thereof, is provided.

2. The method of embodiment 1, wherein the compound is administered at a dose between about 500 micrograms and 1 microgram.
3. The method of embodiment 1 or embodiment 2, wherein the compound is administered for multiple days with a drug holiday in between subsequent treatment cycles.
4. The method of embodiment 3, wherein the compound is administered once or twice a day for at least 13, 14 15, 16, 17, 18, 19, 20, 21, 22, 23, 24, 25, 26 or 27 continuous days, and then the drug holiday is taken until the next 28-day cycle.
5. The method of embodiment 3, wherein the compound is administered once or twice a day for 21 days followed by a 7-day holiday.
6. The method of any one of embodiments 1-5, wherein the dose is less than or equal to about 400 μg.
7. The method of any one of embodiments 1-5, wherein the dose is less than or equal to about 300 μg.
8. The method of any one of embodiments 1-5, wherein the dose is less than or equal to about 200 μg.
9. The method of any one of embodiments 1-5, wherein the dose is less than or equal to about 100 μg.
10. The method of any one of embodiments 1-5, wherein the dose is less than or equal to about 50 μg.
11. The method of any one of embodiments 1-5, wherein the dose is less than or equal to about 25 μg.
12. The method of any one of embodiments 1-5, wherein the dose is less than or equal to about 10 μg.
13. The method of any one of embodiments 1-5, wherein the dose is less than or equal to about 5 μg.
14. The method of any one of embodiments 1-5, wherein the dose is about 50 μg.
15. The method of any one of embodiments 1-5, wherein the dose is about 25 μg.
16. The method of any one of embodiments 1-5, wherein the dose is about 10 μg.
17. The method of any one of embodiments 1-5, wherein the dose is about 5 μg.
18. The method of any one of embodiments 1-17, wherein the disorder is a diffuse large B-cell lymphoma.
19. The method of embodiment 18, wherein the diffuse large B-cell lymphoma is an activated B-cell lymphoma.
20. The method of embodiment 18, wherein the diffuse large B-cell lymphoma is a germinal center B-cell lymphoma.
21. The method of any one of embodiments 1-17, wherein the disorder is an anaplastic large cell lymphoma.
22. The method of any one of embodiments 1-17, wherein the disorder is a cutaneous T-cell lymphoma.
23. The method of any one of embodiments 1-17, wherein the disorder is mantle cell lymphoma.
24. The method of any one of embodiments 1-17, wherein the disorder is multiple myeloma.
25. The method of any one of embodiments 1-24, wherein the disorder is resistant to treatment with first generation IMiD drugs.
26. The method of embodiment 25, wherein the disorder is resistant to treatment with thalidomide.
27. The method of embodiment 25, wherein the disorder is resistant to treatment with pomalidomide.
28. The method of embodiment 25, wherein the disorder is resistant to treatment with lenalidomide.
29. The method of embodiment 25, wherein the disorder is resistant to treatment with iberdomide.
30. In certain embodiments a method of treating a disorder mediated by Ikaros (IKZF1) and/or Aiolos (IKZF3) wherein a blood or tissue sample is taken from a patient and the concentration of one or more biomarkers selected from IRF-1, caspase-3, IL-2, and IFN-γ, is determined, wherein if the patient has a statistically lower concentration of the biomarker(s) than a healthy person then a compound selected from Compound 1, Compound 2, Compound 3, Compound 4, Compound 5, Compound 6, Compound 7, Compound 8, Compound 9, Compound 10, Compound 11, Compound 12, and Compound 13, or a pharmaceutically acceptable salt thereof is administered to the patient, is provided.

31. The method of embodiment 30, wherein the statistically lower concentration of the biomarker(s) is 5% lower than an average healthy patient.
32. The method of embodiment 30, wherein the statistically lower concentration of the biomarker(s) is 20% lower than an average healthy patient.
33. A method of treating a disorder mediated by Ikaros (IKZF1) and/or Aiolos (IKZF3) wherein a blood or tissue sample is taken from a patient and the concentration of one or more biomarkers selected from cyclin D1, E2F1, ZFP91, SALL4, IRF-4, BLIMP1, and MYC is determined, wherein if the patient has a statistically higher concentration of the biomarker(s) than a healthy person then a compound selected Compound 1, Compound 2, Compound 3, Compound 4, Compound 5, Compound 6, Compound 7, Compound 8, Compound 9, Compound 10, Compound 11, Compound 12, and Compound 13, or a pharmaceutically acceptable salt thereof is administered to the patient.
34. The method of embodiment 33, wherein the statistically higher concentration of the biomarker(s) is 5% higher than an average healthy patient.
35. The method of embodiment 33, wherein the statistically higher concentration of the biomarker(s) is 20% higher than an average healthy patient.
36. In certain embodiments a method of treating a disorder mediated by Ikaros (IKZF1) and/or Aiolos (IKZF3) wherein a patient is administered a compound selected from Compound 1, Compound 2, Compound 3, Compound 4, Compound 5, Compound 6, Compound 7, Compound 8, Compound 9, Compound 10, Compound 11, Compound 12, and Compound 13, or a pharmaceutically acceptable salt thereof, and then a blood or tissue sample is taken from the patient and the concentration of one or more biomarkers selected from IRF-1, caspase-3, IL-2, and IFN-γ, is determined, wherein if the concentration of the biomarker(s) is not significantly increased, then the dose of the compound is increased, is provided.
37. The method of embodiment 36, wherein the dose of the compound is increased if the concentration of the biomarkers(s) is not increased by at least about 25%.
38. The method of embodiment 36, wherein the dose of the compound is increased if the concentration of the biomarkers(s) is not increased by at least about 100%.
39. The method of embodiment 36, wherein the dose of the compound is increased if the concentration of the biomarkers(s) is not increased by at least about 200%.
40. In certain embodiments a method of treating a disorder mediated by Ikaros (IKZF1) and/or Aiolos (IKZF3) wherein a patient is administered a compound selected from Compound 1, Compound 2, Compound 3, Compound 4, Compound 5, Compound 6, Compound 7, Compound 8, Compound 9, Compound 10, Compound 11, Compound 12, and Compound 13, or a pharmaceutically acceptable salt thereof, and then a blood or tissue sample is taken from the patient and the concentration of one or more biomarkers selected from cyclin D1, E2F1, ZFP91, SALL4, IRF-4, BLIMP1, and MYC is determined, wherein if the concentration of the biomarker(s) is not significantly decreased, then the dose of the compound is increased, is provided.
41. The method of embodiment 40, wherein the dose of the compound is increased if the concentration of the biomarkers(s) is not decreased by at least about 10%.
42. The method of embodiment 40, wherein the dose of the compound is increased if the concentration of the biomarkers(s) is not decreased by at least about 25%.
43. The method of embodiment 40, wherein the dose of the compound is increased if the concentration of the biomarkers(s) is not decreased by at least about 50%.
44. In certain embodiments a method of treating a disorder mediated by Ikaros and/or Aiolos comprising administering an effective amount of a compound selected from Compound 1, Compound 2, Compound 3, Compound 4, Compound 5, Compound 6, Compound 7, Compound 8, Compound 9, Compound 10, Compound 11, Compound 12, and Compound 13 or a pharmaceutically acceptable salt thereof, to a patient in need thereof, wherein the Ikaros or Aiolos mediated disorder is an activated diffuse large B-cell lymphoma or germinal center large B-cell lymphoma, is provided.
45. In certain embodiments a method of treating a disorder mediated by Ikaros and/or Aiolos comprising administering an effective amount of a compound selected from Compound 1, Compound 2, Compound 3, Compound 4, Compound 5, Compound 6, Compound 7, Compound 8, Compound 9, Compound 10, Compound 11, Compound 12, and Compound 13, or a pharmaceutically acceptable salt thereof, wherein the patient also receives a BTK inhibitor selected from acalabrutinib, spebrutinib, zanubrutinib, LOXO-305, evobrutinib, TG-1701, tolebrutinib, B1113091, DZD-9008, HZ-A-018, orelabrutinib, AC0058TA, SN1011, rilzabrutinib, ARQ 531, DTRMWXHS-12, JNJ-64264681, branebrutinib, and fenebrutinib, is provided.
46. In certain embodiments a method of treating a disorder mediated by Ikaros and/or Aiolos comprising administering an effective amount of a compound selected from Compound 1, Compound 2, Compound 3, Compound 4, Compound 5, Compound 6, Compound 7, Compound 8, Compound 9, Compound 10, Compound 11, Compound 12, and Compound 13 or a pharmaceutically acceptable salt thereof, wherein the patient also receives a CD38 antibody selected from felzartamab, GBR 1342, TAK-573, CID-103, OKT10, STI-6129, SGX301, TAK-079, and mezagitamab, is provided.
47. In certain embodiments a method of treating a disorder mediated by Ikaros and/or Aiolos comprising administering an effective amount of a compound selected from Compound 1, Compound 2, Compound 3, Compound 4, Compound 5, Compound 6, Compound 7, Compound 8, Compound 9, Compound 10, Compound 11, Compound 12, and Compound 13 or a pharmaceutically acceptable salt thereof, wherein the patient also receives a proteasome inhibitor selected from ixazomib citrate, oprozomib, delanzomib, lactacystin, epoxomicin, MG132, MG-262, CEP-18770, NEOSH101, TQB3602, and KZR-616, is provided.
48. In certain embodiments a method of treating a disorder mediated by Ikaros and/or Aiolos comprising administering an effective amount of a compound selected from Compound 1, Compound 2, Compound 3, Compound 4, Compound 5, Compound 6, Compound 7, Compound 8, Compound 9, Compound 10, Compound 11, Compound 12, and Compound 13 or a pharmaceutically acceptable salt thereof, to a patient in need thereof, wherein the patient also receives an IMiD selected from CC-92480, CC-90009, and CC-99282, is provided.

49. In certain embodiments a method of treating a disorder mediated by Ikaros and/or Aiolos comprising administering an effective amount of a compound selected from Compound 1, Compound 2, Compound 3, Compound 4, Compound 5, Compound 6, Compound 7, Compound 8, Compound 9, Compound 10, Compound 11, Compound 12, and Compound 13 or a pharmaceutically acceptable salt thereof, to a patient in need thereof, wherein the patient also receives a HDAC inhibitor selected from trapoxin B, sodium phenylbutyrate, tacedinaline, mocetinostat, BRD73954, BG45, domatinostat, cay10603, HPOB, TMP269, nexturastat A, Santacruzamate A, splitomicin, LMK-235, sodium butyrate, pivaloyloxymethyl butyrate, pyroxamide, abexinostat, resminostat, givinostat, quisinostat, Psammaplin A, KD5170, 1-Alaninechlamydocin, depudecin, and CUDC-101, is provided.

50. In certain embodiments a method of treating a disorder mediated by Ikaros and/or Aiolos comprising administering an effective amount of a compound selected from Compound 1, Compound 2, Compound 3, Compound 4, Compound 5, Compound 6, Compound 7, Compound 8, Compound 9, Compound 10, Compound 11, Compound 12, and Compound 13 or a pharmaceutically acceptable salt thereof, to a patient in need thereof, wherein the patient also receives a compound selected from selinexor, oxaphenamide, belantamab mafodotin, denosumab, zoledronic acid, plerixafor, eltrombopag, ipilumumab, palbociclib, ricolinostat, afuresertib, dinaciclib, filanesib, indatuximab ravtansine, masitinib, sonidegib, sotatercept, ulocuplumab, and urelumab, is provided.

51. The method of any one of embodiments 1-50, wherein the compound is (Compound 1)

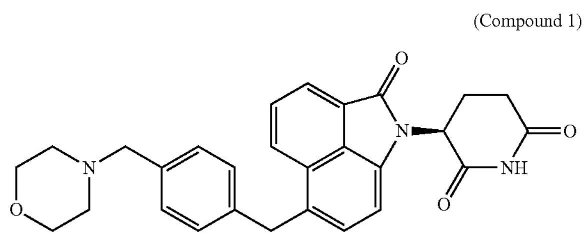 [SMILES: O=C1CC[C@H](N2C(=O)c3cccc4c(Cc5ccc(CN6CCOCC6)cc5)ccc2c34)C(=O)N1]

or a pharmaceutically acceptable salt thereof.

52. The method of any one of embodiments 1-50, wherein the compound is (Compound 2)

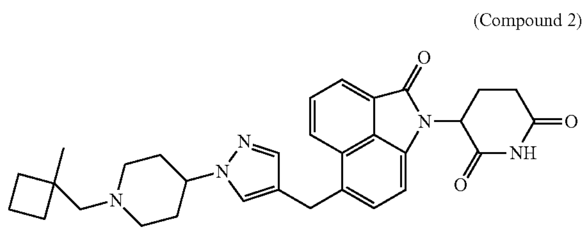 [SMILES: CC1(CN2CCC(n3cc(Cc4ccc5c6c(cccc46)C(=O)N5C4CCC(=O)NC4=O)cn3)CC2)CCC1]

or a pharmaceutically acceptable salt thereof.

53. The method of any one of embodiments 1-50, wherein the compound is (Compound 3)

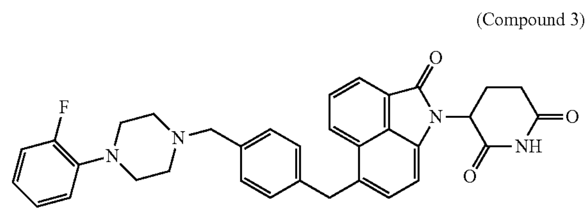 [SMILES: O=C1CCC(N2C(=O)c3cccc4c(Cc5ccc(CN6CCN(c7ccccc7F)CC6)cc5)ccc2c34)C(=O)N1]

or a pharmaceutically acceptable salt thereof

54. The method of any one of embodiments 1-50, wherein the compound is (Compound 4)

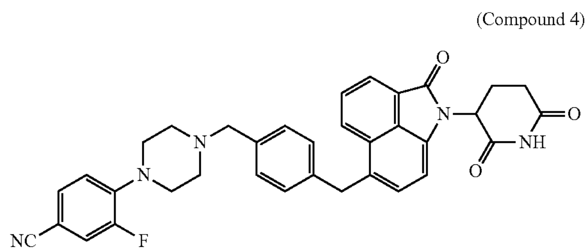 [SMILES: N#Cc1ccc(N2CCN(Cc3ccc(Cc4ccc5c6c(cccc46)C(=O)N5C4CCC(=O)NC4=O)cc3)CC2)c(F)c1]

or a pharmaceutically acceptable salt thereof

55. The method of any one of embodiments 1-50, wherein the compound is (Compound 5)

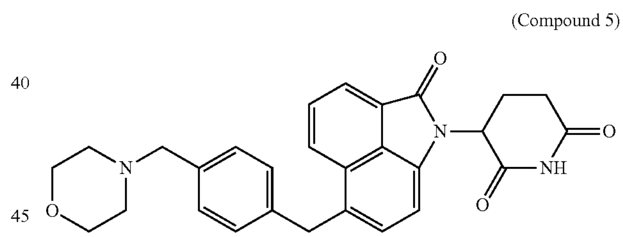

or a pharmaceutically acceptable salt thereof

56. The method of any one of embodiments 1-50, wherein the compound is (Compound 6)

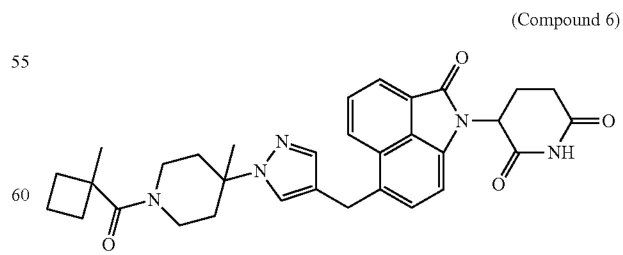

or a pharmaceutically acceptable salt thereof

57. The method of any one of embodiments 1-50, wherein the compound is (Compound 7)

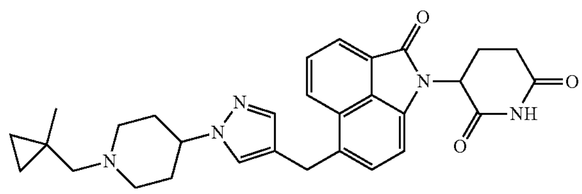

or a pharmaceutically acceptable salt thereof

58. The method of any one of embodiments 1-50, wherein the compound is (Compound 8)

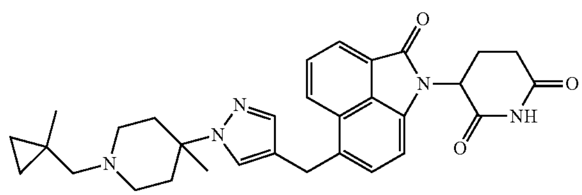

or a pharmaceutically acceptable salt thereof

59. The method of any one of embodiments 1-50, wherein the compound is (Compound 9)

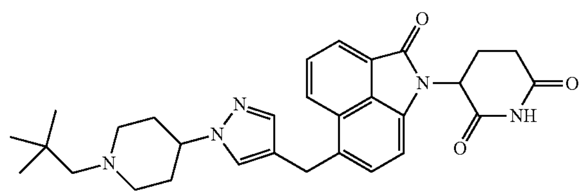

or a pharmaceutically acceptable salt thereof

60. The method of any one of embodiments 1-50, wherein the compound is (Compound 10)

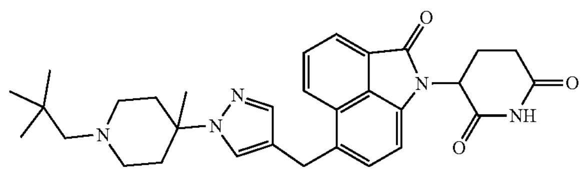

or a pharmaceutically acceptable salt thereof

61. The method of any one of embodiments 1-50, wherein the compound is (Compound 11)

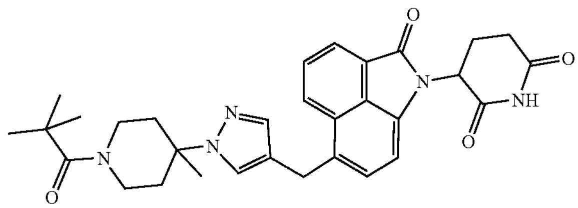

or a pharmaceutically acceptable salt thereof

62. The method of any one of embodiments 1-50, wherein the compound is (Compound 12)

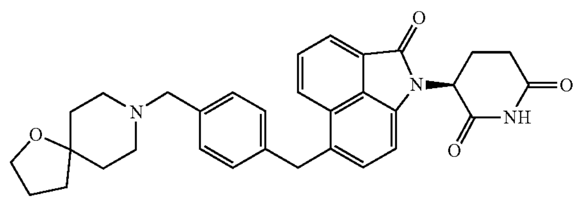

or a pharmaceutically acceptable salt thereof.

63. The method of any one of embodiments 1-50, wherein the compound is (Compound 13)

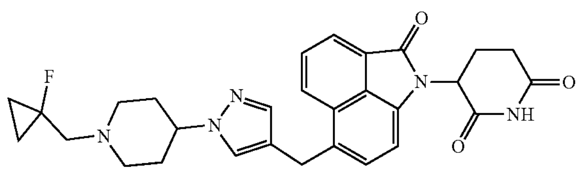

or a pharmaceutically acceptable salt thereof.

64. The method of any one of embodiments 1-63, wherein a Bruton tyrosine kinase inhibitor is also administered to the patient.

65. The method of embodiment 64, wherein the Bruton tyrosine kinase inhibitor is ibrutinib.

66. The method of any one of embodiments 1-65, wherein a corticosteroid is also administered to the patient.

67. The method of embodiment 66, wherein the corticosteroid is dexamethasone.

68. The method of any one of embodiments 1-67, wherein CAR T-cell therapy is also administered to the patient.

69. The method of any one of embodiments 1-67, wherein an antibody-drug conjugate is also administered to the patient.

70. The method of any one of embodiments 1-67, wherein BiTE therapy is also administered to the patient.

71. The method of any one of embodiments 1-67, wherein a bispecific antibody is also administered to the patient.

72. The method of any one of embodiments 1-67, wherein a monoclonal antibody is also administered to the patient.

73. The method of any one of embodiments 1-67, wherein a BTK inhibitor selected from acalabrutinib, spebrutinib, zanubrutinib, LOXO-305, evobrutinib, TG-1701, tolebrutinib, BIIB091, DZD-9008, HZ-A-018, orelabrutinib, AC0058TA, SN1011, rilzabrutinib, ARQ 531, DTRMWXHS-12, JNJ-64264681, branebrutinib, ibrutinib, and fenebrutinib is also administered to the patient.

74. The method of any one of embodiments 1-67, wherein a CD38 antibody selected from felzartamab, daratumumab, GBR 1342, TAK-573, CID-103, OKT10, STI-6129, SGX301, TAK-079, and mezagitamab is also administered to the patient.
75. The method of any one of embodiments 1-67, wherein a proteasome inhibitor selected from ixazomib citrate, oprozomib, delanzomib, lactacystin, bortezomib, carfilzomib, VLX1570, epoxomicin, MG132, MG-262, CEP-18770, NEOSH101, TQB3602, and KZR-616 is also administered to the patient.
76. The method of any one of embodiments 1-67, wherein an IMiD selected from pomalidomide, lenalidomide, thalidomide, iberdomide CC-92480, CC-90009, and CC-99282 is also administered to the patient.
77. The method of any one of embodiments 1-67, wherein an HDAC inhibitor selected from trapoxin B, sodium phenylbutyrate, tacedinaline, mocetinostat, BRD73954, BG45, domatinostat, cay10603, HPOB, TMP269, nexturastat A, Santacruzamate A, splitomicin, LMK-235, sodium butyrate, pivaloyloxymethyl butyrate, pyroxamide, abexinostat, resminostat, givinostat, quisinostat, Psammaplin A, KD5170, 1-Alaninechlamydocin, depudecin, and CUDC-101 is also administered to the patient.
78. The method of any one of embodiments 1-67, wherein a compound selected from selinexor, oxaphenamide, belantamab mafodotin, denosumab, zoledronic acid, plerixafor, eltrombopag, ipilumumab, palbociclib, ricolinostat, afuresertib, dinaciclib, filanesib, indatuximab ravtansine, masitinib, sonidegib, sotatercept, ulocuplumab, and urelumab is also administered to the patient.
79. The method of any one of embodiments 1-78, wherein the compound selected from Compound 1, Compound 2, Compound 3, Compound 4, Compound 5, Compound 6, Compound 7, Compound 8, Compound 9, Compound 10, Compound 11, Compound 12, and Compound 13, or a pharmaceutically acceptable salt thereof is administered once a day.
80. The method of any one of embodiments 1-78, wherein the compound selected from Compound 1, Compound 2, Compound 3, Compound 4, Compound 5, Compound 6, Compound 7, Compound 8, Compound 9, Compound 10, Compound 11, Compound 12, and Compound 13, or a pharmaceutically acceptable salt thereof is administered twice a day.
81. The method of any one of embodiments 1-80, wherein the disorder is Non-Hodgkin's Lymphoma.
82. The method of any one of embodiments 1-80, wherein the disorder is Multiple Myeloma.
83. The method of any one of embodiments 1-82, wherein the disorder is relapsed.
84. The method of any one of embodiments 1-82, wherein the disorder is refractory.
85. The method of any one of embodiments 1-82, wherein the disorder is relapsed and refractory.

IV. Treatment of Disorders Mediated by Ikaros and/or Aiolos

Advantageous treatments of disorders mediated by Ikaros and/or Aiolos are provided. In certain embodiments, the treatment includes the administration of a low dosage form once or twice a day, optionally with a drug holiday, that are highly effective treatment modalities. For example, it has been discovered that treatment can be effective for a patient using one of the compounds described herein with a dosage of not more than about 500, 450, 400, 350, 325, 300, 275, 250, 225, 200, 175, 150, 125 or even 100, 75, 50 or 25 micrograms (μg) once a day (QD) or twice a day (BID) optionally with a treatment holiday. In some embodiments the patient is an adult (typically a human of at least 100 pounds or more, and typically 18 years old or more). In an alternative embodiment, the patient is pediatric (and may be less than 100 pounds and typically less than 18 years old).

The selected compound, for example Compound 1 may be administered as monotherapy or may be combined with a standard of care therapy for the target tumor or cancer, including but not limited to any of those described in the Background of the Invention, or such as a proteasome inhibitor and/or an anti-CD38 monoclonal antibody (mAbs). In MCL, the selected compound can be used, for example, in combination with a Bruton tyrosine kinase (BTK) inhibitor, or an anti-CD20 monoclonal antibody. In PTCL, in particular ALCL, the selected compound may be administered, for example, in combination with anti-CD30 or anti-CD38 monoclonal antibody.

In certain embodiments, Compound 1 is used to treat a disorder mediated by Ikaros or Aiolos according to a treatment regimen described herein.

In certain embodiments, Compound 2 is used to treat a disorder mediated by Ikaros or Aiolos according to a treatment regimen described herein.

In certain embodiments, Compound 3 is used to treat a disorder mediated by Ikaros or Aiolos according to a treatment regimen described herein.

In certain embodiments, Compound 4 is used to treat a disorder mediated by Ikaros or Aiolos according to a treatment regimen described herein.

In certain embodiments, Compound 5 is used to treat a disorder mediated by Ikaros or Aiolos according to a treatment regimen described herein.

In certain embodiments, Compound 6 is used to treat a disorder mediated by Ikaros or Aiolos according to a treatment regimen described herein.

In certain embodiments, Compound 7 is used to treat a disorder mediated by Ikaros or Aiolos according to a treatment regimen described herein.

In certain embodiments, Compound 8 is used to treat a disorder mediated by Ikaros or Aiolos according to a treatment regimen described herein.

In certain embodiments, Compound 9 is used to treat a disorder mediated by Ikaros or Aiolos according to a treatment regimen described herein.

In certain embodiments, Compound 10 is used to treat a disorder mediated by Ikaros or Aiolos according to a treatment regimen described herein.

In certain embodiments, Compound 11 is used to treat a disorder mediated by Ikaros or Aiolos according to a treatment regimen described herein.

In certain embodiments, Compound 12 is used to treat a disorder mediated by Ikaros or Aiolos according to a treatment regimen described herein.

In certain embodiments, Compound 13 is used to treat a disorder mediated by Ikaros or Aiolos according to a treatment regimen described herein.

In certain embodiments a compound described herein, for example Compound 1, is used to treat a cancer that has metastasized. In certain embodiments a compound described herein, for example Compound 1, is used to treat a cancer that has metastasized to the brain.

Treatment Cycles

In certain embodiments, the dosage includes a drug holiday. A drug holiday is a time period during which the patient is not administered the active compound. For example, the patient may be administered the active compound or its pharmaceutically acceptable salt for 21 continuous days and not administered the chemotherapeutic for 7 days during a 28 day cycle, and then optionally the regimen is repeated once, several or more times. In certain examples, one of the compounds described herein may be administered once or twice a day for at least 18, 19, 20, 21, 22, 23, 24, 25, 26 or 27 continuous days, and then a holiday taken until the next 28 day cycle. In some embodiments, the compound is administered once or twice a day for at least 20, 21, 22, 23 or 24 continuous days followed by a drug holiday until the end of the 28 day cycle. In yet another embodiment, the drug is administered every day without a holiday to achieve continuous dosing during the dosing regimen period, which may be 2, 3, or 4 weeks, or even 1, 2, 3, 4, 5 or 6 or more continual months. In another embodiment, the use of a compound described herein eliminates the need for an off-cycle period, drug holiday, or reduction in co-administered anti-neoplastic compound concentration during treatment. In yet another embodiment, the cycle period is greater than 28 days, such as greater than 30 or 35 days.

In certain embodiments, the compound of the present invention is administered for 10, 11, 12, 13, 14, 15, 16, 17, 18, 19, 20, 21, 22, 23, 24, 25, 26, 27, or 28 days of a 28-day treatment cycle. In certain embodiments, the compound of the present invention is administered for 14 consecutive days followed by a 14-day dosage holiday. In certain embodiments, the compound of the present invention is administered for 21 consecutive days followed by a 7-day dosage holiday.

In certain embodiments, the compound of the present invention is administered once a day for 10, 11, 12, 13, 14, 15, 16, 17, 18, 19, 20, 21, 22, 23, 24, 25, 26, 27, or 28 days of a 28-day treatment cycle. In certain embodiments, the compound of the present invention is administered daily for 14 consecutive days followed by a 14-day dosage holiday. In certain embodiments, the compound of the present invention is administered daily for 21 consecutive days followed by a 7-day dosage holiday.

In certain embodiments, the compound of the present invention is administered twice a day for 10, 11, 12, 13, 14, 15, 16, 17, 18, 19, 20, 21, 22, 23, 24, 25, 26, 27, or 28 days of a 28-day treatment cycle. In certain embodiments, the compound of the present invention is administered twice a day for 14 consecutive days followed by a 14-day dosage holiday. In certain embodiments, the compound of the present invention is administered twice a day for 21 consecutive days followed by a 7-day dosage holiday.

In certain embodiments, Compound 1 is administered orally daily for 21 days followed by a 7-day holiday within each 28-day treatment cycle.

Dosing

In certain alternative embodiments the compound of the present invention is administered at a dose of about 800 μg. In certain embodiments, the compound of the present invention is administered at a dose of less than about 600 μg. In certain embodiments, the compound of the present invention is administered at a dose of less than about 400 μg. In certain embodiments, the compound of the present invention is administered at a dose of less than about 300 μg. In certain embodiments, the compound of the present invention is administered at a dose of less than about 200 μg. In certain embodiments, the compound of the present invention is administered at a dose of less than about 100 μg.

In certain embodiments, the compound of the present invention is administered at a dose of less than about 50 μg. In certain embodiments, the compound of the present invention is administered at a dose of less than about 25 μg.

In certain embodiments, the compound of the present invention is administered at a dose of about 50 μg.

In certain embodiments, the compound of the present invention is administered at a dose of about 45 μg.

In certain embodiments, the compound of the present invention is administered at a dose of about 40 μg.

In certain embodiments, the compound of the present invention is administered at a dose of about 35 μg.

In certain embodiments, the compound of the present invention is administered at a dose of about 30 μg.

In certain embodiments, the compound of the present invention is administered at a dose of about 25 μg.

In certain embodiments, the compound of the present invention is administered at a dose of about 20 μg.

In certain embodiments, the compound of the present invention is administered at a dose of about 15 μg.

In certain embodiments, the compound of the present invention is administered at a dose of about 10 μg.

In certain embodiments, the compound of the present invention is administered at a dose of about 5 μg.

In certain embodiments, the compound of the present invention is administered at a dose of about 1 μg.

In certain embodiments, Compound 1 is given at a dose of less than about 800 μg. In certain embodiments, Compound 1 is given at a dose of less than about 600 μg. In certain embodiments, Compound 1 is given at a dose of less than about 400 μg. In certain embodiments, Compound 1 is given at a dose of less than about 300 μg. In certain embodiments, Compound 1 is given at a dose of less than about 200 μg. In certain embodiments, Compound 1 is given at a dose of less than about 100 μg.

In certain embodiments, Compound 1 is given at a dose of about 800 μg. In certain embodiments, Compound 1 is given at a dose of about 600 μg. In certain embodiments, Compound 1 is given at a dose of about 400 μg. In certain embodiments, Compound 1 is given at a dose of about 300 μg. In certain embodiments, Compound 1 is given at a dose of about 200 μg. In certain embodiments, Compound 1 is given at a dose of about 100 μg.

In certain embodiments, Compound 1 is administered at a dose of at least about or between 25, 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, or 1,000 μg.

In certain embodiments, Compound 1 is administered at a dose of about 25 μg. In certain embodiments, Compound 1 is administered at a dose of about 50 or 75 μg. In certain embodiments, Compound 1 is administered at a dose of about 100 or 150 μg. In certain embodiments, Compound 1 is administered at a dose of about 175 or 200 μg. In certain embodiments, Compound 1 is administered at a dose of about 225 or 250 μg. In certain embodiments, Compound 1 is administered at a dose of about 275, 300, 325 or 350 μg. In certain embodiments, Compound 1 is administered at a dose of about 400 or 450 μg. In certain embodiments, Compound 1 is administered at a dose of about 550 μg. In certain embodiments, Compound 1 is administered at a dose of about 650 μg. In certain embodiments, Compound 1 is administered at a dose of about 725 μg. In certain embodiments, Compound 1 is administered at a dose of about 800 μg.

The present invention includes at least the following low-dose features:

(a) a low dose treatment regimen for an Ikaros or Aiolos mediated disorder in a host comprising administering a dose of not more than 500, 450, 400, 350, 300, 250 200, 150 or even 100 micrograms (μg) once a day (QD) or twice a day (BID) to a patient in need thereof of a compound selected from Compound 1, Compound 2, Compound 3, Compound 4, Compound 5, Compound 6, Compound 7, Compound 8, Compound 9, Compound 10, Compound 11, Compound 12, and Compound 13;

(b) the treatment of (a) wherein the treatment regimen includes a drug holiday;

(c) the treatment of (b) wherein the drug holiday is accomplished with a regimen of therapy once or twice a day for at least 13, 14 15, 16, 17, 18, 19, 20, 21, 22, 23, 24, 25, 26 or 27 continuous days, and then a holiday taken until the next 28 day cycle;

(d) the treatment of (c) wherein therapy is given once or twice a day for 21 days followed by a 7 day holiday;

(e) the treatment of (a)-(d) wherein a single dose is not more than 400 micrograms;

(f) the treatment of (a)-(d) wherein a single dose is not more than 300, 200 or 100 micrograms;

(g) the treatment of (a)-(d) wherein a single dose is not more than 25, 50 or 75 micrograms;

(h) the treatment of (b), which may be 2, 3, 4, 5 or 6 weeks, or even 1, 2, 3, 4, 5 or 6 or more months, with dispersed holiday periods;

(i) the treatment of (a) that does not include a holiday period;

(j) the treatment of (a) wherein the cycle period is greater than 28 days, such as greater than 30 or 35 days, and includes a drug holiday;

(k) the treatment of (a)-(j) wherein the disorder selected from diffuse large B-cell lymphoma, anaplastic large cell lymphoma, cutaneous T-cell lymphoma, mantle cell lymphoma, and multiple myeloma, comprising administering an effective amount of Compound 1, Compound 2, Compound 3, Compound 4, Compound 5, Compound 6, Compound 7, Compound 8, Compound 9, Compound 10, Compound 11, Compound 12, or Compound 13 to a patient in need thereof;

(l) the treatment of (a)-(j) wherein the disorder that is resistant to treatment with other cereblon ligands, comprising administering an effective amount of Compound 1, Compound 2, Compound 3, Compound 4, Compound 5, Compound 6, Compound 7, Compound 8, Compound 9, Compound 10, Compound 11, Compound 12, or Compound 13 to a patient in need thereof;

(m) the treatment of (a)-(j) wherein a patient with a cereblon-mediated disorder comprising monitoring the concentration of one or more biomarkers selected from IRF-1 and caspase-3;

(n) the treatment of (a)-(j) wherein a combination treatment of a patient with a cereblon-mediated disorder comprising administering an effective amount of Compound 1, Compound 2, Compound 3, Compound 4, Compound 5, Compound 6, Compound 7, Compound 8, Compound 9, Compound 10, Compound 11, Compound 12, or Compound 13 to a patient in need thereof in combination or alternation with a Bruton tyrosine kinase inhibitor, corticosteroid, CAR T-cell therapy, antibody-drug conjugate, BiTE therapy, bispecific antibody, or monoclonal antibody;

(o) a low does pharmaceutical composition of a compound described herein, or a pharmaceutically acceptable salt, isotopic derivative (including a deuterated derivative), or prodrug thereof in a pharmaceutically acceptable carrier;

(p) the treatment according to (a)-(j) of any disorder described herein comprising administering an effective amount of Compound 1, Compound 2, Compound 3, Compound 4, Compound 5, Compound 6, Compound 7, Compound 8, Compound 9, Compound 10, Compound 11, Compound 12, or Compound 13 to a patient in need thereof, (q) a compound described herein, or a pharmaceutically acceptable salt, isotopic derivative, or prodrug thereof, for the treatment according to (a)-(j) of a disorder that is mediated by Ikaros or Aiolos;

(r) use of a compound described herein, or a pharmaceutically acceptable salt, isotopic derivative, or prodrug thereof, in an effective amount in the treatment according to (a)-(j) of a patient, typically a human, with any one of the disorders described herein, including those mediated by Ikaros or Aiolos;

(s) a method of manufacturing a low dose medicament for the treatment of a disorder described herein in a host characterized in that a compound described herein is used in the manufacture in the low dosage amounts specified herein;

(t) use of a compound described herein, or a pharmaceutically acceptable salt, isotopic derivative, or prodrug thereof in the manufacture of a medicament for the treatment according to (a)-(j) of cancer, including any of the cancers described herein;

(u) a method of manufacturing a medicament for the treatment according to (a)-(j) of cancer in a host, including any of the cancers described herein, characterized in that a compound described herein is used in the manufacture;

(v) a compound described herein, or a pharmaceutically acceptable salt, isotopic derivative, or prodrug thereof, for the treatment according to (a)-(j) of a tumor in a host, including any of the tumors described herein;

(w) use of a compound described herein, or a pharmaceutically acceptable salt, isotopic derivative, or prodrug thereof in the manufacture of a medicament for the treatment according to (a)-(j) of a tumor, including any of the tumors described herein;

(x) a method of manufacturing a medicament for the treatment according to (a)-(j) of a tumor in a host, including any of the tumors described herein, characterized in that a compound described herein is used in the manufacture;

(y) a compound described herein, or a pharmaceutically acceptable salt, isotopic derivative, or prodrug thereof, for the treatment according to (a)-(j) of an immune, autoimmune, or inflammatory disorder in a host;

(z) use of a compound described herein, or a pharmaceutically acceptable salt, isotopic derivative, or prodrug thereof in the manufacture of a medicament for the treatment according to (a)-(j) of an immune, autoimmune, or inflammatory disorder;

(aa) a method of manufacturing a medicament for the treatment according to (a)-(j) of an immune, autoimmune, or inflammatory disorder in a host characterized in that a compound described herein is used in the manufacture;

(bb) a compound described herein, or a pharmaceutically acceptable salt, isotopic derivative, or prodrug thereof, for the treatment according to (a)-(j) of a hematological malignancy such as multiple myeloma, leukemia, lymphoblastic leukemia, chronic lymphocytic leukemia, Hodgkin's lymphoma, or Non-Hodgkin's Lymphoma;

(cc) use of a compound described herein, or a pharmaceutically acceptable salt, isotopic derivative, or prodrug thereof in the manufacture of a medicament for the treatment according to (a)-(j) of a hematological malignancy such as multiple myeloma, leukemia, lymphoblastic leukemia, chronic lymphocytic leukemia, Hodgkin's lymphoma, or Non-Hodgkin's Lymphoma;

(dd) a method of manufacturing a medicament for the treatment according to (a)-(j) of a hematological malignancy in a host such as multiple myeloma, leukemia, lymphoblastic leukemia, chronic lymphocytic leukemia, Hodgkin's lymphoma, or Non-Hodgkin's Lymphoma, characterized in that a compound described herein is used in the manufacture;

(ee) a pharmaceutical composition comprising an effective host-treating amount according to (a)-(j) of a compound described herein or a pharmaceutically acceptable salt, isotopic derivative, or prodrug thereof with a pharmaceutically acceptable carrier or diluent;

(ff) the treatment according to (a)-(j) wherein the compound described herein is a mixture of enantiomers or diastereomers (as relevant), including the racemate;

(gg) The treatment according to (a)-(j) wherein a compound described herein in enantiomerically or diastereomerically (as relevant) enriched form, including an isolated enantiomer or diastereomer (i.e. greater than 85, 90, 95, 97, or 99% pure); and (hh) a process for the preparation of therapeutic products that contain a low dose effective amount of a compound described herein.

In certain alternative embodiments the compound of the present invention is given at a dose of less than about 800 mg. In certain embodiments, the compound of the present invention is given at a dose of less than about 600 mg. In certain embodiments, the compound of the present invention is given at a dose of less than about 400 mg. In certain embodiments, the compound of the present invention is given at a dose of less than about 300 mg. In certain embodiments, the compound of the present invention is given at a dose of less than about 200 mg. In certain embodiments, the compound of the present invention is given at a dose of less than about 100 mg.

In certain embodiments, the compound of the present invention is administered at a dose of about 1,000, 950, 900, 850, 800, 750, 700, 650, 600, 550, 500, 475, 450, 425, 400, 375, 350, 325, 300, 275, 250, 225, 200, 175, 150, 125, 100, 90, 80, 75, 70, 65, 60, 55, 50, 45, 40, 35, 30, 25, 20, 15, 10, 5, or 1 mg.

In certain embodiments, the compound of the present invention is administered at a dose of about 1,000, 950, 900, 850, 800, 750, 700, 650, 600, 550, 500, 475, 450, 425, 400, 375, 350, 325, 300, 275, 250, 225, 200, 175, 150, 125, 100, 90, 80, 75, 70, 65, 60, 55, 50, 45, 40, 35, 30, 25, 20, 15, 10, 5, or 1 μg.

In certain embodiments, the compound of the present invention is administered at a dose of at least about 1,000, 950, 900, 850, 800, 750, 700, 650, 600, 550, 500, 475, 450, 425, 400, 375, 350, 325, 300, 275, 250, 225, 200, 175, 150, 125, 100, 90, 80, 75, 70, 65, 60, 55, 50, 45, 40, 35, 30, 25, 20, 15, 10, 5, or 1 μg.

In certain embodiments, the compound of the present invention is administered at a dose of less than least about 1,000, 950, 900, 850, 800, 750, 700, 650, 600, 550, 500, 475, 450, 425, 400, 375, 350, 325, 300, 275, 250, 225, 200, 175, 150, 125, 100, 90, 80, 75, 70, 65, 60, 55, 50, 45, 40, 35, 30, 25, 20, 15, 10, 5, or 1 μg.

Disorders Mediated by Ikaros and/or Aiolos

In one aspect of the present invention a disorder mediated by Ikaros or Aiolos is treated by Compound 1, or a pharmaceutically acceptable salt thereof, or another compound described herein. In certain embodiments, the cancer is a hematopoietic cancer. In some embodiments, the cancer is a lymphoma, leukemia or myeloma. In certain aspects, the cancer is a Non-Hodgkin's Lymphoma or a Hodgkin's lymphoma.

In certain embodiments, the compound of the present invention is administered to a patient in need thereof in an effective amount to treat diffuse large B-cell lymphoma. In certain embodiments, the diffuse large B-cell lymphoma is an activated B-cell lymphoma or a germinal center B-cell lymphoma. In certain embodiments, the diffuse large B-cell lymphoma is a BCL2/6 translocation bearing cancer. In certain embodiments, the diffuse large B-cell lymphoma is a double hit bearing cancer. In certain embodiments, the diffuse large B-cell lymphoma is a BCL2/6 MYC wild type cancer.

In certain embodiments the compound of the present invention increases the concentration of Caspase-3 and/or Caspase-7. In certain embodiments this increased concentration of Caspase-3 and/or caspase-7 drives cancer cell death, for example mediating the treatment of diffuse large B-cell lymphoma.

In certain embodiments, the compound of the present invention is administered to a patient in need thereof in an effective amount to treat anaplastic large cell lymphoma.

In certain embodiments, the compound of the present invention is administered to a patient in need thereof in an effective amount to treat cutaneous T-cell lymphoma.

In certain embodiments, the compound of the present invention is administered to a patient in need thereof in an effective amount to treat mantle cell lymphoma.

In certain embodiments, the compound of the present invention is administered to a patient in need thereof in an effective amount to treat multiple myeloma.

In certain embodiments, the compound of the present invention is administered to a patient in need thereof in an effective amount to treat a disorder that is resistant to treatment with other cereblon ligands. In certain embodiments, the compound of the present invention is used to treat an IMiD-refractory disorder.

In certain embodiments, Compound 1 is administered to a patient in need thereof in an effective amount to treat diffuse large B-cell lymphoma. In certain embodiments, the diffuse large B-cell lymphoma is an activated B-cell lymphoma or a germinal center B-cell lymphoma. In certain embodiments, the diffuse large B-cell lymphoma is a BCL2/6 translocation bearing cancer.

In certain embodiments, the diffuse large B-cell lymphoma is a double hit bearing cancer. In certain embodiments, the diffuse large B-cell lymphoma is a BCL2/6 MYC wild type cancer.

In certain embodiments, Compound 1 is administered to a patient in need thereof in an effective amount to treat anaplastic large cell lymphoma.

In certain embodiments, Compound 1 is administered to a patient in need thereof in an effective amount to treat cutaneous T-cell lymphoma.

In certain embodiments, Compound 1 is administered to a patient in need thereof in an effective amount to treat mantle cell lymphoma.

In certain embodiments, Compound 1 is administered to a patient in need thereof in an effective amount to treat multiple myeloma.

In certain embodiments, Compound 1 is administered to a patient in need thereof in an effective amount to treat a disorder that is resistant to treatment with other cereblon ligands. In certain embodiments, Compound 1 is administered to a patient in need thereof in an effective amount to treat an IMiD-refractory disorder.

In one aspect an effective amount of a compound described herein, or a pharmaceutically acceptable salt thereof, is administered to a patient to treat a CNS involved cancer, for example a lymphoma in the CNS. In certain embodiments, the patient with a CNS involved cancer, for example a lymphoma in the CNS, is also administered one or more additional therapeutic agents, for example ibrutinib or rituximab. In certain embodiments, a compound described herein is used in the treatment of a peripheral central nervous system lymphoma.

In certain embodiments, Compound 1 is administered for the treatment of PTCL-NOS (i.e. PTCL that is not otherwise specified). In other embodiments Compound 1 is administered for the treatment of PTCL with a specified subtype for example anaplastic large cell lymphoma (ALCL), angioimmunoblastic T-Cell lymphoma (AITL), enteropathy-type T-cell lymphoma, extranodal natural killer (NK) cell lymphoma, or extranodal T-cell lymphoma.

In certain embodiments, the disorder treated by a compound of the present invention is an immunomodulatory disorder. In certain embodiments, the disorder treated by a compound of the present invention is mediated by angiogenesis. In certain embodiments, the disorder treated by a compound of the present invention is related to the lymphatic system.

In certain embodiments, a compound of the present invention or pharmaceutical salt thereof, optionally in a pharmaceutical composition as described herein is administered to a patient in need thereof in an effective amount to degrade Ikaros or Aiolos, which is a mediator of the disorder affecting the patient, such as a human. The control of protein level afforded by any of the compounds of the present invention provides treatment of a disease state or condition, which is modulated through Ikaros or Aiolos by lowering the level of that protein in the cell, e.g., cell of a patient, or by lowering the level of downstream proteins in the cell. In certain embodiments, the treatment comprises administering an effective amount of the compound as described herein, optionally including a pharmaceutically acceptable excipient, carrier, adjuvant (i.e., a pharmaceutically acceptable composition), optionally in combination or alternation with another bioactive agent or combination of agents.

In certain embodiments, a compound of the present invention is administered to a patient in need thereof in an effective amount to treat a disorder including, but not limited to, benign growth, neoplasm, tumor, cancer, abnormal cellular proliferation, immune disorder, inflammatory disorder, graft-versus-host rejection, viral infection, bacterial infection, an amyloid-based proteinopathy, a proteinopathy, or a fibrotic disorder.

The term "disease state" or "condition" when used in connection with any of the compounds is meant to refer to any disease state or condition that is mediated by Ikaros or Aiolos, such as cellular proliferation, or by proteins that are downstream of Ikaros or Aiolos, and where degradation of such protein in a patient may provide beneficial therapy or relief of symptoms to a patient in need thereof. In certain instances, the disease state or condition may be cured.

In certain embodiments, a compound or its corresponding pharmaceutically acceptable salt, isotopic derivative, or prodrug as described herein can be administered in an effective amount to treat a host, for example a human, with a lymphoma or lymphocytic or myelocytic proliferation disorder or abnormality. For example, a compound as described herein can be administered to a host suffering from a Hodgkin Lymphoma or a Non-Hodgkin Lymphoma. For example, the host can be suffering from a Non-Hodgkin Lymphoma such as, but not limited to: an AIDS-Related Lymphoma; Anaplastic Large-Cell Lymphoma; Angioimmunoblastic Lymphoma; Blastic NK-Cell Lymphoma; Burkitt's Lymphoma; Burkitt-like Lymphoma (Small Non-Cleaved Cell Lymphoma); diffuse small-cleaved cell lymphoma (DSCCL); Chronic Lymphocytic Leukemia, Small Lymphocytic Lymphoma; Non-Hodgkin lymphoma NOS, Cutaneous T-Cell Lymphoma; Diffuse Large B-Cell Lymphoma; Enteropathy-Type T-Cell Lymphoma; Follicular Lymphoma; Hepatosplenic Gamma-Delta T-Cell Lymphoma; Lymphoblastic Lymphoma; Mantle Cell Lymphoma; Marginal Zone Lymphoma; Nasal T-Cell Lymphoma; Pediatric Lymphoma; Peripheral Lymphoma, Peripheral T-Cell Lymphomas; Primary Central Nervous System Lymphoma; T-Cell Leukemias; Transformed Lymphomas; Treatment-Related T-Cell Lymphomas; Langerhans cell histiocytosis; or Waldenstrom's Macroglobulinemia.

In another embodiment, a compound or its corresponding pharmaceutically acceptable salt, isotopic derivative, or prodrug as described herein can be administered in an effective amount to treat a host, for example a human, with a Hodgkin lymphoma, such as, but not limited to: Nodular Sclerosis Classical Hodgkin's Lymphoma (CHL); Mixed Cellularity CHL; Lymphocyte-depletion CHL; Lymphocyte-rich CHL; Lymphocyte Predominant Hodgkin Lymphoma; or Nodular Lymphocyte Predominant HL.

In another embodiment, a compound or its corresponding pharmaceutically acceptable salt, isotopic derivative, or prodrug as described herein can be administered in an effective amount to treat a host, for example a human, with an immunomodulatory condition. Non-limiting examples of immunomodulatory conditions include: arthritis, lupus, celiac disease, Sjogren's syndrome, polymyalgia rheumatia, multiple sclerosis, ankylosing spondylitis, type 1 diabetes, alopecia areata, vasculitis, and temporal arteritis.

In certain embodiments, the condition treated with a compound of the present invention is a disorder related to abnormal cellular proliferation. Abnormal cellular proliferation, notably hyperproliferation, can occur as a result of a wide variety of factors, including genetic mutation, infection, exposure to toxins, autoimmune disorders, and benign or malignant tumor induction.

Abnormal proliferation of B-cells, T-cells, and/or NK cells can result in a wide range of diseases such as cancer, proliferative disorders and inflammatory/immune diseases. A host, for example a human, afflicted with any of these disorders can be treated with an effective amount of a compound as described herein to achieve a decrease in symptoms (palliative agent) or a decrease in the underlying disease (a disease modifying agent).

In certain embodiments, a compound or its corresponding pharmaceutically acceptable salt, isotopic derivative, or prodrug as described herein can be administered in an effective amount to treat a host, for example a human, with a specific B-cell lymphoma or proliferative disorder such as, but not limited to: multiple myeloma; Diffuse large B cell lymphoma; Follicular lymphoma; Mucosa-Associated Lymphatic Tissue lymphoma (MALT); Small cell lymphocytic lymphoma; diffuse poorly differentiated lymphocytic lymphoma; Mediastinal large B cell lymphoma; Nodal marginal zone B cell lymphoma (NMZL); Splenic marginal zone lymphoma (SMZL); Intravascular large B-cell lymphoma; Primary effusion lymphoma; or Lymphomatoid granulomatosis; B-cell prolymphocytic leukemia; Hairy cell leukemia; Splenic lymphoma/leukemia, unclassifiable; Splenic diffuse red pulp small B-cell lymphoma; Hairy cell leukemia-variant; Lymphoplasmacytic lymphoma; Heavy chain diseases, for example, Alpha heavy chain disease, Gamma heavy chain disease, Mu heavy chain disease; Plasma cell myeloma; Solitary plasmacytoma of bone; Extraosseous plasmacytoma; Primary cutaneous follicle center lymphoma; T cell/histiocyte rich large B-cell lymphoma; DLBCL associated with chronic inflammation; Epstein-Barr virus (EBV)+ DLBCL of the elderly; Primary mediastinal (thymic) large B-cell lymphoma; Primary cutaneous DLBCL, leg type; ALK+ large B-cell lymphoma; Plasmablastic lymphoma; Large B-cell lymphoma arising in HHV8-associated multicentric; Castleman disease; B-cell lymphoma, unclassifiable, with features intermediate between diffuse large B-cell lymphoma; or B-cell lymphoma, unclassifiable, with features intermediate between diffuse large B-cell lymphoma and classical Hodgkin lymphoma.

In certain embodiments, a compound or its corresponding pharmaceutically salt, isotopic derivative, or prodrug as described herein can be administered in an effective amount to treat a host, for example a human, with a T-cell or NK-cell lymphoma such as, but not limited to: anaplastic lymphoma kinase (ALK) positive, ALK negative anaplastic large cell lymphoma, or primary cutaneous anaplastic large cell lymphoma; angioimmunoblastic lymphoma; cutaneous T-cell lymphoma, for example mycosis fungoides, Sézary syndrome, primary cutaneous anaplastic large cell lymphoma, primary cutaneous CD30+ T-cell lymphoproliferative disorder; primary cutaneous aggressive epidermotropic CD8+ cytotoxic T-cell lymphoma; primary cutaneous gamma-delta T-cell lymphoma; primary cutaneous small/medium CD4+ T-cell lymphoma, and lymphomatoid papulosis; Adult T-cell Leukemia/Lymphoma (ATLL); Blastic NK-cell Lymphoma; Enteropathy-type T-cell lymphoma; Hematosplenic gamma-delta T-cell Lymphoma; Lymphoblastic Lymphoma; Nasal NK/T-cell Lymphomas; Treatment-related T-cell lymphomas; for example lymphomas that appear after solid organ or bone marrow transplantation; T-cell prolymphocytic leukemia; T-cell large granular lymphocytic leukemia; Chronic lymphoproliferative disorder of NK-cells; Aggressive NK cell leukemia; Systemic EBV+ T-cell lymphoproliferative disease of childhood (associated with chronic active EBV infection); Hydroa vacciniforme-like lymphoma; Adult T-cell leukemia/lymphoma; Enteropathy-associated T-cell lymphoma; Hepatosplenic T-cell lymphoma; or Subcutaneous panniculitis-like T-cell lymphoma.

In certain embodiments, a compound or its corresponding pharmaceutically acceptable salt, isotopic derivative, or prodrug as described herein can be administered to treat a host, for example a human, with leukemia. For example, the host may be suffering from an acute or chronic leukemia of a lymphocytic or myelogenous origin, such as, but not limited to: Acute lymphoblastic leukemia (ALL); Acute myelogenous leukemia (AML); Chronic lymphocytic leukemia (CLL); Chronic myelogenous leukemia (CML); juvenile myelomonocytic leukemia (JMML); hairy cell leukemia (HCL); acute promyelocytic leukemia (a subtype of AML); large granular lymphocytic leukemia; or Adult T-cell chronic leukemia. In certain embodiments, the patient suffers from an acute myelogenous leukemia, for example an undifferentiated AML (M0); myeloblastic leukemia (M1; with/without minimal cell maturation); myeloblastic leukemia (M2; with cell maturation); promyelocytic leukemia (M3 or M3 variant [M3V]); myelomonocytic leukemia (M4 or M4 variant with eosinophilia [M4E]); monocytic leukemia (M5); erythroleukemia (M6); or megakaryoblastic leukemia (M7).

There are a number of skin disorders associated with cellular hyperproliferation. Psoriasis, for example, is a benign disease of human skin generally characterized by plaques covered by thickened scales. The disease is caused by increased proliferation of epidermal cells of unknown cause. Chronic eczema is also associated with significant hyperproliferation of the epidermis. Other diseases caused by hyperproliferation of skin cells include atopic dermatitis, lichen planus, warts, pemphigus vulgaris, actinic keratosis, basal cell carcinoma and squamous cell carcinoma.

Other hyperproliferative cell disorders include blood vessel proliferation disorders, fibrotic disorders, autoimmune disorders, graft-versus-host rejection, tumors and cancers.

Blood vessel proliferative disorders include angiogenic and vasculogenic disorders. Proliferation of smooth muscle cells in the course of development of plaques in vascular tissue cause, for example, restenosis, retinopathies and atherosclerosis. Both cell migration and cell proliferation play a role in the formation of atherosclerotic lesions.

Fibrotic disorders are often due to the abnormal formation of an extracellular matrix. Examples of fibrotic disorders include hepatic cirrhosis and mesangial proliferative cell disorders. Hepatic cirrhosis is characterized by the increase in extracellular matrix constituents resulting in the formation of a hepatic scar. Hepatic cirrhosis can cause diseases such as cirrhosis of the liver. An increased extracellular matrix resulting in a hepatic scar can also be caused by viral infection such as hepatitis. Lipocytes appear to play a major role in hepatic cirrhosis.

Mesangial disorders are brought about by abnormal proliferation of mesangial cells. Mesangial hyperproliferative cell disorders include various human renal diseases, such as glomerulonephritis, diabetic nephropathy, malignant nephrosclerosis, thrombotic micro-angiopathy syndromes, transplant rejection, and glomerulopathies.

Another disease with a proliferative component is rheumatoid arthritis. Rheumatoid arthritis is generally considered an autoimmune disease that is thought to be associated with activity of autoreactive T cells, and to be caused by autoantibodies produced against collagen and IgE.

Other disorders that can include an abnormal cellular proliferative component include Bechet's syndrome, acute respiratory distress syndrome (ARDS), ischemic heart disease, post-dialysis syndrome, leukemia, acquired immune deficiency syndrome, vasculitis, lipid histiocytosis, septic shock and inflammation in general.

A compound or its pharmaceutically acceptable salt, isotopic analog, or prodrug as described herein can be administered in an effective amount to treat a host, for example a human, with a proliferative condition such as myeloproliferative disorder (MPD), polycythemia vera (PV), essential thrombocythemia (ET), myeloid metaplasia with myelofibrosis (MMM), chronic myelomonocytic leukemia (CMML), hypereosinophilic syndrome (HES), system mast cell disease (SMCD), and the like. In another embodiment, a compound provided herein is useful for the treatment of primary myelofibrosis, post-polycythemia vera myelofibrosis, post-essential thrombocythemia myelofibrosis, and secondary acute myelogenous leukemia.

In certain embodiments, a compound or its pharmaceutically acceptable salt, isotopic analog, or prodrug as described herein can be administered in an effective amount to treat a host, for example a human, with a myelodysplastic syndrome (MDS) such as, but not limited to: refractory cytopenia with unilineage dysplasia, refractory anemia with ring sideroblasts (RARS), refractory anemia with ring sideroblasts-thrombocytosis (RARS-t), refractory cytopenia with multilineage dysplasia (RCMD) including RCMD with multilineage dysplasia and ring sideroblasts (RCMD-RS), Refractory amenias with excess blasts I (RAEB-I) and II (RAEB-II), 5q-syndrome, refractory cytopenia of childhood, and the like.

In certain embodiments, a compound of the present invention can provide a therapeutic effect by direct degradation of Ikaros or Aiolos which may change the transcriptional regulation of a protein downstream of Ikaros or Aiolos.

The term "neoplasia" or "cancer" is used to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors. Exemplary cancers which may be treated by the present compounds either alone or in combination with at least one additional anti-cancer agent include squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's Lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using compounds according to the present invention include, for example, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML.

Additional cancers which may be treated using the disclosed compounds according to the present invention include, for example, acute granulocytic leukemia, acute lymphocytic leukemia (ALL), acute myelogenous leukemia (AML), adenocarcinoma, adenosarcoma, adrenal cancer, adrenocortical carcinoma, anal cancer, anaplastic astrocytoma, angiosarcoma, appendix cancer, astrocytoma, Basal cell carcinoma, B-Cell lymphoma, bile duct cancer, bladder cancer, bone cancer, bone marrow cancer, bowel cancer, brain cancer, brain stem glioma, breast cancer, triple (estrogen, progesterone and HER-2) negative breast cancer, double negative breast cancer (two of estrogen, progesterone and HER-2 are negative), single negative (one of estrogen, progesterone and HER-2 is negative), estrogen-receptor positive, HER2-negative breast cancer, estrogen receptor-negative breast cancer, estrogen receptor positive breast cancer, metastatic breast cancer, luminal A breast cancer, luminal B breast cancer, Her2-negative breast cancer, HER2-positive or negative breast cancer, progesterone receptor-negative breast cancer, progesterone receptor-positive breast cancer, recurrent breast cancer, carcinoid tumors, cervical cancer, cholangiocarcinoma, chondrosarcoma, chronic lymphocytic leukemia (CLL), chronic myelogenous leukemia (CML), colon cancer, colorectal cancer, craniopharyngioma, cutaneous lymphoma, cutaneous melanoma, diffuse astrocytoma, ductal carcinoma in situ (DCIS), endometrial cancer, ependymoma, epithelioid sarcoma, esophageal cancer, ewing sarcoma, extrahepatic bile duct cancer, eye cancer, fallopian tube cancer, fibrosarcoma, gallbladder cancer, gastric cancer, gastrointestinal cancer, gastrointestinal carcinoid cancer, gastrointestinal stromal tumors (GIST), germ cell tumor glioblastoma multiforme (GBM), glioma, hairy cell leukemia, head and neck cancer, hemangioendothelioma, Hodgkin lymphoma, hypopharyngeal cancer, infiltrating ductal carcinoma (IDC), infiltrating lobular carcinoma (ILC), inflammatory breast cancer (IBC), intestinal Cancer, intrahepatic bile duct cancer, invasive/infiltrating breast cancer, Islet cell cancer, jaw cancer, Kaposi sarcoma, kidney cancer, laryngeal cancer, leiomyosarcoma, leptomeningeal metastases, leukemia, lip cancer, liposarcoma, liver cancer, lobular carcinoma in situ, low-grade astrocytoma, lung cancer, lymph node cancer, lymphoma, male breast cancer, medullary carcinoma, medulloblastoma, melanoma, meningioma, Merkel cell carcinoma, mesenchymal chondrosarcoma, mesenchymous, mesothelioma metastatic breast cancer, metastatic melanoma metastatic squamous neck cancer, mixed gliomas, monodermal teratoma, mouth cancer mucinous carcinoma, mucosal melanoma, multiple myeloma, Mycosis Fungoides, myelodysplastic syndrome, nasal cavity cancer, nasopharyngeal cancer, neck cancer, neuroblastoma, neuroendocrine tumors (NETs), Non-Hodgkin's Lymphoma, non-small cell lung cancer (NSCLC), oat cell cancer, ocular cancer, ocular melanoma, oligodendroglioma, oral cancer, oral cavity cancer, oropharyngeal cancer, osteogenic sarcoma, osteosarcoma, ovarian cancer, ovarian epithelial cancer ovarian germ cell tumor, ovarian primary peritoneal carcinoma, ovarian sex cord stromal tumor, Paget's disease, pancreatic cancer, papillary carcinoma, paranasal sinus cancer, parathyroid cancer, pelvic cancer, penile cancer, peripheral nerve cancer, peritoneal cancer, pharyngeal cancer, pheochromocytoma, pilocytic astrocytoma, pineal region tumor, pineoblastoma, pituitary gland cancer, primary central nervous system (CNS) lymphoma, prostate cancer, rectal cancer, renal cell carcinoma, renal pelvis cancer, rhabdomyosarcoma, salivary gland cancer, soft tissue sarcoma, bone sarcoma, sarcoma, sinus cancer, skin cancer, small cell lung cancer (SCLC), small intestine cancer, spinal cancer, spinal column cancer, spinal cord cancer, squamous cell carcinoma, stomach cancer, synovial sarcoma, T-cell lymphoma, testicular cancer, throat cancer, thymoma/thymic carcinoma, thyroid cancer, tongue cancer, tonsil cancer, transitional cell cancer, tubal cancer, tubular carcinoma, undiagnosed cancer, ureteral cancer, urethral cancer, uterine adenocarcinoma, uterine cancer, uterine sarcoma, vaginal cancer, vulvar cancer, T-cell lineage acute lymphoblastic leukemia (T-ALL), T-cell lineage lymphoblastic lymphoma (T-LL), peripheral T-cell lymphoma, Adult T-cell leukemia, Pre-B ALL, Pre-B lymphomas, large B-cell lymphoma, Burkitts lymphoma, B-cell ALL, Philadelphia chromosome positive ALL, Philadelphia chromosome positive CML, juvenile myelomonocytic leukemia (JMML), acute promyelocytic leukemia (a subtype of AML), large granular lymphocytic leukemia, Adult T-cell chronic leukemia, diffuse large B cell lymphoma, follicular lymphoma; Mucosa-Associated Lymphatic Tissue lymphoma (MALT), small cell lymphocytic lymphoma, mediastinal large B cell lymphoma, nodal marginal zone B cell lymphoma (NMZL); splenic marginal zone lymphoma (SMZL); intravascular large B-cell lymphoma; primary effusion lymphoma; or lymphomatoid granulomatosis; B-cell prolymphocytic leukemia; splenic lymphoma/leukemia, unclassifiable, splenic diffuse red pulp small B-cell lymphoma; lymphoplasmacytic lymphoma; heavy chain diseases, for example, Alpha heavy chain disease, Gamma heavy chain disease, Mu heavy chain disease, plasma cell myeloma, solitary plasmacytoma of bone; extraosseous plasmacytoma; primary cutaneous follicle center lymphoma, T cell/histocyte rich large B-cell lymphoma, DLBCL associated with chronic inflammation; Epstein-Barr virus (EBV)+DLBCL of the elderly; primary mediastinal (thymic) large B-cell lymphoma, primary cutaneous DLBCL, leg type, ALK+ large B-cell lymphoma, plasmablastic lymphoma; large B-cell lymphoma arising in HHV8-associated multicentric, Castleman disease; B-cell lymphoma, unclassifiable, with features intermediate between diffuse large B-cell lymphoma, or B-cell lymphoma, unclassifiable, with features intermediate between diffuse large B-cell lymphoma and classical Hodgkin lymphoma. In certain embodiments, the disorder is adenoid cystic carcinoma. In certain embodiments, the disorder is NUT midline carcinoma.

In another embodiment, a compound or its pharmaceutically acceptable salt, isotopic derivative or prodrug as described herein can be used in an effective amount to treat a host, for example a human, with an autoimmune disorder. Examples include, but are not limited to: Acute disseminated encephalomyelitis (ADEM); Addison's disease; Agammaglobulinemia; Alopecia areata; Amyotrophic lateral sclerosis (Also Lou Gehrig's disease; Motor Neuron Disease); Ankylosing Spondylitis; Antiphospholipid syndrome; Antisynthetase syndrome; Atopic allergy; Atopic dermatitis; Autoimmune aplastic anemia; Autoimmune arthritis; Autoimmune cardiomyopathy; Autoimmune enteropathy; Autoimmune granulocytopenia; Autoimmune hemolytic anemia; Autoimmune hepatitis; Autoimmune hypoparathyroidism; Autoimmune inner ear disease; Autoimmune lymphoproliferative syndrome; Autoimmune myocarditis; Autoimmune pancreatitis; Autoimmune peripheral neuropathy; Autoimmune ovarian failure; Autoimmune polyendocrine syndrome; Autoimmune progesterone dermatitis; Autoimmune thrombocytopenic purpura; Autoimmune thyroid disorders; Autoimmune urticarial; Autoimmune uveitis; Autoimmune vasculitis; Balo disease/Balo concentric sclerosis; Behçet's disease; Berger's disease; Bickerstaffs encephalitis; Blau syndrome; Bullous pemphigoid; Cancer; Castleman's disease; Celiac disease; Chagas disease; Chronic inflammatory demyelinating polyneuropathy; Chronic inflammatory demyelinating polyneuropathy; Chronic obstructive pulmonary disease; Chronic recurrent multifocal osteomyelitis; Churg-Strauss syndrome; Cicatricial pemphigoid; Cogan syndrome; Cold agglutinin disease; Complement component 2 deficiency; Contact dermatitis; Cranial arteritis; CREST syndrome; Crohn's disease; Cushing's Syndrome; Cutaneous leukocytoclastic angiitis; Dego's disease; Dercum's disease; Dermatitis herpetiformis; Dermatomyositis; Diabetes mellitus type 1; Diffuse cutaneous systemic sclerosis; Discoid lupus erythematosus; Dressler's syndrome; Drug-induced lupus; Eczema; Endometriosis; Enthesitis-related arthritis; Eosinophilic fasciitis; Eosinophilic gastroenteritis; Eosinophilic pneumonia; Epidermolysis bullosa acquisita; Erythema nodosum; Erythroblastosis fetalis; Essential mixed cryoglobulinemia; Evan's syndrome; Extrinsic and intrinsic reactive airways disease (asthma); Fibrodysplasia ossificans progressive; Fibrosing alveolitis (or Idiopathic pulmonary fibrosis); Gastritis; Gastrointestinal pemphigoid; Glomerulonephritis; Goodpasture's syndrome; Graves' disease; Guillain-Barre syndrome (GBS); Hashimoto's encephalopathy; Hashimoto's thyroiditis; Hemolytic anemia; Henoch-Schonlein purpura; Herpes gestationis (Gestational Pemphigoid); Hidradenitis suppurativa; Hughes-Stovin syndrome; Hypogammaglobulinemia; Idiopathic inflammatory demyelinating diseases; Idiopathic pulmonary fibrosis; Idiopathic thrombocytopenic purpura; IgA nephropathy; Immune glomerulonephritis; Immune nephritis; Immune pneumonitis; Inclusion body myositis; inflammatory bowel disease; Interstitial cystitis; Juvenile idiopathic arthritis aka Juvenile rheumatoid arthritis; Kawasaki's disease; Lambert-Eaton myasthenic syndrome; Leukocytoclastic vasculitis; Lichen planus; Lichen sclerosus; Linear IgA disease (LAD); Lupoid hepatitis aka Autoimmune hepatitis; Lupus erythematosus; Majeed syndrome; microscopic polyangiitis; Miller-Fisher syndrome; mixed connective tissue disease; Morphea; Mucha-Habermann disease aka *Pityriasis lichenoides* et varioliformis *acuta*; Multiple sclerosis; Myasthenia gravis; Myositis; Meniere's disease; Narcolepsy; Neuromyelitis optica (also Devic's disease); Neuromyotonia; Occular cicatricial pemphigoid; Opsoclonus myoclonus syndrome; Ord's thyroiditis; Palindromic rheumatism; PANDAS (pediatric autoimmune neuropsychiatric disorders associated with *Streptococcus*); Paraneoplastic cerebellar degeneration; Paroxysmal nocturnal hemoglobinuria (PNH); Parry Romberg syndrome; Pars planitis; Parsonage-Turner syndrome; Pemphigus vulgaris; Perivenous encephalomyelitis; Pernicious anaemia; POEMS syndrome; Polyarteritis nodosa; Polymyalgia rheumatic; Polymyositis; Primary biliary cirrhosis; Primary sclerosing cholangitis; Progressive inflammatory neuropathy; Psoriasis; Psoriatic arthritis; pure red cell aplasia; Pyoderma gangrenosum; Rasmussen's encephalitis; Raynaud phenomenon; Reiter's syndrome; relapsing polychondritis; restless leg syndrome; retroperitoneal fibrosis; rheumatic fever; rheumatoid arthritis; Sarcoidosis; Schizophrenia; Schmidt syndrome; Schnitzler syndrome; Scleritis; Scleroderma; Sclerosing cholangitis; serum sickness; Sjogren's syndrome; Spondyloarthropathy; Stiff person syndrome; Still's disease; Subacute bacterial endocarditis (SBE); Susac's syndrome; Sweet's syndrome; Sydenham chorea; sympathetic ophthalmia; systemic lupus erythematosus; Takayasu's arteritis; temporal arteritis (also known as "giant cell arteritis"); thrombocytopenia; Tolosa-Hunt syndrome; transverse myelitis; ulcerative colitis; undifferentiated connective tissue disease; undifferentiated spondyloarthropathy; urticarial vasculitis; vasculitis; vitiligo; viral diseases such as Epstein Barr Virus (EBV), Hepatitis B, Hepatitis C, HIV, HTLV 1, Varicella-Zoster Virus (VZV) and Human Papilloma Virus (HPV); or Wegener's granulomatosis. In some embodiments, the autoimmune disease is an allergic condition, including those from asthma, food allergies, atopic dermatitis, chronic pain, and rhinitis.

Cutaneous contact hypersensitivity and asthma are just two examples of immune responses that can be associated with significant morbidity. Others include atopic dermatitis, eczema, Sjogren's Syndrome, including keratoconjunctivitis sicca secondary to Sjogren's Syndrome, alopecia areata, allergic responses due to arthropod bite reactions, Crohn's disease, aphthous ulcer, iritis, conjunctivitis, keratoconjunctivitis, ulcerative colitis, cutaneous lupus erythematosus, scleroderma, vaginitis, proctitis, and drug eruptions. These conditions may result in any one or more of the following symptoms or signs: itching, swelling, redness, blisters, crusting, ulceration, pain, scaling, cracking, hair loss, scarring, or oozing of fluid involving the skin, eye, or mucosal membranes.

In atopic dermatitis, and eczema in general, immunologically mediated leukocyte infiltration (particularly infiltration of mononuclear cells, lymphocytes, neutrophils, and eosinophils) into the skin importantly contributes to the pathogenesis of these diseases. Chronic eczema also is associated with significant hyperproliferation of the epidermis. Immunologically mediated leukocyte infiltration also occurs at sites other than the skin, such as in the airways in asthma and in the tear producing gland of the eye in keratoconjunctivitis sicca.

A compound or its pharmaceutically acceptable salt, isotopic variant, or prodrug as described herein can be administered in an effective amount to treat a host, for example a human, with a skin disorder such as psoriasis (for example, psoriasis vulgaris), atopic dermatitis, skin rash, skin irritation, skin sensitization (e.g., contact dermatitis or allergic contact dermatitis). For example, certain substances including some pharmaceuticals when topically applied can cause skin sensitization. In some embodiments, the skin disorder is treated by topical administration of compounds known in the art in combination with the compounds disclosed herein. In one non-limiting embodiment compounds of the present invention are used as topical agents in treating contact dermatitis, atopic dermatitis, eczematous dermatitis, psoriasis, Sjogren's Syndrome, including keratoconjunctivitis sicca secondary to Sjogren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, and drug eruptions.

Disease states of conditions which may be treated using compounds according to the present invention include, for example, asthma, autoimmune diseases such as multiple sclerosis, various cancers, ciliopathies, cleft palate, diabetes, heart disease, hypertension, inflammatory bowel disease, mental retardation, mood disorder, obesity, refractive error, infertility, Angelman syndrome, Canavan disease, Coeliac disease, Charcot-Marie-Tooth disease, Cystic fibrosis, Duchenne muscular dystrophy, Haemochromatosis, Haemophilia, Klinefelter's syndrome, Neurofibromatosis, Phenylketonuria, Polycystic kidney disease 1 (PKD1) or 2 (PKD2) Prader-Willi syndrome, Sickle-cell disease, Tay-Sachs disease, Turner syndrome.

Further disease states or conditions which may be treated by compounds according to the present invention include Alzheimer's disease, Amyotrophic lateral sclerosis (Lou Gehrig's disease), Anorexia nervosa, Anxiety disorder, Atherosclerosis, Attention deficit hyperactivity disorder, Autism, Bipolar disorder, Chronic fatigue syndrome, Chronic obstructive pulmonary disease, Crohn's disease, Coronary heart disease, Dementia, Depression, Diabetes mellitus type 1, Diabetes mellitus type 2, Epilepsy, Guillain-Barre syndrome, Irritable bowel syndrome, Lupus, Metabolic syndrome, Multiple sclerosis, Myocardial infarction, Obesity, Obsessive-compulsive disorder, Panic disorder, Parkinson's disease, Psoriasis, Rheumatoid arthritis, Sarcoidosis, Schizophrenia, Stroke, Thromboangiitis obliterans, Tourette syndrome, Vasculitis.

Still additional disease states or conditions which can be treated by compounds according to the present invention include aceruloplasminemia, Achondrogenesis type II, achondroplasia, Acrocephaly, Gaucher disease type 2, acute intermittent porphyria, Canavan disease, Adenomatous Polyposis Co/i, ALA dehydratase deficiency, adenylosuccinate lyase deficiency, Adrenogenital syndrome, Adrenoleukodystrophy, ALA-D porphyria, ALA dehydratase deficiency, Alkaptonuria, Alexander disease, Alkaptonuric ochronosis, alpha 1-antitrypsin deficiency, alpha-1 proteinase inhibitor, emphysema, amyotrophic lateral sclerosis Alstrom syndrome, Alexander disease, Amelogenesis imperfecta, ALA dehydratase deficiency, Anderson-Fabry disease, androgen insensitivity syndrome, Anemia Angiokeratoma Corporis Diffusum, Angiomatosis retinae (von Hippel-Lindau disease) Apert syndrome, Arachnodactyly (Marfan syndrome), Stickler syndrome, Arthrochalasis multiplex congenital (Ehlers-Danlos syndrome#arthrochalasia type) ataxia telangiectasia, Rett syndrome, primary pulmonary hypertension, Sandhoff disease, neurofibromatosis type II, Beare-Stevenson cutis gyrata syndrome, Mediterranean fever, familial, Benjamin syndrome, beta-thalassemia, Bilateral Acoustic Neurofibromatosis (neurofibromatosis type II), factor V Leiden thrombophilia, Bloch-Sulzberger syndrome (incontinentia pigmenti), Bloom syndrome, X-linked sideroblastic anemia, Bonnevie-Ullrich syndrome (Turner syndrome), Bourneville disease (tuberous sclerosis), prion disease, Birt-Hogg-Dube syndrome, Brittle bone disease (osteogenesis imperfecta), Broad Thumb-Hallux syndrome (Rubinstein-Taybi syndrome), Bronze Diabetes/Bronzed Cirrhosis (hemochromatosis), Bulbospinal muscular atrophy (Kennedy's disease), Burger-Grutz syndrome (lipoprotein lipase deficiency), CGD Chronic granulomatous disorder, Campomelic dysplasia, biotinidase deficiency, Cardiomyopathy (Noonan syndrome), Cri du chat, CAVD (congenital absence of the vas deferens), Caylor cardiofacial syndrome (CBAVD), CEP (congenital erythropoietic porphyria), cystic fibrosis, congenital hypothyroidism, Chondrodystrophy syndrome (achondroplasia), otospondylomegaepiphyseal dysplasia, Lesch-Nyhan syndrome, galactosemia, Ehlers-Danlos syndrome, Thanatophoric dysplasia, Coffin-Lowry syndrome, Cockayne syndrome, (familial adenomatous polyposis), Congenital erythropoietic porphyria, Congenital heart disease, Methemoglobinemia/Congenital methaemoglobinaemia, achondroplasia, X-linked sideroblastic anemia, Connective tissue disease, Conotruncal anomaly face syndrome, Cooley's Anemia (beta-thalassemia), Copper storage disease (Wilson's disease), Copper transport disease (Menkes disease), hereditary coproporphyria, Cowden syndrome, Craniofacial dysarthrosis (Crouzon syndrome), Creutzfeldt-Jakob disease (prion disease), Cockayne syndrome, Cowden syndrome, Curschmann-Batten-Steinert syndrome (myotonic dystrophy), Beare-Stevenson cutis gyrata syndrome, primary hyperoxaluria, spondyloepimetaphyseal dysplasia (Strudwick type), muscular dystrophy, Duchenne and Becker types (DBMD), Usher syndrome, Degenerative nerve diseases including de Grouchy syndrome and Dejerine-Sottas syndrome, developmental disabilities, distal spinal muscular atrophy, type V, androgen insensitivity syndrome, Diffuse Globoid Body Sclerosis (Krabbe disease), Di George's syndrome, Dihydrotestosterone receptor deficiency, androgen insensitivity syndrome, Down syndrome, Dwarfism, erythropoietic protoporphyria Erythroid 5-aminolevulinate synthetase deficiency, Erythropoietic porphyria, erythropoietic protoporphyria, erythropoietic uroporphyria, Friedreich's ataxia-familial paroxysmal polyserositis, porphyria cutanea tarda, familial pressure sensitive neuropathy, primary pulmonary hypertension (PPH), Fibrocystic disease of the pancreas, fragile X syndrome, galactosemia, genetic brain disorders, Giant cell hepatitis (Neonatal hemochromatosis), Gronblad-Strandberg syndrome (pseudoxanthoma elasticum), Gunther disease (congenital erythropoietic porphyria), haemochromatosis, Hallgren syndrome, sickle cell anemia, hemophilia, hepatoerythropoietic porphyria (HEP), Hippel-Lindau disease (von Hippel-Lindau disease), Huntington's disease, Hutchinson-Gilford progeria syndrome (progeria), Hyperandrogenism, Hypochondroplasia, Hypochromic anemia, Immune system disorders, including X-linked severe combined immunodeficiency, Insley-Astley syndrome, Jackson-Weiss syndrome, Joubert syndrome, Lesch-Nyhan syndrome, Jackson-Weiss syndrome, Kidney diseases, including hyperoxaluria, Klinefelter's syndrome, Kniest dysplasia, Lacunar dementia, Langer-Saldino achondrogenesis, ataxia telangiectasia, Lynch syndrome, Lysylhydroxylase deficiency, Machado-Joseph disease, Metabolic disorders, including Kniest dysplasia, Marfan syndrome, Movement disorders, Mowat-Wilson syndrome, cystic fibrosis, Muenke syndrome, Multiple neurofibromatosis, Nance-Insley syndrome, Nance-Sweeney chondrodysplasia, Niemann-Pick disease, Noack syndrome (Pfeiffer syndrome), Osler-Weber-Rendu disease, Peutz-Jeghers syndrome, Polycystic kidney disease, polyostotic fibrous dysplasia (McCune-Albright syndrome), Peutz-Jeghers syndrome, Prader-Labhart-Willi syndrome, hemochromatosis, primary hyperuricemia syndrome (Lesch-Nyhan syndrome), primary pulmonary hypertension, primary senile degenerative dementia, prion disease, progeria (Hutchinson Gilford Progeria Syndrome), progressive chorea, chronic hereditary (Huntington) (Huntington's disease), progressive muscular atrophy, spinal muscular atrophy, propionic acidemia, protoporphyria, proximal myotonic dystrophy, pulmonary arterial hypertension, PXE (pseudoxanthoma elasticum), Rb (retinoblastoma), Recklinghausen disease (neurofibromatosis type I), Recurrent polyserositis, Retinal disorders, Retinoblastoma, Rett syndrome, RFALS type 3, Ricker syndrome, Riley-Day syndrome, Roussy-Levy syndrome, severe achondroplasia with developmental delay and acanthosis nigricans (SADDAN), Li-Fraumeni syndrome, sarcoma, breast, leukemia, and adrenal gland (SBLA) syndrome, sclerosis tuberose (tuberous sclerosis), SDAT, SED congenital (spondyloepiphyseal dysplasia congenita), SED Strudwick (spondyloepimetaphyseal dysplasia, Strudwick type), SEDc (spondyloepiphyseal dysplasia congenita) SEMD, Strudwick type (spondyloepimetaphyseal dysplasia, Strudwick type), Shprintzen syndrome, Skin pigmentation disorders, Smith-Lemli-Opitz syndrome, South-African genetic porphyria (variegate porphyria), infantile-onset ascending hereditary spastic paralysis, Speech and communication disorders, sphingolipidosis, Tay-Sachs disease, spinocerebellar ataxia, Stickler syndrome, stroke, androgen insensitivity syndrome, tetrahydrobiopterin deficiency, beta-thalassemia, Thyroid disease, Tomaculous neuropathy (hereditary neuropathy with liability to pressure palsies), Treacher Collins syndrome, Triplo X syndrome (triple X syndrome), Trisomy 21 (Down syndrome), Trisomy X, VHL syndrome (von Hippel-Lindau disease), Vision impairment and blindness (Alstrom syndrome), Vrolik disease, Waardenburg syndrome, Warburg Sjo Fledelius Syndrome, Wolf-Hirschhorn syndrome, Wolff Periodic disease, Weissenbacher-Zweymuller syndrome and Xeroderma pigmentosum, among others.

In certain embodiments, a treatment is provided for treating multiple myeloma comprising administering to a patient an effective amount of a compound described herein, or a pharmaceutically acceptable salt, isotopic analog, or prodrug thereof, optionally in a pharmaceutically acceptable carrier to form a composition. In another embodiment, a compound described herein, or a pharmaceutically acceptable salt, isotopic analog, or prodrug thereof, optionally in a pharmaceutically acceptable carrier to form a composition, for use in a treatment of multiple myeloma, wherein the treatment comprises administering the compound to a patient.

In certain embodiments, a treatment is provided for managing the progression of multiple myeloma comprising administering to a patient an effective amount of a compound described herein, or a pharmaceutically acceptable salt, isotopic analog, or prodrug thereof, optionally in a pharmaceutically acceptable carrier to form a composition. In another embodiment, a compound described herein, or a pharmaceutically acceptable salt, isotopic analog, or prodrug thereof, optionally in a pharmaceutically acceptable carrier to form a composition, for use in a treatment for managing the progression of multiple myeloma, wherein the treatment comprises administering the compound to a patient.

Treatments are also provided for patients who have been previously treated for multiple myeloma but are non-responsive to standard therapies in addition to those who have not been previously treated. Additional treatments are provided for patients who have undergone surgery in an attempt to treat multiple myeloma in addition to those who have not undergone surgery. Treatments are also provided for patients who have previously undergone transplant therapy in addition to those who have not.

In certain embodiments, the disorder treated by the present invention is a wild-type cancer, wherein the term "wild-type" refers to a cancer that has not developed resistance to a previously effective treatment (i.e. a relapsed cancer) and does not have any resistance imparting mutations (i.e. a refractory cancer). In certain embodiments, the disorder treated by the present invention is a relapsed cancer. In certain embodiments, the disorder treated by the present invention is a refractory cancer. In certain embodiments, the disorder treated by the present invention is a relapsed and refractory cancer.

A compound described herein, for example, Compound 1 or a pharmaceutically acceptable salt thereof, can be administered in the treatment or management of multiple myeloma or Non-Hodgkin's Lymphoma that is relapsed, refractory, or resistant. In some embodiments, the disorder is primary, secondary, tertiary, quadruply or quintuply relapsed. In certain embodiments, the compounds described herein may be used to reduce, maintain, or eliminate minimal residual disease (MRD).

The types of multiple myeloma that may be treated with the compounds described herein include, but are not limited to: monoclonal gammopathy of undetermined significance (MGUS); low risk, intermediate risk, or high risk multiple myeloma; newly diagnosed multiple myeloma, including low risk, intermediate risk, or high risk newly diagnosed multiple myeloma); transplant eligible and transplant ineligible multiple myeloma; smoldering (indolent) multiple myeloma (including low risk, intermediate risk, or high risk smoldering multiple myeloma); active multiple myeloma; solitary plasmocytoma; plasma cell leukemia; central nervous system multiple myeloma; light chain myeloma; non-secretory myeloma; Immunoglobulin D myeloma; and Immunoglobulin E myeloma.

In certain embodiments, a treatment is provided for managing multiple myeloma comprising administering to a patient an effective amount of a compound described herein, or a pharmaceutically acceptable salt, isotopic analog, or prodrug thereof, optionally in a pharmaceutically acceptable carrier to form a composition, as induction therapy.

In certain embodiments, a treatment is provided for treating or managing multiple myeloma comprising administering to a patient an effective amount of a compound described herein, or a pharmaceutically acceptable salt, isotopic analog, or prodrug thereof, optionally in a pharmaceutically acceptable carrier to form a composition, as consolidation therapy.

In certain embodiments, a method is provided for treating or managing multiple myeloma comprising administering to a patient an effective amount of a compound described herein, or a pharmaceutically acceptable salt, isotopic analog, or prodrug thereof, optionally in a pharmaceutically acceptable carrier to form a composition, as maintenance therapy.

In certain embodiments, the multiple myeloma is plasma cell leukemia.

In certain embodiments, the multiple myeloma is high risk multiple myeloma. In some embodiments, the high-risk multiple myeloma is relapsed or refractory. In certain embodiments, the high-risk multiple myeloma has relapsed within 12 months of the first treatment. In another embodiment, the high-risk multiple myeloma is characterized by genetic abnormalities, for example, one or more of del(17/17p) and t(14;16)(q32;q32). In some embodiments, the high risk multiple myeloma is relapsed or refractory to one, two or three previous treatments.

In some embodiments, the multiple myeloma is transplant eligible newly diagnosed multiple myeloma. In other embodiments, the multiple myeloma is transplant ineligible newly diagnosed multiple myeloma.

In some embodiments, the multiple myeloma shows early progression (for example less than 12 months) following initial treatment. In other embodiments, the multiple myeloma shows early progression (for example less than 12 months) following autologous stem cell transplant. In another embodiment, the multiple myeloma is refractory to lenalidomide. In another embodiment, the multiple myeloma is refractory to pomalidomide. In some such embodiments, the multiple myeloma is predicted to be refractory to pomalidomide (for example, by molecular characterization). In another embodiment, the multiple myeloma is relapsed or refractory to 3 or more treatments and was exposed to a proteasome inhibitor (for example, bortezomib, carfilzomib, ixazomib, oprozomib, or marizomib) and an immunomodulatory compound (for example thalidomide, lenalidomide, pomalidomide, iberdomide, or avadomide), or double refractory to a proteasome inhibitor and an immunomodulatory compound. In still other embodiments, the multiple myeloma is relapsed or refractory to 3 or more prior therapies, including for example, a CD38 monoclonal antibody (CD38 mAb, for example, daratumumab or isatuximab), a proteasome inhibitor (for example, bortezomib, carfilzomib, ixazomib, or marizomib), and an immunomodulatory compound (for example thalidomide, lenalidomide, pomalidomide, iberdomide, or avadomide) or double refractory to a proteasome inhibitor or immunomodulatory compound and a CD38 mAb. In still other embodiments, the multiple myeloma is triple refractory, for example, the multiple myeloma is refractory to a proteasome inhibitor (for example, bortezomib, carfilzomib, ixazomib, oprozomib or marizomib), an immunomodulatory compound (for example thalidomide, lenalidomide, pomalidomide, iberdomide, or avadomide), and one other active agent, as described herein.

In certain embodiments, a treatment is provided for managing relapsed or refractory multiple myeloma in patients with impaired renal function or a symptom thereof comprising administering to a patient an effective amount of a compound described herein, or a pharmaceutically acceptable salt, isotopic analog, or prodrug thereof, optionally in a pharmaceutically acceptable carrier to form a composition.

In another embodiment, a treatment is provided for managing relapsed or refractory multiple myeloma in frail patients comprising administering to a patient an effective amount of a compound described herein, or a pharmaceutically acceptable salt, isotopic analog, or prodrug thereof, optionally in a pharmaceutically acceptable carrier to form a composition, wherein the frail patient is characterized by ineligibility for induction therapy or intolerance to dexamethasone treatment. In other embodiments, the frail patient is elderly, for example, older than 65 years old.

In another embodiment, a treatment is provided for managing fourth line relapsed or refractory multiple myeloma comprising administering to a patient an effective amount of a compound described herein, or a pharmaceutically acceptable salt, isotopic analog, or prodrug thereof, optionally in a pharmaceutically acceptable carrier to form a composition.

In another embodiment, a treatment is provided for managing newly diagnosed, transplant-ineligible multiple myeloma comprising administering to a patient an effective amount of a compound described herein, or a pharmaceutically acceptable salt, isotopic analog, or prodrug thereof, optionally in a pharmaceutically acceptable carrier to form a composition.

In another embodiment, a treatment is provided for managing newly diagnosed, transplant-ineligible multiple myeloma comprising administering to a patient an effective amount of a compound described herein, or a pharmaceutically acceptable salt, isotopic analog, or prodrug thereof, optionally in a pharmaceutically acceptable carrier to form a composition, as maintenance therapy after another therapy or transplant.

In another embodiment, a treatment is provided for managing high risk multiple myeloma that is relapsed or refractory to one, two, or three previous treatments comprising administering to a patient an effective amount of a compound described herein, or a pharmaceutically acceptable salt, isotopic analog, or prodrug thereof, optionally in a pharmaceutically acceptable carrier to form a composition.

In certain embodiments, the disorder treated by the present invention is a relapsed and/or refractory Non-Hodgkin's Lymphoma. In certain embodiments, the disorder treated by the present invention is a relapsed Non-Hodgkin's Lymphoma. In certain embodiments, the disorder treated by the present invention is a refractory Non-Hodgkin's Lymphoma.

In certain embodiments, the disorder treated by the present invention is a relapsed and refractory Non-Hodgkin's Lymphoma.

In certain embodiments, the disorder treated by the present invention is a relapsed and/or refractory multiple myeloma. In certain embodiments, the disorder treated by the present invention is a relapsed multiple myeloma. In certain embodiments, the disorder treated by the present invention is a refractory multiple myeloma. In certain embodiments, the disorder treated by the present invention is a relapsed and refractory multiple myeloma.

In certain embodiments, the disorder treated by the present invention is a relapsed and/or refractory peripheral T-cell lymphoma. In certain embodiments, the disorder treated by the present invention is a relapsed peripheral T-cell lymphoma. In certain embodiments, the disorder treated by the present invention is a refractory peripheral T-cell lymphoma. In certain embodiments, the disorder treated by the present invention is a relapsed and refractory peripheral T-cell lymphoma.

In certain embodiments, Compound 1 is administered for the treatment of PTCL-NOS (i.e. PTCL that is not otherwise specified). In other embodiments Compound 1 is administered for the treatment of PTCL with a specified subtype for example anaplastic large cell lymphoma (ALCL), angioimmunoblastic T-Cell lymphoma (AITL), enteropathy-type T-cell lymphoma, or extranodal natural killer (NK) cell/T-cell lymphoma.

In certain embodiments, the disorder treated by the present invention is a relapsed and/or refractory systemic anaplastic large cell lymphoma (ALK+). In certain embodiments, the disorder treated by the present invention is a relapsed systemic anaplastic large cell lymphoma (ALK+). In certain embodiments, the disorder treated by the present invention is a refractory systemic anaplastic large cell lymphoma (ALK+). In certain embodiments, the disorder treated by the present invention is a relapsed and refractory systemic anaplastic large cell lymphoma (ALK+).

In certain embodiments, the disorder treated by the present invention is a relapsed and/or refractory systemic anaplastic large cell lymphoma ($ALK^-$). In certain embodiments, the disorder treated by the present invention is a relapsed systemic anaplastic large cell lymphoma ($ALK^-$). In certain embodiments, the disorder treated by the present invention is a refractory systemic anaplastic large cell lymphoma ($ALK^-$). In certain embodiments, the disorder treated by the present invention is a relapsed and refractory systemic anaplastic large cell lymphoma ($ALK^-$).

In certain embodiments, the disorder treated by the present invention is a relapsed and/or refractory angioimmunoblastic T-cell lymphoma. In certain embodiments, the disorder treated by the present invention is a relapsed angioimmunoblastic T-cell lymphoma. In certain embodiments, the disorder treated by the present invention is a refractory angioimmunoblastic T-cell lymphoma. In certain embodiments, the disorder treated by the present invention is a relapsed and refractory angioimmunoblastic T-cell lymphoma.

In certain embodiments, the disorder treated by the present invention is a relapsed and/or refractory anaplastic large cell lymphoma. In certain embodiments, the disorder treated by the present invention is a relapsed anaplastic large cell lymphoma. In certain embodiments, the disorder treated by the present invention is a refractory anaplastic large cell lymphoma. In certain embodiments, the disorder treated by the present invention is a relapsed and refractory anaplastic large cell lymphoma.

In certain embodiments, the disorder treated by the present invention is a relapsed and/or refractory mantle cell lymphoma. In certain embodiments, the disorder treated by the present invention is a relapsed mantle cell lymphoma. In certain embodiments, the disorder treated by the present invention is a refractory mantle cell lymphoma. In certain embodiments, the disorder treated by the present invention is a relapsed and refractory mantle cell lymphoma.

In certain embodiments, the disorder treated by the present invention is a relapsed and/or refractory follicular lymphoma. In certain embodiments, the disorder treated by the present invention is a relapsed follicular lymphoma. In certain embodiments, the disorder treated by the present invention is a refractory follicular lymphoma. In certain embodiments, the disorder treated by the present invention is a relapsed and refractory follicular lymphoma.

In certain embodiments, the disorder treated by the present invention is a relapsed and/or refractory follicular T-cell lymphoma. In certain embodiments, the disorder treated by the present invention is a relapsed follicular T-cell lymphoma. In certain embodiments, the disorder treated by the present invention is a refractory follicular T-cell lymphoma. In certain embodiments, the disorder treated by the present invention is a relapsed and refractory follicular T-cell lymphoma.

In certain embodiments, the disorder treated by the present invention is a relapsed and/or refractory peripheral T-cell lymphoma. In certain embodiments, the disorder treated by the present invention is a relapsed peripheral T-cell lymphoma. In certain embodiments, the disorder treated by the present invention is a refractory peripheral T-cell lymphoma. In certain embodiments, the disorder treated by the present invention is a relapsed and refractory peripheral T-cell lymphoma.

In certain embodiments, the disorder treated by the present invention is a relapsed and/or refractory diffuse large B-cell lymphoma. In certain embodiments, the disorder treated by the present invention is a relapsed diffuse large B-cell lymphoma. In certain embodiments, the disorder treated by the present invention is a refractory diffuse large B-cell lymphoma. In certain embodiments, the disorder treated by the present invention is a relapsed and refractory diffuse large B-cell lymphoma.

In certain embodiments, Compound 1 is administered to a patient in need thereof in an effective amount to treat follicular T-cell lymphoma. In certain embodiments, Compound 1 is administered to a patient in need thereof in an effective amount to treat angioimmunoblastic T-cell lymphoma. In certain embodiments, Compound 1 is administered to a patient in need thereof in an effective amount to treat systemic anaplastic large cell lymphoma ($ALK^-$). In certain embodiments, Compound 1 is administered to a patient in need thereof in an effective amount to treat systemic anaplastic large cell lymphoma (ALK+).

Additional examples of Non-Hodgkin's Lymphomas that can be treated with a compound described herein include Double hit lymphoma, triple hit lymphoma, extranodal marginal zone B-cell lymphoma of MALT, extranodal NK/T-cell lymphoma, and myeloid-lineage lymphoma.

Pharmacodynamic Dose Modification and Biomarkers

In certain embodiments, the compound of the present invention is administered in an effective amount to treat a patient with a cereblon-mediated disorder comprising administering to the patient an effective amount of the compound and monitoring the concentration of a biomarker selected from IRF-1, caspase-1, caspase-3, caspase-7, cyclin D1, E2F1, ZFP91, SALL4, IRF-4, BLIMP1, MYC, IL-2, T-cell activation and/or proliferation, BCMA, M-protein, PARP, BIM, survivin, IKZF1, IKZF3, ZFP91, WIZ, and/or IFN-γ or a combination thereof.

In certain embodiments, the concentration of IRF-1 and/or caspase 3 increases upon treating a patient with a compound described herein. The size of the increase can be used to determine whether or not the dose of the compound described herein should be increased, decreased, or kept the same. For example, if the concentration of IRF-1 and/or caspase 3 increases by less than 1.25, 1.5, 1.75, or 2-fold then the physician may increase the dose of Compound 1 administered to a patient being treated for a lymphoma.

In certain embodiments, the concentration of cyclin D and/or E2F1 decreases upon treating a patient with a compound described herein. The size of the decrease can be used to determine whether or not the dose of the compound described herein should be increased, decreased, or kept the same. For example, if the concentration of cyclin D and E2F1 decreases by less than 1.25, 1.5, 1.75, or 2-fold then the physician may increase the dose of Compound 1 administered to a patient being treated for a lymphoma.

In certain embodiments, the concentration of cyclin D, E2F1, ZFP91, SALL4, IRF-4, BLIMP1, and/or MYC decreases upon treating a patient with a compound described herein. In certain embodiments, the patient has a lymphoma. The size of the decrease can be used to determine whether or not the dose of the compound described herein should be increased, decreased, or kept the same.

In certain embodiments, the concentration of IL-2 and/or IFN-γ increases upon treating a patient with a compound described herein. In certain embodiments, the patient has a myeloma. The size of the increase can be used to determine whether or not the dose of the compound described herein should be increased, decreased, or kept the same.

In certain embodiments the concentration of the biomarker increases by about 3, 4, 5, 6, 7, or 8 fold upon delivery of an effective dose of a compound described herein, for example Compound 1. For example, as shown in FIG. 51 the activity level of caspase-3 and caspase-7 is increased by more than 800% upon treatment of Compound 1. In certain embodiments the level of caspase 3/7 activity is assayed and if less than about 2, 3, 4, 5, 6, 7, or 8-fold then the dose of Compound 1 is increased.

In certain embodiments the biomarker is STAT3.

In certain embodiments the biomarker is Ki67.

In certain embodiments the concentration of the biomarker decreases by about 3, 4, 5, 6, 7, or 8-fold upon delivery of an effective dose of a compound described herein, for example Compound 1.

In certain embodiments, the patient treated with a compound selected from Compound 1, Compound 2, Compound 3, Compound 4, Compound 5, Compound 6, Compound 7, Compound 8, Compound 9, Compound 10, Compound 11, Compound 12, and Compound 13, is selected based on the concentration of a biomarker. For example, the patient treated with Compound 1 may be selected based on the concentration of a biomarker.

In certain embodiments, the biomarker is selected from IKZF1, IKZF3, MYC, i12, INFy, TNFa, sFLC, and sBCMA.

In certain embodiments, the biomarker is selected from IRF-1, caspase-3, cyclin D1, E2F1, ZFP91, SALL4, IRF-4, BLIMP1, MYC, IL-2, and/or IFN-γ.

In certain embodiments the biomarker is a tumor immunity marker (e.g., a cytokine, tumor infiltrating lymphocyte, T-cell activation and/or proliferation, and B-cell markers such as BCMA or M-protein, or a combination thereof).

In certain embodiments the biomarker is an apoptotic marker (e.g., total and/or cleaved caspase-1, caspase-3, caspase-7, PARP, BIM, or survivin, or a combination thereof).

In certain embodiments the biomarker is a zinc finger protein (e.g., IKZF1, IKZF3, ZFP91, WIZ, or SALL4, or a combination thereof).

Treatment Advantages

In one aspect of the present invention a treatment described herein has one or more advantages over presently approved treatments of cancer, for example treatments of multiple myeloma or Non-Hodgkin's Lymphoma. For example, Compound 1 or a pharmaceutically acceptable salt thereof as administered using the treatments described herein has a better outcome in one or more of the measures described below than currently approved treatments, for example thalidomide, pomalidomide or lenalidomide (see Examples 9 12 13 15-19, 26-31, and 35 demonstrating the superior efficacy of Compound 1 in multiple myeloma and Non-Hodgkin's Lymphoma models).

In certain embodiments the advantage provided by Compound 1 over currently known treatments is a decreased propensity to develop resistance. For example, mice that had developed resistance to treatment with pomalidomide still responded rapidly to treatment with Compound 1 (see FIG. 40). Additionally, when treatment was withdrawn from mice for a long enough period for their tumors to regrow and rechallenged with Compound 1 the tumors still rapidly decreased in size (see FIG. 33).

In other embodiments the advantage over currently approved therapies is the ability to treat refractory tumors. For example, in mice doses of Compound 1 as low as 30 μg/kg were effective in the treatment of NCI-H929 tumors that were nonresponsive to 3,000 μg/kg dosing (see FIG. 33). Additionally, across a panel of cell lines Compound 1 was consistently 2-3 magnitudes more potent than pomalidomide and even demonstrated efficacy against cells that were refractory to pomalidomide (see FIG. 32). This effect is also demonstrated by tracking biomarkers concentration such as caspase 3 (see FIG. 31).

In other embodiments the advantage over currently approved therapies is a more rapid degradation of IKZF1 and IKZF3 and thus a more rapid treatment of cancer. For example, Compound 1 degrades more IKZF1 in one hour than pomalidomide degrades in two hours when dosed at the same concentration (see FIG. 29).

In certain embodiments, a treatment is provided for inducing a therapeutic response as assessed by the International Uniform Response Criteria (IURC) for Multiple Myeloma (described in Durie B. G. M; et al. "International uniform response criteria for multiple myeloma. *Leukemia* 2006, 10(10):1-7) in a patient having multiple myeloma comprising administering to the patient an effective amount of a compound described herein, or a pharmaceutically acceptable salt, isotopic analog, or prodrug thereof, optionally in a pharmaceutically acceptable carrier to form a composition.

In another embodiment, a treatment is provided to achieve a stringent complete response, complete response, or very good partial response, as assessed by the IURC for Multiple Myeloma in a patient having multiple myeloma comprising administering to the patient an effective amount of a compound described herein, or a pharmaceutically acceptable salt, isotopic analog, or prodrug thereof, optionally in a pharmaceutically acceptable carrier to form a composition.

In another embodiment, a treatment is provided to achieve an increase in overall survival, progression-free survival, event-free survival, time to process, or disease-free survival in a patient having multiple myeloma comprising administering to the patient an effective amount of a compound described herein, or a pharmaceutically acceptable salt, isotopic analog, or prodrug thereof, optionally in a pharmaceutically acceptable carrier to form a composition (see Examples 21 and 22 which demonstrate a dose dependent increase in overall survival in animal models).

The advantages of Compound 1 can be further enhanced by administering an additional bioactive agent in combination therapy. For example, in mouse studies when Compound 1 was administered in a treatment regimen that included weekly dexamethasone it was far more efficacious than the same dose of Compound 1 or dexamethasone alone (see FIG. 41).

Treatment of IKZF1/IKZF3 Mediated Cancers with Prominent Mutations

In certain embodiments, a compound described herein is administered in an effective amount to treat a cancer that is mediated by a protein with one or more mutations, for example a multiple myeloma mediated by a protein with one or more mutations.

In some embodiments, the compounds described herein may be administered in an effective amount in the treatment or management of multiple myeloma characterized by a genetic abnormality, for example but not limited to: Cyclin D translocations (for example, t(11;14)(q13;q32); t(6;14)(p21;32); t(12;14)(p13;q32); or t(6;20)); MMSET translocations (for example t(4;14)(p16;q32); MAF translocations (for example t(14;16)(q32;a32); t(20;22); t(16;22)(q11;q13); or t(14;20)(q32;q11); or other chromosome factor (for example deletion of 17p13 or chromosome 13; del(17/17p), nonhyperdiploidy, and gain (1q)).

In certain embodiments, the multiple myeloma has a p53 mutation. In certain embodiments, the p53 mutation is a Q331 mutation. In certain embodiments, the p53 mutation is a R273H mutation. In certain embodiments, the p53 mutation is a K132 mutation. In certain embodiments, the p53 mutation is a K132N mutation. In certain embodiments, the p53 mutation is a R337 mutation. In certain embodiments, the p53 mutation is a R337L mutation. In certain embodiments, the p53 mutation is a W146 mutation. In certain embodiments, the p53 mutation is a S261 mutation. In certain embodiments, the p53 mutation is a S261T mutation. In certain embodiments, the p53 mutation is a E286 mutation. In certain embodiments, the p53 mutation is a E286K mutation. In certain embodiments, the p53 mutation is a R175 mutation. In certain embodiments, the p53 mutation is a R175H mutation. In certain embodiments, the p53 mutation is a E258 mutation. In certain embodiments, the p53 mutation is a E258K mutation. In certain embodiments, the p53 mutation is a A161 mutation. In certain embodiments, the p53 mutation is a A161T mutation.

In certain embodiments, the multiple myeloma has a homozygous deletion of p53. In certain embodiments, the multiple myeloma has a homozygous deletion of wild-type p53. In certain embodiments, the multiple myeloma has wild-type p53.

In certain embodiments, the multiple myeloma shows activation of one or more oncogenic drivers. In certain embodiments, the one or more oncogenic drivers are selected from the group consisting of C-MAF, MAFB, FGFR3, MMset, Cyclin D1, and Cyclin D. In certain embodiments, the multiple myeloma shows activation of C-MAF. In certain embodiments, the multiple myeloma shows activation of MAFB. In certain embodiments, the multiple myeloma shows activation of FGFR3 and MMset. In certain embodiments, the multiple myeloma shows activation of C-MAF, FGFR3, and MMset. In certain embodiments, the multiple myeloma shows activation of Cyclin D1. In certain embodiments, the multiple myeloma shows activation of MAFB and Cyclin D1. In certain embodiments, the multiple myeloma shows activation of Cyclin D.

In certain embodiments, the multiple myeloma has one or more chromosomal translocations. In certain embodiments, the chromosomal translocation is t(14;16). In certain embodiments, the chromosomal translocation is t(14;20). In certain embodiments, the chromosomal translocation is t(4;14). In certain embodiments, the chromosomal translocations are t(4;14) and t(14;16). In certain embodiments, the chromosomal translocation is t(11;14). In certain embodiments, the chromosomal translocation is t(6;20). In certain embodiments, the chromosomal translocation is t(20;22). In certain embodiments, the chromosomal translocations are t(6;20) and t(20;22). In certain embodiments, the chromosomal translocation is t(16;22). In certain embodiments, the chromosomal translocations are t(14;16) and t(16;22). In certain embodiments, the chromosomal translocations are t(14;20) and t(11;14).

In certain embodiments, the multiple myeloma has a Q331 p53 mutation, activation of C-MAF, and a chromosomal translocation at t(14; 16). In certain embodiments, the multiple myeloma has homozygous deletion of p53, activation of C-MAF, and a chromosomal translocation at t(14; 16). In certain embodiments, the multiple myeloma has a K132N p53 mutation, activation of MAFB, and a chromosomal translocation at t(14;20). In certain embodiments, the multiple myeloma has wild type p53, activation of FGFR3 and MMset, and a chromosomal translocation at t(4; 14). In certain embodiments, the multiple myeloma has wild type p53, activation of C-MAF, and a chromosomal translocation at t(14;16). In certain embodiments, the multiple myeloma has homozygous deletion of p53, activation of FGFR3, MMset, and C-MAF, and chromosomal translocations at t(4;14) and t(14;16). In certain embodiments, the multiple myeloma has homozygous deletion of p53, activation of Cyclin D1, and a chromosomal translocation at t(11;14). In certain embodiments, the multiple myeloma has a R337L p53 mutation, activation of Cyclin D1, and a chromosomal translocation at t(11;14). In certain embodiments, the multiple myeloma has a W146 p53 mutation, activation of FGFR3 and MMset, and a chromosomal translocation at t(4; 14). In certain embodiments, the multiple myeloma has a S261T p53 mutation, activation of MAFB, and chromosomal translocations at t(6;20) and t(20;22). In certain embodiments, the multiple myeloma has a E286K p53 mutation, by activation of FGFR3 and MMset, and a chromosomal translocation at t(4; 14). In certain embodiments, the multiple myeloma has a R175H p53 mutation, activation of FGFR3 and MMset, and a chromosomal translocation at t(4; 14). In certain embodiments, the multiple myeloma has a E258K p53 mutation, activation of C-MAF, and chromosomal translocations at t(14;16) and t(16;22). In certain embodiments, the multiple myeloma has wild type p53, activation of MAFB and Cyclin D1, and chromosomal translocations at t(14;20) and t(11;14). In certain embodiments, the multiple myeloma has a A161T p53 mutation, activation of Cyclin D, and a chromosomal translocation at t(11;14).

Patient Selection

In certain embodiments, the patient treated with a compound described herein has received a prior treatment with an IMiD, for example thalidomide, lenalidomide, or pomalidomide.

In certain embodiments, the patient treated with a compound described herein has received a prior treatment with an CD20 antibody for example rituximab, ocrelizumab, obinutuzumab, ofatumumab, ibritumomab, tositumomab, or ublituximab.

In certain embodiments, the patient treated with a compound described herein has received a prior treatment with an CD38 antibody for example daratumumab or isatuximab.

In certain embodiments, the patient treated with a compound described herein has received a prior treatment with an CD30 antibody for example brentuximab.

In certain embodiments, the patient treated with a compound described herein has received a prior treatment with a BTK inhibitor for example ibrutinib, acalabrutinib, or zanubrutinib.

In certain embodiments, the patient treated with a compound described herein has received a prior treatment with an alkylator for example cyclophosphomide, melphan, melphalan flufenamide, or bendamustine.

In certain embodiments, the patient treated with a compound described herein has received a prior treatment with a proteasome inhibitor for example bortezomib, carfilzomib, or ixazomib.

In certain embodiments, the patient treated with a compound described herein has received a prior treatment with a glucocorticoid, for example dexamethasone, predinisone, or methylprednisolone.

In certain embodiments, the patient treated with a compound described herein has received a prior treatment with a bone-modifying agent, for example denosumab, zoledronic acid, or pamidronate.

In certain embodiments, the patient treated with a compound described herein has received a prior treatment with a HDAC inhibitor, for example panobinostat.

In certain embodiments, the patient treated with a compound described herein has received a prior treatment with a nuclear export inhibitor, for example selinexor.

In certain embodiments, the patient treated for multiple myeloma has received at least 1, 2, 3, or 4 prior anti-myeloma or lymphoma regimens, for example lenalidomide, pomalidomide, a proteasome inhibitor, a glucocorticoid, or an anti-CD38 antibody. For example, a patient that has received at least 3 prior anti-myeloma regimens including at least two consecutive cycles of lenalidomide, pomalidomide, a proteasome inhibitor, a glucocorticoid, or an anti-CD38 antibody.

In certain embodiments, the patient treated for multiple myeloma has a M-protein level of ≥about 0.5 g/dL by serum protein electophoresis (sPEP), ≥200 mg/24-hour urine collection by Urine Protein Electrophoresis (uPEP), Serum Free Light Chain (FLC) levels >100 mg/L involved light chain and an abnormal kappa/lambda (κ/λ) ratio in subjects without measurable serum or urine M-protein, and/or a serum IgA level ≥0.50 g/dL.

In certain embodiments, the patient treated has peripheral t-cell lymphoma and has had at least one prior alkylator-based chemotherapy treatment.

In certain embodiments, the patient treated has anaplastic large cell lymphoma (ALCL) and has had at least one prior alkylator-based chemotherapy treatment and also has received CD30 antibody therapy.

In certain embodiments, the patient treated has mantle cell lymphoma and has had at least two prior lines of therapy, including a CD20 antibody and alkylator chemotherapy line, and a Bruton's tyrosine kinase inhibitor.

In certain embodiments, the patient treated has follicular lymphoma and has had at least two prior lines of therapy, including a CD20 antibody and alkylator chemotherapy line.

In certain embodiments, the patient treated has diffuse large B-cell lymphoma and has had at least two prior lines of therapy, including a CD20 antibody therapy and has received a prior autologous bone marrow transplant (or is ineligible for bone marrow transplant).

In certain embodiments, the patient treated for Non-Hodgkin's Lymphoma has a lesion that can be measured in at least two dimensions with PET-CT, for example a lesion with a minimum measurement of at least about 15 mm in the longest diameter.

In some embodiments, the patient to be treated by one of the compounds described herein has not be treated with multiple myeloma therapy prior to administration. In some embodiments, the patient to be treated by one of the compounds described herein has been treated by multiple myeloma therapy prior to administration. In some embodiments, the patient to be treated by one of the compounds described herein has developed drug resistant to the multiple myeloma therapy. In some embodiments, the patient to be treated by one of the compounds described herein has developed resistance to one, two, or three multiple myeloma therapies, wherein the therapies are selected from a CD38 antibody (CD38 mAB, for example, daratumumab or isatuximab), a proteasome inhibitor (for example, bortezomib, carfilzomib, ixazomib, or marizomib), and an immunomodulatory compound (for example thalidomide, lenalidomide, pomalidomide, iberdomide, or avadomide).

The compounds described herein can be administered in an effective amount to treat a patient regardless of patient's age. In some embodiments, the patient is 18 years or older. In other embodiments, the patient is more than 18, 25, 35, 40, 45, 50, 55, 60, 65, or 70 years old. In other embodiments, the patient is less than 65 years old. In other embodiments, the patient is more than 65 years old. In certain embodiments, the patient is an elderly multiple myeloma patient, such as a patient older than 65 years old. In certain embodiments, the patient is an elderly multiple myeloma patient, such as a patient older than 75 years old.

V. Combination Therapy

Any of the compounds described herein can be administered in an effective amount alone or in combination to treat a host such as a human with a disorder as described herein. In certain embodiments, a compound described herein is administered with an additional bioactive agent.

The term "bioactive agent" is used to describe an agent, other than the compound according to the present invention, which can be administered in combination or alternation with a compound of the present invention to achieve a desired result of therapy. In certain embodiments, the compound of the present invention and the bioactive agent are administered in a manner that they are active in vivo during overlapping time periods, for example, have time-period overlapping Cmax, Tmax, AUC or another pharmacokinetic parameter. In another embodiment, the compound of the present invention and the bioactive agent are administered to a host in need thereof that do not have overlapping pharmacokinetic parameter, however, one has a therapeutic impact on the therapeutic efficacy of the other.

As used herein when a compound is administered in combination with another this combination can be as one dosage form or multiple dosage forms at the same time or different times. Additionally, the compounds administered in combination can be administered with different dosing schedules. For example the combination of Compound 1 with dexamethasone includes a treatment regimen where Compound 1 is administered once a day for 21 consecutive days in a 28 day treatment cycle and dexamethasone is administered once a week during the treatment cycle.

In certain embodiments, Compound 1 is administered to a patient in need thereof in an effective amount in combination with one or more additional therapeutic agents described herein.

In certain embodiments, Compound 2 is administered to a patient in need thereof in an effective amount in combination with one or more additional therapeutic agents described herein.

In certain embodiments, Compound 3 is administered to a patient in need thereof in an effective amount in combination with one or more additional therapeutic agents described herein.

In certain embodiments, Compound 4 is administered to a patient in need thereof in an effective amount in combination with one or more additional therapeutic agents described herein.

In certain embodiments, Compound 5 is administered to a patient in need thereof in an effective amount in combination with one or more additional therapeutic agents described herein.

In certain embodiments, Compound 6 is administered to a patient in need thereof in an effective amount in combination with one or more additional therapeutic agents described herein.

In certain embodiments, Compound 7 is administered to a patient in need thereof in an effective amount in combination with one or more additional therapeutic agents described herein.

In certain embodiments, Compound 8 is administered to a patient in need thereof in an effective amount in combination with one or more additional therapeutic agents described herein.

In certain embodiments, Compound 9 is administered to a patient in need thereof in an effective amount in combination with one or more additional therapeutic agents described herein.

In certain embodiments, Compound 10 is administered to a patient in need thereof in an effective amount in combination with one or more additional therapeutic agents described herein.

In certain embodiments, Compound 11 is administered to a patient in need thereof in an effective amount in combination with one or more additional therapeutic agents described herein.

In certain embodiments, Compound 12 is administered to a patient in need thereof in an effective amount in combination with one or more additional therapeutic agents described herein.

In certain embodiments, Compound 13 is administered to a patient in need thereof in an effective amount in combination with one or more additional therapeutic agents described herein.

Corticosteroids

In certain embodiments, the compound of the present invention is administered in combination with a corticosteroid. In certain embodiments, the corticosteroid is dexamethasone. In certain embodiments, Compound 1 is administered with a corticosteroid. In certain embodiments, Compound 1 is administered with dexamethasone, for example in the dosage regimen shown below:

| Study Drug(s) | Dosage Formulation | Dose Level(s) | Frequency | Route of Administration |
|---|---|---|---|---|
| Compound 1 | Capsule | Table A | QD 21/7 | Oral |
| ≤75 years old Dexamethasone | Tablet | 40 mg | Once/week (QW) on days 1, 8, 15, | Oral |
| >75 years old Dexamethasone | Tablet | 20 mg | Once/week (QW) on days 1, 8, 15, and 22 | Oral |

In certain aspects Compound 1 is dosed QD on a dosing 21/7 schedule for each 28-day cycle in combination with another bioactive agent, for example once a week dosing of dexamethasone. In certain embodiments, the dexamethasone dose for an adult ≤75 years old is 40 mg QW on days 1, 8, 15, and 22 of a 28-day cycle. In certain embodiments, the dexamethasone dose for an adult >75 years old is 20 mg QW on days 1, 8, 15, and 22 of a 28-day cycle.

In certain embodiments, a compound described herein is administered in combination with a corticosteroid. Non-limiting examples of corticosteroids include dexamethasone, prednisone, fludrocortisone, hydrocortisone, cortisone, betamethasone, methylprednisolone.

In certain embodiments, Compound 1 is administered in combination with a corticosteroid. In certain embodiments, Compound 2 is administered in combination with a corticosteroid. In certain embodiments, Compound 3 is administered in combination with a corticosteroid. In certain embodiments, Compound 4 is administered in combination with a corticosteroid. In certain embodiments, Compound 5 is administered in combination with a corticosteroid. In certain embodiments, Compound 6 is administered in combination with a corticosteroid. In certain embodiments, Compound 7 is administered in combination with a corticosteroid. In certain embodiments, Compound 8 is administered in combination with a corticosteroid. In certain embodiments, Compound 9 is administered in combination with a corticosteroid. In certain embodiments, Compound 10 is administered in combination with a corticosteroid. In certain embodiments, Compound 11 is administered in combination with a corticosteroid. In certain embodiments, Compound 12 is administered in combination with a corticosteroid. In certain embodiments, Compound 13 is administered in combination with a corticosteroid. In certain embodiments, the corticosteroid is dexamethasone.

Additional non-limiting examples of corticosteroids include corticosterone, aldosterone, prednisolone, triamcinolone, budesonide, deflazacort, flugestone, fluorometholone, medrysone, prebediolone acetate, chloroprednisone, cloprednol, difluprednate, fluocinolone, fluperolone, fluperolone acetate, fluprednisolone, loteprednol, prednicarbate, tixocortol, alclometasone, alclometasone dipropionate, beclometasone, clobetasol, clobetasone, clocortolone, desoximetasone, diflorasone, diflorasone diacetate, difluocortolone, difluocortolone valerate, fluprednidene, fluprednidene acetate, fluticasone, fluticasone furoate, halometasone, meprednisone, mometasone, mometasone furoate, paramethasone, prednylidene, rimexolone, ulobetasol, amcinonide, ciclesonide, desonide, formocortal, fluclorolone, fluclorolone acetonide, fludroxycortide, flunisolide, fluocinolone, fluocinolone acetonide, fluocinonide, halcinonide, triamcinolone, triamcinolone acetonide, cortivazol, RU-28362, dexamethasone acefurate, dexamethasone acetate, dexamethasone cipecilate, dexamethasone diethylaminoacetate, dexamethasone dipropionate, dexamethasone isonicotinate, dexamethasone linoleate, dexamethasone metasulphobenzoate, dexamethasone palmitate, dexamethasone phosphate, dexamethasone pivalate, dexamethasone succinate, dexamethasone sulfate, dexamethasone tebutate, dexamethasone troxundate, and dexamethasone valerate.

Kinase Inhibitors

In certain embodiments, the bioactive agent is a kinase inhibitor, for example a Bruton's tyrosine kinase (BTK) inhibitor. In certain embodiments, the kinase inhibitor is selected from a phosphoinositide 3-kinase (PI3K) inhibitor, a Bruton's tyrosine kinase (BTK) inhibitor, or a spleen tyrosine kinase (Syk) inhibitor, or a combination thereof.

In certain embodiments, the compound of the present invention is administered in combination with a BTK inhibitor. In certain embodiments, the BTK inhibitor is Ibrutinib. In certain embodiments, the embodiments the BTK inhibitor is Acalabrutinib. In certain embodiments, Compound 1 is administered in combination with a BTK inhibitor. In certain embodiments, Compound 1 is administered in combination BTK inhibitor is Zanubrutinib. In certain with Ibrutinib. In certain embodiments, Compound 1 is administered in combination with Zanubrutinib. In certain embodiments, Compound 1 is administered in combination with Acalabrutinib.

In certain embodiments, Compound 2 is administered in combination with a BTK inhibitor. In certain embodiments, Compound 3 is administered in combination with a BTK inhibitor. In certain embodiments, Compound 4 is administered in combination with a BTK inhibitor. In certain embodiments, Compound 5 is administered in combination with a BTK inhibitor. In certain embodiments, Compound 6 is administered in combination with a BTK inhibitor. In certain embodiments, Compound 7 is administered in combination with a BTK inhibitor. In certain embodiments, Compound 8 is administered in combination with a BTK inhibitor. In certain embodiments, Compound 9 is administered in combination with a BTK inhibitor. In certain embodiments, Compound 10 is administered in combination with a BTK inhibitor. In certain embodiments, Compound 11 is administered in combination with a BTK inhibitor. In certain embodiments, Compound 12 is administered in combination with a BTK inhibitor. In certain embodiments, Compound 13 is administered in combination with a BTK inhibitor. In certain embodiments, the BTK inhibitor is selected from Ibrutinib, Zanubrutinib, and Acalabrutinib.

Examples of BTK inhibitors include ibrutinib (also known as PCI-32765)(Imbruvica™)(1-[(3R)-3-[4-amino-3-(4-phenoxy-phenyl)pyrazolo[3,4-d]pyrimidin-1-yl]piperidin-1-yl]prop-2-en-1-one), dianilinopyrimidine-based inhibitors such as AVL-101 and AVL-291/292 (N-(3-((5-fluoro-2-((4-(2-methoxyethoxy)phenyl)amino)pyrimidin-4-yl)amino)phenyl)acrylamide) (Avila Therapeutics) (see US Patent Publication No 2011/0117073, incorporated herein in its entirety), Dasatinib ([N-(2-chloro-6-methylphenyl)-2-(6-(4-(2-hydroxyethyl)piperazin-1-yl)-2-methylpyrimidin-4-ylamino)thiazole-5-carboxamide], LFM-A13 (alpha-cyano-beta-hydroxy-beta-methyl-N-(2,5-ibromophenyl) propenamide), GDC-0834 ([R—N-(3-(6-(4-(1,4-dimethyl-3-oxopiperazin-2-yl)phenylamino)-4-methyl-5-oxo-4,5-dihydropyrazin-2-yl)-2-methylphenyl)-4,5,6,7-tetrahydrobenzo[b]thiophene-2-carboxamide], CGI-560 4-(tert-butyl)-N-(3-(8-(phenylamino)imidazo[1,2-a]pyrazin-6-yl) phenyl)benzamide, CGI-1746 (4-(tert-butyl)-N-(2-methyl-3-(4-methyl-6-((4-(morpholine-4-carbonyl)phenyl)amino)-5-oxo-4,5-dihydropyrazin-2-yl)phenyl)benzamide), CNX-774 (4-(4-((4-((3-acrylamidophenyl)amino)-5-fluoropyrimidin-2-yl)amino)phenoxy)-N-methylpicolinamide), CTA056 (7-benzyl-1-(3-(piperidin-1-yl)propyl)-2-(4-(pyridin-4-yl)phenyl)-1H-imidazo[4,5-g]quinoxalin-6(5H)-one), GDC-0834 ((R)—N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide), GDC-0837 ((R)—N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide), HM-71224, ACP-196, ONO-4059 (Ono Pharmaceuticals), PRT062607 (4-((3-(2H-1,2,3-triazol-2-yl)phenyl)amino)-2-(((1R,2S)-2-aminocyclohexyl)amino) pyrimidine-5-carboxamide hydrochloride), QL-47 (1-(1-acryloylindolin-6-yl)-9-(1-methyl-1H-pyrazol-4-yl)benzo[h][1,6]naphthyridin-2(1H)-one), and RN486 (6-cyclopropyl-8-fluoro-2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-2H-isoquinolin-1-one), and other molecules capable of inhibiting BTK activity, for example those BTK inhibitors disclosed in Akinleye et ah, Journal of Hematology & Oncology, 2013, 6:59, the entirety of which is incorporated herein by reference.

In certain embodiments, the BTK inhibitor is selected from acalabrutinib, spebrutinib, zanubrutinib, LOXO-305, evobrutinib, TG-1701, tolebrutinib, BIIB091, DZD-9008, HZ-A-018, orelabrutinib, AC0058TA, SN1011, rilzabrutinib, ARQ 531, DTRMWXHI-S-12, JNJ-64264681, branebrutinib, and fenebrutinib. In certain embodiments, Compound 1 is administered in combination with an BTK inhibitor selected from acalabrutinib, spebrutinib, zanubrutinib, LOXO-305, evobrutinib, TG-1701, tolebrutinib, B11B091, DZD-9008, HZ-A-018, orelabrutinib, AC0058TA, SN1011, rilzabrutinib, ARQ 531, DTRIWXS-12, JNJ-64264681, branebrutinib, and fenebrutini b.

Examples of PI3 kinase inhibitors include but are not limited to Wortmannin, demethoxyviridin, perifosine, idelalisib, Pictilisib, Palomid 529, ZSTK474, PWT33597, CUDC-907, and AEZS-136, duvelisib, GS-9820, BKM120, GDC-0032 (Taselisib) (2-[4-[2-(2-Isopropyl-5-methyl-1,2,4-triazol-3-yl)-5,6-dihydroimidazo[1,2-d][1,4]benzoxazepin-9-yl]pyrazol-1-yl]-2-methylpropanamide), MLN-1117 ((2R)-1-Phenoxy-2-butanyl hydrogen (S)-methylphosphonate; or Methyl(oxo) {[(2R)-1-phenoxy-2-butanyl]oxy}phosphonium)), BYL-719 ((2S)—N1-[4-Methyl-5-[2-(2,2,2-trifluoro-1,1-dimethylethyl)-4-pyridinyl]-2-thiazolyl]-1,2-pyrrolidinedicarboxamide), GSK2126458 (2,4-Difluoro-N-{2-(methyloxy)-5-[4-(4-pyridazinyl)-6-quinolinyl]-3-pyridinyl}benzenesulfonamide) (omipalisib), TGX-221 ((+)-7-Methyl-2-(morpholin-4-yl)-9-(1-phenylaminoethyl)-pyrido[1,2-a]-pyrimidin-4-one), GSK2636771 (2-Methyl-1-(2-methyl-3-(trifluoromethyl) benzyl)-6-morpholino-1H-benzo[d]imidazole-4-carboxylic acid dihydrochloride), KIN-193 ((R)-2-((1-(7-methyl-2-morpholino-4-oxo-4H-pyrido[1,2-a]pyrimidin-9-yl)ethyl) amino)benzoic acid), TGR-1202/RP5264, GS-9820 ((S)-1-(4-((2-(2-aminopyrimidin-5-yl)-7-methyl-4-mohydroxypropan-1-one), GS-1101 (5-fluoro-3-phenyl-2-([S)]-1-[9H-purin-6-ylamino]-propyl)-3H-quinazolin-4-one), AMG-319, GSK-2269557, SAR245409 (N-(4-(N-(3-((3,5-dimethoxyphenyl)amino)quinoxalin-2-yl)sulfamoyl) phenyl)-3-methoxy-4 methylbenzamide), BAY80-6946 (2-amino-N-(7-methoxy-8-(3-morpholinopropoxy)-2,3-dihydroimidazo[1,2-c]quinaz), AS 252424 (5-[1-[5-(4-Fluoro-2-hydroxy-phenyl)-furan-2-yl]-meth-(Z)-ylidene]-thiazolidine-2,4-dione), CZ 24832 (5-(2-amino-8-fluoro-[1,2,4] triazolo[1,5-a]pyridin-6-yl)-N-tert-butylpyridine-3-sulfonamide), Buparlisib (5-[2,6-Di(4-morpholinyl)-4-pyrimidinyl]-4-(trifluoromethyl)-2-pyridinamine), GDC- 0941 (2-(1H-Indazol-4-yl)-6-[[4-(methylsulfonyl)-1-piperazinyl]methyl]-4-(4-morpholinyl)thieno[3,2-d]pyrimidine), GDC-0980 ((S)-1-(4-((2-(2-aminopyrimidin-5-yl)-7-methyl-4-morpholinothieno[3,2-d]pyrimidin-6 yl)methyl)piperazin-1-yl)-2-hydroxypropan-1-one (also known as RG7422)), SF1126 ((8S,14S,17S)-14-(carboxymethyl)-8-(3-guanidinopropyl)-17-(hydroxymethyl)-3,6,9,12,15-pentaoxo-1-(4-(4-oxo-8-phenyl-4H-chromen-2-yl)morpholino-4-ium)-2-oxa-7,10,13,16-tetraazaoctadecan-18-oate), PF-05212384 (N-[4-[[4-(Dimethylamino)-1-piperidinyl]carbonyl]phenyl]-N'-[4-(4,6-di-4-morpholinyl-1,3,5-triazin-2-yl)phenyl]urea) (gedatolisib), LY3023414, BEZ235 (2-Methyl-2-{4-[3-methyl-2-oxo-8-(quinolin-3-yl)-2,3-dihydro-1H-imidazo[4,5-c]quinolin-1-yl] phenyl}propanenitrile) (dactolisib), XL-765 (N-(3-(N-(3-(3,5-dimethoxyphenylamino)quinoxalin-2-yl)sulfamoyl) phenyl)-3-methoxy-4-methylbenzamide), and GSK1059615 (5-[[4-(4-Pyridinyl)-6-quinolinyl]methylene]-2,4-thiazolidenedione), PX886 ([(3aR,6E,9S,9aR,10R,11aS)-6-[[bis (prop-2-enyl)amino]methylidene]-5-hydroxy-9-(methoxymethyl)-9a,11a-dimethyl-1,4,7-trioxo-2,3,3a,9,10,11-hexahydroindeno[4,5h]isochromen-10-yl] acetate (also known as sonolisib)), LY294002, AZD8186, PF-4989216, pilaralisib, GNE-317, PI-3065, PI-103, NU7441 (KU-57788), HS 173, VS-5584 (SB2343), CZC24832, TG100-115, A66, YM201636, CAY10505, PIK-75, PIK-93, AS-605240, BGT226 (NVP-BGT226), AZD6482, voxtalisib, alpelisib, IC-87114, TGI100713, CH5132799, PKI-402, copanlisib (BAY 80-6946), XL 147, PIK-90, PIK-293, PIK-294, 3-MA (3-methyladenine), AS-252424, AS-604850, apitolisib (GDC-0980; RG7422), and the structure described in WO2014/071109.

Syk inhibitors include, for example, Cerdulatinib (4-(cyclopropylamino)-2-((4-(4-(ethylsulfonyl)piperazin-1-yl) phenyl)amino)pyrimidine-5-carboxamide), entospletinib (6-(1H-indazol-6-yl)-N-(4-morpholinophenyl)imidazo[1,2-a] pyrazin-8-amine), fostamatinib ([6-({5-Fluoro-2-[(3,4,5-trimethoxyphenyl)amino]-4-pyrimidinyl}amino)-2,2-dimethyl-3-oxo-2,3-dihydro-4H-pyrido[3,2-b][1,4]oxazin-4-yl]methyl dihydrogen phosphate), fostamatinib disodium salt (sodium (6-((5-fluoro-2-((3,4,5-trimethoxyphenyl) amino)pyrimidin-4-yl)amino)-2,2-dimethyl-3-oxo-2H-pyrido[3,2-b][1,4]oxazin-4(3H)-yl)methyl phosphate), BAY 61-3606 (2-(7-(3,4-Dimethoxyphenyl)-imidazo[1,2-c]pyrimidin-5-ylamino)-nicotinamide HCl), R09021 (6-[(1R,2S)-2-Amino-cyclohexylamino]-4-(5,6-dimethyl-pyridin-2-ylamino)-pyridazine-3-carboxylic acid amide), imatinib (Gleevac; 4-[(4-methylpiperazin-1-yl)methyl]-N-(4-methyl-3-{[4-(pyridin-3-yl)pyrimidin-2-yl]amino}phenyl)benzamide), staurosporine, GSK143 (2-(((3R,4R)-3-aminotetrahydro-2H-pyran-4-yl)amino)-4-(p-tolylamino)pyrimidine-5-carboxamide), PP2 (1-(tert-butyl)-3-(4-chlorophenyl)-1H-pyrazolo[3,4-d]pyrimidin-4-amine), PRT-060318 (2-(((1R,2S)-2-aminocyclohexyl)amino)-4-(m-tolylamino) pyrimidine-5-carboxamide), PRT-062607 (4-((3-(2H-1,2,3-triazol-2-yl)phenyl)amino)-2-(((1R,2S)-2-aminocyclohexyl)amino)pyrimidine-5-carboxamide hydrochloride), R112 (3,3'-((5-fluoropyrimidine-2,4-diyl) bis(azanediyl))diphenol), R348 (3-Ethyl-4-methylpyridine), R406 (6-((5-fluoro-2-((3,4,5-trimethoxyphenyl)amino)pyrimidin-4-yl)amino)-2,2-dimethyl-2H-pyrido[3,2-b][1,4] oxazin-3(4H)-one), piceatannol (3-Hydroxyresveratol), YM193306 (see Singh et al. Discovery and Development of Spleen Tyrosine Kinase (SYK) Inhibitors, J. Med. Chem. 2012, 55, 3614-3643), 7-azaindole, piceatannol, ER-27319 (see Singh et al. Discovery and Development of Spleen Tyrosine Kinase (SYK) Inhibitors, J. Med. Chem. 2012, 55, 3614-3643 incorporated in its entirety herein), Compound D (see Singh et al. Discovery and Development of Spleen Tyrosine Kinase (SYK) Inhibitors, J. Med. Chem. 2012, 55, 3614-3643 incorporated in its entirety herein), PRT060318 (see Singh et al. Discovery and Development of Spleen Tyrosine Kinase (SYK) Inhibitors, J. Med. Chem. 2012, 55, 3614-3643 incorporated in its entirety herein), luteolin (see Singh et al. Discovery and Development of Spleen Tyrosine Kinase (SYK) Inhibitors, J. Med. Chem. 2012, 55, 3614-3643 incorporated in its entirety herein), apigenin (see Singh et al. Discovery and Development of Spleen Tyrosine Kinase (SYK) Inhibitors, J. Med. Chem. 2012, 55, 3614-3643 incorporated in its entirety herein), quercetin (see Singh et al. Discovery and Development of Spleen Tyrosine Kinase (SYK) Inhibitors, J. Med. Chem. 2012, 55, 3614-3643 incorporated in its entirety herein), fisetin (see Singh et al. Discovery and Development of Spleen Tyrosine Kinase (SYK) Inhibitors, J. Med. Chem. 2012, 55, 3614-3643 incorporated in its entirety herein), myricetin (see Singh et al. Discovery and Development of Spleen Tyrosine Kinase (SYK) Inhibitors, J. Med. Chem. 2012, 55, 3614-3643 incorporated in its entirety herein), morin (see Singh et al. Discovery and Development of Spleen Tyrosine Kinase (SYK) Inhibitors, J. Med. Chem. 2012, 55, 3614-3643 incorporated in its entirety herein).

Proteasome Inhibitors

In certain embodiments, the compound of the present invention is administered in combination with a proteasome inhibitor. In certain embodiments, the proteasome inhibitor is Bortezomib. In certain embodiments, the proteasome inhibitor is Ixazomib. In certain embodiments, the proteasome inhibitor is Carfilzomib. In certain embodiments, Compound 1 is administered in combination with a proteasome inhibitor. In certain embodiments, Compound 1 is administered in combination with Bortezomib. In certain embodiments, Compound 1 is administered in combination with Ixazomib. In certain embodiments, Compound 1 is administered in combination with Carfilzomib. In certain embodiments, Compound 1 is administered in combination with carfilzomib and daratumumab.

In certain embodiments, Compound 2 is administered in combination with a proteasome inhibitor. In certain embodiments, Compound 3 is administered in combination with a proteasome inhibitor. In certain embodiments, Compound 4 is administered in combination with a proteasome inhibitor. In certain embodiments, Compound 5 is administered in combination with a proteasome inhibitor. In certain embodiments, Compound 6 is administered in combination with a proteasome inhibitor. In certain embodiments, Compound 7 is administered in combination with a proteasome inhibitor. In certain embodiments, Compound 8 is administered in combination with a proteasome inhibitor. In certain embodiments, Compound 9 is administered in combination with a proteasome inhibitor. In certain embodiments, Compound 10 is administered in combination with a proteasome inhibitor. In certain embodiments, Compound 11 is administered in combination with a proteasome inhibitor. In certain embodiments, Compound 12 is administered in combination with a proteasome inhibitor. In certain embodiments, Compound 13 is administered in combination with a proteasome inhibitor. In certain embodiments, the proteasome inhibitor is selected from Bortezomib, Ixazomib, VLX1570, and Carfilzomib.

Additional examples of proteasome inhibitors include ixazomib citrate, oprozomib, delanzomib, lactacystin, epoxomicin, MG132, MG-262, CEP-18770, NEOSH101, TQ13602, and KZR-616. In certain embodiments, Compound 1 is administered in combination with a proteasome inhibitor selected from ixazomib citrate, oprozomib, delanzomib, lactacystin, epoxomicin, MG132, MG-262, CEP-18770, NEOSH101, TQB3602, VLX1570, and KZR-616.

HDAC Inhibitors

In certain embodiments, the compound of the present invention is administered in combination with an HDAC inhibitor. In certain embodiments, the HDAC inhibitor is Vorinostat. In certain embodiments, the HDAC inhibitor is Romidepsin. In certain embodiments, the HDAC inhibitor is Panobinostat. In certain embodiments, the HDAC inhibitor is Belinostat. In certain embodiments, Compound 1 is administered in combination with an HDAC inhibitor. In certain embodiments, Compound 1 is administered in combination with Vorinostat. In certain embodiments, Compound 1 is administered in combination with Romidepsin. In certain embodiments, Compound 1 is administered in combination with Panobinostat. In certain embodiments, Compound 1 is administered in combination with Belinostat.

In certain embodiments, Compound 2 is administered in combination with a HDAC inhibitor. In certain embodiments, Compound 3 is administered in combination with a HDAC inhibitor. In certain embodiments, Compound 4 is administered in combination with a HDAC inhibitor. In certain embodiments, Compound 5 is administered in combination with a HDAC inhibitor. In certain embodiments, Compound 6 is administered in combination with a HDAC inhibitor. In certain embodiments, Compound 7 is administered in combination with a HDAC inhibitor. In certain embodiments, Compound 8 is administered in combination with a HDAC inhibitor. In certain embodiments, Compound 9 is administered in combination with a HDAC inhibitor. In certain embodiments, Compound 10 is administered in combination with a HDAC inhibitor. In certain embodiments, Compound 11 is administered in combination with a HDAC inhibitor. In certain embodiments, Compound 12 is administered in combination with a HDAC inhibitor. In certain embodiments, Compound 13 is administered in combination with a HDAC inhibitor. In certain embodiments, the HDAC inhibitor is selected from Vorinostat, Romidepsin, Panobinostat, and Belinostat.

In certain embodiments, the HDAC inhibitor is selected from trapoxin B, sodium phenylbutyrate, tacedinaline, mocetinostat, BRD73954, BG45, domatinostat, cay10603, HPOB, TMP269, nexturastat A, Santacruzamate A, splitomicin, LMK-235, sodium butyrate, pivaloyloxymethyl butyrate, pyroxamide, abexinostat, resminostat, givinostat, quisinostat, Psammaplin A, KD5170, 1-Alaninechlamydocin, depudecin, and CUDC-101. In certain embodiments, Compound 1 is administered in combination with an HDAC inhibitor selected from trapoxin B, sodium phenylbutyrate, tacedinaline, mocetinostat, BRD73954, BG45, domatinostat, cay10603, HPOB, TMP269, nexturastat A, Santacruzamate A, splitomicin, LMK-235, sodium butyrate, pivaloyloxymethyl butyrate, pyroxamide, abexinostat, resminostat, givinostat, quisinostat, Psammaplin A, KD5170, 1-Alaninechlamydocin, depudecin, and CUDC-101.

IMiDs

In certain embodiments, the compound of the present invention is administered in combination with an IMiD. In certain embodiments, the IMiD is thalidomide. In certain embodiments, the IMiD is lenalidomide. In certain embodiments, the IMiD is pomalidomide. In certain embodiments, Compound 1 is administered in combination with thalidomide. In certain embodiments, Compound 1 is administered in combination with lenalidomide. In certain embodiments, Compound 1 is administered in combination with pomalidomide.

In certain embodiments, Compound 2 is administered in combination with an IMiD. In certain embodiments, Compound 3 is administered in combination with an IMiD. In certain embodiments, Compound 4 is administered in combination with an IMiD. In certain embodiments, Compound 5 is administered in combination with an IMiD. In certain embodiments, Compound 6 is administered in combination with an IMiD. In certain embodiments, Compound 7 is administered in combination with an IMiD. In certain embodiments, Compound 8 is administered in combination with an IMiD. In certain embodiments, Compound 9 is administered in combination with an IMiD. In certain embodiments, Compound 10 is administered in combination with an IMiD. In certain embodiments, Compound 11 is administered in combination with an IMiD. In certain embodiments, Compound 12 is administered in combination with an IMiD. In certain embodiments, Compound 13 is administered in combination with an IMiD. In certain embodiments, the IMiD is selected from pomalidomide, thalidomide, and lenalidomide.

In certain embodiments, the IMiD is CC-90009. In certain embodiments, the IMiD is CC-99282. In certain embodiments, the IMiD is CC-92480. In certain embodiments, Compound 1 is administered in combination with CC-90009. In certain embodiments, Compound 1 is administered in combination with CC-99282. In certain embodiments, Compound 1 is administered in combination with CC-92480.

In certain embodiments, Compound 2, Compound 3, Compound 4, Compound 5, Compound 6, Compound 7, Compound 8, Compound 9, Compound 10, Compound 11, Compound 12, or Compound 13 is administered in combination with an IMiD. In certain embodiments, the IMiD is selected from CC-90009, CC-99282, and CC-92480.

Antibodies

In certain embodiments, the compound of the present invention is administered in combination with an antibody targeting CD20, CD30, or CD38. In certain embodiments, the targeted antibody is Rituximab. In certain embodiments, the targeted antibody is Daratumumab. In certain embodiments, the targeted antibody is Elotuzumab. In certain embodiments, the targeted antibody is Isatuximab. In certain embodiments, Compound 1 is administered in combination with an antibody targeting CD20, CD30, or CD38. In certain embodiments, Compound 1 is administered in combination with Rituximab. In certain embodiments, Compound 1 is administered in combination with Daratumumab. In certain embodiments, Compound 1 is administered in combination with Elotuzumab. In certain embodiments, Compound 1 is administered in combination with Isatuximab.

In certain embodiments, Compound 2 is administered in combination with an antibody targeting CD20, CD30, or CD38. In certain embodiments, Compound 3 is administered in combination with an antibody targeting CD20, CD30, or CD38. In certain embodiments, Compound 4 is administered in combination with an antibody targeting CD20, CD30, or CD38. In certain embodiments, Compound 5 is administered in combination with an antibody targeting CD20, CD30, or CD38. In certain embodiments, Compound 6 is administered in combination with an antibody targeting CD20, CD30, or CD38. In certain embodiments, Compound 7 is administered in combination with an antibody targeting CD20, CD30, or CD38. In certain embodiments, Compound 8 is administered in combination with an antibody targeting CD20, CD30, or CD38. In certain embodiments, Compound 9 is administered in combination with an antibody targeting CD20, CD30, or CD38. In certain embodiments, Compound 10 is administered in combination with an antibody targeting CD20, CD30, or CD38. In certain embodiments, Compound 11 is administered in combination with an antibody targeting CD20, CD30, or CD38. In certain embodiments, Compound 12 is administered in combination with an antibody targeting CD20, CD30, or CD38. In certain embodiments, Compound 13 is administered in combination with an antibody targeting CD20, CD30, or CD38. In certain embodiments, the targeted antibody is selected from Rituximab, Daratumumab, Elotuzumab, and Isatuximab.

In certain embodiments, the compound of the present invention is administered in combination with an antibody-drug conjugate. In certain embodiments, the antibody-drug conjugate is Brentuximab vedotin. In certain embodiments, the antibody-drug conjugate is Ibritumomab tiuxetan. In certain embodiments, the antibody-drug conjugate is Mogamulizumab. In certain embodiments, the antibody-drug conjugate is Obinutuzumab. In certain embodiments, the antibody-drug conjugate is Polatuzumab vedotin. In certain embodiments, the antibody-drug conjugate is Belantamab mafodotin (GSK2857916). In certain embodiments, the antibody-drug conjugate is MEDI2228. In certain embodiments, the antibody-drug conjugate is CC-99712. In certain embodiments, Compound 1 is administered in combination with an antibody-drug conjugate. In certain embodiments, Compound 1 is administered in combination with Brentuximab vedotin. In certain embodiments, Compound 1 is administered in combination with Ibritumomab tiuxetan. In certain embodiments, Compound 1 is administered in combination with Mogamulizumab. In certain embodiments, Compound 1 is administered in combination with Obinutuzumab. In certain embodiments, Compound 1 is administered in combination with Polatuzumab vedotin. In certain embodiments, Compound 1 is administered in combination with Belantamab mafodotin (GSK2857916). In certain embodiments, Compound 1 is administered in combination with MEDI2228. In certain embodiments, Compound 1 is administered in combination with CC-99712. In certain embodiments, Compound 1 is administered in combination with tafasitamab.

In certain embodiments, Compound 2 is administered in combination with an antibody-drug conjugate. In certain embodiments, Compound 3 is administered in combination with an antibody-drug conjugate. In certain embodiments, Compound 4 is administered in combination with an antibody-drug conjugate. In certain embodiments, Compound 5 is administered in combination with an antibody-drug conjugate. In certain embodiments, Compound 6 is administered in combination with an antibody-drug conjugate. In certain embodiments, Compound 7 is administered in combination with an antibody-drug conjugate. In certain embodiments, Compound 8 is administered in combination with an antibody-drug conjugate. In certain embodiments, Compound 9 is administered in combination with an antibody-drug conjugate. In certain embodiments, Compound 10 is administered in combination with an antibody-drug conjugate. In certain embodiments, Compound 11 is administered in combination with an antibody-drug conjugate. In certain embodiments, Compound 12 is administered in combination with an antibody-drug conjugate. In certain embodiments, Compound 13 is administered in combination with an antibody-drug conjugate. In certain embodiments, the antibody-drug conjugate is selected from Brentuximab vedotin, Ibritumomab tiuxetan, Mogamulizumab, Obinutuzumab, Polatuzumab vedotin, Belantamab mafodotin (GSK2857916), MEDI2228, and CC-99712.

In certain embodiments, the compound of the present invention is administered in combination with a bispecific antibody. In certain embodiments, the bispecific antibody is PF-06863135. In certain embodiments, the bispecific antibody is TNB-383B. In certain embodiments, the bispecific antibody is REGN5458. In certain embodiments, the bispecific antibody is JNJ-64007957. In certain embodiments, Compound 1 is administered in combination with a bispecific antibody. In certain embodiments, Compound 1 is administered in combination with PF-06863135. In certain embodiments, Compound 1 is administered in combination with TNB-383B. In certain embodiments, Compound 1 is administered in combination with REGN5458. In certain embodiments, Compound 1 is administered in combination with JNJ-64007957.

In certain embodiments, Compound 2 is administered in combination with a bispecific antibody. In certain embodiments, Compound 3 is administered in combination with a bispecific antibody. In certain embodiments, Compound 4 is administered in combination with a bispecific antibody. In certain embodiments, Compound 5 is administered in combination with a bispecific antibody. In certain embodiments, Compound 6 is administered in combination with a bispecific antibody. In certain embodiments, Compound 7 is administered in combination with a bispecific antibody. In certain embodiments, Compound 8 is administered in combination with a bispecific antibody. In certain embodiments, Compound 9 is administered in combination with a bispecific antibody. In certain embodiments, Compound 10 is administered in combination with a bispecific antibody. In certain embodiments, Compound 11 is administered in combination with a bispecific antibody. In certain embodiments, Compound 12 is administered in combination with a bispecific antibody. In certain embodiments, Compound 13 is administered in combination with a bispecific antibody. In certain embodiments, the bispecific antibody is selected from PF-06863135, TNB-383B, REGN5458, and JNJ-64007957.

In certain embodiments, the compound of the present invention is administered in combination with a naked monoclonal antibody (mAb). In certain embodiments, the naked mAb is SEA-BCMA. In certain embodiments, Compound 1 is administered in combination with a naked mAb. In certain embodiments, Compound 1 is administered in combination with SEA-BCMA.

In certain embodiments, Compound 2 is administered in combination with a naked mAb. In certain embodiments, Compound 3 is administered in combination with a naked mAb. In certain embodiments, Compound 4 is administered in combination with a naked mAb. In certain embodiments, Compound 5 is administered in combination with a naked mAb. In certain embodiments, Compound 6 is administered in combination with a naked mAb. In certain embodiments, Compound 7 is administered in combination with a naked mAb. In certain embodiments, Compound 8 is administered in combination with a naked mAb. In certain embodiments, Compound 9 is administered in combination with a naked mAb. In certain embodiments, Compound 10 is administered in combination with a naked mAb. In certain embodiments, Compound 11 is administered in combination with a naked mAb. In certain embodiments, Compound 12 is administered in combination with a naked mAb. In certain embodiments, Compound 13 is administered in combination with a naked mAb. In certain embodiments, the naked mAb is SEA-BCMA.

Additional non-limiting examples of CD38 antibodies include felzartamab, GBR 1342, TAK-573, CID-103, OKT10, STI-6129, SGX301, and mezagitamab. In certain embodiments, Compound 1 is administered in combination with a CD38 antibody selected from felzartamab, GBR 1342, TAK-573, CID-103, OKT10, STI-6129, SGX301, TAK-079, and mezagitamab.

CAR T-Cell Therapy

In certain embodiments, the compound of the present invention is administered in combination with a CAR T-cell therapy. In certain embodiments, the CAR T-cell therapy is Axicabtagene ciloleucel. In certain embodiments, the CAR T-cell therapy is Tisagenlecleucel. In certain embodiments, the CAR T-cell therapy is Idecabtagene vicleucel (ide-cel; bb2121). In certain embodiments, the CAR T-cell therapy is LCAR-B38M (JNJ-4528; JNJ-68284528). In certain embodiments, the CAR T-cell therapy is P-BCMA-101. In certain embodiments, the CAR T-cell therapy is PBCAR269A. In certain embodiments, the CAR T-cell therapy is bb21217. In certain embodiments, the CAR T-cell therapy is JCARK125 (orva-cel; orvacabtagene autoleucel). In certain embodiments, the CAR T-cell therapy is ALLO-715. In certain embodiments, the CAR T-cell therapy is Descartes-08. In certain embodiments, the CAR T-cell therapy is FCARH143. In certain embodiments, the CAR T-cell therapy is CT053.

In certain embodiments, Compound 1 is administered in combination with a CAR T-cell therapy. In certain embodiments, Compound 1 is administered in combination with Axicabtagene ciloleucel. In certain embodiments, Compound 1 is administered in combination with Tisagenlecleucel. In certain embodiments, Compound 1 is administered in combination with Idecabtagene vicleucel (ide-cel; bb2121). In certain embodiments, Compound 1 is administered in combination with LCAR-B38M (JNJ-4528; JNJ-68284528). In certain embodiments, Compound 1 is administered in combination with P-BCMA-101. In certain embodiments, Compound 1 is administered in combination with PBCAR269A. In certain embodiments, Compound 1 is administered in combination with bb21217. In certain embodiments, Compound 1 is administered in combination with JCARK125 (orva-cel; orvacabtagene autoleucel). In certain embodiments, Compound 1 is administered in combination with ALLO-715. In certain embodiments, Compound 1 is administered in combination with Descartes-08. In certain embodiments, Compound 1 is administered in combination with FCARH143. In certain embodiments, Compound 1 is administered in combination with CT053.

In certain embodiments, Compound 2 is administered in combination with CAR T-cell therapy. In certain embodiments, Compound 3 is administered in combination with CAR T-cell therapy. In certain embodiments, Compound 4 is administered in combination with CAR T-cell therapy. In certain embodiments, Compound 5 is administered in combination with CAR T-cell therapy. In certain embodiments, Compound 6 is administered in combination with CAR T-cell therapy. In certain embodiments, Compound 7 is administered in combination with CAR T-cell therapy. In certain embodiments, Compound 8 is administered in combination with CAR T-cell therapy. In certain embodiments, Compound 9 is administered in combination with CAR T-cell therapy. In certain embodiments, Compound 10 is administered in combination with CAR T-cell therapy. In certain embodiments, Compound 11 is administered in combination with CAR T-cell therapy. In certain embodiments, Compound 12 is administered in combination with CAR T-cell therapy. In certain embodiments, Compound 13 is administered in combination with CAR T-cell therapy. In certain embodiments, the CAR T-cell therapy is selected from Axicabtagene ciloleucel, Tisagenlecleucel, Idecabtagene vicleucel (ide-cel; bb2121), LCAR-B38M (JNJ-4528; JNJ-68284528), and P-BCMA-101. In certain embodiments, the CAR T-cell therapy is selected from PBCAR269A, bb21217, JCARK125 (orva-cel; orvacabtagene autoleucel), ALLO-715, Descartes-08, FCARH143, and CT053.

In certain embodiments the CAR T-cell Therapy is selected from ALLO-715, bb21217, BCMA CAR-T, CD138 CAR-T, CD19 CAR-T, ciltacabtagene autoleucel, CS1 (SLAMF7) CAR-T, CT053, Descartes-11, idecabtagene vicleucel, NKG2D CAR-T, orvacabtagene autoleucel, P-BCMA-101, and UCARTCS1.

Cellular Therapy

In certain embodiments, the compound of the present invention is administered in combination with a cellular therapy. In certain embodiments Compound 1 is used in combination with a cellular therapy.

Non-limiting examples of cellular therapy include allo-HSCT, allo-NKT, auto-HSCT, and auto-NKT.

T-cell Engagers

In certain embodiments, the compound of the present invention is administered in combination with a bi-specific T-cell engagers (BiTEs). In certain embodiments, the BiTE is Blinatumomab. In certain embodiments, the BiTE is CC-93268. In certain embodiments, the BiTE is AMG 420. In certain embodiments, the BiTE is AMG 701. In certain embodiments, Compound 1 is administered in combination with a bi-specific T-cell engagers (BiTEs). In certain embodiments, Compound 1 is administered in combination with Blinatumomab. In certain embodiments, Compound 1 is administered in combination with AMG 420. In certain embodiments, Compound 1 is administered in combination with CC-93269. In certain embodiments, Compound 1 is administered in combination with AMG 701.

In certain embodiments, Compound 2 is administered in combination with a BiTE. In certain embodiments, Compound 3 is administered in combination with a BiTE. In certain embodiments, Compound 4 is administered in combination with a BiTE. In certain embodiments, Compound 5 is administered in combination with a BiTE. In certain embodiments, Compound 6 is administered in combination with a BiTE. In certain embodiments, Compound 7 is administered in combination with a BiTE. In certain embodiments, Compound 8 is administered in combination with a BiTE. In certain embodiments, Compound 9 is administered in combination with a BiTE. In certain embodiments, Compound 10 is administered in combination with a BiTE. In certain embodiments, Compound 11 is administered in combination with a BiTE. In certain embodiments, Compound 12 is administered in combination with a BiTE. In certain embodiments, Compound 13 is administered in combination with a BiTE. In certain embodiments, the BiTE is selected from Blinatumomab, AMG 420, CC-93269, and AMG 4701.

In certain embodiments Compound 1 is used in combination with a bispecific antibody selected from AMG 420, AMG 701, BFCR4350A, blinatumomab, CC-93269, elranatamab, EM801, REGN5458, talquetamab, teclistamab, and TNB-383B.

Immune Modulators Checkpoint Inhibitors

In certain embodiments, the compound of the present invention is administered in combination with a checkpoint inhibitor. In certain embodiments, the compound of the present invention is administered in combination with a PD-1 checkpoint inhibitor. In certain embodiments, the compound of the present invention is administered in combination with a PD-L1 checkpoint inhibitor. In certain embodiments, the compound of the present invention is administered in combination with an IFNAR checkpoint inhibitor. In certain embodiments, the checkpoint inhibitor is Nivolumab. In certain embodiments, the checkpoint inhibitor is Pembrolizumab. In certain embodiments, the checkpoint inhibitor is Interferon alfa-2b. In certain embodiments, Compound 1 is administered in combination with a checkpoint inhibitor. In certain embodiments, Compound 1 is administered in combination with a PD-1 checkpoint inhibitor. In certain embodiments, Compound 1 is administered in combination with a PD-L1 checkpoint inhibitor. In certain embodiments, Compound 1 is administered in combination with an IFNAR checkpoint inhibitor. In certain embodiments, Compound 1 is administered in combination with Nivolumab. In certain embodiments, Compound 1 is administered in combination with Pembrolizumab. In certain embodiments, Compound 1 is administered in combination with Interferon alfa-2b.

In certain embodiments, Compound 2 is administered in combination with a checkpoint inhibitor. In certain embodiments, Compound 3 is administered in combination with a checkpoint inhibitor. In certain embodiments, Compound 4 is administered in combination with a checkpoint inhibitor. In certain embodiments, Compound 5 is administered in combination with a checkpoint inhibitor. In certain embodiments, Compound 6 is administered in combination with a checkpoint inhibitor. In certain embodiments, Compound 7 is administered in combination with a checkpoint inhibitor. In certain embodiments, Compound 8 is administered in combination with a checkpoint inhibitor. In certain embodiments, Compound 9 is administered in combination with a checkpoint inhibitor. In certain embodiments, Compound 10 is administered in combination with a checkpoint inhibitor. In certain embodiments, Compound 11 is administered in combination with a checkpoint inhibitor. In certain embodiments, Compound 12 is administered in combination with a checkpoint inhibitor. In certain embodiments, Compound 13 is administered in combination with a checkpoint inhibitor. In certain embodiments, the checkpoint inhibitor is a PD-1 checkpoint inhibitor. In certain embodiments, the checkpoint inhibitor is a PD-L1 checkpoint inhibitor. In certain embodiments, the checkpoint inhibitor is an IFNAR checkpoint inhibitor. In certain embodiments, the checkpoint inhibitor is selected from Nivolumab, Pembrolizumab, and Interferon alfa-2b.

PD-1 inhibitors that blocks the interaction of PD-1 and PD-L1 by binding to the PD-1 receptor, and in turn inhibit immune suppression include, for example, nivolumab (Opdivo), pembrolizumab (Keytruda), pidilizumab, AMP-224 (AstraZeneca and MedImmune), PF-06801591 (Pfizer), MEDI0680 (AstraZeneca), PDR001 (Novartis), REGN2810 (Regeneron), SHR-12-1 (Jiangsu Hengrui Medicine Company and Incyte Corporation), TSR-042 (Tesaro), and the PD-L1/VISTA inhibitor CA-170 (Curis Inc.). PD-L1 inhibitors that block the interaction of PD-1 and PD-L1 by binding to the PD-L1 receptor, and in turn inhibits immune suppression, include for example, atezolizumab (Tecentriq), durvalumab (AstraZeneca and MedImmune), KN035 (Alphamab), and BMS-936559 (Bristol-Myers Squibb). CTLA-4 checkpoint inhibitors that bind to CTLA-4 and inhibits immune suppression include, but are not limited to, ipilimumab, tremelimumab (AstraZeneca and MedImmune), AGEN1884 and AGEN2041 (Agenus). LAG-3 checkpoint inhibitors, include, but are not limited to, BMS-986016 (Bristol-Myers Squibb), GSK2831781 (GlaxoSmithKline), IMP321 (Prima BioMed), LAG525 (Novartis), and the dual PD-1 and LAG-3 inhibitor MGD013 (MacroGenics). An example of a TIM-3 inhibitor is TSR-022 (Tesaro).

In certain embodiments, the checkpoint inhibitor is selected from nivolumab/OPDIVO®; pembrolizumab/KEYTRUDA®; and pidilizumab/CT-011, MPDL3280A/RG7446; MEDI4736; MSB0010718C; BMS 936559, a PDL2/lg fusion protein such as AMP 224 or an inhibitor of B7-H3 (e.g., MGA271), B7-H4, BTLA, HVEM, TIM3, GAL9, LAG 3, VISTA, KIR, 2B4, CD160, CGEN-15049, CHK 1, CHK2, A2aR, B-7 family ligands, or a combination thereof.

In certain embodiments, the PD-1 inhibitor is BGB-A317. In certain embodiments, the PD-L1 inhibitor is MED14736. In certain embodiments, the PD-L2 inhibitor is rHIgM12B7A.

In certain embodiments, the checkpoint inhibitor is a B7 inhibitor, for example a B7-H3 inhibitor or a B7-H4 inhibitor. In certain embodiments, the B7-H3 inhibitor is MGA271.

In certain embodiments, the checkpoint inhibitor is an OX40 agonist. In certain embodiments, the checkpoint inhibitor is an anti-OX40 antibody, for example anti-OX-40 or MEDI6469.

In certain embodiments, the checkpoint inhibitor is a GITR agonist. In certain embodiments, the GITR agonist is an anti-GITR antibody, for example TRX518.

In certain embodiments, the checkpoint inhibitor is a CD137 agonist. In certain embodiments, the CD137 agonist is an anti-CD137 antibody, for example PF-05082566.

In certain embodiments, the checkpoint inhibitor is a CD40 agonist. In certain embodiments, the CD40 agonist is an anti-CD40 antibody, for example CF-870,893.

In certain embodiments, the checkpoint inhibitor is an IDO inhibitor, for example INCB24360 or indoximod.

In certain embodiments the checkpoint inhibitor is selected from atezolizumab, avelumab, durvalumab, nivolumab, and pembrolizumab.

Additional Bioactive Agents

In another embodiment, an active compounds described herein can be administered in an effective amount for the treatment of abnormal tissue of the male reproductive system such as prostate or testicular cancer, in combination or alternation with an effective amount of an androgen (such as testosterone) inhibitor including but not limited to a selective androgen receptor modulator, a selective androgen receptor degrader, a complete androgen receptor degrader, or another form of partial or complete androgen antagonist. In certain embodiments, the prostate or testicular cancer is androgen-resistant. Non-limiting examples of anti-androgen compounds are provided in WO 2011/156518 and U.S. Pat. Nos. 8,455,534 and 8,299,112. Additional non-limiting examples of anti-androgen compounds include: enzalutamide, apalutamide, cyproterone acetate, chlormadinone acetate, spironolactone, canrenone, drospirenone, ketoconazole, topilutamide, abiraterone acetate, and cimetidine.

In certain embodiments, the bioactive agent is an ALK inhibitor. Examples of ALK inhibitors include but are not limited to Crizotinib, Alectinib, ceritinib, TAE684 (NVP-TAE684), GSK1838705A, AZD3463, ASP3026, PF-06463922, entrectinib (RXDX-101), and AP26113.

In certain embodiments, the bioactive agent is an EGFR inhibitor. Examples of EGFR inhibitors include erlotinib (Tarceva), gefitinib (Iressa), afatinib (Gilotrif), rociletinib (CO-1686), osimertinib (Tagrisso), olmutinib (Olita), naquotinib (ASP8273), nazartinib (EGF816), PF-06747775

(Pfizer), icotinib (BPI-2009), neratinib (HKI-272; PB272); avitinib (AC0010), EAI045, tarloxotinib (TH-4000; PR-610), PF-06459988 (Pfizer), tesevatinib (XL647; EXEL-7647; KD-019), transtinib, WZ-3146, WZ8040, CNX-2006, and dacomitinib (PF-00299804; Pfizer).

In certain embodiments, the bioactive agent is an HER-2 inhibitor. Examples of HER-2 inhibitors include trastuzumab, lapatinib, ado-trastuzumab emtansine, and pertuzumab.

In certain embodiments, the bioactive agent is a CD20 inhibitor. Examples of CD20 inhibitors include obinutuzumab, rituximab, fatumumab, ibritumomab, tositumomab, and ocrelizumab.

In certain embodiments, the bioactive agent is a JAK3 inhibitor. Examples of JAK3 inhibitors include tasocitinib.

In certain embodiments the bioactive agent is a JAK inhibitor, for example ruxolitinib.

In certain embodiments, the bioactive agent is a BCL-2 inhibitor. Examples of BCL-2 inhibitors include venetoclax, ABT-199 (4-[4-[[2-(4-Chlorophenyl)-4,4-dimethylcyclohex-1-en-1-yl]methyl]piperazin-1-yl]-N-[[3-nitro-4-[[(tetrahydro-2H-pyran-4-yl)methyl]amino]phenyl]sulfonyl]-2-[(1H-pyrrolo[2,3-b]pyridin-5-yl)oxy]benzamide), ABT-737 (4-[4-[[2-(4-chlorophenyl)phenyl]methyl]piperazin-1-yl]-N-[4-[[(2R)-4-(dimethylamino)-1-phenylsulfanylbutan-2-yl]amino]-3-nitrophenyl]sulfonylbenzamide) (navitoclax), ABT-263 ((R)-4-(4-((4'-chloro-4,4-dimethyl-3,4,5,6-tetrahydro-[1,1'-biphenyl]-2-yl)methyl)piperazin-1-yl)-N-((4-((4-morpholino-1-(phenylthio)butan-2-yl)amino)-3((trifluoromethyl)sulfonyl)phenyl)sulfonyl)benzamide), GX15-070 (obatoclax mesylate, (2Z)-2-[(5Z)-5-[(3,5-dimethyl-1H-pyrrol-2-yl)methylidene]-4-methoxypyrrol-2-ylidene]indole; methanesulfonic acid))), 2-methoxy-antimycin A3, YC137 (4-(4,9-dioxo-4,9-dihydronaphtho[2,3-d]thiazol-2-ylamino)-phenyl ester), pogosin, ethyl 2-amino-6-bromo-4-(1-cyano-2-ethoxy-2-oxoethyl)-4H-chromene-3-carboxylate, Nilotinib-d3, TW-37 (N-[4-[[2-(1,1-Dimethylethyl) phenyl]sulfonyl]phenyl]-2,3,4-trihydroxy-5-[[2-(1-methylethyl)phenyl]methyl]benzamide), Apogossypolone (ApoG2), HA14-1, AT101, sabutoclax, gambogic acid, or G3139 (Oblimersen).

In certain embodiments the bioactive agent is venetoclax.

In certain embodiments, the bioactive agent is a MEK inhibitor. MEK inhibitors are well known, and include, for example, trametinib/GSK1120212 (N-(3-{3-Cyclopropyl-5-[(2-fluoro-4-iodophenyl)amino]-6,8-dimethyl-2,4,7-trioxo-3,4,6,7-tetrahydropyrido[4,3-d]pyrimidin-l(2H-yl}phenyl) acetamide), selumetinib (6-(4-bromo-2-chloroanilino)-7-fluoro-N-(2-hydroxyethoxy)-3-methylbenzimidazole-5-carboxamide), pimasertib/AS703026/MSC 1935369 ((S)—N-(2,3-dihydroxypropyl)-3-((2-fluoro-4-iodophenyl)amino) isonicotinamide), XL-518/GDC-0973 (1-({3,4-difluoro-2-[(2-fluoro-4-iodophenyl)amino]phenyl}carbonyl)-3-[(2S)-piperidin-2-yl]azetidin-3-ol), refametinib/BAY869766/RDEAl 19 (N-(3,4-difluoro-2-(2-fluoro-4-iodophenylamino)-6-methoxyphenyl)-1-(2,3-dihydroxypropyl)cyclopropane-1-sulfonamide), PD-0325901 (N-[(2R)-2,3-Dihydroxypropoxy]-3,4-difluoro-2-[(2-fluoro-4-iodophenyl)amino]-benzamide), TAK733 ((R)-3-(2,3-Dihydroxypropyl)-6-fluoro-5-(2-fluoro-4-iodophenylamino)-8-methylpyrido[2,3-d]pyrimidine-4,7(3H,8H)-dione), MEK162/ARRY438162 (5-[(4-Bromo-2-fluorophenyl)amino]-4-fluoro-N-(2-hydroxyethoxy)-1-methyl-1H-benzimidazole-6-carboxamide), R05126766 (3-[[3-Fluoro-2-(methylsulfamoylamino)-4-pyridyl]methyl]-4-methyl-7-pyrimidin-2-yloxychromen-2-one), WX-554, R04987655/CH4987655 (3,4-difluoro-2-((2-fluoro-4-iodophenyl) amino)-N-(2-hydroxyethoxy)-5-((3-oxo-1,2-oxazinan-2yl) methyl)benzamide), or AZD8330 (2-((2-fluoro-4-iodophenyl)amino)-N-(2 hydroxyethoxy)-1,5-dimethyl-6-oxo-1,6-dihydropyridine-3-carboxamide), U0126-EtOH, PD184352 (CI-1040), GDC-0623, BI-847325, cobimetinib, PD98059, BIX 02189, BIX 02188, binimetinib, SL-327, TAK-733, PD318088.

In certain embodiments, the bioactive agent is a Raf inhibitor. Raf inhibitors are known and include, for example, Vemurafinib (N-[3-[[5-(4-Chlorophenyl)-1H-pyrrolo[2,3-b] pyridin-3-yl]carbonyl]-2,4-difluorophenyl]-1-propanesulfonamide), sorafenib tosylate (4-[4-[[4-chloro-3-(trifluoromethyl)phenyl]carbamoylamino]phenoxy]-N-methylpyridine-2-carboxamide; 4-methylbenzenesulfonate), AZ628 (3-(2-cyanopropan-2-yl)-N-(4-methyl-3-(3-methyl-4-oxo-3,4-dihydroquinazolin-6-ylamino)phenyl)benzamide), NVP-BHG712 (4-methyl-3-(1-methyl-6-(pyridin-3-yl)-1H-pyrazolo[3,4-d]pyrimidin-4-ylamino)-N-(3-(trifluoromethyl)phenyl)benzamide), RAF-265 (1-methyl-5-[2-[5-(trifluoromethyl)-1H-imidazol-2-yl] pyridin-4-yl]oxy-N-[4-(trifluoromethyl)phenyl] benzimidazol-2-amine), 2-Bromoaldisine (2-Bromo-6,7-dihydro-1H,5H-pyrrolo[2,3-c]azepine-4,8-dione), Raf Kinase Inhibitor IV (2-chloro-5-(2-phenyl-5-(pyridin-4-yl)-1H-imidazol-4-yl)phenol), Sorafenib N-Oxide (4-[4-[[[[4-Chloro-3(trifluoroMethyl)phenyl]aMino]carbonyl]aMino] phenoxy]-N-Methyl-2pyridinecarboxaMide 1-Oxide), PLX-4720, dabrafenib (GSK2118436), GDC-0879, RAF265, AZ 628, SB590885, ZM336372, GW5074, TAK-632, CEP-32496, LY3009120, and GX818 (Encorafenib).

In certain embodiments, the bioactive agent is an AKT inhibitor, including but not limited to, MK-2206, GSK690693, Perifosine, (KRX-0401), GDC-0068, Triciribine, AZD5363, Honokiol, 5 PF-04691502, and Miltefosine, a FLT-3 inhibitor, including but not limited to, P406, Dovitinib, Quizartinib (AC220), Amuvatinib (MP-470), Tandutinib (MLN518), ENMD-2076, and KW-2449, or a combination thereof.

In certain embodiments, the bioactive agent is an mTOR inhibitor. Examples of mTOR inhibitors include but are not limited to rapamycin and its analogs, everolimus (Afinitor), temsirolimus, ridaforolimus, sirolimus, and deforolimus. Examples of MEK inhibitors include but are not limited to tametinib/GSK1120212 (N-(3-{3-Cyclopropyl-5-[(2-fluoro-4-iodophenyl)amino]-6,8-dimethyl-2,4,7-trioxo-3,4,6,7-tetrahydropyrido[4,3-d]pyrimidin-l(2H-yl}phenyl)acetamide), selumetinob (6-(4-bromo-2-chloroanilino)-7-fluoro-N-(2-hydroxyethoxy)-3-methylbenzimidazole-5-carboxamide), pimasertib/AS703026/MSC1935369 ((S)—N-(2,3-dihydroxypropyl)-3-((2-fluoro-4-iodophenyl)amino) isonicotinamide), XL-518/GDC-0973 (1-({3,4-difluoro-2-[(2-fluoro-4-iodophenyl)amino]phenyl}carbonyl)-3-[(2S)-piperidin-2-yl]azetidin-3-ol) (cobimetinib), refametinib/BAY869766/RDEA119 (N-(3,4-difluoro-2-(2-fluoro-4-iodophenylamino)-6-methoxyphenyl)-1-(2,3-dihydroxypropyl)cyclopropane-1-sulfonamide), PD-0325901 (N-[(2R)-2,3-Dihydroxypropoxy]-3,4-difluoro-2-[(2-fluoro-4-iodophenyl)amino]-benzamide), TAK733 ((R)-3-(2,3-Dihydroxypropyl)-6-fluoro-5-(2-fluoro-4-iodophenylamino)-8-methylpyrido[2,3d]pyrimidine-4,7(3H,8H)-dione), MEK162/ARRY438162 (5-[(4-Bromo-2-fluorophenyl)amino]-4-fluoro-N-(2-hydroxyethoxy)-1-methyl-1H-benzimidazole-6 carboxamide), R05126766 (3-[[3-Fluoro-2-(methylsulfamoylamino)-4-pyridyl]methyl]-4-methyl-7-pyrimidin-2-yloxychromen-2-one), WX-554, R04987655/CH4987655

(3,4-difluoro-2-((2-fluoro-4-iodophenyl)amino)-N-(2-hydroxyethoxy)-5-((3-oxo-1,2-oxazinan-2 yl)methyl)benzamide), or AZD8330 (2-((2-fluoro-4-iodophenyl)amino)-N-(2-hydroxyethoxy)-1,5-dimethyl-6-oxo-1,6-dihydropyridine-3-carboxamide).

In certain embodiments, the bioactive agent is a RAS inhibitor. Examples of RAS inhibitors include but are not limited to Reolysin and siG12D LODER.

In certain embodiments, the bioactive agent is a HSP inhibitor. HSP inhibitors include but are not limited to Geldanamycin or 17-N-Allylamino-17-demethoxygeldanamycin (17AAG), and Radicicol.

In certain embodiments the bioactive agent is a biphosphonate. Examples of biphosphonates include but are not limited to clodronate, pamidronate, and zoledronic acid.

Additional bioactive compounds include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, aFLT-3 inhibitor, a VEGFR inhibitor, an aurora kinase inhibitor, a PIK-1 modulator, an HDAC inhibitor, a c-MET inhibitor, a PARP inhibitor, a Cdk inhibitor, an IGFR-TK inhibitor, an anti-HGF antibody, a focal adhesion kinase inhibitor, a Map kinase (mek) inhibitor, a VEGF trap antibody, pemetrexed, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, $IPdR_1$ KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo [2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258); 3-[5-(methylsulfonylpiperadinemethyl)-indolyl-quinolone, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, *Bacillus* Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezomib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

In certain embodiments, the bioactive agent is selected from, but are not limited to, Imatinib mesylate (Gleevac®), Dasatinib (Sprycel®), Nilotinib (Tasigna®), Bosutinib (Bosulif®), Trastuzumab (Herceptin®), trastuzumab-DM1, Pertuzumab (Perjeta™), Lapatinib (Tykerb®), Gefitinib (Iressa®), Erlotinib (Tarceva®), Cetuximab (Erbitux®), Panitumumab (Vectibix®), Vandetanib (Caprelsa®), Vemurafenib (Zelboraf®), Vorinostat (Zolinza®), Romidepsin (Istodax®), Bexarotene (Tagretin®), Alitretinoin (Panretin®), Tretinoin (Vesanoid®), Carfilizomib (Kyprolis™), Pralatrexate (Folotyn®), Bevacizumab (Avastin®), Ziv-aflibercept (Zaltrap®), Sorafenib (Nexavar®), Sunitinib (Sutent®), Pazopanib (Votrient®), Regorafenib (Stivarga®), and Cabozantinib (Cometriq™).

In certain aspects, the bioactive agent is an anti-inflammatory agent, a chemotherapeutic agent, a radiotherapeutic, an additional therapeutic agent, or an immunosuppressive agent.

Suitable chemotherapeutic bioactive agents include, but are not limited to, a radioactive molecule, a toxin, also referred to as cytotoxin or cytotoxic agent, which includes any agent that is detrimental to the viability of cells, and liposomes or other vesicles containing chemotherapeutic compounds. General anti-cancer pharmaceutical agents include: Vincristine (Oncovin®) or liposomal vincristine (Marqibo®), Daunorubicin (daunomycin or Cerubidine®) or doxorubicin (Adriamycin®), Cytarabine (cytosine arabinoside, ara-C, or Cytosar®), L-asparaginase (Elspar®) or PEG-L-asparaginase (pegaspargase or Oncaspar®), Etoposide (VP-16), Teniposide (Vumon®), 6-mercaptopurine (6-MP or Purinethol®), Methotrexate, Cyclophosphamide (Cytoxan®), Prednisone, Dexamethasone (Decadron), imatinib (Gleevec®), dasatinib (Sprycel®), nilotinib (Tasigna®), bosutinib (Bosulif®), and ponatinib (Iclusig™). Examples of additional suitable chemotherapeutic agents include but are not limited to 1-dehydrotestosterone, 5-fluorouracil decarbazine, 6-mercaptopurine, 6-thioguanine, actinomycin D, adriamycin, aldesleukin, an alkylating agent, allopurinol sodium, altretamine, amifostine, anastrozole, anthramycin (AMC)), an anti-mitotic agent, cis-dichlorodiamine platinum (II) (DDP) cisplatin), diamino dichloro platinum, anthracycline, an antibiotic, an antimetabolite, asparaginase, BCG live (intravesical), betamethasone sodium phosphate and betamethasone acetate, bicalutamide, bleomycin sulfate, busulfan, calcium leucouorin, calicheamicin, capecitabine, carboplatin, lomustine (CCNU), carmustine (BSNU), Chlorambucil, Cisplatin, Cladribine, Colchicin, conjugated estrogens, Cyclophosphamide, Cyclothosphamide, Cytarabine, Cytarabine, cytochalasin B, Cytoxan, Dacarbazine, Dactinomycin, dactinomycin (formerly actinomycin), daunirubicin HCL, daunorucbicin citrate, denileukin diftitox, Dexrazoxane, Dibromomannitol, dihydroxy anthracin dione, Docetaxel, dolasetron mesylate, doxorubicin HCL, dronabinol, *E. coli* L-asparaginase, emetine, epoetin-α, *Erwinia* L-asparaginase, esterified estrogens, estradiol, estramustine phosphate sodium, ethidium bromide, ethinyl estradiol, etidronate, etoposide citrororum factor, etoposide phosphate, filgrastim, floxuridine, fluconazole, fludarabine phosphate, fluorouracil, flutamide, folinic acid, gemcitabine HCL, glucocorticoids, goserelin acetate, gramicidin D, granisetron HCL, hydroxyurea, idarubicin HCL, ifosfamide, interferon α-2b, irinotecan HCL, letrozole, leucovorin calcium, leuprolide acetate, levamisole HCL, lidocaine, lomustine, maytansinoid, mechlorethamine HCL, medroxyprogesterone acetate, megestrol acetate, melphalan HCL, mercaptipurine, mesna, methotrexate, methyltestosterone, mithramycin, mitomycin C, mitotane, mitoxantrone, nilutamide, octreotide acetate, ondansetron HCL, paclitaxel, pamidronate disodium, pentostatin, pilocarpine HCL, plimycin, polifeprosan 20 with carmustine implant, porfimer sodium, procaine, procarbazine HCL, propranolol, rituximab, sargramostim, streptozotocin, tamoxifen, taxol, teniposide, tenoposide, testolactone, tetracaine, thioepa chlorambucil, thioguanine, thiotepa, topotecan HCL, toremifene citrate, trastuzumab, tretinoin, valrubicin, vinblastine sulfate, vincristine sulfate, and vinorelbine tartrate.

In some embodiments, the compound of the present invention is administered in combination with a chemotherapeutic agent (e.g., a cytotoxic agent or another chemical compound useful in the treatment of cancer). Examples of chemotherapeutic agents include alkylating agents, antimetabolites, folic acid analogs, pyrimidine analogs, purine analogs and related inhibitors, *vinca* alkaloids, epipodopyllotoxins, antibiotics, L-Asparaginase, topoisomerase inhibitors, interferons, platinum coordination complexes, anthracenedione substituted urea, methyl hydrazine derivatives, adrenocortical suppressant, adrenocorticosteroides, progestins, estrogens, antiestrogen, androgens, antiandrogen, and gonadotropin-releasing hormone analog. Also included is 5-fluorouracil (5-FU), leucovorin (LV), irenotecan, oxaliplatin, capecitabine, paclitaxel, and doxetaxel. Non-limiting examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammall and calicheamicin omegall (see, e.g., Agnew, Chem. Inti. Ed Engl. 33:183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin, including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, OR); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, NJ), ABRAXANE®, cremophor-free, albumin-engineered nanoparticle formulation of paclitaxel (American Pharmaceutical Partners, Schaumberg, IL), and TAXOTERE® doxetaxel (Rhone-Poulenc Rorer, Antony, France); chloranbucil; GEMZAR® gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DMFO); retinoids such as retinoic acid; capecitabine; and pharmaceutically acceptable salts, acids or derivatives of any of the above. Two or more chemotherapeutic agents can be used in a cocktail to be administered in combination with the compound of the present invention. Suitable dosing regimens of combination chemotherapies are known in the ar. For example, combination dosing regimens are described in Saltz et al., Proc. Am. Soc. Clin. Oncol. 18:233a (1999) and Douillard et al., Lancet 355(9209): 1041-1047 (2000).

Additional therapeutic agents that can be administered in combination with a compound disclosed herein can include bevacizumab, sutinib, sorafenib, 2-methoxyestradiol or 2ME2, finasunate, vatalanib, vandetanib, aflibercept, volociximab, etaracizumab (MEDI-522), cilengitide, erlotinib, cetuximab, panitumumab, gefitinib, trastuzumab, dovitinib, figitumumab, atacicept, rituximab, alemtuzumab, aldesleukine, atlizumab, tocilizumab, temsirolimus, everolimus, lucatumumab, dacetuzumab, HLL1, huN901-DM1, atiprimod, natalizumab, bortezomib, carfilzomib, marizomib, tanespimycin, saquinavir mesylate, ritonavir, nelfinavir mesylate, indinavir sulfate, belinostat, panobinostat, mapatumumab, lexatumumab, dulanermin, ABT-737, oblimersen, plitidepsin, talmapimod, P276-00, enzastaurin, tipifarnib, perifosine, imatinib, dasatinib, lenalidomide, thalidomide, simvastatin, celecoxib, bazedoxifene, AZD4547, rilotumumab, oxaliplatin (Eloxatin), PD0332991, ribociclib (LEE011), amebaciclib (LY2835219), HDM201, fulvestrant (Faslodex), exemestane (Aromasin), PIM447, ruxolitinib (INC424), BGJ398, necitumumab, pemetrexed (Alimta), and ramucirumab (IMC-1121B).

In certain embodiments, the additional therapy is a monoclonal antibody (MAb). Some MAbs stimulate an immune response that destroys cancer cells. Similar to the antibodies produced naturally by B cells, these MAbs may "coat" the cancer cell surface, triggering its destruction by the immune system. For example, bevacizumab targets vascular endothelial growth factor (VEGF), a protein secreted by tumor cells and other cells in the tumor's microenvironment that promotes the development of tumor blood vessels. When bound to bevacizumab, VEGF cannot interact with its cellular receptor, preventing the signaling that leads to the growth of new blood vessels. Similarly, cetuximab and panitumumab target the epidermal growth factor receptor (EGFR), and trastuzumab targets the human epidermal growth factor receptor 2 (HER-2). MAbs that bind to cell surface growth factor receptors prevent the targeted receptors from sending their normal growth-promoting signals. They may also trigger apoptosis and activate the immune system to destroy tumor cells.

In one aspect of the present invention, the bioactive agent is an immunosuppressive agent. The immunosuppressive agent can be a calcineurin inhibitor, e.g. a cyclosporin or an ascomycin, e.g. Cyclosporin A (NEORAL®), FK506 (tacrolimus), pimecrolimus, a mTOR inhibitor, e.g. rapamycin or a derivative thereof, e.g. Sirolimus (RAPAMUNE®), Everolimus (Certican®), temsirolimus, zotarolimus, biolimus-7, biolimus-9, a rapalog, e.g. ridaforolimus, azathioprine, campath 1H, a SiP receptor modulator, e.g. fingolimod or an analogue thereof, an anti IL-8 antibody, mycophenolic acid or a salt thereof, e.g. sodium salt, or a prodrug thereof, e.g. Mycophenolate Mofetil (CELLCEPT®), OKT3 (ORTHOCLONE OKT3@), Prednisone, ATGAM®, THYMOGLOBULIN®, Brequinar Sodium, OKT4, T10B9.A-3A, 33B3.1, 15-deoxyspergualin, tresperimus, Leflunomide ARAVA®, CTLAI-Ig, anti-CD25, anti-IL2R, Basiliximab (SIMULECT®), Daclizumab (ZENAPAX®), mizorbine, methotrexate, dexamethasone, ISAtx-247, SDZ ASM 981 (pimecrolimus, Elidel®), CTLA4lg (Abatacept), belatacept, LFA3lg, etanercept (sold as Enbrel® by Immunex), adalimumab (Humira®), infliximab (Remicade®), an anti-LFA-1 antibody, natalizumab (Antegren®), Enlimomab, gavilimomab, antithymocyte immunoglobulin, siplizumab, Alefacept efalizumab, pentasa, mesalazine, asacol, codeine phosphate, benorylate, fenbufen, naprosyn, diclofenac, etodolac and indomethacin, aspirin and ibuprofen.

In some embodiments, the bioactive agent is a therapeutic agent which is a biologic such a cytokine (e.g., interferon or an interleukin (e.g., IL-2)) used in cancer treatment. In some embodiments the biologic is an anti-angiogenic agent, such as an anti-VEGF agent, e.g., bevacizumab (AVASTIN®). In some embodiments the biologic is an immunoglobulin-based biologic, e.g., a monoclonal antibody (e.g., a humanized antibody, a fully human antibody, an Fc fusion protein or a functional fragment thereof) that agonizes a target to stimulate an anti-cancer response, or antagonizes an antigen important for cancer. Such agents include RITUXAN® (rituximab); ZENAPAX® (daclizumab); SIMULECT® (basiliximab); SYNAGIS® (palivizumab); REMICADE® (infliximab); HERCEPTIN® (trastuzumab); MYLOTARG® (gemtuzumab ozogamicin); CAMPATH® (alemtuzumab); ZEVALIN® (ibritumomab tiuxetan); HUMIRA® (adalimumab); XOLAIR® (omalizumab); BEXXAR® (tositumomab-l-131); RAPTIVA® (efalizumab); ERBITUX® (cetuximab); AVASTIN® (bevacizumab); TYSABRI® (natalizumab); ACTEMRA® (tocilizumab); VECTIBIX® (panitumumab); LUCENTIS® (ranibizumab); SOURIS® (eculizumab); CIMZIA® (certolizumab pegol); SIMPONI® (golimumab); ILARIS® (canakinumab); STELARA® (ustekinumab); ARZERRA® (ofatumumab); PROLIA® (denosumab); NUMAX® (motavizumab); ABTHRAX® (raxibacumab); BENLYSTA® (belimumab); YERVOY® (ipilimumab); ADCETRIS® (brentuximab vedotin); PERJETA® (pertuzumab); KADCYLA® (ado-trastuzumab emtansine); and GAZYVA® (obinutuzumab). Also included are antibody-drug conjugates.

In certain embodiments, the additional therapy is bendamustine. In certain embodiments, the additional therapy is obinutuzmab. In certain embodiments, the additional therapy is a proteasome inhibitor, for example ixazomib or oprozomib. In certain embodiments, the additional therapy is a histone deacetylase inhibitor, for example ACY241. In certain embodiments, the additional therapy is a BET inhibitor, for example GSK525762A, OTX015, BMS-986158, TEN-010, CPI-0610, INCB54329, BAY1238097, FT-1101, ABBV-075, BI 894999, GS-5829, GSK1210151A (I-BET-151), CPI-203, RVX-208, XD46, MS436, PFI-1, RVX2135, ZEN3365, XD14, ARV-771, MZ-1, PLX5117, 4-[2-(cyclopropylmethoxy)-5-(methanesulfonyl)phenyl]-2-methylisoquinolin-1(2H)-one, EP11313 and EP11336. In certain embodiments, the additional therapy is an MCL-1 inhibitor, for example AZD5991, AMG176, MIK665, S64315, or S63845. In certain embodiments, the additional therapy is an LSD-1 inhibitor, for example ORY-1001, ORY-2001, INCB-59872, IMG-7289, TAK-418, GSK-2879552, 4-[2-(4-amino-piperidin-1-yl)-5-(3-fluoro-4-methoxy-phenyl)-1-methyl-6-oxo-1,6-dihydropyrimidin-4-yl]-2-fluorobenzonitrile or a salt thereof. In certain embodiments, the additional therapy is a CS1 antibody, for example elotuzumab. In certain embodiments, the additional therapy is a CD38 antibody, for example daratumumab or isatuximab. In certain embodiments, the additional therapy is a BCMA antibody or antibody-conjugate, for example GSK2857916 or BI 836909.

In certain embodiments, the bioactive agent is selinexor. In certain embodiments, Compound 1 is administered in combination with selinexor. In certain embodiments, Compound 1 is administered in combination with aspirin.

In certain embodiments, Compound 2, Compound 3, Compound 4, Compound 5, Compound 6, Compound 7, Compound 8, Compound 9, Compound 10, Compound 11, Compound 12, or Compound 13 is administered in combination with selinexor. In certain embodiments, Compound 2, Compound 3, Compound 4, Compound 5, Compound 6, Compound 7, Compound 8, Compound 9, Compound 10, Compound 11, Compound 12, or Compound 13 is administered in combination with aspirin.

In other embodiments a compound described herein is administered in combination with a drug selected from selinexor, oxaphenamide, belantamab mafodotin, denosumab, zoledronic acid, plerixafor, eltrombopag, ipilumumab, palbociclib, ricolinostat, afuresertib, dinaciclib, filanesib, indatuximab ravtansine, masitinib, sonidegib, sotatercept, ulocuplumab, and urelumab.

In certain embodiments Compound 1 is used in combination with a chemokine receptor antagonist, for example plerixafor.

In certain embodiments Compound 1 is used in combination with a vaccine, for example PVX-410.

In certain embodiments Compound 1 is used in combination with a chemotherapeutic agent, for example bendamustine, busulfan, carmustine, cyclophosphamide, doxorubicin, etoposide, fludarabine, melphalan, or vincristine.

In certain embodiments Compound 1 is used in combination with a conjugated antibody, for example belantamab mafodotin, CC-99712, HDP-101, or MEDI2228.

In certain embodiments Compound 1 is used in combination with a phospholipid-drug conjugate, for example CLR 131.

In certain embodiments a compound described herein is used in combination with a chemokine receptor antagonist, for example plerixafor.

In certain embodiments a compound described herein is used in combination with a vaccine, for example PVX-410.

In certain embodiments a compound described herein is used in combination with a chemotherapeutic agent, for example bendamustine, busulfan, carmustine, cyclophosphamide, doxorubicin, etoposide, fludarabine, melphalan, or vincristine.

In certain embodiments a compound described herein is used in combination with a conjugated antibody, for example belantamab mafodotin, CC-99712, HDP-101, or MEDI2228.

In certain embodiments a compound described herein is used in combination with a phospholipid-drug conjugate, for example CLR 131.

In certain embodiments a compound described herein is used in combination with a CHOP regimen (cyclophosphamide, vincristine, prednisone, and daunorubicin). In certain embodiments Compound 1 is used in combination with a CHOP regimen (cyclophosphamide, vincristine, prednisone, and daunorubicin). In certain embodiments Compound 1, rituximab, and CHOP are administered in combination.

In certain embodiments a compound described herein is used in combination with a CVP regimen (cyclophosphamide, vincristine, and prednisone). In certain embodiments Compound 1 is used in combination with a CVP regimen (cyclophosphamide, vincristine, and prednisone). In certain embodiments Compound 1, rituximab, and CVP are administered in combination.

In certain embodiments a compound described herein is used in combination with a romidepsin, belinostat, or brentuximab to treat cancer, for example T-NHL. In certain embodiments Compound 1 is used in combination with a romidepsin, belinostat, or brentuximab to treat cancer, for example T-NHL.

In certain embodiments a compound described herein is used in combination with a polatuzumab, tafastamab, CAR-T, a BTK inhibitor, or a PI3Kinase inhibitor to treat cancer, for example B-NHL. In certain embodiments Compound 1 is used in combination with a polatuzumab, tafastamab, CAR-T, a BTK inhibitor, or a PI3Kinase inhibitor to treat cancer, for example B-NHL In certain embodiments Compound 1 is used in the treatment of relapsed and/or refractory mantle cell leukemia. In certain embodiments Compound 1 and rituximab are used in the treatment of relapsed and/or refractory mantle cell leukemia. In certain embodiments Compound 1, rituximab, and bendamustine are used in the treatment of relapsed and/or refractory mantle cell leukemia. In certain embodiments Compound 1, rituximab, and ibrutinib are used in the treatment of relapsed and/or refractory mantle cell leukemia.

In certain embodiments Compound 1 is used in the treatment of relapsed and/or refractory marginal zone leukemia. In certain embodiments Compound 1 and rituximab are used in the treatment of relapsed and/or refractory marginal zone leukemia. In certain embodiments Compound 1, rituximab, and dexamethasone are used in the treatment of relapsed and/or refractory marginal zone leukemia.

In certain embodiments Compound 1 is used in combination with rituximab and DHAP (dexamethasone, cytarabine, and cisplatin). In certain embodiments Compound 1 is used in combination with DHAP (dexamethasone, cytarabine, and cisplatin). In certain embodiments Compound 1 is used in combination with rituximab and ICE (ifosfamide, carboplatin, and etoposide). In certain embodiments Compound 1 is used in combination with ICE (ifosfamide, carboplatin, and etoposide). In certain embodiments Compound 1 is used in combination with rituximab and GemOx (gemcitabine and oxaliplatin). In certain embodiments Compound 1 is used in combination with GemOx (gemcitabine and oxaliplatin). In certain embodiments Compound 1 is used in combination with polatuzumab and brentuximab. In certain embodiments Compound 1 is used in combination with polatuzumab. In certain embodiments Compound 1 is used in combination with tafasitimab. In certain embodiments Compound 1 is used in combination with tafasitimab and lenolidomide. In certain embodiments Compound 1 is used in combination with rituximab and lenolidomide. In certain embodiments Compound 1 is used in combination with anti CD19 CART (for example axicabtagene, lisocabtagene, tisafenlucleucel, loncastuximab, or tesirine). In certain embodiments one of the above combinations is used in the treatment of DLBCL or B-NHL.

In certain embodiments Compound 1 is used in combination with praltrexate. In certain embodiments Compound 1 is used in combination with bendamustine. In certain embodiments Compound 1 is used in combination with brexucabtagene. In certain embodiments Compound 1 is used in combination with bortezomib and rituximab. In certain embodiments Compound 1 is used in combination with bendamustine and rituximab. In certain embodiments Compound 1 is used in combination with VR-CAP (rituximab, cyclophospharmide, doxorubicin, prednisone, and bortzomib).

In certain embodiments Compound 1 is used in combination with carfilzomib and daratumumab.

In certain embodiments Compound 1 is used in combination with abecma. In certain embodiments Compound 1 is used in combination with melfiufen. In certain embodiments Compound 1 is used in combination with ciltacabtagene autoleucel.

In certain embodiments a compound described herein, for example Compound 1 is used in a therapy in the table below. In other embodiments Compound 1 is replaced with a different compound described herein.

| Disease | Characterization | Agent(s) |
|---|---|---|
| MCL | Relapsed and/or refractory | Compound 1 |
| MCL | Relapsed and/or refractory | Compound 1 and rituximab |
| MCL | Relapsed and/or refractory | Compound 1, rituximab, and bendamustine |
| MCL | Relapsed and/or refractory | Compound 1, rituximab, and ibrutinib |
| Follicular or marginal zone lymphoma | Relapsed and/or refractory | Compound 1 |
| Follicular, marginal zone, mucosa-associated lymphoid tissue, or small lymphocytic, lymphoma | Relapsed and/or refractory | Compound 1 and rituximab |
| Mantle cell lymphoma | Relapsed and/or refractory | Compound 1 and rituximab |
| Follicular, marginal zone, mucosa-associated lymphoid tissue, or small lymphocytic, lymphoma | Relapsed and/or refractory | Compound 1, rituximab, and dexamethasone |
| Mantle cell lymphoma | Relapsed and/or refractory | Compound 1, rituximab, and dexamethasone |
| Diffuse large b-cell, mantle cell, or follicular lymphoma | Relapsed and/or refractory | Compound 1 |
| Transformed: diffuse large b-cell, mantle cell, or follicular lymphoma | Relapsed and/or refractory | Compound 1 |
| Diffuse large b-cell, mantle cell, or follicular lymphoma | Relapsed and/or refractory | Compound 1 and rituximab |
| Transformed: diffuse large b-cell, mantle cell, or follicular lymphoma | Relapsed and/or refractory | Compound 1, rituximab, and benadmustine |
| MCL | Frontline | Compound 1 |
| MCL | Frontline | Compound 1 and rituximab |
| MCL | Frontline | Compound 1, rituximab, and bendamustine |
| Follicular, marginal zone, or small lymphocytic lymphoma | Frontline | Compound 1 and rituximab |
| Follicular, marginal zone, or small lymphocytic lymphoma | Frontline | Compound 1, rituximab, and CHOP |
| Diffuse large b-cell lymphoma | Frontline | Compound 1, rituximab, and CHOP |

VI. Pharmaceutical Compositions

Any of the compounds as disclosed herein can be administered as the neat chemical, but are more typically administered as a pharmaceutical composition that includes an effective amount for a host, typically a human, in need of such treatment for any of the disorders described herein. Accordingly, the disclosure provides pharmaceutical compositions comprising an effective amount of compound or pharmaceutically acceptable salt together with at least one pharmaceutically acceptable carrier for any of the uses described herein. The pharmaceutical composition may contain a compound or salt as the only active agent, or, in an alternative embodiment, the compound and at least one additional active agent.

In certain embodiments, the pharmaceutical composition is in a dosage form that contains from about 0.1 mg to about 2000 mg, from about 10 mg to about 1000 mg, from about 50 mg to about 600 mg, or from about 100 mg to about 400 mg of the active compound. In another embodiment the pharmaceutical composition is in a dosage form that contains from about 0.1 mg to about 100 mg, from about 0.5 mg to about 100 mg, from about 1 mg to about 50 mg, or from about 2 mg to about 25 mg of the active compound. In another embodiment the pharmaceutical composition is in a dosage form that contains from about 0.1 mg to about 10 mg, from about 0.5 mg to about 8 mg, from about 0.5 mg to about 6 mg, or from about 0.5 mg to about 5 mg of the active compound. Examples are dosage forms with at least, or in some embodiments, not more than, 0.1, 1, 5, 10, 25, 50, 100, 200, 250, 300, 400, 500, 600, 700, or 750 mg of active compound, or its salt.

In certain embodiments, the pharmaceutical composition is in a dosage form that contains from about 1 μg to about 2000 μg, from about 10 μg to about 1000 μg, from about 50 μg to about 600 μg, or from about 100 μg to about 400 μg of the active compound. In another embodiment the pharmaceutical composition is in a dosage form that contains from about 1 μg to about 400 μg, from about 5 μg to about 400 μg, from about 10 mg to about 250 μg, or from about 25 μg to about 250 μg of the active compound. Examples are dosage forms with at least, or in some embodiments, not more than, 0.1, 1, 5, 10, 25, 50, 100, 200, 250, 300, 400, 500, 600, 700, or 750 μg of active compound, or its salt.

The pharmaceutical composition may also include a molar ratio of the active compound and an additional bioactive agent. For example, the pharmaceutical composition may contain a molar ratio of about 0.0005:1, about 0.001:1, about 0.01:1, about 0.05:1, or about 0.1:1 of active compound to an anti-inflammatory or immunosuppressing agent. For example, the pharmaceutical composition may contain a molar ratio of about 0.5:1, about 1:1, about 2:1, about 3:1 or from about 1.5:1 to about 4:1 of active compound to an anti-inflammatory or immunosuppressing agent. Compounds disclosed herein may be administered orally, topically, parenterally, by inhalation or spray, sublingually, via implant, including ocular implant, transdermally, via buccal administration, rectally, as an ophthalmic solution, injection, including ocular injection, intravenous, intra-aortal, intracranial, subdermal, intraperitioneal, subcutaneous, transnasal, sublingual, or rectal or by other means, in dosage unit formulations containing conventional pharmaceutically acceptable carriers. For ocular delivery, the compound can be administered, as desired, for example, via intravitreal, intrastromal, intracameral, sub-tenon, sub-retinal, retro-bulbar, peribulbar, suprachorodial, conjunctival, subconjunctival, episcleral, periocular, transscleral, retrobulbar, posterior juxtascleral, circumcorneal, or tear duct injections, or through a mucus, mucin, or a mucosal barrier, in an immediate or controlled release fashion or via an ocular device.

The pharmaceutical composition may be formulated as any pharmaceutically useful form, e.g., as an aerosol, a cream, a gel, a pill, an injection or infusion solution, a capsule, a tablet, a syrup, a transdermal patch, a subcutaneous patch, a dry powder, an inhalation formulation, in a medical device, suppository, buccal, or sublingual formulation, parenteral formulation, or an ophthalmic solution. Some dosage forms, such as tablets and capsules, are subdivided into suitably sized unit doses containing appropriate quantities of the active components, e.g., an effective amount to achieve the desired purpose.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, flavorants, glidants, lubricants, preservatives, stabilizers, surfactants, tableting agents, and wetting agents. Some carriers may be listed in more than one class, for example vegetable oil may be used as a lubricant in some formulations and a diluent in others. Pharmaceutically acceptable carriers are carriers that do not cause any severe adverse reactions in the human body when dosed in the amount that would be used in the corresponding pharmaceutical composition. Exemplary pharmaceutically acceptable carriers include sugars, starches, celluloses, powdered tragacanth, malt, gelatin; talc, and vegetable oils. Optional active agents may be included in a pharmaceutical composition, which do not substantially interfere with the activity of the compound of the present invention.

The pharmaceutical compositions/combinations can be formulated for oral administration. These compositions can contain any amount of active compound that achieves the desired result, for example between 0.1 and 99 weight % (wt. %) of the compound and usually at least about 5 wt. % of the compound. Some embodiments contain from about 25 wt. % to about 50 wt. % or from about 5 wt. % to about 75 wt. % of the compound.

Formulations suitable for rectal administration are typically presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, Pharmaceutical Research 3 (6):318 (1986)) and typically take the form of an optionally buffered aqueous solution of the active compound. In certain embodiments, microneedle patches or devices are provided for delivery of drugs across or into biological tissue, particularly the skin. The microneedle patches or devices permit drug delivery at clinically relevant rates across or into skin or other tissue barriers, with minimal or no damage, pain, or irritation to the tissue.

Formulations suitable for administration to the lungs can be delivered by a wide range of passive breath driven and active power driven single/-multiple dose dry powder inhalers (DPI). The devices most commonly used for respiratory delivery include nebulizers, metered-dose inhalers, and dry powder inhalers. Several types of nebulizers are available, including jet nebulizers, ultrasonic nebulizers, and vibrating mesh nebulizers. Selection of a suitable lung delivery device depends on parameters, such as nature of the drug and its formulation, the site of action, and pathophysiology of the lung.

In certain embodiments, a compound described herein, for example Compound 1, is formulated as described in Table A.

TABLE A

Example Drug Product Composition

| Item # | Ingredients | A mg/ca | B mg/ca | C mg/caps |
|---|---|---|---|---|
| 1 | Compound 1 | 0.40 | 0.10 | 0.025 |
| 2 | PEG 400 | 1187.4 | 296.87 | 249.21 |
| | TOTAL | 1200.0 | 300.00 | 250.00 |

In certain embodiments, the present invention provides a pharmaceutical composition comprising Compound 1, a nonaqueous solvent, a preservative, and/or a pH control agent.

In certain embodiments, a compound described herein, for example Compound 1, is formulated as described herein for example as described in Table B or Table C.

Non-limiting examples of preservatives include alcohols (for example, ethanol, benzyl alcohol), aluminum acetate, benzalkonium chloride, benzethonium chloride, benzoic acid and salts thereof (for example, potassium benzoate, sodium benzoate), boric acid and salts thereof (for example, sodium borate), bronopol, butylene glycol, butylated hydroxyanisole, calcium acetate, calcium chloride, cetrimide, chlorhexidine, chlorobutanol, chlorocresol, chloroxylenol, citric acid monohydrate, cresol, dimethyl ether, edetic acid and salts thereof, gelatin, glycerin, hexetidine, imidurea, lactic acid and salts thereof (for example, calcium lactate, sodium lactate), monothioglycerol, parabens (for example, butylparaben, ethylparaben methylparaben, propylparaben, propylparaben sodium), pentetic acid and salts thereof, phenol, phenoxyethanol, phenylethyl alcohol, phenylmercuric acetate, phenylmercuric borate, phenylmercuric nitrate, propyl gallate, potassium metabisulfite, sorbic acid and salts thereof (for example, potassium sorbate), propionic acid and salts thereof (for example, sodium propionate), propylene glycol, sodium acetate, sodium sulfite, sulfur dioxide, thimerosal, and xylitol.

The term pH control agent can be used interchangeably with pH adjustment agent, pH regulator, and/or buffering agent. Non-limiting examples of pH control agents include acetic acid, glacial acetic acid, adipic acid, strong ammonia solution and salts thereof (for example, ammonium carbonate, ammonium chloride, ammonium phosphate), arginine, boric acid and salts thereof (for example, sodium borate), calcium carbonate, calcium hydroxide, calcium lactate, calcium phosphate, tribasic, citric acid (anhydrous or monohydrate) and salts thereof (for example, potassium citrate, sodium citrate), diethanolamine, fumaric acid and salts thereof, glycine, gluconic acid, hydrochloric acid, diluted hydrochloric acid, alpha-lactalbumin, lactic acid and salts thereof (for example, sodium lactate solution), lysine hydrochloride, maleic acid, malic acid, methionine, monoethanolamine, monosodium glutamate, meglumine, nitric acid, phosphoric acid and salts thereof (for example, dibasic sodium phosphate, monobasic sodium phosphate, potassium phosphate, potassium hydrogen phosphate, dibasic, potassium phosphate), diluted phosphoric acid, potassium bicarbonate, potassium hydroxide, potassium metaphosphate, monobasic, propionic acid, racemethionine, sodium acetate, sodium bicarbonate, sodium carbonate, sodium hydroxide, succinic acid, sulfuric acid, tartaric acid, trolamine, a hydroxide, an amine, and salts thereof.

Non-limiting examples of buffering agents include, but are not limited to, adipic acid, ammonia solution, boric acid, calcium carbonate, calcium hydroxide, calcium lactate, calcium phosphate, citric acid, sodium phosphate, diethanolamine, maleic acid, malic acid, methionine, monoethanolamine, sodium glutamate, phosphoric acid, potassium citrate, sodium acetate, sodium bicarbonate, sodium borate, sodium carbonate, sodium citrate, sodium hydroxide, sodium lactate and triethanolamine.

In certain embodiments, the buffering agent is selected from carbonates, citrates, gluconates, lactates, phosphates, tartrates, potassium metaphosphate, potassium phosphate, monobasic, sodium acetate, sodium citrate, anhydrous and dihydrate.

In certain embodiments, the pharmaceutical composition includes water.

In certain embodiments, the pharmaceutical composition includes a non-aqueous or anhydrous solvent.

Nonlimiting examples of non-aqueous solvents include alcohols (for example, ethanol), PEG 300, PEG 400, propylene glycol, cremophor, caplex 355, Capryol™ 90, Lauroglycol™ 90, TranscutolHP, butylated hydroxytoluene, benzyl alcohol, citric acid, triacetin, propylene glycol, fats and oils.

TABLE B

| 25 μg strength formulation | | | |
|---|---|---|---|
| Ingredient | mg/capsule (25 μg) | Percent w/w | Function |
| Compound 1 | 0.0250 | 0.010 | Drug Substance |
| PEG 400 | 247.4125 | 98.965 | Nonaqueous solvent |
| Butylated Hydroxytoluene | 0.0625 | 0.025 | Preservative |
| Citric Acid, Anhydrous | 2.500 | 1.000 | pH control |
| Total | 250.0000 | 100.000 | |

TABLE C

| 100 μg strength formulation | | | |
|---|---|---|---|
| Ingredient | mg/capsule (100 μg) | Percent w/w | Function |
| Compound 1 | 0.100 | 0.033 | Drug Substance |
| PEG 400 | 296.825 | 98.942 | Nonaqueous solvent |
| Butylated Hydroxytoluene, | 0.075 | 0.025 | Preservative |
| Citric Acid, Anhydrous | 3.000 | 1.000 | pH control |
| Total | 300.0000 | 100.000 | |

1. In certain embodiments, Compound 1 is provided in a liquid filled capsule comprising a solvent, preservative, and pH control agent.
2. The pharmaceutical composition of embodiment 1, wherein the capsule is filled with a solution comprising about 0.001, 0.005, 0.01, 0.015, 0.02, 0.025, 0.03, 0.033, 0.035, 0.04, 0.045, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.5, 2, 2.5, 3, 3.5, 4, 4.5, or 500 Compound 1 by weight.
3. The pharmaceutical composition of embodiment 1, wherein the capsule is filled with a solution comprising at least about 0.001, 0.005, 0.01, 0.015, 0.02, 0.025, 0.03, 0.033, 0.035, 0.04, 0.045, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.5, 2, 2.5, 3, 3.5, 4, 4.5, or 5% Compound 1 by weight.
4. The pharmaceutical composition of any one of embodiments 1-3, wherein the solvent is not aqueous.
5. The pharmaceutical composition of embodiment 4, wherein the solvent is PEG.
6. The pharmaceutical composition of embodiment 5, wherein the solvent is PEG 400.
7. The pharmaceutical composition of any one of embodiments 1-6, wherein the capsule is filled with a solution comprising about 95, 95.5, 96, 96.5, 97, 97.5, 98, 98.1, 98.2, 98.3, 98.4, 98.5, 98.6, 98.65. 98.7. 98.75, 98.8, 98.85, 98.9, 99, 99.1, 99.2, 99.3, 99.4, or 99.5% solvent by weight.
8. The pharmaceutical composition of any one of embodiments 1-6, wherein the capsule is filled with a solution comprising at least about 85, 90, 95, 95.5, 96, 96.5, 97, 97.5, 98, 98.1, 98.2, 98.3, 98.4, 98.5, 98.6, 98.65. 98.7. 98.75, 98.8, 98.85, 98.9, 99, 99.1, 99.2, 99.3, 99.4, or 99.5% solvent by weight.
9. The pharmaceutical composition of any one of embodiments 1-8, wherein the preservative is butylated hydroxytoluene.
10. The pharmaceutical composition of any one of embodiments 1-9, wherein the capsule is filled with a solution comprising at least about 0.01, 0.05, 0.1, 0.15, 0.2, 0.25, 0.3, 0.35, 0.4, 0.45, 0.5, 0.55, 0.6, 065, 0.8, 0.85, 0.9, 0.95, or 1% preservative by weight.
11. The pharmaceutical composition of any one of embodiments 1-9, wherein the capsule is filled with a solution comprising about 0.01, 0.05, 0.1, 0.15, 0.2, 0.25, 0.3, 0.35, 0.4, 0.45, 0.5, 0.55, 0.6, 065, 0.8, 0.85, 0.9, 0.95, or 1% preservative by weight.
12. The pharmaceutical composition of any one of embodiments 1-11, wherein the pH control agent is citric acid.
13. The pharmaceutical composition of any one of embodiments 1-11, wherein the pH control agent is anhydrous citric acid.
14. The pharmaceutical composition of any one of embodiments 1-13, wherein the capsule is filled with a solution comprising at least about 0.01, 0.05, 0.1, 0.15, 0.2, 0.25, 0.3, 0.35, 0.4, 0.45, 0.5, 0.55, 0.6, 065, 0.8, 0.85, 0.9, 0.95, 1, 1.1, 1.2, 1.3, 1.4, 1.5, 1.6, 1.7, 1.8, 1.9, 2, 2.25, 2.5, 2.75, or 3% pH control agent by weight.
15. The pharmaceutical composition of any one of embodiments 1-13, wherein the capsule is filled with a solution comprising about 0.01, 0.05, 0.1, 0.15, 0.2, 0.25, 0.3, 0.35, 0.4, 0.45, 0.5, 0.55, 0.6, 065, 0.8, 0.85, 0.9, 0.95, 1, 1.1, 1.2, 1.3, 1.4, 1.5, 1.6, 1.7, 1.8, 1.9, 2, 2.25, 2.5, 2.75, or 3% pH control agent by weight.

Additional Excipients

In certain embodiments, a compound described herein is administered as a pharmaceutical composition comprising one or more excipients from the Handbook of Pharmaceutical Excipients $9^{th}$ Edition (or earlier).

In certain embodiments, a compound described herein is dissolved or dispersed in oil or fat components. Upon oral administration, the oil or fat component may form a microemulsion in the digestive system so that the compound is more quickly absorbed in the body.

In certain embodiments, the oil is an edible oil, a medicament oil, a pharmaceutically acceptable fat and oil, or a food-acceptable fats and oil. For example, the pharmaceutically acceptable fat and oil, or a food-acceptable fats and oil includes, but is not limited, to a vegetable oil, an animal oil, a fish oil or a mineral oil.

In certain embodiments, the edible oil is selected from the group consisting of medium chain fatty acid triglyceride, amaranth oil, apricot oil, apple oil, argan oil, artichokes oil, avocado oil, almond oil, acai berry extract, arachis oil, buffalo pumpkin oil, borage seed oil, borage oil, babassu oil, coconut oil, corn oil, cottonseed oil (cotton seed oil), cashew oil, carob oil, Coriander oil, camellia oil (Camellia oil), Cauliflower oil, cape chestnut oil, cassis oil, deer oil, evening primrose oil, grape syrup Oila oil (hibiscus oil), grape seed oil, gourd oil, hazelnut oil, hemp oil, kapok oil, krill oil, linseed oil, macadamia nut oil, Mongolia oil, moringa oil, malula oil, meadowfoam oil, mustard oil, niger seed oil, olive oil, okrao oil Hibiscus oil), palm oil, palm kernel oil, peanut oil, pecan oil, pine oil, pistachio oil, pumpkin oil, papaya oil, perilla oil (perilla oil), poppy seed oil, prune oil, saw palm oil, quinoa oil, rapeseed oil, rice germ oil, rice bran oil, rice oil, rarelman cheer oil, Safflower oil (safflower oil), soybean oil, sesame oil, sunflower oil, thistle oil, tomato oil, wheat germ oil, walnut oil, watermelon oil, docosahexaenoic acid (DHA), eicosapentaenoic acid (EPA), and any combination thereof.

In certain embodiments, the fat-soluble oil is a vitamin including, but is not limited, to vitamin A oil, vitamin D oil, vitamin E oil, vitamin K oil, and derivatives thereof; and glycerophospholipids such as lecithin, and any combination thereof, can also be used as fats and oils in the present invention.

In certain embodiments, the oil in the present invention may be a liquid (such as a fat oil) or a solid (a fat or the like) at room temperature. In certain embodiments, the oil in the present invention is a liquid at the temperature in the living body (in particular, the temperature of the stomach, around 37° C.). In certain embodiments, the fat includes many saturated fatty acids (for example, palmitic acid, stearic acid), and/or fatty oils contain many unsaturated fatty acids (for example, oleic acid, linoleic acid, linolenic acid); and wherein these fatty acids and oils may be esterified.

In certain embodiments, the fatty acids having 2 to 4 carbon atoms are called short chain fatty acids (lower fatty acids), 5 to 12 fatty acids as medium chain fatty acids, and fatty acids with 12 or more carbon atoms as long chain fatty acids (higher fatty acids). Since fatty acids generally have a high hydrophilicity when the number of carbon atoms is small, oils of the present invention include medium chain fatty acids (for example, medium chain fatty acid triglycerides such as tri (caprylic/capric acid) glycerol and glyceryl tricaprylate) and long Chain fatty acid.

In certain embodiments, the fatty acid is used in combination with a saturated polyglycolated glyceride obtained by polyglycolysis of hydrogenated vegetable oil with polyethylene glycol, a mono-, di- or triglyceride, and a mono- or di-fatty acid ester of polyethylene glycol.

In certain embodiments, the pharmaceutical composition includes a diluent. Nonlimiting examples of the diluent used in capsules include, but are not limited to, calcium carbonate, calcium phosphate di or tri basic, kaolin, lactose, lactitol, mannitol, microcrystalline cellulose, powdered cellulose, cellulose acetate, sorbitol, starch, calcium sulfate, dextrates, dextrin, dextrose, maltodextrin, erythritol, glyceryl palmitostearate, isomalt, magnesium carbonate, magnesium oxide, mannitol, sodium chloride, sucrose, sulfobutylether b-cyclodextrin, talc, and xylitol.

VII. Metabolites

In certain aspects of the present invention a metabolite of Compound 1 is used as either (i) an active agent administered to a patient in need thereof in an effective amount to treat any of the disorders and in any of the methods described herein or (ii) as a synthetic process intermediate. Examples of Compound 1 metabolites are:

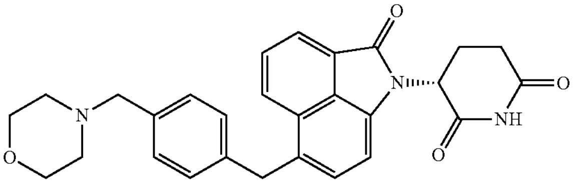

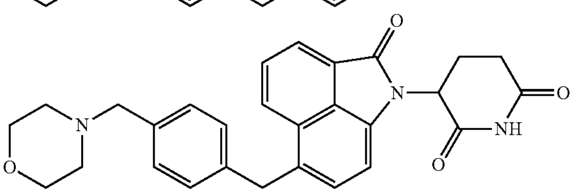

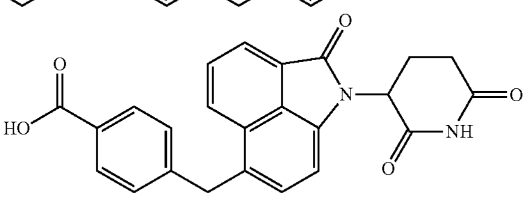

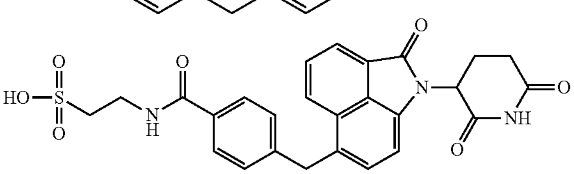

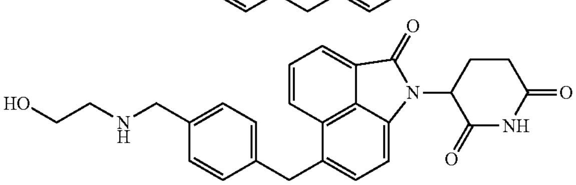

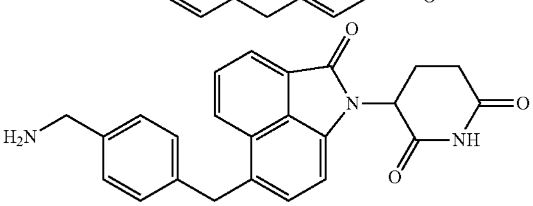

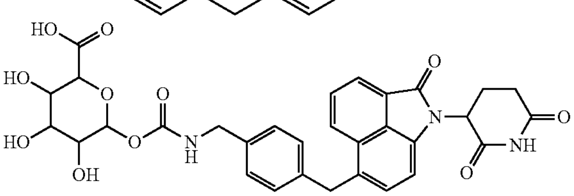

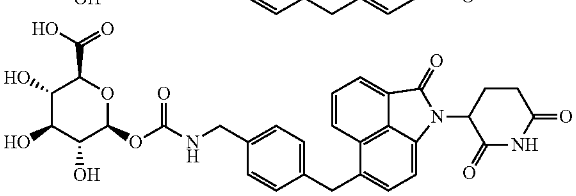

-continued
+ 0, 1, 2, or 3 O
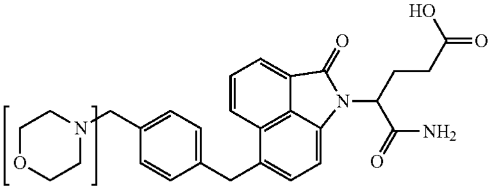
+ 0, 1, 2, or 3 O
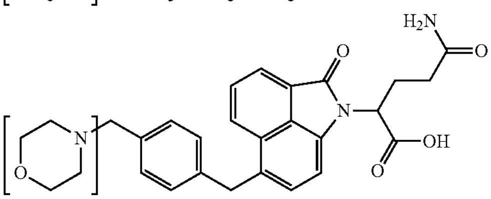
+ 0, 1, 2, or 3 O
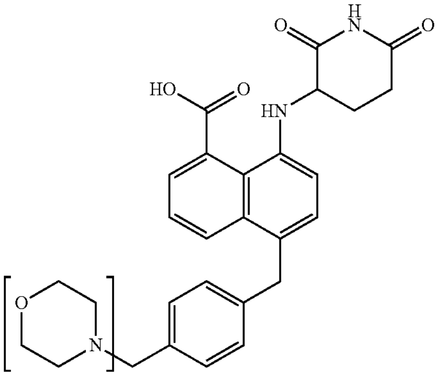
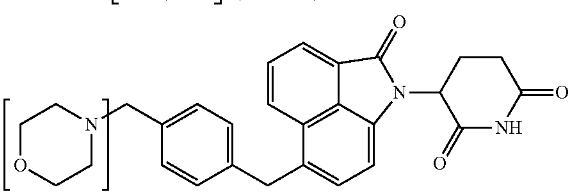
- 2 H
+ 1, 2, or 3 O
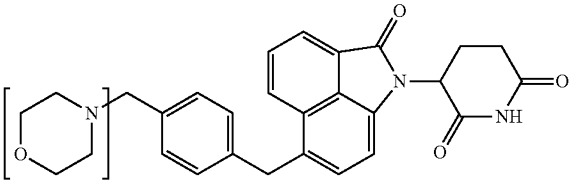
- 4 H
+ 1, 2, or 3 O
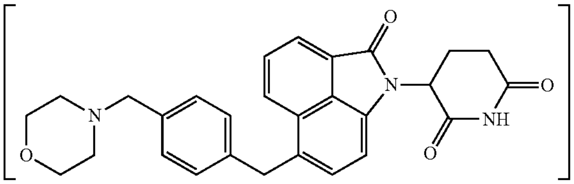
+O
+glucoronide
In certain embodiments, the metabolite of Compound 1 is enantiomerically or diastereomerically enriched:
+ 0, 1, 2, or 3 O
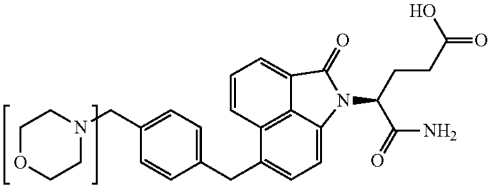
+ 0, 1, 2, or 3 O
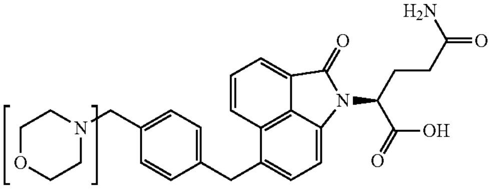
+ 0, 1, 2, or 3 O
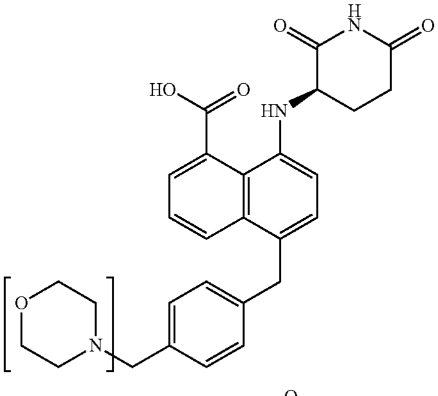
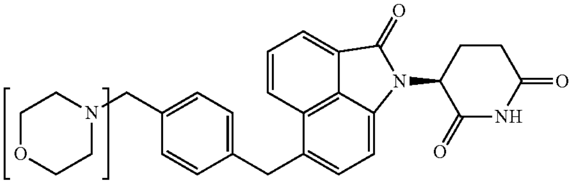
- 2 H
+ 1, 2, or 3 O
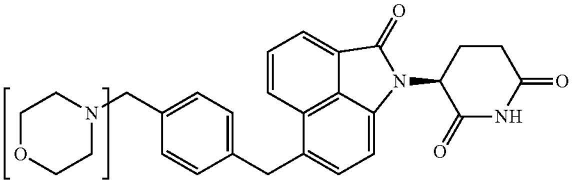
- 4 H
+ 1, 2, or 3 O
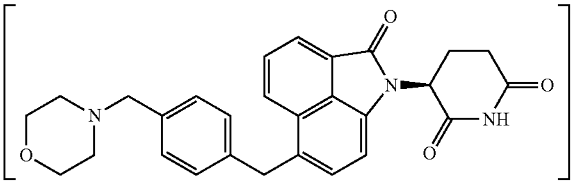
+O
+glucoronide
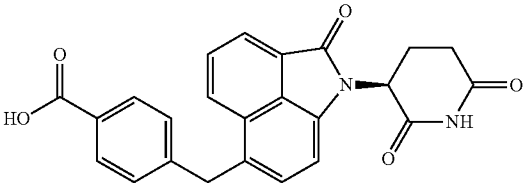

-continued
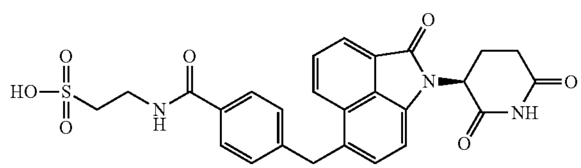
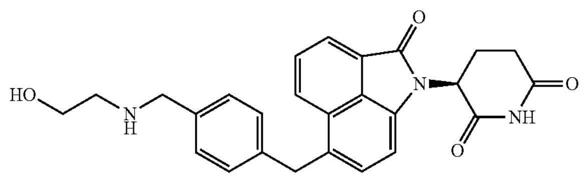
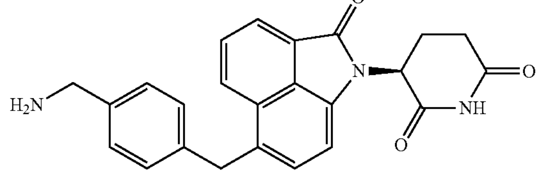
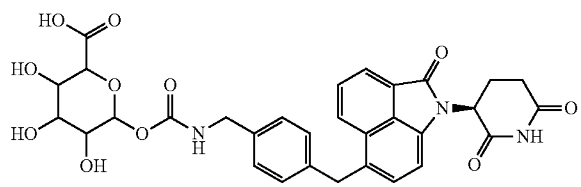
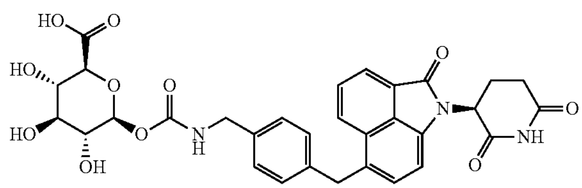
+ 0, 1, 2, or 3 O
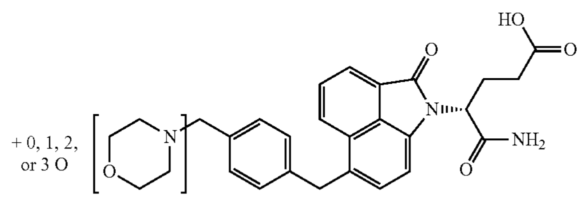
+ 0, 1, 2, or 3 O
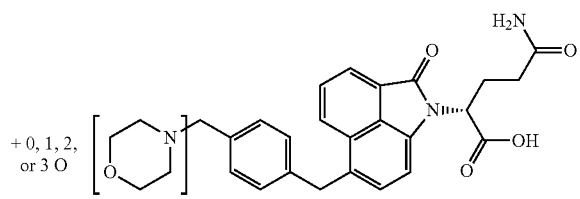
+ 0, 1, 2, or 3 O
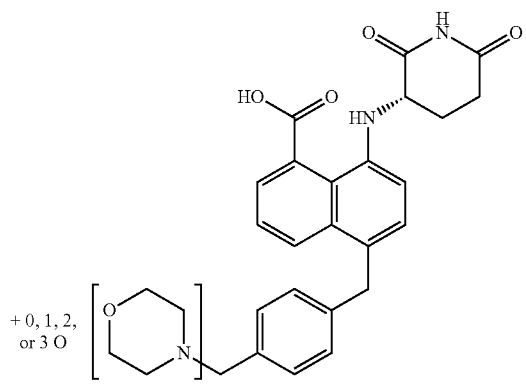
-continued
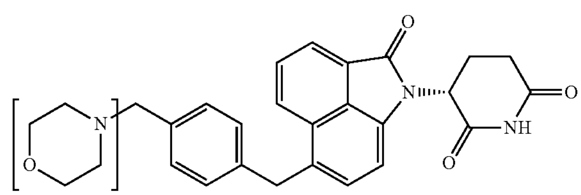
- 2 H
+ 1, 2, or 3 O
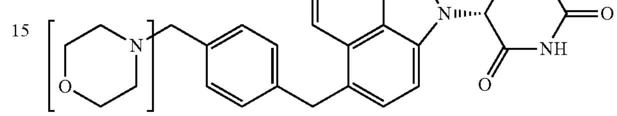
- 4 H
+ 1, 2, or 3 O
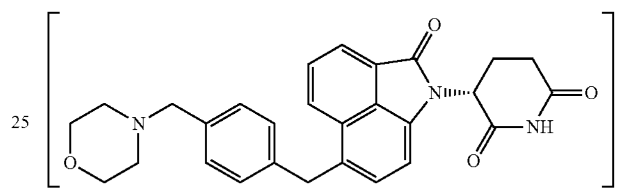
+O
+glucoronide
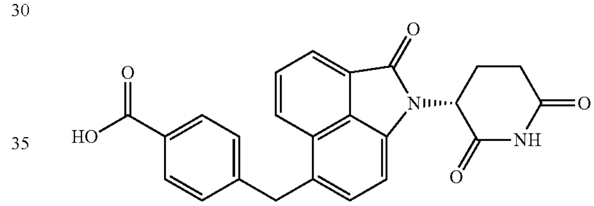
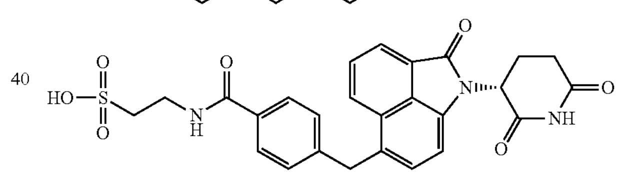
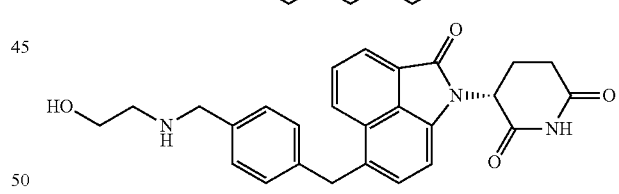
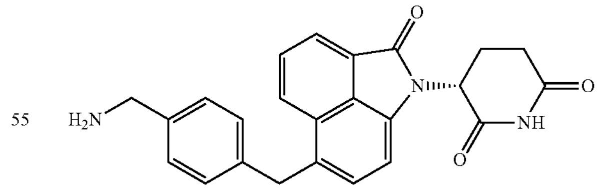
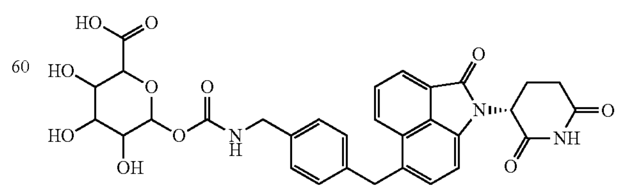

-continued

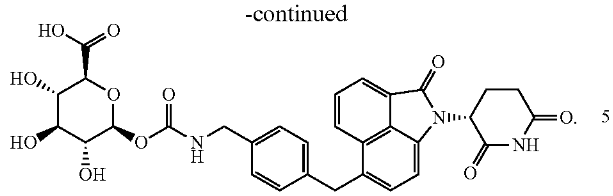

In certain embodiments, a Compound 1 metabolite is used in a treatment described herein.

In certain embodiments, a Compound 1 metabolite is used as an intermediate in the preparation of Compound 1.

VIII. General Synthesis

The compounds described herein can be prepared by methods known by those skilled in the art. In one non-limiting example, the disclosed compounds can be made using the schemes below.

Compounds of the present invention with stereocenters may be drawn without stereochemistry for convenience. One skilled in the art will recognize that pure or enriched enantiomers and diastereomers can be prepared by methods known in the art. Examples of methods to obtain optically active materials include at least the following:

i) physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization—a technique whereby the individual enantiomers are separately crystallized from a solution of the racemate, possible only if the enantiomer is a conglomerate in the solid state;

iii) enzymatic resolutions—a technique whereby partial or complete separation of a racemate by virtue of differing rates of reaction for the enantiomers with an enzyme;

iv) enzymatic asymmetric synthesis—a synthetic technique whereby at least one step in the synthesis uses an enzymatic reaction to obtain an enantiomerically pure or enriched synthetic precursor of the desired enantiomer;

v) chemical asymmetric synthesis—a synthetic technique whereby the desired enantiomer is synthesized from an achiral precursor under conditions that produce asymmetry (i.e. chirality) in the product, which may be achieved by chiral catalysts or chiral auxiliaries;

vi) diastereomer separations—a technique whereby a racemic compound is reaction with an enantiomerically pure reagent (the chiral auxiliary) that converts the individual enantiomers to diastereomers. The resulting diastereomers are then separated by chromatography or crystallization by virtue of their now more distinct structural differences the chiral auxiliary later removed to obtain the desired enantiomer;

vii) first- and second-order asymmetric transformations—a technique whereby diastereomers from the racemate quickly equilibrate to yield a preponderance in solution of the diastereomer from the desired enantiomer of where preferential crystallization of the diastereomer from the desired enantiomer perturbs the equilibrium such that eventually in principle all the material is converted to the crystalline diastereomer from the desired enantiomers. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase (including vial chiral HPLC). The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase; xii) extraction with chiral solvents—a technique whereby the enantiomers are separated by virtue of preferential dissolution of one enantiomer into a particular chiral solvent;

xiii) transport across chiral membranes—a technique whereby a racemate is place in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane that allows only one enantiomer of the racemate to pass through;

xiv) simulated moving bed chromatography is used in one embodiment. A wide variety of chiral stationary phases are commercially available.

EXAMPLES OF THE PRESENT INVENTION

Example 1. Synthesis of 3-(6-(4-(morpholinomethyl)benzyl)-2-oxobenzo[cd]indol-1(2H)-yl)piperidine-2,6-dione (Compound 5) and enantiomer 1 3-(6-(4-(morpholinomethyl)benzyl)-2-oxobenzo[cd]indol-1(2H)-yl)piperidine-2,6-dione (Compound 1)

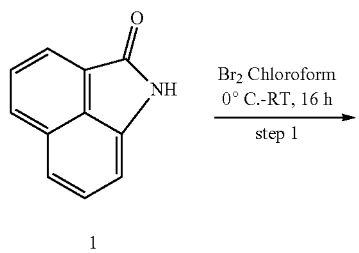

1

-continued

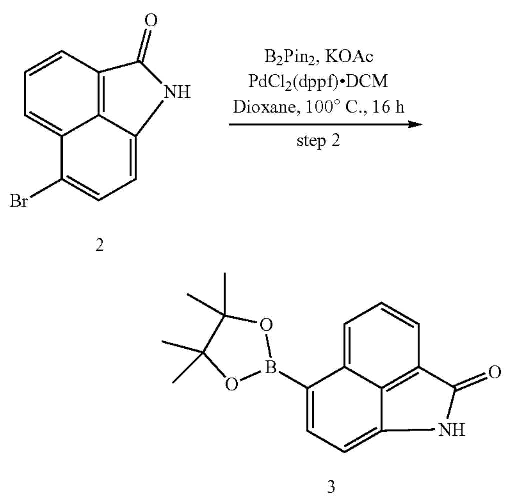

2

3

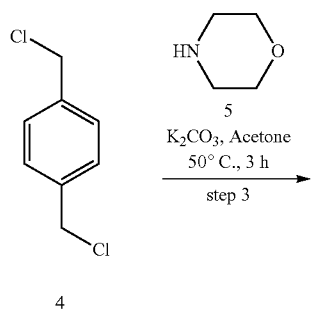

5

4

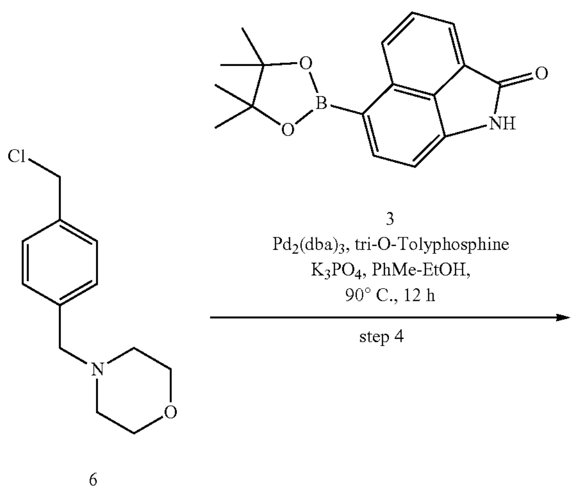

3

6

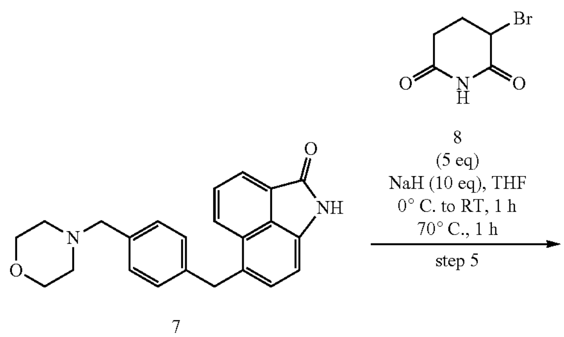

8

7

-continued

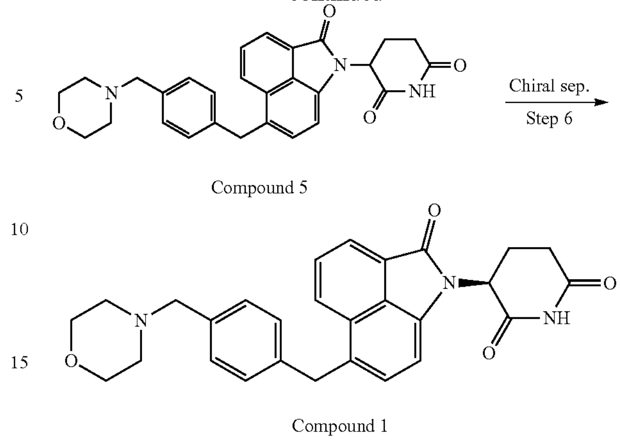

Compound 5

Compound 1

Step 1: Synthesis of 6-bromo-1H-benzo[cd]indol-2-one (2): A solution of molecular bromine (354.23 g, 2.22 mol, 113.53 mL) in chloroform (500 mL) was added drop wise at 0° C. to a stirred suspension of 1H-benzo[cd]indol-2-one (1) (250 g, 1.48 mol) in chloroform (2.5 L), and the reaction mixture was stirred at room temperature for 16 hours. After completion of the reaction (monitored by TLC), the reaction mass was poured into a saturated solution of sodium thiosulphate in water. The yellow solid formed was filtered through a sintered funnel, washed with water, washed with pentane, and stripped with toluene to afford 6-bromo-1H-benzo[cd]indol-2-one (2) (350 g, 90% yield) as yellow solid which was stored in a Tarson plastic bottle at ambient temperature. LC MS: ES+2 (248.2 and 250.2).

Step 2: Synthesis of 6-(4,4,5,5-tetramethyl-1,3,2-dioxaborolan-2-yl)-1H-benzo[cd]indol-2-one (3): Bis(pinacolato) diboron (30.71 g, 120.93 mmol) followed by well dried potassium acetate (23.74 g, 241.86 mmol, 15.12 mL) was added to a stirred solution of 6-bromo-1H-benzo[cd]indol-2-one (2) (20 g, 80.62 mmol) in 1,4 dioxane (500 mL). The resultant reaction mass was degassed well with argon for 15 minutes. $Pd_2(dba)_3$ (6.58 g, 8.06 mmol) was then added and the reaction mass was heated at 100° C. for 16 hours. After completion of the reaction (monitored by TLC), the reaction mixture was cooled to room temperature (RT), filtered through a pad of celite, and washed with ethyl acetate (1 L). The combined filtrate was then washed with cold water (3×300 mL), dried over anhydrous sodium sulphate, and concentrated under reduced pressure to afford crude 6-(4,4,5,5-tetramethyl-1,3,2-dioxaborolan-2-yl)-1H-benzo[cd]indol-2-one (3) (23 g, 46.76 mmol, 58.00% yield) as a brown gum which was stored in a round bottom flask at 5° C. inside a refrigerator. This was forwarded without further purification; LC MS: ES+295.7.

Step 3: Synthesis of 4-(4-(chloromethyl)benzyl)morpholine (6): To a stirred solution of morpholine (5) (8 g, 91.83 mmol, 8.03 mL) in analytical grade acetone (15 mL) was added 99% potassium carbonate, anhydrous, (12.69 g, 91.83 mmol, 5.54 mL) at room temperature and the resultant reaction mixture was heated at 50° C. for 20 minutes. 1,4-bis(chloromethyl)benzene (4) (16.07 g, 91.83 mmol, 11.32 mL) was then added to the reaction mixture and heating was continued for 3 hours. After completion of the reaction (monitored by TLC and LCMS), volatiles were removed under vacuum and the solid thus obtained was taken in ethyl acetate (50 mL), washed with water (3×25 ml) and brine (2×15 mL), dried over anhydrous sodium sulfate and concentrated under reduced pressure. The crude mass was purified by column chromatography (silica, gradient: 10-30% ethyl acetate in hexane) to afford 4-[[4-(chloromethyl)phenyl]methyl]morpholine (6) (10 g, 44.30 mmol, 48.25% yield) as a colourless sticky solid which was stored in a round bottom flask at 5° C. inside a refrigerator; LC MS: ES+226.2.

Step 4: Synthesis of 6-(4-(morpholinomethyl)benzyl) benzo[cd]indol-2(1H)-one (7): To a well degassed solution of 4-[[4-(chloromethyl)phenyl]methyl]morpholine (6) (8 g, 35.44 mmol) and 6-(4,4,5,5-tetramethyl-1,3,2-dioxaborolan-2-yl)-1H-benzo[cd]indol-2-one (3) (20.92 g, 70.89 mmol) in a mixture of ethanol (20 mL) and toluene (40 mL), was added anhydrous tribasic potassium phosphate (22.57 g, 106.33 mmol) followed by the addition of tri-o-tolyl phosphine (2.16 g, 7.09 mmol) and $Pd_2(dba)_3$ (3.25 g, 3.54 mmol). The resulting mixture was then heated at 90° C. for 12 hours. After completion of the reaction (as monitored by LCMS), the reaction mixture was filtered through a bed of celite and washed with ethyl acetate (200 mL). The combined filtrate was then washed with water (3×50 mL) and brine (2×40 mL), dried over anhydrous sodium sulfate and concentrated under reduced pressure. The crude mass was purified by column chromatography (silica, gradient: 0-20% ethyl acetate in DCM) to obtain 6-[[4-(morpholinomethyl) phenyl]methyl]-1H-benzo[cd]indol-2-one (7) (6.5 g, 17.59 mmol, 49.63% yield) as yellow solid which was stored in a Tarson plastic bottle at ambient temperature. LC MS: ES+359.3.

Step 5: Synthesis of 3-(6-(4-(morpholinomethyl)benzyl)-2-oxobenzo[cd]indol-1(2H)-yl)piperidine-2,6-dione: To an ice cooled solution of 6-[[4-(morpholinomethyl)phenyl] methyl]-1H-benzo[cd]indol-2-one (7) (4.8 g, 13.39 mmol) in dry THE (50 mL), sodium hydride (60% dispersion in mineral oil) (3.08 g, 133.92 mmol) was added portion wise, maintaining the temperature at <5° C. Once the addition was complete, the resultant mixture was stirred for 15 minutes at room temperature. Then the reaction mixture was again cooled to 0° C. and 3-bromopiperidine-2,6-dione (8) (12.86 g, 66.96 mmol) was added to it portion wise. After complete addition, the resulting solution was heated at 70° C. for 1 hour. After completion (evidenced from TLC), the reaction mixture was again cooled to 0° C. and quenched with ice cooled water (40 mL). The aqueous layer was extracted with ethyl acetate (3×50 mL). Combined extracts were dried over anhydrous sodium sulfate and concentrated under reduced pressure. The crude mass was purified by flash chromatography (silica, gradient: 2.5% MeOH in DCM) to afford 3-[6-[[4-(morpholinomethyl)phenyl]methyl]-2-oxo-benzo [cd]indol-1-yl]piperidine-2,6-dione Compound 5 (4 g, 8.36 mmol, 62.44% yield) as a yellow solid which was stored in a round bottom flask at 5° C. inside a refrigerator. $^1H$ NMR (400 MHz, DMSO-$d_6$) δ 11.12 (s, 1H), 8.31 (d, J=8.2 Hz, 1H), 8.06 (d, J=6.92 Hz, 1H), 7.80 (t, J=7.58 Hz, 1H), 7.39 (d, J=7.24 Hz, 1H), 7.24-7.17 (m, 4H), 7.10 (d, J=7.2 Hz, 1H), 5.44 (dd, J=12.36, 4.76 Hz, 1H), 4.36 (s, 1H), 3.51 (br s, 4H), 3.36 (s, 2H), 2.98-2.90 (m, 1H), 2.79-2.73 (m, 1H), 2.69-2.62 (m, 1H), 2.28 (br s, 4H), 2.10-2.07 (m, 1H); LC MS: ES+470.2.

Step 6: Chiral separation: Preparation of R- and S-3-(6-(4-(morpholinomethyl)benzyl)-2-oxobenzo[cd]indol-1 (2H)-yl)piperidine-2,6-dione: 3.8 g of 3-(6-(4-(morpholinomethyl)benzyl)-2-oxobenzo[cd]indol-1(2H)-yl) piperidine-2,6-dione Compound 5 was separated into enantiomers by the chiral normal phase preparative HPLC method below. The fractions were first evaporated separately under reduced pressure to obtain a solid mass. The solid was then suspended in a mixture of acetonitrile and water (2:3) and they were then put in a dry-ice/acetone bath until the acetonitrile-water mixture solidified. The frozen mixture was then freeze dried with a lyophilizer for 20 hours to afford 3-(6-(4-(morpholinomethyl)benzyl)-2-oxobenzo[cd] indol-1(2H)-yl)piperidine-2,6-dione Compound 1 (first eluted peak, retention time=9.33 min, 'S' ABS) (1.3 g, % ee 99.9).

Preparative Chiral HPLC Method:

Column: Chiralpak IC (20×250 mm), 5
Detector wavelength: 258 nm
Injection Volume: 500 μL
Flow rate: 18 ml/minute
Column temperature: NA
Sample temperature: NA
Run time: 25 minutes
Diluent: Mobile phase
Needle wash: DCM
Seal wash: NA
Mobile phase: 500 mL of DCM and 500 mL of isopropyl alcohol were mixed and sonicated to degas.

Example 2. Synthesis of Compound 2, Compound 7, Compound 9, and Compound 13

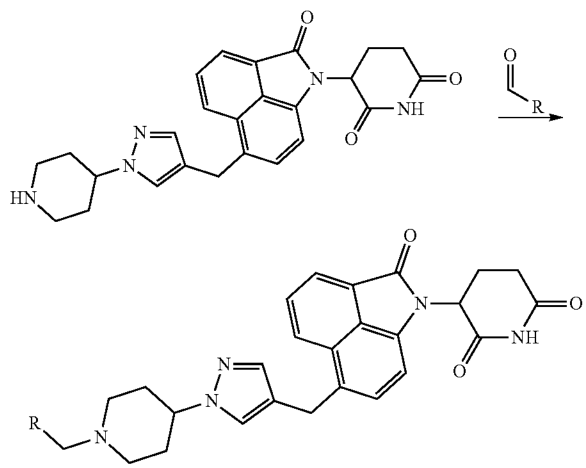

To a stirred solution of amine (1.0 equiv) in THE (6 mL/mmol) was added triethylamine (2.0 equiv) at 0° C. Then aldehyde (1.0 equiv), phenylsilane (1.0 equiv) and dibutyltindichloride (1.2 equiv) were added to the reaction mixture. The resulting solution was stirred at 90° C. for 16 hours. The reaction mixture was then diluted with ethyl acetate and washed with aqueous $NaHCO_3$ solution, water (×3), and brine. The organic layer was then dried over anhydrous $Na_2SO_4$ and concentrated under reduced pressure. The crude mass was then purified by a CombiFlash ISCO column, eluting with 3% methanol in DCM to afford the final compound.

Compound 2:

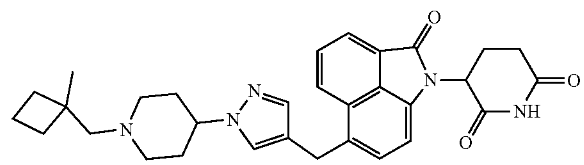 [SMILES: CC1(CN2CCC(n3cc(Cc4ccc5c6c(cccc46)C(=O)N5C4CCC(=O)NC4=O)cn3)CC2)CCC1]

Yellow solid, 3.8 g, 71.92% yield, 99.49% purity. $^1$H NMR (400 MHz, DMSO-$d_6$) δ 11.11 (s, 1H), 8.37 (d, J=8.2 Hz, 1H), 8.08 (d, J=6.96 Hz, 1H), 7.82 (t, J=7.6 Hz, 1H), 7.57 (s, 1H), 7.35 (d, J=7.24 Hz, 1H), 7.28 (s, 1H), 7.06 (d, J=7.24 Hz, 1H), 5.43 (dd, J=12.64, 4.8 Hz, 1H), 4.17 (s, 2H), 3.99-3.96 (m, 1H), 2.94-2.90 (m, 1H), 2.75-2.62 (m, 4H), 2.22 (s, 2H), 2.09-2.02 (m, 3H), 1.99-1.69 (m, 8H), 1.61-1.56 (m, 2H), 1.13 (s, 3H); LC MS: ES+526.4.

Compound 7:

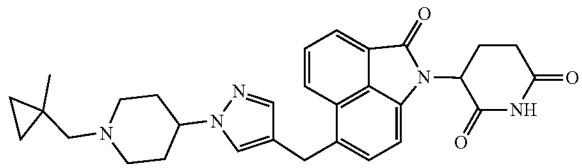 [SMILES: CC1(CN2CCC(n3cc(Cc4ccc5c6c(cccc46)C(=O)N5C4CCC(=O)NC4=O)cn3)CC2)CC1]

Yellow solid, 119.0 mg, 43.26% yield, 96.88% purity. $^1$H NMR (400 MHz, DMSO-$d_6$) δ 11.11 (s, 1H), 8.37 (d, J=8.16 Hz, 1H), 8.08 (d, J=6.88 Hz, 1H), 7.83 (t, J=7.64 Hz, 1H), 7.58 (s, 1H), 7.35 (d, J=7.24 Hz, 1H), 7.29 (s, 1H), 7.07 (d, J=7.24 Hz, 1H), 5.44-5.42 (m, 1H), 4.18 (s, 2H), 4.00-3.99 (m, 1H), 3.00-2.91 (m, 3H), 2.80-2.73 (m, 1H), 2.67-2.62 (m, 1H), 2.11-2.10 (m, 3H), 1.91-1.88 (m, 6H), 1.01 (s, 3H), 0.26-0.21 (m, 4H); LC MS: ES+512.3.

Compound 9:

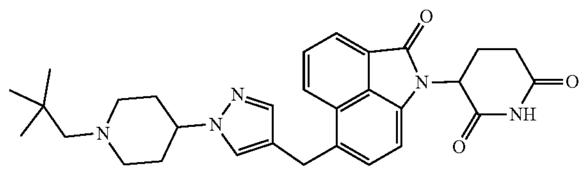 [SMILES: CC(C)(C)CN1CCC(n2cc(Cc3ccc4c5c(cccc35)C(=O)N4C3CCC(=O)NC3=O)cn2)CC1]

Yellow solid, 75.0 mg, 42.55% yield, 97.14% purity. $^1$H NMR (400 MHz, DMSO-$d_6$) δ 11.12 (s, 1H), 8.38 (d, J=8.32 Hz, 1H), 8.08 (d, J=6.76 Hz, 1H), 7.83 (t, J=7.54 Hz, 1H), 7.57 (s, 1H), 7.36 (d, J=7.64 Hz, 1H), 7.29 (s, 1H), 7.07 (d, J=7.24 Hz, 1H), 5.44-5.42 (m, 1H), 4.17 (s, 2H), 3.99-3.97 (m, 1H), 2.99-2.91 (m, 1H), 2.81-2.77 (m, 2H), 2.67-2.62 (m, 1H), 2.33-2.27 (m, 2H), 2.05-2.04 (m, 3H), 1.89-1.83 (m, 4H), 1.60-1.58 (m, 1H), 0.83 (s, 9H); LC MS: ES+514.7.

Compound 13:

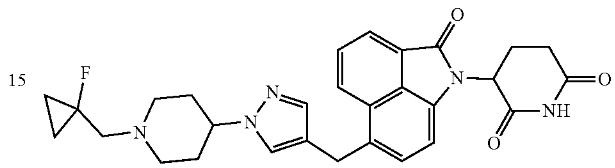

Yellow solid, 100.0 mg, 59.76% yield, 96.30% purity. H NMR (400 MHz, DMSO-$d_6$) δ 11.11 (s, 1H), 8.37 (d, J=8.24 Hz, 1H), 8.08 (d, J=6.96 Hz, 1H), 7.83 (t, J=7.6 Hz, 1H), 7.59 (s, 1H), 7.35 (d, J=7.32 Hz, 1H), 7.30 (s, 1H), 7.07 (d, J=7.28 Hz, 1H), 5.43 (dd, J=12.6, 5.0 Hz, 1H), 4.18 (s, 2H), 4.03-4.01 (m, 1H), 3.12-2.90 (m, 3H), 2.80-2.62 (m, 4H), 2.22-2.19 (m, 2H), 2.09-2.07 (m, 1H), 1.90-1.88 (m, 4H), 0.99-0.95 (m, 2H), 0.66-0.65 (m, 2H); LC MS: ES+516.3.

Example 3. Synthesis of 3-[6-[[4-[[4-(2-fluorophenyl)piperazin-1-yl]methyl]phenyl]methyl]-2-oxo-benzo[cd]indol-1-yl]piperidine-2,6-dione (Compound 3)

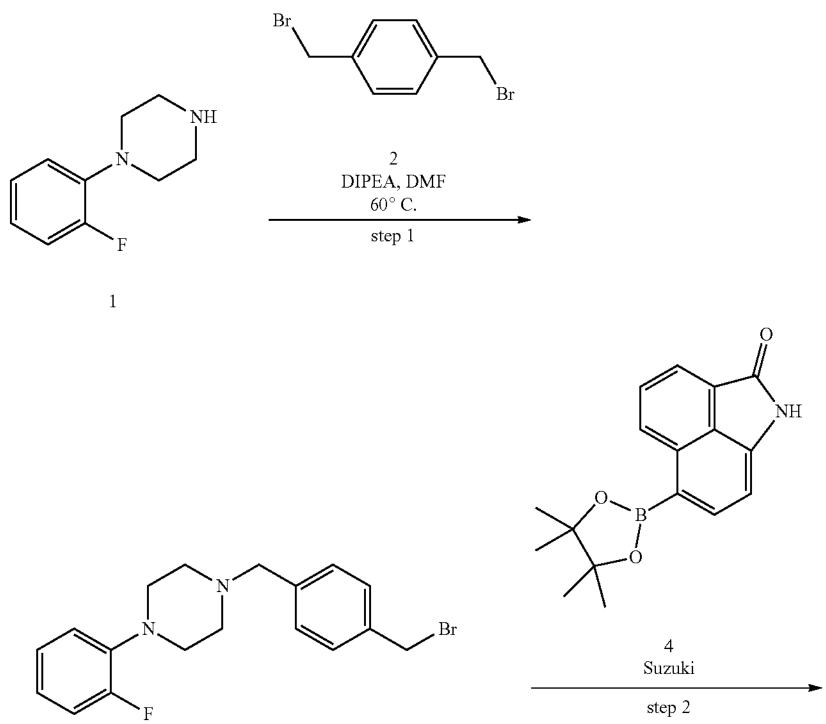

-continued

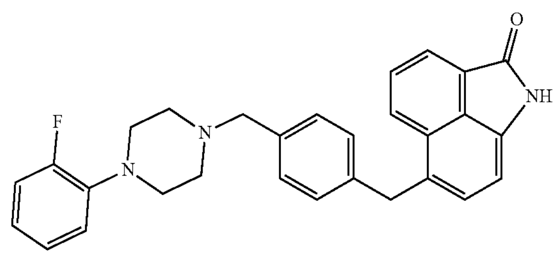

5

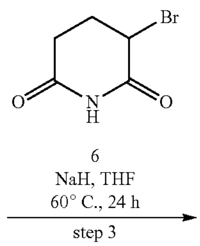

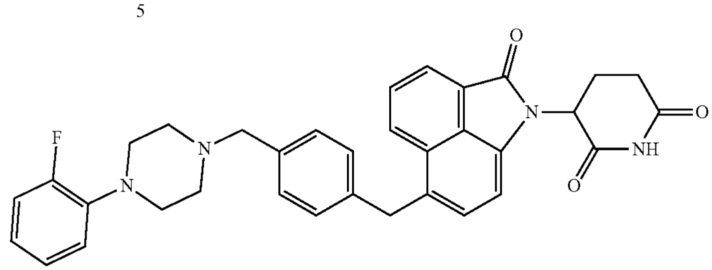

Compound 3

Step 1: Synthesis of 1-[[4-(chloromethyl)phenyl]methyl]-4-(2-fluorophenyl)piperazine (3): To a stirred solution of 1-(2-fluorophenyl)piperazine (1) (2 g, 11.10 mmol) in dry grade DMF (5 mL), DIPEA (4.30 g, 33.29 mmol, 5.80 mL) was added followed by 1,4-bis(chloromethyl)benzene (2) (3.89 g, 22.19 mmol, 2.74 mL). The resulting reaction mixture was heated at 60° C. for 12 hours. After completion of the reaction (evidenced from LC MS), ice cooled water (25 mL) was added to the reaction mixture and extracted with ethyl acetate (3×30 mL). The organic portion was separated, dried over anhydrous sodium sulfate and concentrated under reduced pressure. The crude reaction mass was purified by column chromatography (silica, gradient: 0-40% ethyl acetate in hexane) to afford 1-[[4-(chloromethyl)phenyl]methyl]-4-(2-fluorophenyl)piperazine (3) (3 g, 8.47 mmol, 76.31% yield, 90% purity) as a yellow solid; LC MS: ES+319.4.

Step 2: Synthesis of 6-[[4-[[4-(2-fluorophenyl)piperazin-1-yl]methyl]phenyl]methyl]-1H-benzo[cd]indol-2-one (5): To the stirred solution of 6-(4,4,5,5-tetramethyl-1,3-dioxolan-2-yl)-1H-benzo[cd]indol-2-one (4) (500 mg, 1.68 mmol) and 1-[[4-(chloromethyl)phenyl]methyl]-4-(2-fluorophenyl) piperazine (3) (536.10 mg, 1.68 mmol) in ethanol (1 mL) and toluene (2 mL) was added tripotassium phosphate (892.33 mg, 4.20 mmol) followed by 0.5 ml water and the reaction mass was degassed under nitrogen atmosphere over 10 minutes. Then tris-o-tolylphosphane (102.36 mg, 336.31 umol) and (1E,4E)-1,5-diphenylpenta-1,4-dien-3-one palladium (153.98 mg, 168.15 umol) were added to this reaction mass and resultant reaction mixture was heated at 90° C. overnight. After completion of reaction, the reaction mixture was filtered through a celite bed and washed with ethyl acetate (50 mL). The filtrate was collected and washed with water (2×20 mL)/brine (20 mL). The combined organic layers were separated, dried over sodium sulfate and concentrated under vacuum. The crude was purified by column chromatography (silica, gradient: 0-40% ethylacetate in hexane) to afford 6-[[4-[[4-(2-fluorophenyl)piperazin-1-yl]methyl]phenyl]methyl]-1H-benzo[cd]indol-2-one (5) (280 mg, 539.49 umol, 32.08% yield, 87% purity) as a yellow solid; LC MS: 452.4.

Step 3: Preparation of 3-[6-[[4-[[4-(2-fluorophenyl)piperazin-1-yl]methyl]phenyl]methyl]-2-oxo-benzo[cd]indol-1-yl]piperidine-2,6-dione: To an ice cooled solution of 6-[[4-[[4-(2-fluorophenyl)piperazin-1-yl]methyl]phenyl]methyl]-1H-benzo[cd]indol-2-one 5 (80 mg, 177.17 umol) in dry THE (8 mL), sodium hydride (in oil dispersion) 60% dispersion in mineral oil (67.89 mg, 1.77 mmol, 60% purity) was added portion wise, while the temperature was maintained at <5° C. Once the addition was over, the resultant mixture was stirred for 15 minutes at room temperature. Then the reaction mixture was again cooled to 0° C. and 3-bromopiperidine-2,6-dione 6 (170.10 mg, 885.87 umol) was added to it portion wise. After complete addition, the resulting solution was heated at 70° C. for 1 hour. After completion (evidenced from TLC), the reaction mixture was again cooled to 0° C. and quenched with ice cooled water (40 mL). The aqueous layer was extracted with ethyl acetate (3×50 mL). Combined extracts were dried over anhydrous sodium sulfate and concentrated under reduced pressure. The crude mass was purified by flash chromatography (silica, gradient: 3% MeOH in DCM) to afford 3-[6-[[4-[[4-(2-fluorophenyl)piperazin-1-yl]methyl]phenyl]methyl]-2-oxo-benzo[cd]indol-1-yl]piperidine-2,6-dione Compound 3 (20 mg, 34.69 umol, 19.58% yield, 97.59% purity). 1H NMR (400 MHz, DMSO-$d_6$) δ 11.12 (s, 1H), 8.32 (d, J=8.16 Hz, 1H), 8.07 (d, J=6.92 Hz, 1H), 7.81 (t, J=7.92 Hz, 1H), 7.41 (d, J=7.24 Hz, 1H), 7.26-7.20 (m, 4H), 7.11-7.05 (m, 3H), 7.0-6.93 (br m, 2H), 5.43 (dd, J=12.64, 4.76 Hz, 1H), 4.38 (s, 2H), 3.45 (s, 2H), 2.96 (br s, 5H), 2.76-2.73 (m, 1H), 2.66-2.62 (m, 1H), 2.50 (br s, 4H), 2.10-2.09 (m, 1H); LC MS: ES+563.5.

Example 4. Synthesis of 4-[4-[[4-[[1-(2,6-dioxo-3-piperidyl)-2-oxo-benzo[cd]indol-6 yl] methyl] phenyl] methyl] piperazin-1-yl]-3-fluoro-benzonitrile (Compound 4)
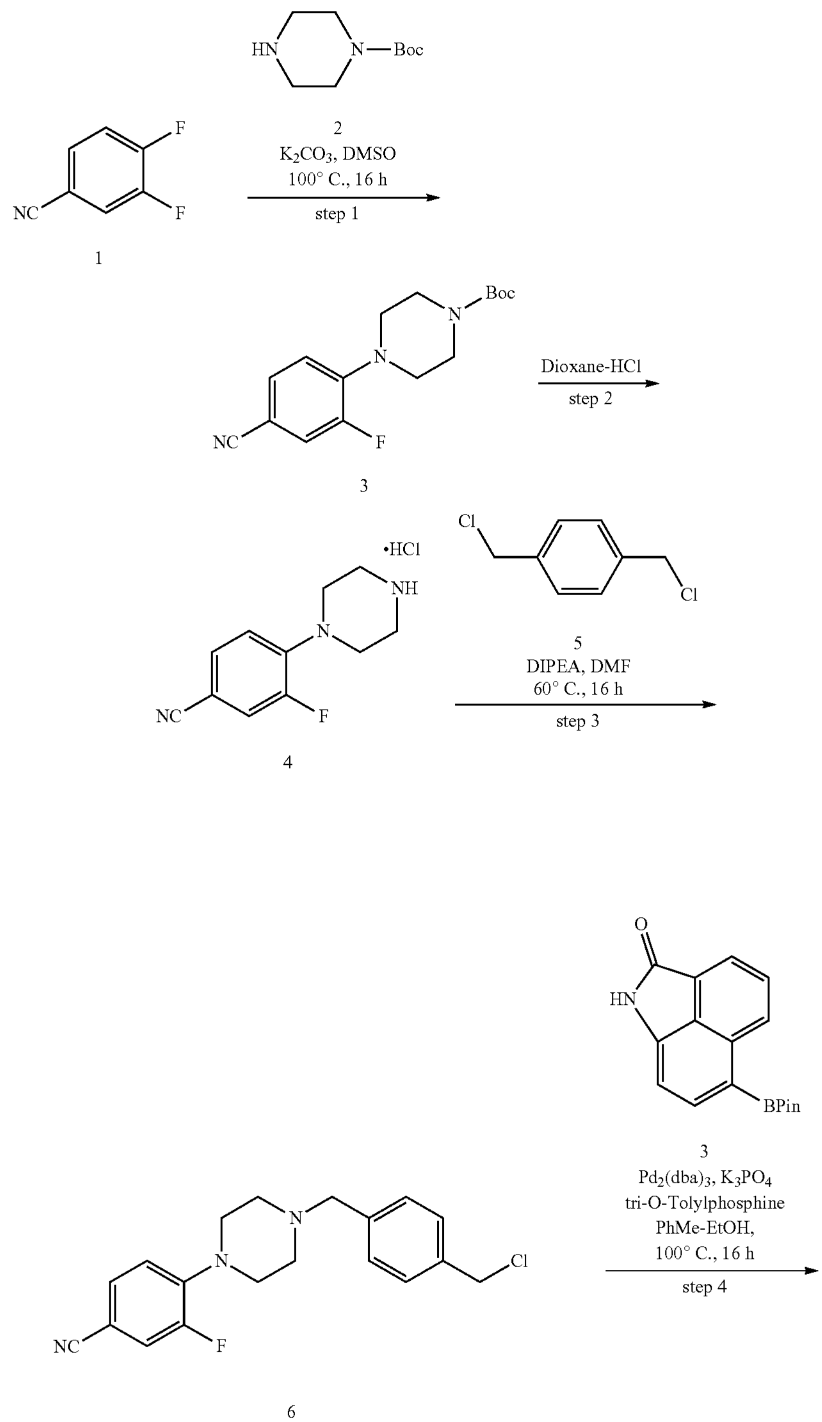

-continued

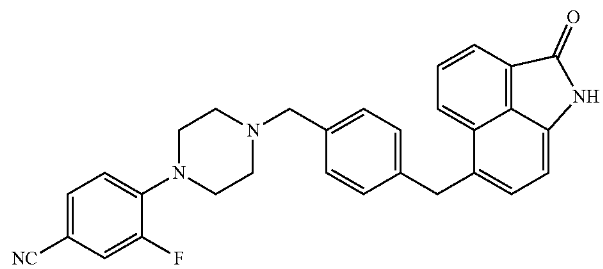

7

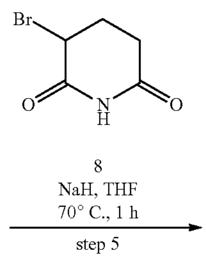

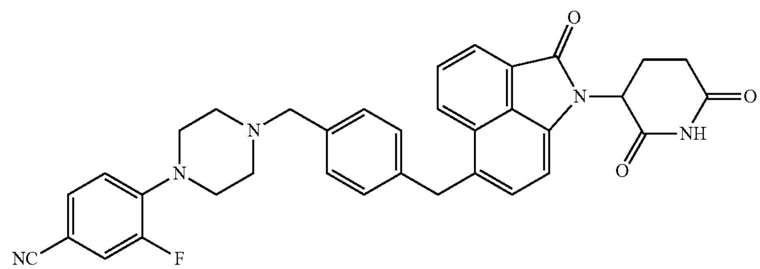

Compound 4

Step-1: Synthesis of tert-butyl 4-(4-cyano-2-fluoro-phenyl)piperazine-1-carboxylate (3): To a stirred solution of 3,4-difluorobenzonitrile (1) (13 g, 93.46 mmol) in DMSO (80 mL), potassium carbonate (19.37 g, 140.18 mmol, 8.46 mL) and tert-butyl piperazine-1-carboxylate (2) (19.15 g, 102.80 mmol) were added and the resulting reaction mixture was heated at 100° C. for 16 hours. After completion (monitored by TLC), the reaction mixture was allowed to cool and water (500 ml) was added to it. The solid that formed was then filtered off, washed with water, and dried under vacuum to obtain tert-butyl 4-(4-cyano-2-fluoro-phenyl)piperazine-1-carboxylate (3) (20 g, 66% yield) as a white solid. LC MS: ES+306.2.

Step-2: Synthesis of 3-fluoro-4-piperazin-1-yl-benzonitrile Hydrochloride salt (4): To a stirred solution of tert-butyl 4-(4-cyano-2-fluoro-phenyl)piperazine-1-carboxylate (3) (20 g, 65.50 mmol) in dioxane (15 mL) was added dioxane-HCl (65.50 mmol, 50 mL) and the reaction mixture was stirred at room temperature for 3 hours. All the volatiles were removed under reduced pressure. The solid obtained was triturated with ether to afford 3-fluoro-4-piperazin-1-yl-benzonitrile; hydrochloride (4) (17 g, 88% yield) as a white solid. LC MS: ES+206.4.

Step-3: Synthesis of 4-[4-[[4-(chloromethyl)phenyl] methyl]piperazin-1-yl]-3-fluoro-benzonitrile (6): To a stirred solution of 3-fluoro-4-piperazin-1-yl-benzonitrile; hydrochloride (4) (15 g, 62.06 mmol) in DMF (75 mL) was added DIPEA (24.06 g, 186.19 mmol, 32.43 mL) and the reaction mixture was stirred for 5 minutes. Then 1,4-bis (chloromethyl)benzene (5) (10.86 g, 62.06 mmol, 7.65 mL) was added in one portion and the reaction was heated at 60° C. for 16 hours. After completion (monitored by TLC), the reaction mixture was diluted with ethyl acetate and washed with water and brine, dried over sodium sulfate and concentrated. The crude thus obtained was purified by column chromatography (silica, gradient: 10-30% EtOAc in Hexane) to afford 4-[4-[[4-(chloromethyl)phenyl]methyl] piperazin-1-yl]-3-fluoro-benzonitrile (6) (7 g, 32% yield) as a white solid. LC MS: (Es, ES+2) 344.2, 346.4.

Step-4: Synthesis of 3-fluoro-4-[4-[[4-[(2-oxo-1H-benzo [cd]indol-6-yl)methyl]phenyl]methyl]piperazin-1-yl]benzonitrile (7): To a well degassed solution of 4-[4-[[4-(chloromethyl)phenyl]methyl]piperazin-1-yl]-3-fluoro-benzonitrile (6) (7 μg, 20.36 mmol) and 6-(4,4,5,5-tetramethyl-1,3-dioxolan-2-yl)-1H-benzo[cd]indol-2-one (3) (9.08 g, 30.54 mmol) in ethanol (30 mL) and toluene (60 mL), anhydrous potassium phosphate tribasic, (10.80 g, 50.90 mmol) was added followed by the addition of tri-o-tolyl phosphine (1.24 g, 4.07 mmol) and $Pd_2(dba)_3$ (1.86 g, 2.04 mmol). The resulting mixture was then heated at 100° C. for 16 hours. After completion of reaction (as monitored by LCMS), the reaction mixture was filtered through a bed of celite, and washed with ethyl acetate. The combined filtrate was washed with water and brine, dried over sodium sulfate, and concentrated under reduced pressure. Crude mass was purified by column chromatography (silica, gradient: 0-40% ethyl acetate in hexane) to obtain 3-fluoro-4-[4-[[4-[(2-oxo-1H-benzo[cd]indol-6-yl) methyl]phenyl] methyl]piperazin-1-yl]benzonitrile (7) (5.5 g, 52% yield) as yellow solid. LC MS: ES+477.4.

Step-5: Synthesis of 4-[4-[[4-[[1-(2,6-dioxo-3-piperidyl)-2-oxo-benzo[cd]indol-6 yl] methyl]phenyl] methyl] piperazin-1-yl]-3-fluoro-benzonitrile: To a cooled solution of fluoro-4-[4-[[4-[(2-oxo-1H-benzo[cd]indol-6-yl)methyl] phenyl]methyl]piperazin-1-yl]benzonitrile (7) (5.5 g, 11.54 mmol) in dry THE (30 mL), sodium hydride (60% dispersion in mineral oil) (2.65 g, 115.41 mmol) was added portion wise, maintaining the temperature at <5° C. Once the addition is over, the resultant mixture was stirred for 15 minutes at room temperature. Then the reaction mixture was again cooled to 0° C. and 3-bromopiperidine-2,6-dione (8) (11.08 g, 57.71 mmol) was added to it portion wise. After complete addition, the resulting solution was heated at 70° C. 1 hour. After completion (evidenced from TLC), the reaction mixture was cooled to 0° C. and quenched with the addition of ice cooled water. The aqueous layer was extracted with ethyl acetate (3×100 mL). The combined organics were separated, dried over sodium sulfate, and concentrated under reduced pressure. Crude mass was purified by column chromatography (silica, gradient: 30-100% EtOAc in DCM) to afford 4-[4-[[4-[[1-(2,6-dioxo-3-piperidyl)-2-oxo-benzo[cd]indol-6-yl]methyl]phenyl]methyl]piperazin-1-yl]-3-fluoro-benzonitrile Compound 4 (4.4 g, 63% yield) as yellow solid. $^{1}H$ NMR (400 MHz, DMSO-$d_6$) δ 11.12 (s, 1H), 8.32 (d, J=8.28 Hz, 1H), 8.07 (d, J=6.92 Hz, 1H), 7.80 (t, J=7.66 Hz, 1H), 7.66 (d, J=12.4 Hz, 1H), 7.54 (d, J=8.36 Hz, 1H), 7.40 (d, J=7.28 Hz, 1H), 7.26-7.19 (m, 4H), 7.11-7.05 (m, 2H), 5.44 (dd, J=12.64, 4.84 Hz, 1H), 4.37 (s, 2H), 3.49 (s, 2H), 3.12 (br s, 4H), 2.98-2.90 (m, 1H), 2.79-2.73 (m, 1H), 2.70-2.62 (m, 1H), 2.45 (br s, 4H), 2.10-2.07 (m, 1H); LC MS: ES+588.48.

Example 5. Amide Coupling Conditions

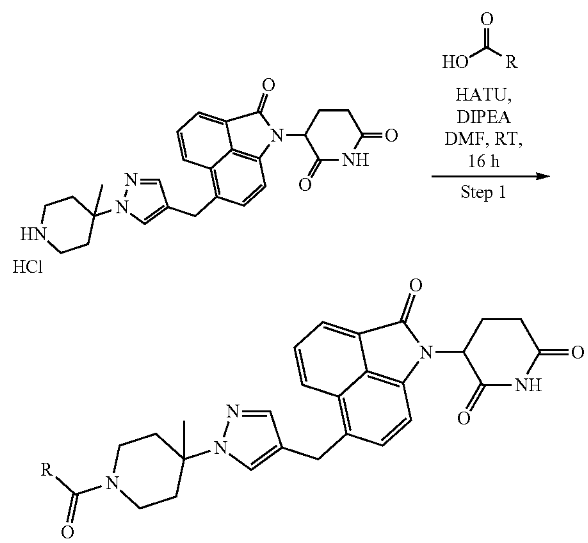

To an equi-molar mixture of amine and acid in DMF (6 mL/mmol) were added HATU (1.5 equiv) and DIPEA (5.0 equiv) at 0° C. The resulting solution was stirred at ambient temperature for 16 hours. The reaction mixture was then diluted with ethyl acetate and washed with aqueous $NaHCO_3$ solution, water (×3) and brine. The organic layer was then dried over anhydrous $Na_2SO_4$ and concentrated under reduced pressure. The crude mass was then purified by a CombiFlash ISCO column, eluting with 2% methanol in DCM.

Compound 6:

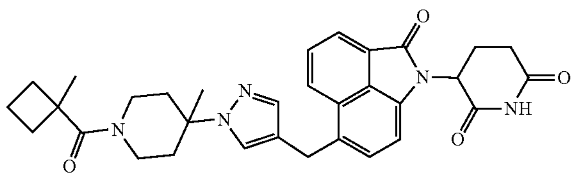 [SMILES: CC1(C(=O)N2CCC(C)(n3cc(Cc4ccc5c6c(cccc46)C(=O)N5C4CCC(=O)NC4=O)cn3)CC2)CCC1]

Yellow solid, 110 mg, 48.55% yield, 98.94% purity. $^{1}H$ NMR (400 MHz, DMSO-$d_6$) δ 11.11 (s, 1H), 8.39 (d, J=Hz, 1H), 8.08 (d, J=Hz, 1H), 7.82 (t, J=Hz, 1H), 7.78 (s, 1H), 7.36-7.33 (m, 2H), 7.07 (d, J=Hz, 1H), 5.43 (dd, J=Hz, 1H), 4.20 (s, 2H), 3.69-3.67 (m, 1H), 3.29-3.28 (m, 1H), 3.07-3.05 (m, 2H), 2.99-2.90 (m, 1H), 2.80-2.69 (m, 1H), 2.67-2.62 (m, 1H), 2.39-2.28 (m, 4H), 2.09-2.07 (m, 1H), 1.94-1.83 (m, 1H), 1.78-1.74 (m, 4H), 1.62-1.55 (m, 1H), 1.34 (s, 3H), 1.31 (s, 3H); LC MS: ES+554.2.

Compound 11:

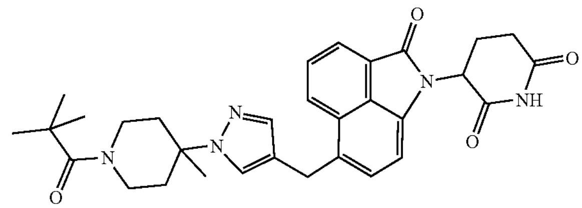 [SMILES: CC(C)(C)C(=O)N1CCC(C)(n2cc(Cc3ccc4c5c(cccc35)C(=O)N4C3CCC(=O)NC3=O)cn2)CC1]

Yellow solid, 120 mg, 43.48% yield, 99.32% purity. $^{1}H$ NMR (400 MHz, DMSO-$d_6$) δ 11.11 (s, 1H), 8.39 (d, J=8.2 Hz, 1H), 8.08 (d, J=6.92 Hz, 1H), 7.83 (t, J=7.58 Hz, 1H), 7.78 (s, 1H), 7.35-7.33 (m, 1H), 7.07 (d, J=7.08 Hz, 1H), 5.44-5.42 (m, 1H), 4.21 (s, 2H), 3.70-3.68 (m, 2H), 3.25-3.22 (m, 2H), 2.98-2.91 (m, 1H), 2.76-2.72 (m, 1H), 2.67-2.62 (m, 1H), 2.27-2.26 (m, 2H), 2.09-2.08 (m, 1H), 1.76-1.71 (m, 2H), 1.35 (s, 3H), 1.16 (s, 9H); LC MS: ES+542.2.

Example 6. Synthesis of Compound 8 and Compound 10

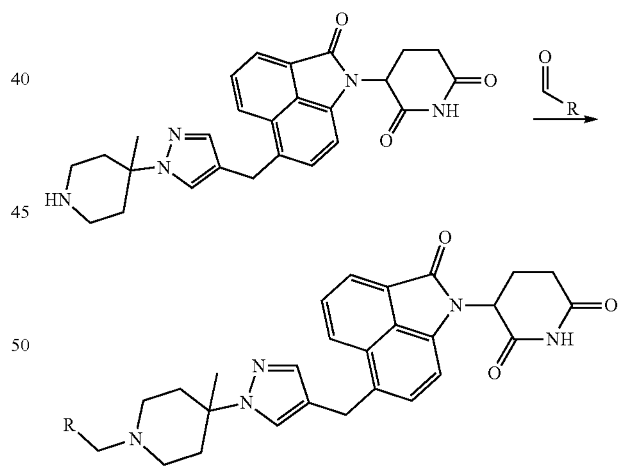

To a stirred solution of amine (1.0 equiv) in THE (6 mL/mmol) was added triethylamine (2.0 equiv) at 0° C. Then aldehyde (1.0 equiv), phenylsilane (1.0 equiv) and dibutyltindichloride (1.2 equiv) were added to the reaction mixture. The resulting solution was stirred at 90° C. for 16 hours. The reaction mixture was then diluted with ethyl acetate and washed with aqueous $NaHCO_3$ solution, water (×3) and brine. The organic layer was then dried over anhydrous $Na_2SO_4$ and concentrated under reduced pressure. The crude mass was then purified by CombiFlash ISCO column, eluting with 3% methanol in DCM.

Compound 8

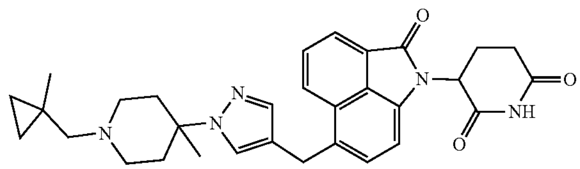 [SMILES: CC1(CN2CCC(C)(n3cc(Cc4ccc5c6c(cccc46)C(=O)N5C4CCC(=O)NC4=O)cn3)CC2)CC1]

Yellow solid, 130.0 mg, 60.22% yield, 98.59% purity. H NMR (400 MHz, DMSO-$d_6$) δ 11.11 (s, 1H), 8.38 (d, J=8.24 Hz, 1H), 8.08 (d, J=6.88 Hz, 1H), 7.81 (t, J=7.58 Hz, 1H), 7.71 (s, 1H), 7.37-7.31 (m, 2H), 7.07 (d, J=7.24 Hz, 1H), 5.43 (dd, J=12.64, 4.8 Hz, 1H), 4.20 (s, 2H), 2.99-2.90 (m, 1H), 2.80-2.69 (m, 1H), 2.66-2.62 (m, 1H), 2.50-2.49 (m, 3H), 2.34-2.32 (m, 2H), 2.15-1.92 (m, 4H), 1.82-1.78 (m, 2H), 1.29 (s, 3H), 1.00 (s, 3H); LC MS: ES+526.6.

Compound 10:

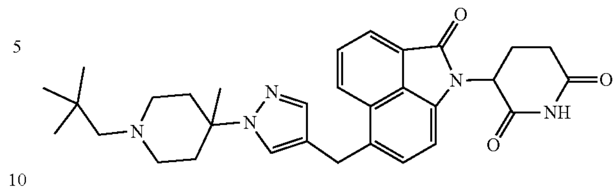

Yellow solid, 130.0 mg, 57% yield, 94.32% purity. $^1$H NMR (400 MHz, DMSO-$d_6$) δ 11.10 (s, 1H), 8.39 (d, J=8.24 Hz, 1H), 8.08 (d, J=6.96 Hz, 1H), 7.82 (t, J=7.62 Hz, 1H), 7.70 (s, 1H), 7.34 (d, J=7.24 Hz, 1H), 7.30 (s, 1H), 7.07 (d, J=7.24 Hz, 1H), 5.43 (dd, J=12.64, 4.88 Hz, 1H), 4.20 (s, 2H), 2.97-2.90 (m, 1H), 2.77-2.72 (m, 1H), 2.67-2.62 (m, 1H), 2.50-2.49 (m, 2H), 2.33-2.29 (m, 4H), 2.09-2.07 (m, 1H), 1.96 (s, 2H), 1.79-1.75 (m, 2H), 1.29 (s, 3H), 0.81 (s, 9H); LC MS: ES+528.5.

Example 7. Synthesis of 3-(6-(4-((1-oxa-8-azaspiro[4.5]decan-8-yl)methyl)benzyl)-2-oxobenzo[cd]indol-1(2H)-yl)piperidine-2,6-dione (Compound 12)

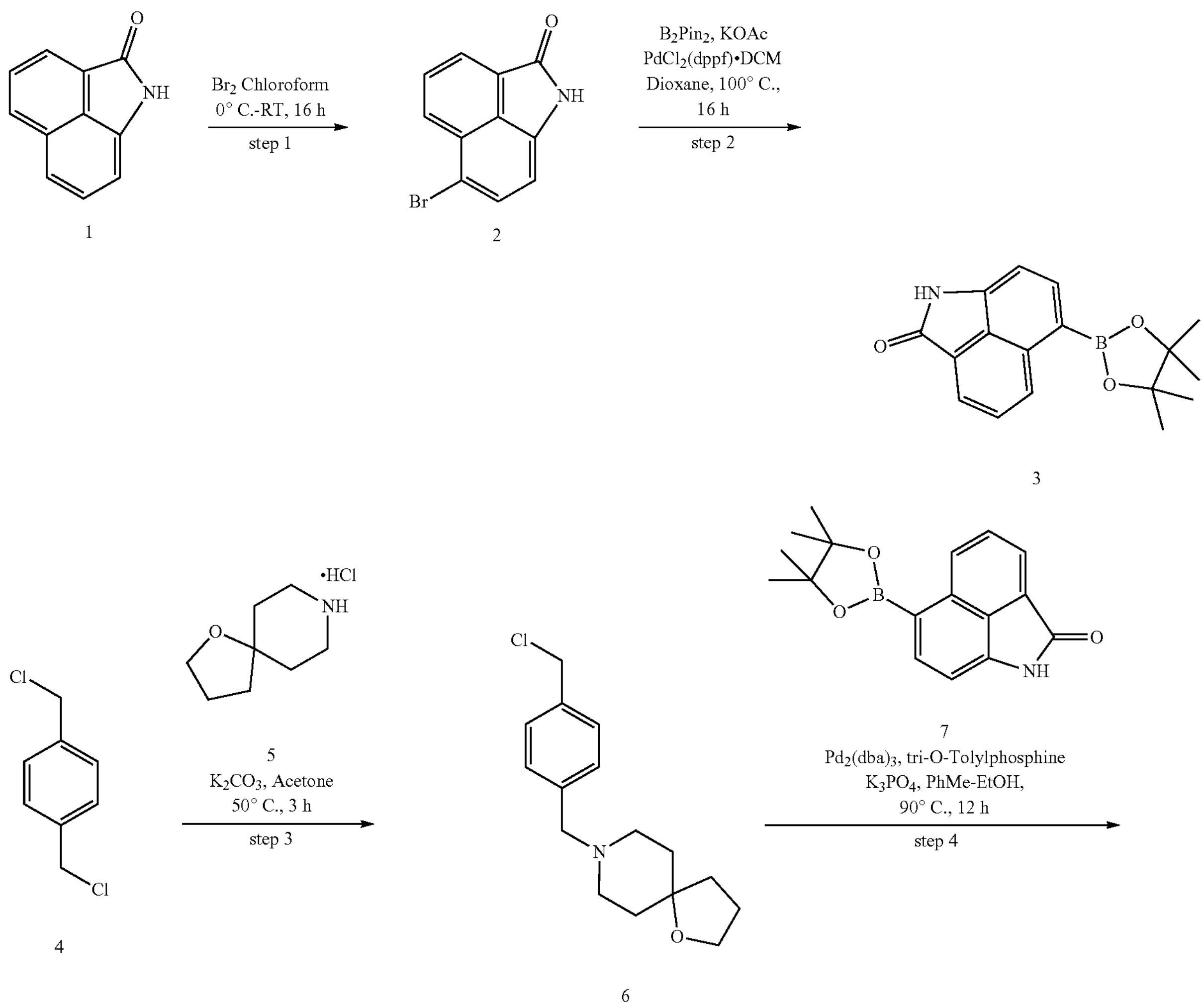

-continued

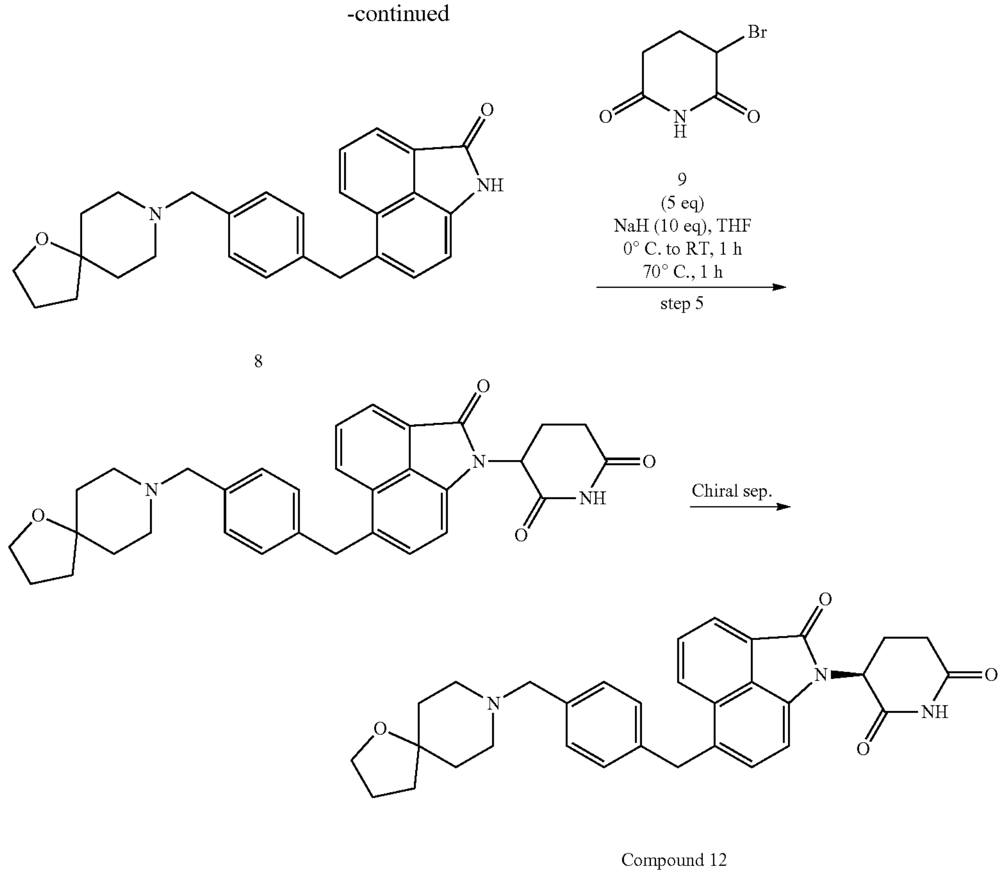

8

9

Compound 12

Step 1: Synthesis of 6-bromo-1H-benzo[cd]indol-2-one (2): To a stirred suspension of 1H-benzo[cd]indol-2-one (1) (250 g, 1.48 mol) in chloroform (2.5 L), a solution of molecular bromine (354.23 g, 2.22 mol, 113.53 mL) in chloroform (500 mL) was added drop wise at 0° C. and the reaction mixture was stirred at room temperature for 16 hours. After completion of the reaction (monitored by TLC), the reaction mass was poured into a saturated solution of sodium thiosulphate in water. The yellow solid formed was filtered through cintered funnel, washed with water, washed with pentane and then stripped with toluene to afford 6-bromo-1H-benzo[cd]indol-2-one (2) (350 g, 90% yield) as yellow solid. LC MS: ES+2 (248.2 and 250.2).

Step 2: Synthesis of 6-(4,4,5,5-tetramethyl-1,3,2-dioxaborolan-2-yl)-1H-benzo[cd]indol-2-one: To a stirred solution of 6-bromo-1H-benzo[cd]indol-2-one (2) (100 g, 403.10 mmol) in 1,4-dioxane (1 L) was added bis(pinacolato)diboron (153.55 g, 604.66 mmol) followed by well dried potassium acetate (118.68 g, 1.21 mol, 75.60 mL). The resultant reaction mass was degassed well with argon for 15 minutes. PdCl2(dppf)·DCM (32.92 g, 40.31 mmol) was added and the reaction mass was heated at 100° C. for 16 hours. After completion of the reaction (monitored by TLC), the reaction mixture was cooled to room temperature, filtered through a pad of celite, and washed with ethyl acetate. The combined filtrate was then washed with cold water, dried over anhydrous sodium sulphate, and concentrated under reduced pressure to afford crude 6-(4,4,5,5-tetramethyl-1,3,2-dioxaborolan-2-yl)-1H-benzo[cd]indol-2-one (3) (110 g, 64% yield) as a brown gum. This was forwarded without further purification, LC MS: ES+295.7.

Step 3: Synthesis of 8-(4-(chloromethyl)benzyl)-1-oxa-8-azaspiro[4.5]decane (6): To a stirred solution of 1-oxa-8-azaspiro[4.5]decane; hydrochloride (5) (5 g, 28.14 mmol) in dry grade acetone (50 mL) was added DIPEA (3.64 g, 28.14 mmol, 4.90 mL) followed by 99% anhydrous potassium carbonate (11.67 g, 84.43 mmol, 5.10 mL) at room temperature and the resulting reaction mixture was heated at 50° C. for 20 minutes. 1,4-bis(chloromethyl)benzene (4) (9.85 g, 56.28 mmol, 6.94 mL) was then added to the reaction mixture and heating was continued for 3 hours. After completion of the reaction (monitored by TLC and LCMS), volatiles were removed under vacuum and the solid thus obtained was taken in ethyl acetate (20 mL), washed with water and brine (×3), dried over anhydrous sodium sulfate and concentrated under reduced pressure. The crude mass was purified by column chromatography (silica, gradient: 0-5% MeOH in DCM) to afford 8-[[4-(chloromethyl)phenyl]methyl]-1-oxa-8-azaspiro[4.5]decane (6) (4.68 g, 16.56 mmol, 58.84% yield, 99% purity) as colorless sticky solid. LC MS: ES+280.4.

Step 4: Synthesis of 6-(4-((1-oxa-8-azaspiro[4.5]decan-8-yl)methyl)benzyl)benzo[cd]indol-2(1H)-one (8): To a well degassed solution of 8-[[4-(chloromethyl)phenyl]methyl]-1-oxa-8-azaspiro[4.5]decane (6) (4.68 g, 16.73 mmol) and 6-(4,4,5,5-tetramethyl-1,3,2-dioxaborolan-2-yl)-1H-benzo[cd]indol-2-one (7) (9.87 g, 33.45 mmol) in ethanol (20.0 mL)-Toluene (40.0 mL), Potassium phosphate tribasic anhydrous (10.65 g, 50.18 mmol) was added followed by the addition Tri-o-Tolyl phosphine (1.02 g, 3.35 mmol) and $Pd_2(dba)_3$ (1.53 g, 1.67 mmol). The resulting mixture was then heated at 90° C. for 12 hours. After completion of reaction (as monitored by LCMS), the reaction mixture was filtered through a bed of celite, washed with Ethyl acetate. The combined filtrate was washed with water and brine, dried over anhydrous sodium sulfate and concentrated under reduced pressure. Crude mass was purified by column chromatography (silica, gradient: 0-5% MeOH in DCM) to obtain 6-[[4-(1-oxa-8-azaspiro[4.5]decan-8-ylmethyl)phenyl]methyl]-1H-benzo[cd]indol-2-one (8) (2.83 g, 6.17 mmol, 36.91% yield, 90% purity) as yellow solid. LC MS: ES+413.0.

Step 5: Synthesis of 3-(6-(4-((1-oxa-8-azaspiro[4.5]decan-8-yl)methyl)benzyl)-2-oxobenzo[cd]indol-1(2H)-yl)piperidine-2,6-dione: To a ice cooled solution of 6-[[4-(1-oxa-8-azaspiro[4.5]decan-8-ylmethyl)phenyl]methyl]-1H-benzo[cd]indol-2-one (8) (2.83 g, 6.86 mmol) in dry THE (20 mL), sodium hydride (60% dispersion in mineral oil) (2.63 g, 68.60 mmol, 60% purity) was added portion wise. The temperature was maintained at <5° C. Once the addition was over, the resultant mixture was stirred for 15 minutes at room temperature. Then the reaction mixture was again cooled to 0° C. and 3-bromopiperidine-2,6-dione (9) (6.59 g, 34.30 mmol) was added to it portion wise. After complete addition, the resulting solution was heated at 70° C. for 1 hour. After completion (evidenced by TLC), the reaction mixture was again cooled to 0° C. and quenched with ice cooled water. The aqueous layer was extracted with ethyl acetate (3×20 mL). The combined extract was dried over anhydrous sodium sulfate and concentrated under reduced pressure. The crude mass was washed with diethyl ether/pentane to afford the racemate which was then chirally separated to afford (S)-3-[6-[[4-(1-oxa-8-azaspiro[4.5]decan-8-ylmethyl)phenyl]methyl]-2-oxo-benzo[cd]indol-1-yl]piperidine-2,6-dione Compound 12 (2.7 g, 5.15 mmol, 75.1% yield) as yellow solid. LC MS: ES+524.3.

Step 6: Chiral separation: 1.2 g of 3-(6-(4-((1-oxa-8-azaspiro[4.5]decan-8-yl)methyl)benzyl)-2-oxobenzo[cd]indol-1(2H)-yl)piperidine-2,6-dione was separated into enantiomers by the chiral normal phase preparative HPLC method below. The fractions were first evaporated separately under reduced pressure to obtain solid mass. The solid was then suspended in a mixture of acetonitrile and water (2:3) and it was kept in a dry-ice/acetone bath until the acetonitrile-water mixture solidified. The frozen mixture was then freeze dried with a lyophilizer for 20 hours to afford 3-[6-[[4-(1-oxa-8-azaspiro[4.5]decan-8-ylmethyl)phenyl]methyl]-2-oxo-benzo[cd]indol-1-yl]piperidine-2,6-dione Compound 12 (first eluted peak, RT=6.29 min 'S' ABS) (420 mg, % ee 99.28).

Preparative Chiral HPLC Method:

- Column: Chiralpak IC (20×250 mm), 5
- Detector wavelength: 224 nm
- Injection Volume: 500 μL
- Flow rate: 18 ml/minute
- Column temperature: NA
- Sample temperature: NA
- Run time: 20 minutes
- Diluent: Mobile phase
- Needle wash: DCM
- Seal wash: NA
- Mobile phase: 600 mL of DCM and 400 mL of Isopropyl alcohol were mixed and sonicated to degas.

General Experimental Information:

The various cell lines described in the Examples below were obtained and cultured as described in Table 1.

TABLE 1

Vendors and Culture Conditions of Cell Lines

| Cell Line | Vendor | Catalog Number | Culture Conditions |
|---|---|---|---|
| NCI-H929 | ATCC | CRL-9068 | RPMI-1640, 10% FBS, 0.05 mM 2-mercaptoethanol |
| KI-JK | ATCC | CRL-9068 | RPMI-1640, 10% FBS |
| DL-40 | JCRB | JCRB1337 | RPMI-1640, 20% FBS |
| TMD8 | Shanghai Rongbo biotech Co. LTD | CVCL_A442 | RPMI-1640, 10% FBS |
| RPMI-8226 | ATCC | CCL-155 | RPMI-1640, 10% FBS |
| MM1.S-Luc | ATCC | CRL-2947 | RPMI + 10% FBS and 1000 ng/mL puromycin |

Example 8 Unique Properties of Compound 1

Biomarker assessment in MM and ALCL tumor bearing studies showed deep degradation (>75%) by Compound 1 of both IKZF1/3 with duration of 24 hours. Compound 1 was effective in MM animal models that were resistant to pomalidomide. Mice bearing RPMI-8226 human MM tumor xenografts showed no response when treated with pomalidomide (3000 μg/kg/day, clinically relevant dose) for 17 days, and once Compound 1 was administered to those animals at 100 pig/kg/day it led to rapid tumor regression.

CB17 SCID mice bearing established RPMI-8226 xenografts were administered pomalidomide (3000 pug/kg/day) on a daily PO regimen for 3 weeks. Pomalidornide treatment was then stopped and mice were treated with Compound 1 (100 μg/kg/day) on a daily regimen for 2 weeks. Data are expressed as mean tumor volumes±SEM.

In a single MM tumor bearing study, Compound 1 alone attained regression; however, the combination of dexamethasone (5 mg/kg, QW) with Compound 1 (10 μg/kg/day) attained longer durability of regression compared to Compound 1 alone or dexamethasone alone.

IKZF1/3 are not degraded in mouse cells treated with thalidomide or its IMiD® analogs because of a single amino acid difference in mouse cereblon compared to human cereblon that causes steric hindrance and prevents recruitment of IKZF1/3. Ex vivo studies were performed in peripheral blood cells (PBMC) of mice, rats, dogs, and monkeys to identify relevant species for IND enabling-toxicity studies based on the degree of IKZF1 degradation by Compound 1. IKZF1 was not degraded in mouse or rat cells by Compound 1, thus, while rat could not be considered a pharmacologically relevant species for human risk assessment, it was chosen as the rodent species for toxicological studies because it is widely used in toxicity testing and a substantial historical toxicology database is available. Compound 1 was highly effective in degrading IKZF1/3 in cynomolgus monkey cells but had no effect on IKZF1/3 in dog cells. Therefore, cynomolgus monkey was chosen for non-rodent toxicological studies.

Secondary pharmacodynamic (PD) studies were conducted to evaluate off-target activity of Compound 1. Global proteomic studies from ALCL tumor xenografts isolated from mice 4 hours post a single dose of Compound 1 (100 μg/kg) demonstrated that Compound 1 is highly selective, degrading only IKZF1/3 out of >7900 proteins detected in the tissue.

Specific studies were carried out to assess the ability of Compound 1 to degrade Sal-like protein 4 (SALL4), a protein implicated in the teratogenicity induced by the IMiD®s class of IKZF1/IKZF3 degraders. In the KELLY neuroblastoma cell line, Compound 1 promoted the degradation of SALL4 by more than 85% at 10 nM, suggesting that Compound 1 has teratogenic potential. A small number of cereblon E3 ligase modulators have been shown to promote degradation of the translation termination factor GSPT1. From a targeted cell-based assay, Compound 1 had no significant effect on G1 to S Phase Transition 1 (GSPT1) up to 10 μM.

In vitro testing for specific binding or activity of Compound 1 (100 nM) against 87 potential unintended molecular targets showed no targets inhibited >50% at 500× the free plasma exposure ($C_{max}$) associated with maximum in vivo efficacy. Viability assays performed in HepG2 liver cancer cells, devoid of IKZF1 and IKZF3, showed no significant effect on viability with Compound 1 at concentrations up to 3.3 μM.

Example 9. Potency and Catalytic Rate of Compound 1

Figure 1A:
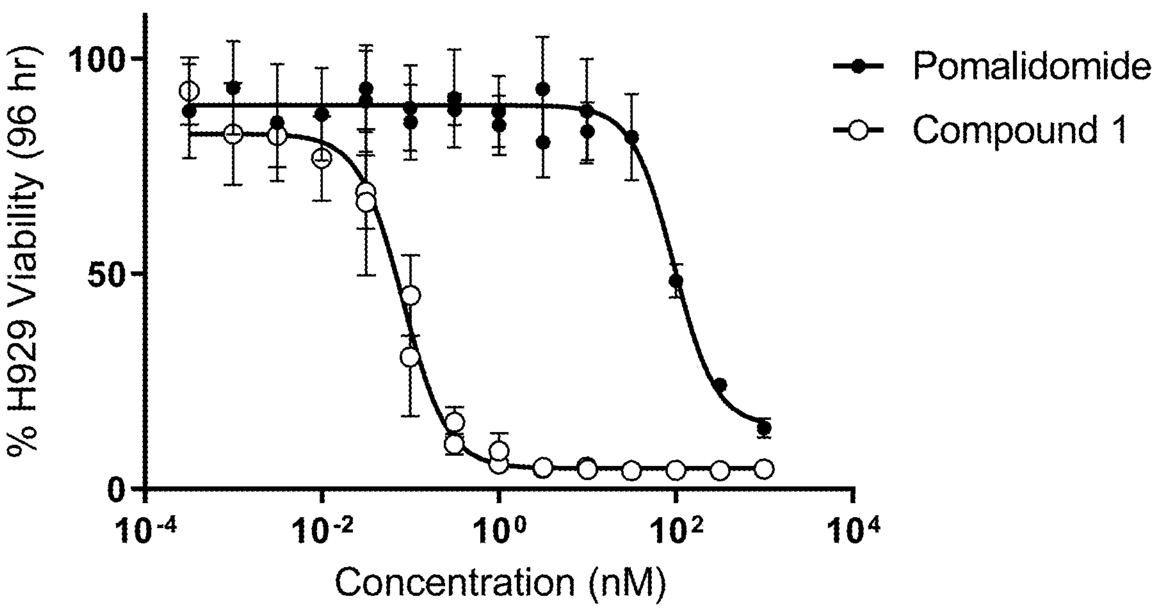
FIG. 1A is a dose-response curve describing the effect of Compound 1 on H929 cell viability compared to pomalidomide as described in Example 9. The x-axis is the concentration of Compound 1 or pomalidomide in nM and the y-axis is the % H929 cell viability after 96 hours.

The potency of Compound 1 was determined using an NCI-H929 viability assay and compared to pomalidomide. NCIH929 cell viability was determined based on quantification of ATP using CellTiter-Glo®2.0 luminescent Assay kit, which signals the presence of metabolically-active cells. Briefly, test compound was added to 384-well plates at a top concentration of 1 μM with 10 points, half log titration in duplicates. NCIH929 cells were seeded into the 384-well plates in RPMI medium containing 10% FBS and 0.05 mM 2-mercaptoethanol at a cell density of 750 cells per well. Cells treated in the absence of the test compound were the negative control and cells treated in the absence of CellTiter-Glo® 2.0 were the positive control. Cells treated with the test compounds were incubated at 37° C. with 5% $CO_2$ for 96 hr. CellTiter-Glo reagent was then added to the cells and Luminescence was acquired on EnVision™ Multilabel Reader (PerkinElmer, Santa Clara, CA, USA). % Viability was determined by normalizing the signal with positive and DMSO treated negative controls on the same microtiter plate. The results are shown in FIG. 1A and Table 2. As shown in Table 2, Compound 1 exhibited an $IC_{502}$ of 0.071 μM. Data in FIG. 1A are expressed as the mean±SD for 3 independent experiments each with n=2. Curve fit and $IC_{502}$ determination was performed by 4 parametric regression analysis. Data in Table 1 are the geometric mean and 95% confidence interval of $IC_{502}$ values and the linear mean±SD for $E_{max}$ values determined for the indicated number of independent experiments.

TABLE 2

The Effect of Compound 1 on H929 Cell Viability and IKZF1 Degradation

| | Treatment | Mean $IC_{50}$ (nM) | $IC_{50}$ 95% CI (nM) | Mean $E_{max}$ (%) ± SD |
|---|---|---|---|---|
| H929 Viability | Pomalidomide (n = 14) | 141 | 97-204 | 15.6 ± 4.2 |
| (96 hours) | Compound 1 (n = 3) | 0.071 | 0.033-0.149 | 4.0 ± 0.5 |
| IKZF1 Degradation | Pomalidomide (n = 24) | >833 | NA | 55.7 ± 6.0 |
| (1.5 hours) | Compound 1 (n = 2) | 0.27 | NA | 22.4 ± 3.1 |

Figure 1B:
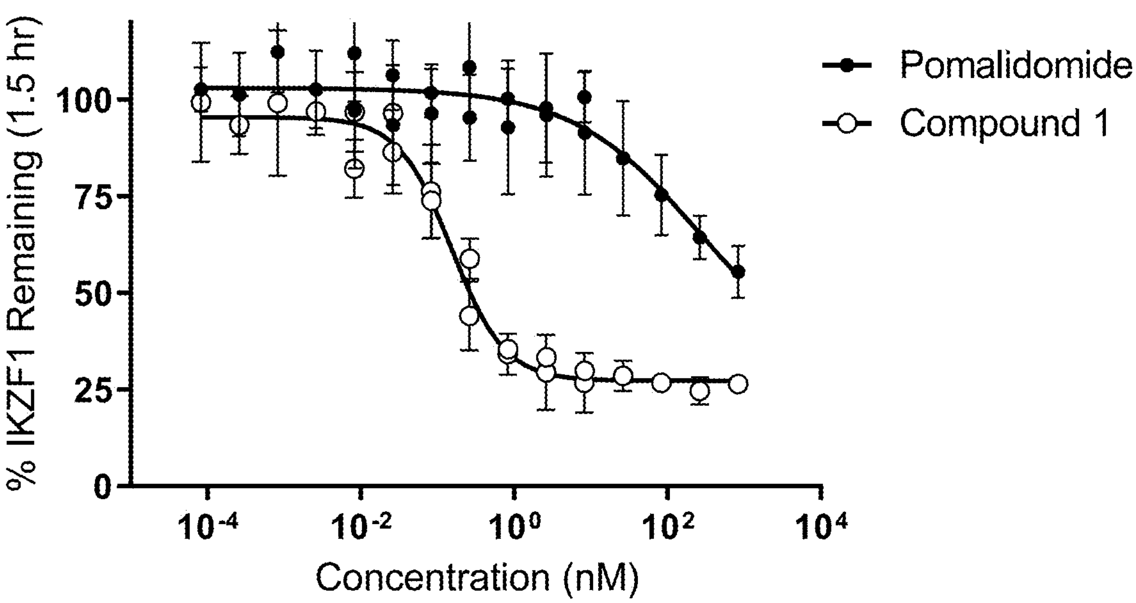
FIG. 1B is a dose-response curve describing the effect of Compound 1 on IKZF1 degradation compared to pomalidomide as described in Example 9. The x-axis is the concentration of Compound 1 or pomalidomide in nM and the y-axis is the % IKZF1 remaining after 1.5 hours.

The effect of Compound 1 on NCI-H929 IKZF1 degradation was also determined. Endogenous expression of IKZF1 in NCIH929 cells was determined by addition of N-terminal HiBiT tag to the NCIH929 cell line using CRISPR-Cas9. Briefly, test compound was added to 384-well plates at a top concentration of 1 μM with 10 points, half log titration in duplicates. NCIH929 cells expressing HiBiT-tagged IKZF1 were seeded into the 384-well plates in RPMI medium containing 10% FBS and 0.05 mM 2-mercaptoethanol at a cell density of 15000 cells per well. Cells treated in the absence of the test compound were the negative control and wells containing media only were the positive control. Following compound treatment, cells were incubated at 37° C. with 5% $CO_2$ for 1.5 hr. HiBiT signal was determined using Nano-Glo™ HiBiT Lytic Assay System (Promega, N3050) and luminescence was acquired on EnVision™ Multilabel Reader (PerkinElmer, Santa Clara, CA, USA). % IKZF1 remaining was determined by normalizing the signal with positive and negative controls on the same microtiter plate. The results are shown in FIG. 1B and Table 2. As shown in Table 2, Compound 1 exhibited an $IC_{50}$ of 0.27 μM. Data in FIG. 1B are expressed as the mean±SD for 2 independent experiments each with n=2. Curve fit and $IC_{50}$ determination was performed by 4 parametric regression analysis. Data in Table 1 are the geometric mean and 95% confidence interval of $IC_{50}$ values and the linear mean±SD determined for the indicated number of independent experiments.

The data in FIG. 29 was produced by measuring IKZF1 degradation after addition of N-terminal HiBiT tag to the endogenously expressed IKZF1 in NCIH929 cell line using CRISPR-Cas9. Test compound was added to 384-well plates at a top concentration of 1 μM for Compound 1 and 10 μM for pomalidomide with 22 points, 2-fold titration in duplicates. NCIH929 cells expressing HiBiT-tagged IKZF1 were seeded into the 384-well plates in RPMI medium containing 10% FBS and 0.05 mM 2-mercaptoethanol at a cell density of 15000 cells per well. Cells treated in the absence of the test compound were the negative control and wells containing media only were the positive control. Following compound treatment, cells were incubated at 37° C. with 5% $CO_2$ for 1 or 2 hr. HiBiT signal was determined using Nano-Glo™ HiBiT Lytic Assay System (Promega, N3050) and luminescence was acquired on EnVision™ Multilabel Reader (PerkinElmer, Santa Clara, CA, USA). % IKZF1 remaining was determined by normalizing the signal with positive and negative controls on the same microtiter plate. Curve fit and $IC_{50}$ determination was performed by 4 parametric regression analysis. Compound 1 induced rapid degradation of IKZF1, resulting in 50% degradation after 1 hour treatment and >80% maximal degradation after 2 hour treatment with a DC50 of 21 pM. Pomalidomide degraded less than 25% of IKZF1 at 1 hour and Compound 1 showed potency >2000-fold greater than pomalidomide at 2 hr.

Example 10. Compound 1 Selectivity in ALCL Tumor Xenografts Using Global Proteomics NOD SCI mouse bearing ALCL ALK+DL40 xenografts were treated orally with 100 μg/kg of Compound 1. After 1, 4, 24 and 48 hour treatment, biological duplicates of tumoral cells were harvested, washed twice with PBS, and snap frozen in liquid nitrogen. Samples were resuspended in lysis buffer [8 M urea, 50 mM EPPS (pH 8.5), 50 mM NaCl, lx protease inhibitor cocktail] and lysed by sonication. Lysates were centrifuged at maximum speed, reduced for 1 hour at room temperature with 5 mM TCEP, and the cysteine residues were then alkylated with 15 mM iodoacetamide (room temperature, in dark, 30 minutes). Protein content was extracted twice by methanol-chloroform precipitation and subsequent ice-cold acetone washes. Protein pellets were resuspended in 8 M urea, 50 mM EPPS (pH 8.5) buffer and protein concentrations were measured by BCA assay. Samples were then diluted to 4 M urea with 50 mM EPPS (pH 8.5) and digested at 37° C. for 1 hour with endoproteinase Lys-C, at a 1/100 enzyme/protein ratio. The mixtures were then diluted to 1 M urea with 50 mM EPPS (pH 8.5) and trypsin was added at a 1/50 enzyme/protein ratio. The reaction was incubated overnight at 37° C. and stopped by acidification with formic acid 0.5% (v/v). Peptides were loaded on tC18 SepPak solid-phase extraction cartridges and lyophilized.

For peptide labeling, 100 μg of peptides per sample was prepared at 1 μg/l concentration in 200 mM EPPS (pH 8.5), ACN was added to a final concentration of 30% and then 50 μg of each TMT 10 reagent. After 1 hour incubation at room temperature, reactions were quenched with 0.3% hydroxylamine for 15 minutes and mixed equally. The mixed sample was desalted using the tC18 SepPak solid-phase extraction cartridges, and lyophilized. Dried peptides were resuspended in 5% ACN, 10 mM $NH_4HCO_3$ pH 8 and fractionated in a basic pH reversed phase chromatography using a HPLC equipped with a 3.5 μm XBridge Peptide BEH C18 column. 96 fractions were collected, which were consolidated into 24, of which only 12 nonadjacent samples were analyzed. Samples were desalted, dried via vacuum centrifugation and reconstituted in 12 μL of 5% formic for LC-MS/MS analysis.

Figure 2A:
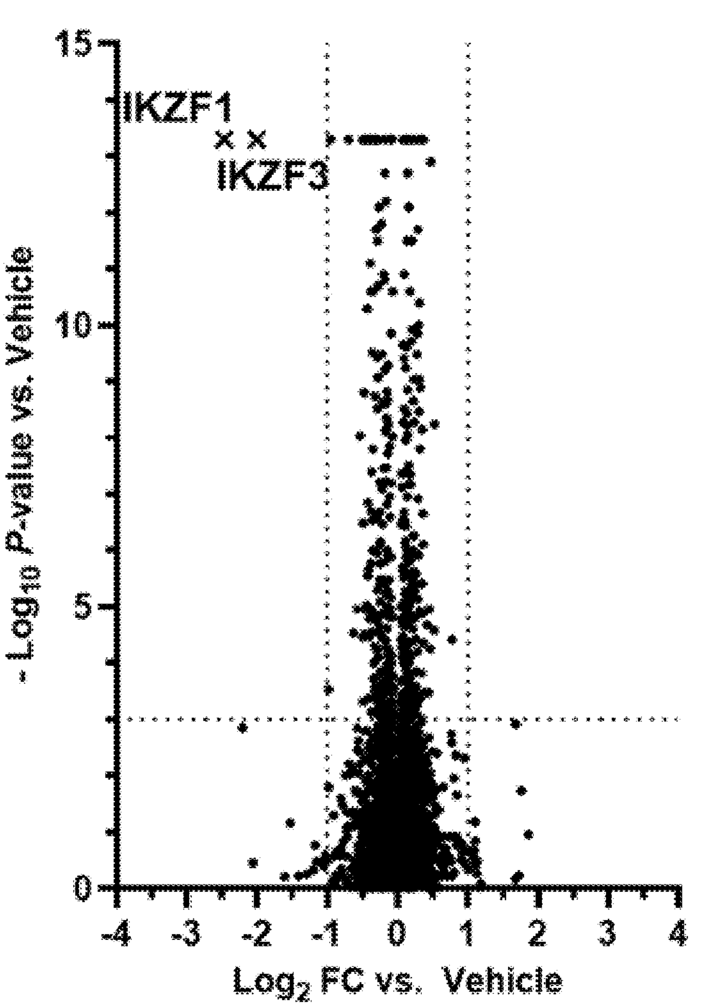
FIG. 2A is a scatter plot of data from tumor lysates analyzed by multiplexed quantitative proteomics in mice treated with Compound 1 for 4 hours. Tumor lysates were analyzed by multiplexed quantitative proteomics and fold changes in relative abundance comparing treatment with Compound 1 to that with DMSO control were depicted in a scatter plot. Log 2 fold changes are shown in the x axis and negative Log 10 adjusted P values are shown on the y axis. The horizontal dashed line marks the statistical significance (P adjusted≤0.01) and the vertical line marks fold change ≥2. IKZF1 and IKZF3 are the only significantly downregulated proteins with a fold change of 5.5 and 4.1, respectively. Data shown are of biological duplicates measured in a single 10-plex TMT experiment with a total of 7,903 proteins quantified. P values were derived from a moderated t-statistic and corrected for multiple hypothesis testing using a Benjamini-Hochberg approach. The experimental procedure is provided in Example 10.
Figure 2B:
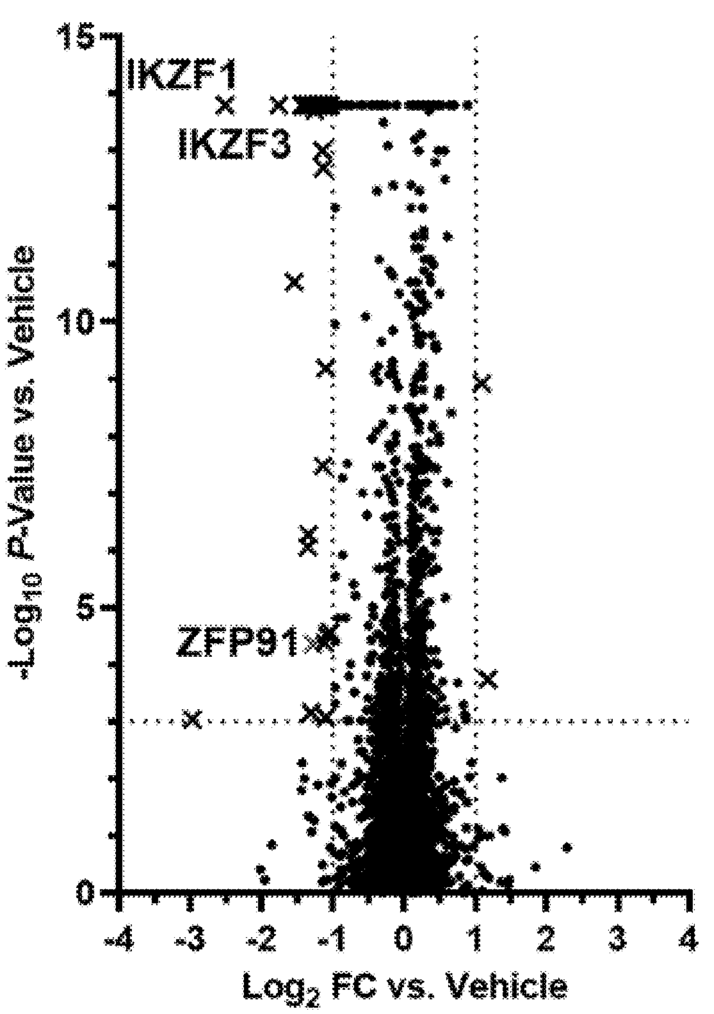
FIG. 2B is a scatter plot of data from tumor lysates analyzed by multiplexed quantitative proteomics in mice treated with Compound 1 for 24 hours. Tumor lysates were analyzed by multiplexed quantitative proteomics and fold changes in relative abundance comparing treatment with Compound 1 to that with DMSO control were depicted in a scatter plot. Log 2 fold changes are shown in the x axis and negative Log 10 adjusted P values are shown on the y axis. The horizontal dashed line marks the statistical significance (P adjusted≤0.01) and the vertical line marks fold change ≥2. The experimental procedure is provided in Example 10.

A third of each sample (4 μL) was separated by reversed phase chromatography using an EASY-Spray C18 column (2 μm particle size, 250 mm length×75 μm ID) mounted in an EASY-nLC 1200 LC pump coupled to an Orbitrap Fusion Lumos Tribid mass spectrometer. Peptides were separated using a 420 min gradient of 2 to 30% acetonitrile at a flow rate of ~300 nL/min. Each analysis was performed using the multi-notch MS3 (SPS-MS3) scan. For the identification and relative quantification, all RAW files obtained from the mass spectrometer were transformed using SEQUEST-based software. Briefly, mass spectra were searched against the human Uniprot database (February 2016) concatenated with a database composed of all protein sequences in the reversed order as well as known contaminants. In all SEQUEST searches, precursor ion tolerance was set at 25 ppm and product ion tolerance at 0.9 Da, including methionine oxidation (+15.9949 Da) and cysteine carbamidomethylation (+57.0215 Da) as variable modifications. TMT tag (+229.1629 Da) on lysine residues and peptide N-termini were set as static modifications. Peptide-spectrum matches (PSMs) were performed using a linear discriminant analysis and adjusted to a 200 FDR2. Peptide intensities were quantified by extracting the signal-to-noise ratio and proteins were further collapsed to a final protein-level FDR of 2%. Protein quantification values were exported to Excel, GraphPad Prism 7 or Perseus14 for further analysis. The resulting data is shown in FIG. 2A and a 24 hour experiment is shown in FIG. 2B.

The identified proteins are shown in Table 3 and Table 4 below

TABLE 3

Identified Proteins From 4-Hour Proteomics Study
4 Hour Proteomics

| Gene Symbol | Total Peptides | Log2 FC vs Vehicle | P-value |
|---|---|---|---|
| IKZF1 | 26 | −2.466 | 4.50E−14 |
| IKZF3 | 11 | −2.006 | 4.70E−14 |

TABLE 4

Identified Proteins From 24-Hour Proteomics Study
24 Hour Proteomics

| Gene Symbol | Total Peptides | Log2 FC vs Vehicle | P-value |
|---|---|---|---|
| MYH7 | 14 | −2.977 | 9.20E−04 |
| IKZF1 | 26 | −2.515 | 1.70E−14 |
| IKZF3 | 11 | −1.761 | 1.70E−14 |
| CKMT2 | 47 | −1.544 | 1.90E−11 |
| MYLPF | 128 | −1.434 | 1.70E−14 |
| ATP2A1 | 102 | −1.427 | 1.70E−14 |
| TNNI2 | 29 | −1.377 | 1.70E−14 |
| MYBPC1 | 58 | −1.366 | 1.70E−14 |
| APOBEC2 | 8 | −1.355 | 8.70E−07 |
| MYL4 | 13 | −1.344 | 5.30E−07 |
| CASQ1 | 25 | −1.333 | 1.70E−14 |
| FHL1 | 21 | −1.311 | 6.90E−04 |
| ACTN2 | 91 | −1.304 | 1.70E−14 |
| MYL1 | 174 | −1.3 | 1.70E−14 |
| ZFP91 | 7 | −1.279 | 4.40E−05 |
| MYH1 | 274 | −1.258 | 1.70E−14 |
| SRL | 33 | −1.252 | 2.00E−14 |
| CKM | 125 | −1.248 | 1.70E−14 |
| MYH7B | 84 | −1.231 | 1.70E−14 |
| MYOM1 | 47 | −1.201 | 1.70E−14 |
| MYH2 | 632 | −1.188 | 1.70E−14 |
| NEB | 241 | −1.184 | 1.70E−14 |
| MYH3 | 49 | −1.165 | 1.70E−14 |
| MYBPC2 | 45 | −1.146 | 1.70E−14 |
| TPM1 | 36 | −1.146 | 9.00E−14 |
| KLHL41 | 13 | −1.142 | 3.30E−08 |
| PYGM | 71 | −1.139 | 1.70E−14 |
| LDB3 | 35 | −1.136 | 2.10E−13 |
| JPH2 | 6 | −1.117 | 4.20E−05 |
| TTN | 1070 | −1.117 | 1.70E−14 |
| PVALB | 5 | −1.105 | 8.50E−04 |
| MYH13 | 14 | −1.102 | 6.40E−10 |
| ACTA1 | 93 | −1.089 | 1.70E−14 |
| TRIM72 | 8 | −1.083 | 3.10E−05 |
| MYH4 | 174 | −1.05 | 1.70E−14 |
| AK1 | 18 | −1.041 | 2.70E−05 |
| TNNC2 | 54 | −1.035 | 1.70E−14 |
| SPR | 9 | 1.088 | 1.20E−09 |
| OAS1 | 5 | 1.172 | 1.80E−04 |

Example 11. Compound 1-Induced Ikaros Degradation in KW-K (ALK+) Cells

Figure 3:
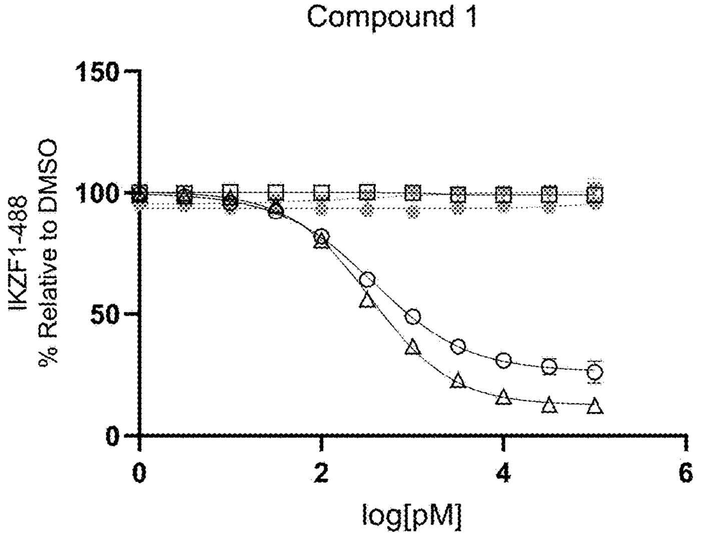
FIG. 3 is a dose-response curve describing the effect of Compound 1 with and without bortezomib (proteasome inhibitor) or MLN-4924 (neddylation inhibitor) on Ikaros degradation. As described in Example 11, Ki-JK cells were exposed to Compound 1 with and without bortezomib or MLN-4924 and the IKZF1 concentration was determined by flow cytometry at 1.5, 3, and 6 hours for Compound 1 and 6 hours for the combination of Compound 1 and bortezomib or MLN-4924. The x-axis is the concentration of Compound 1 alone or in combination with bortezomib or MLN-4924. The y-axis is the remaining concentration of IKZF1-488 measured as a percent relative to DMSO.

Flow cytometry was used to assess the Ikaros degradation characteristics and evaluate the mechanism of Compound 1. Ki-JIK cells (DSMZ, ACC 695) were seeded in 96-well plates pre-spotted with Compound 1 in dose response (11-point, duplicate, 0.001-100 nM), with and without bortezomib (proteasome inhibitor, 10 μM) or MLN-4924 (neddylation inhibitor, 10 μM). The cells were prepared for staining using the FOXP3 Fix/Perm Buffer Set (BioLegend, 421403) according to the manufacturer's instructions at 1.5, 3, and 6 hours. IKZF1-AF488 (564867) and IgG1-488 (557782) (BD Biosciences) were diluted 1:100 in Perm Buffer. Signal was detected using the Guava® easyCyte™ Flow Cytometer. As shown in FIG. 3, potent dose response degradation over time with Compound 1 was observed and the maximal degradation was observed at 6 hours. Degradation was not observed with the combination of Compound 1 and bortezomib or MLN-4924.

Example 12. Compound 1 Anti-Proliferative Activity in Hematological Cancer

The anti-proliferative activity of Compound 1 in hematological cancer cell lines was evaluated and compared to Pomalidomide. The cells were treated for 96 hours and the results are shown in Table 5. Compound 1 is more potent than pomalidomide in every cell line, and in multiple cell lines, it is more than 5,000-fold more active.

TABLE 5

Anti-proliferative activity of Compound 1 in Hematological Cancer Cell Lines

| Cell Line | Description | Compound 1 $IC_{50}$ (nM) | Pomalidomide $IC_{50}$ (nM) |
|---|---|---|---|
| OCI-LY10 | ABC-DLBCL | 0.03 | 47.7 |
| TMD8 | ABC-DLBCL | 0.078 | 326.7 |
| SU-DHL-2 | ABC-DLBCL | 4.55 | >10000 |
| KARPASS422 | GCB-DLBCL | 0.189 | 24.4 |
| Pfeiffer | GCB-DLBCL | 1.08 | >10000 |
| RL | GCB-DLBCL | 2.32 | >10000 |
| DOHH-2 | GCB-DLBCL | 2.73 | 1153 |
| WSU-DLCL2 | GCB-DLBCL | 2.8 | >10000 |
| SU-DHL-5 | GCB-DLBCL | 6.37 | >10000 |
| Farage | GCB-DLBCL | 56.3 | >10000 |
| SU-DHL-1 | ALCL | 0.415 | 378 |
| KIJK | ALCL | 0.583 | 4326 |
| DL40 | ALCL | 0.91 | >10000 |
| SR | ALCL | 16.2 | >10000 |
| HuT 102 | CTCL | 15.4 | >10000 |
| HH | CTCL | 58 | >10000 |
| Mino | MCL | 0.194 | 426 |
| Rec-1 | MCL | 0.353 | 44.8 |
| Maver-1 | MCL | 12.1 | >10000 |
| Jeko-1 | MCL | 43.2 | >10000 |
| MM.1S | MM | 0.036 | 71 |
| OPM-2 | MM | 0.058 | 93.3 |
| KMM-1 | MM | 0.059 | 527 |
| H929 | MM | 0.073 | 171 |
| MM.1R | MM | 0.083 | 193 |
| LP-1 | MM | 0.642 | 576 |
| RPMI 8226 | MM | 0.698 | >10000 |
| KMS-26 | MM | 0.789 | 2093 |

Example 13. Compound 1 Efficacy in Multiple Myeloma

Figure 4:
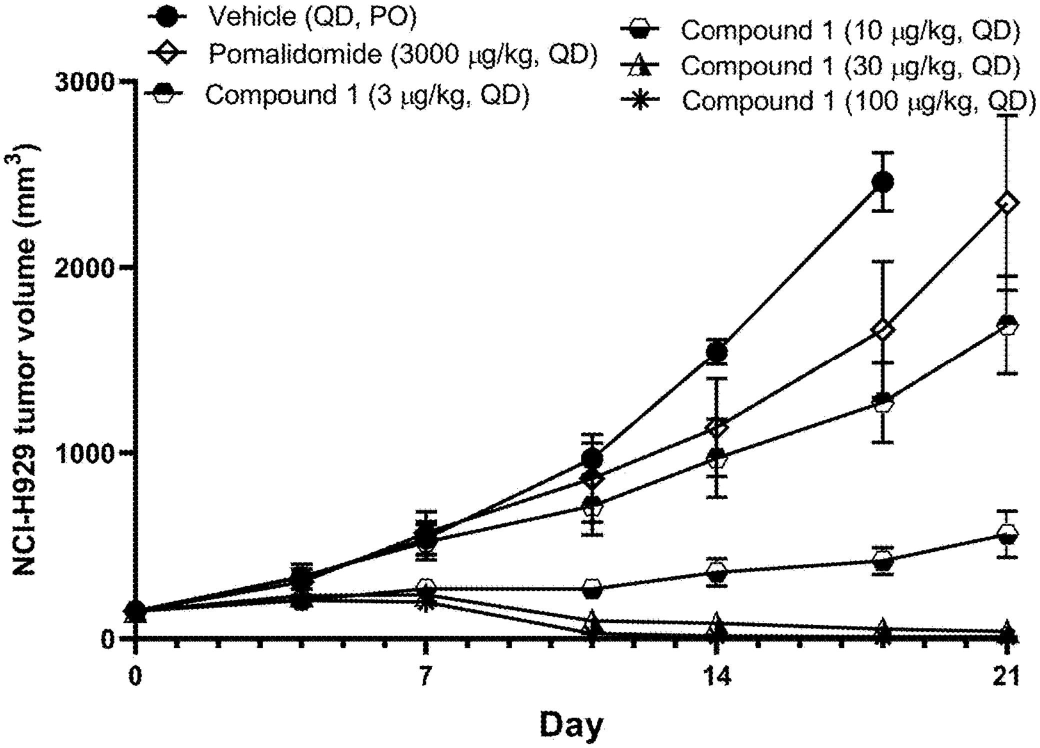
FIG. 4 is a graph of the effect of Compound 1 in mice bearing multiple myeloma NCI-H929 cells as described in Example 13. Compound 1 was administered orally (PO) every day (QD) at four different concentrations (3 μg/kg, 10 μg/kg, 30 μg/kg, and 100 μg/kg) and compared to pomalidomide. The x-axis is the time measured in days and the y-axis is NCI-H929 tumor volume measured in $mm^3$.
Figure 5:
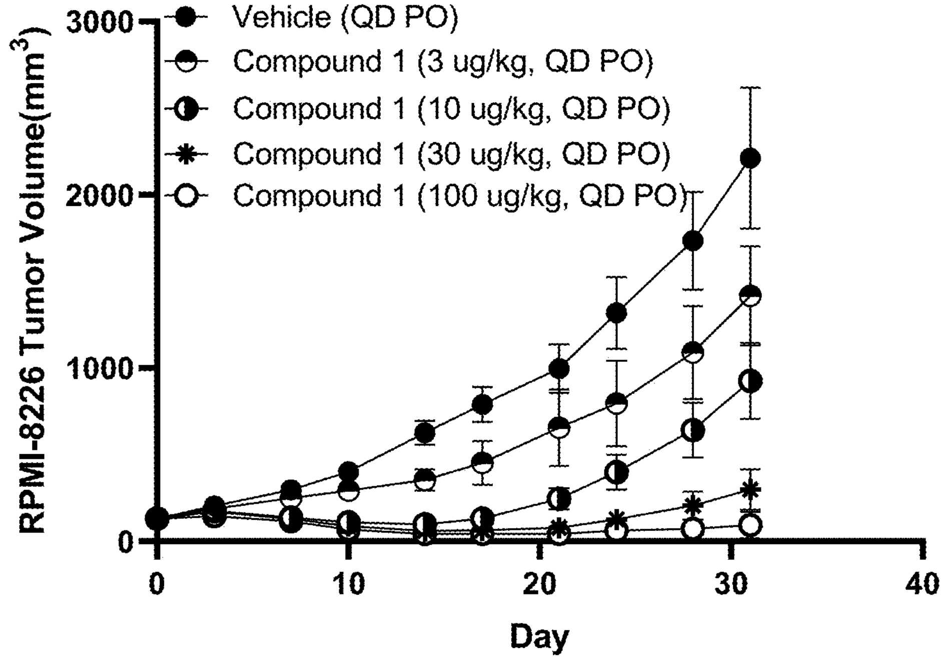
FIG. 5 is a graph of the effect of Compound 1 in mice bearing multiple myeloma RPMI-8226 cells as described in Example 13. Compound 1 was administered orally (PO) every day (QD) at four different concentrations (3 μg/kg, 10 μg/kg, 30 μg/kg, and 100 μg/kg) and compared to pomalidomide. The x-axis is the time measured in days and the y-axis is RPMI-8226 tumor volume measured in $mm^3$.

Compound 1 efficacy in two multiple myeloma cell lines (NC-H929) and (RPMI-8226) was evaluated at four different doses: 3 μg/kg, 10 μg/kg, 30 μg/kg, and 100 μg/kg. Compound 1 was administered QD (every day) orally (PO). The efficacy of Compound 1 was compared to pomalidomide (administered at 3000 μg/kg). The results in the NCI-H929 and RPMI-8826 cells lines are shown in FIGS. 4 and 5, respectively. Table 6 describes the statistical significance of the experiment in each cell line for each dose. Compound 1 at all four concentrations was reduced tumor volume more than pomalidomide administered at 3000 μg/kg.

TABLE 6

Statistical Significance of Compound 1 Compared to Vehicle

| Treatment | Dose Level (μg/kg) | Statistical Significance Compared to Vehicle |
|---|---|---|
| NCI-H929 Cells | | |
| Vehicle | N/A | N/A |
| Compound 1 | 3 | 0.04 |
| Compound 1 | 10 | 0.0002 |
| Compound 1 | 30 | 0.0004 |
| Compound 1 | 100 | 0.0004 |
| Pomalidomide | 3000 | 0.718 |
| RPMI-8226 | | |
| Compound 1 | 3 | NS |
| Compound 1 | 10 | NS |
| Compound 1 | 30 | 0.01 |
| Compound 1 | 100 | 0.009 |

For the NCI-H929 cells, the xenograft study was conducted in female NOD SCID mice bearing NCI-H929 multiple myeloma tumors. Female SCID mice were inoculated subcutaneously in the right flank with $5\times10^6$ tumors cells in 0.2 mL of PBS supplemented with matrigel (PBS: matrigel=1:1). Tumor volume was measured twice weekly in two dimensions using calipers, and volume was calculated using the formula: $(w2\times l)/2=mm^3$, assuming 1 mg is equivalent to 1 $mm^3$ of tumor volume. Once the tumors reached a volume range of 84-267 $mm^3$ (18 days after implantation), the animals were divided randomly into groups of 6, stratified to result in about equal average tumor sizes in each treatment group. Treatment began on Day 0 with established subcutaneous NCI-H929 tumors with a mean tumor volume (MTV) of 149-150 $mm^3$.

All agents were administered to mice bearing NCI-H929 tumors on day 0 and dosed PO daily for 21 days, except for the vehicle group which was dosed for 18 days. Compound 1 was dosed at 3, 10, 30, or 100 μg/kg and was formulated in PEG400 (30% v/v)+70% v/v HPMC (1% w/v) in citrate buffer (pH 5). Pomalidomide was dosed at 3000 μg/kg and used the same formulation as Compound 1. Body weight and MTV were measured on a 2× weekly schedule and the study end point was a MTV of 2460 $mm^3$ in the vehicle control group on Day 18. Statistical analysis was performed using two-way analysis of variance (ANOVA). Data are expressed as MTV±SEM.

For the RPMI-8226 MM model, the female CB17 SCID mice were inoculated subcutaneously in the right flank with $10\times10^6$ RPMI-8226 cells in 0.2 mL of PBS supplemented with matrigel (PBS:matrigel=1:1). Tumor volume was measured twice weekly in two dimensions using calipers, and volume was calculated using the formula: $(w2\times l)/2=mm^3$, assuming 1 mg is equivalent to 1 $mm^3$ of tumor volume. Once the tumors reached a volume range of 109-158 $mm^3$ (28 days after implantation), the animals were divided randomly into groups of 6, stratified to result in about equal average tumor sizes in each treatment group. Treatment began on Day 0 with established subcutaneous RPMI-8226 tumors with a mean tumor volume (MTV) of 130 $mm^3$.

All agents were administered to mice bearing RPMI-8226 tumors on day 0 and dosed PO daily for 31 days. Compound 1 was dosed at 3, 10, 30, or 100 μg/kg and was formulated in PEG400 (30% v/v)+70% v/v HPMC (1% w/v) in citrate buffer (pH 5). Body weight and MTV was measured on a 2× weekly schedule and the study end point was a MTV of 2211 $mm^3$ in the vehicle control group on Day 31. Statistical analysis was performed using two-way analysis of variance (ANOVA). Data are expressed as MTV±SEM.

Example 14. Compound 1 Demonstrates Rapid Tumor Elimination in Multiple Myeloma Model Compound 1 was administered at 300 μg/kg QD (every day) orally to female NOD SCID mice with disseminated MM1.S multiple myeloma tumors with a measurable MM1.S tumor burden on day 0 and dosed PO daily for 3 weeks. Compound 1 was formulated in PEG400 (30% v/v)+70% v/v HPMC (1% w/v) in citrate buffer (pH 5). Body weight and tumor burden were measured on a 2× weekly schedule and the study end point was 20 days post the dosing, day 41. Data are expressed as mean BLI±SEM.

Figure 6:
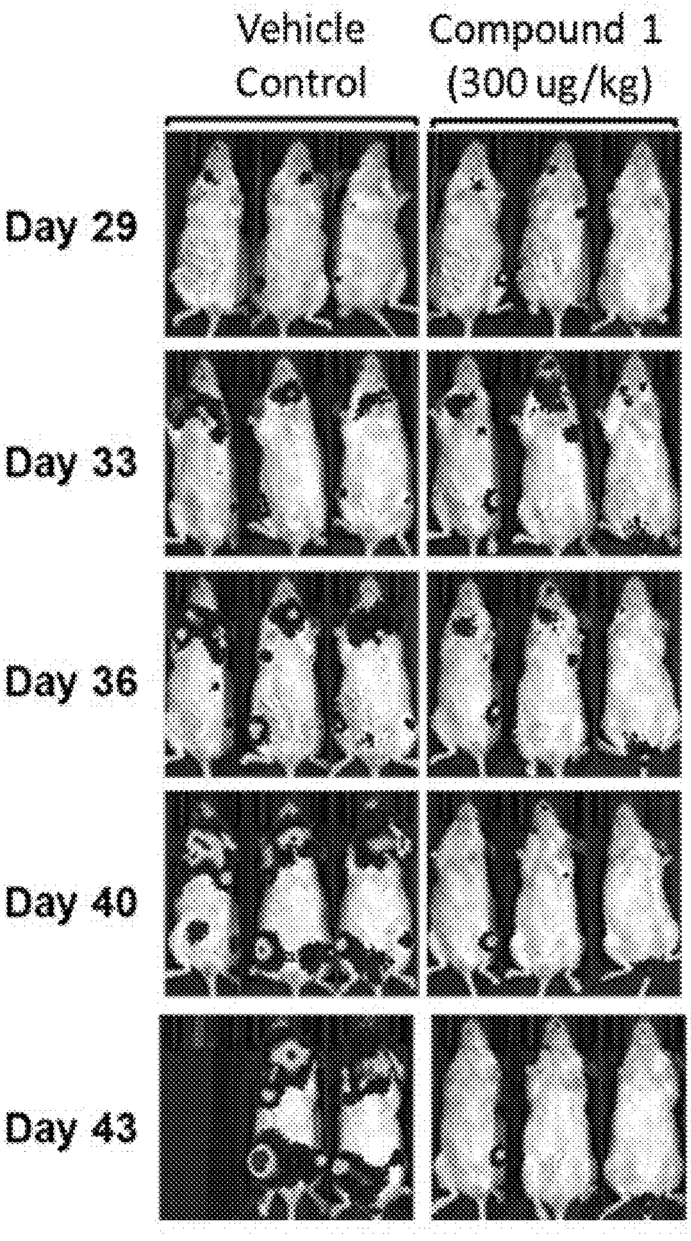
FIG. 6 are images comparing mice administered Compound 1 and vehicle. Mice were imaged using IVIS Lumina II as described in Example 14.
Figure 8:
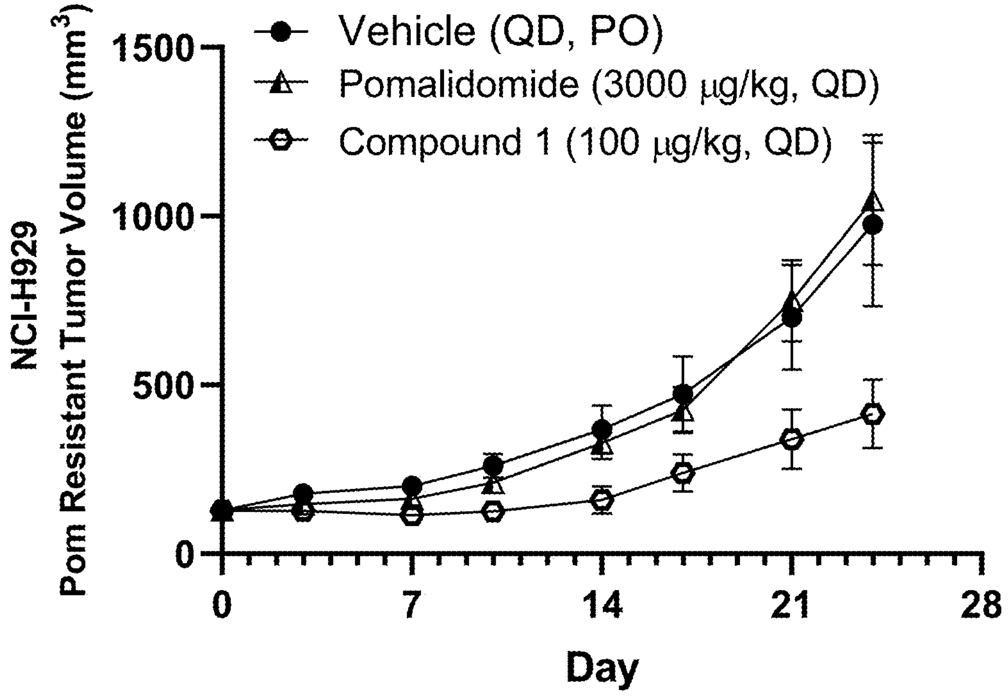
FIG. 8 is a graph of the tumor volume of mice injected with NCI-H929 pomalidomide resistant cells and administered Compound 1 (100 μg/kg) or pomalidomide (3000 μg/kg) orally (PO) every day (QD) as described in Example 15. The x-axis is the time measured in days and the y-axis is the tumor volume measured in $mm^3$.

A xenograft study was conducted. Female SCID animals were irradiated with a 200 rads Co60 irradiator source and after 24 hours, animals were inoculated via tail vein injection with 1×107 MM1.S-Luc in 200 μL PBS. Tumor burden was measured twice weekly using imaging analysis. Mice were injected intraperitoneally with 15 mg/mL of D-luciferin and anesthetized with 1-2% isoflurane inhalation. 10 minutes post luciferin injection, mice were imaged using IVIS Lumina II (Perkin Elmer) and total bioluminescence signal (BLI, photons/s) was measured in a region of interest (ROI). BLI from ROI were quantified and used as an indicator of tumor burden. 29 days post tumor cell inoculation mice were randomized into two groups, with 3 mice per group and an average BLI of $17\times10^6$ photons. FIG. 6 are images of the mice administered Compound 1 compared to the mice administered vehicle. Images were taken on days 4, 7, 11, 14, and 18. As shown in FIG. 8, the total bioluminescence signal of the mice administered Compound 1 was significantly less than the mice administered vehicle. This data is also presented in FIG. 34.

Example 15. Compound 1 in Pomalidomide Resistant or Refractory Myeloma Models Compound 1 was tested in a multiple myeloma cell line resistant to pomalidomide (H929 PomR) and a refractory multiple myeloma cell line (RPMI-8226). The results are shown in FIG. 8 (H929 PomR cells) and FIG. 9 (RPMI-8226 cells).

H929 multiple myeloma cells resistant to pomalidomide (H929 PomR) were generated by continued treatment in vitro with pomalidomide until the proliferation of cells was no longer inhibited. H929 PomR cells were implanted into NOD SCID mice subcutaneously in the right flank at a concentration of $10\times10^6$ tumors cells in 0.2 mL of PBS supplemented with matrigel (PBS:matrigel=1:1). Mice were then treated daily with pomalidomide (5000 μg/kg/day) for 14 days until they were cohorted into groups of 8, stratified to result in about equal average tumor sizes in each treatment group.

Following a single day of drug washout, mice were administered Compound 1 (100 μg/kg/day) or pomalidomide (3000 μg/kg/day) on a daily PO regimen. Both compounds were formulated in PEG400 (30% v/v)+70% v/v HPMC (1% w/v) in citrate buffer (pH 5). Body weight and mean tumor volume (MTV) were measured on a 2× weekly schedule, and the study end point was a MTV of 1048 $mm^3$ in the pomalidomide control group on Day 24. Data are expressed as MTV±SEM. As shown in FIG. 8, the tumors in the mice administered Compound 1 were smaller over the course of the study the mice administered pomalidomide.

For the RPMI-8226 MM model, the female CB17 SCID mice were inoculated subcutaneously in the right flank with $10\times10^6$ RPMI-8226 cells in 0.2 mL of PBS supplemented with matrigel (PBS:matrigel=1:1). Tumor volume was measured twice weekly in two dimensions using calipers, and volume was calculated using the formula: $(w2\times l)/2=mm^3$, assuming 1 mg is equivalent to 1 $mm^3$ of tumor volume. Once the tumors reached a volume range of 109-158 $mm^3$ (28 days after implantation), the animals were divided randomly into groups of 6, stratified to result in about equal average tumor sizes in each treatment group. Treatment began on Day 0 with established subcutaneous RPMI-8226 tumors with a mean tumor volume (MTV) of 130 $mm^3$.

Figure 9:
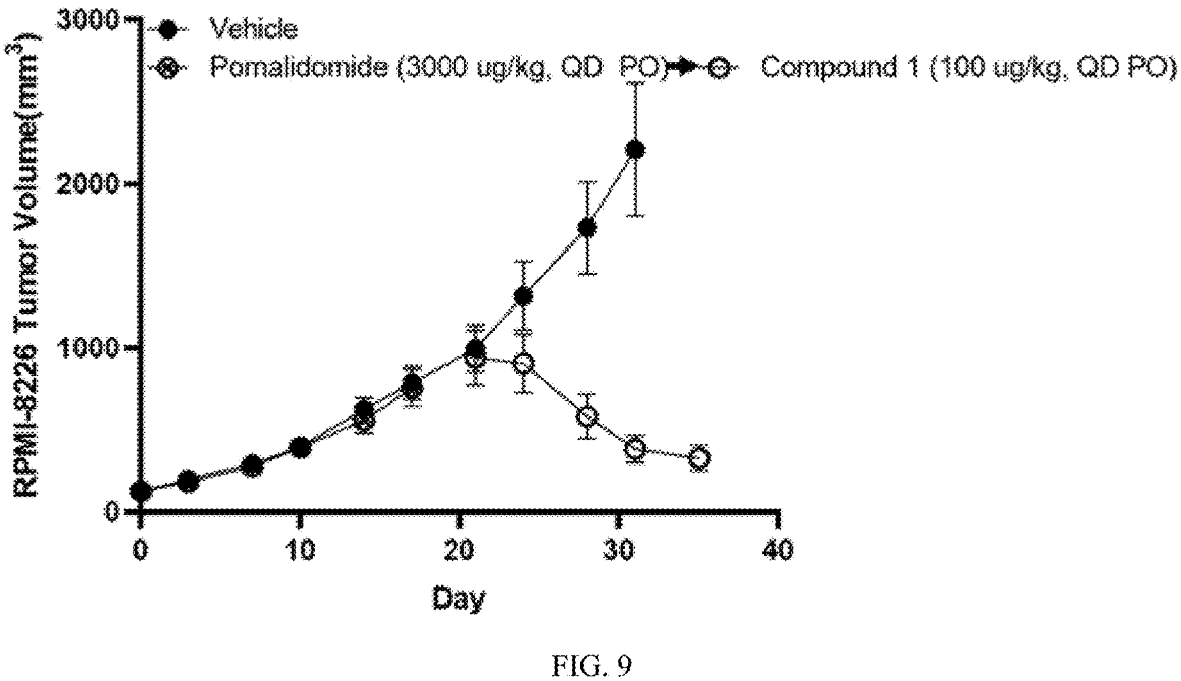
FIG. 9 is a graph of the tumor volume of mice injected with refractory multiple myeloma cell line RPMI-8226. As described in Example 15, mice were injected with RPMI-8226 tumors and the tumors were allowed to grow to a volume of 109-158 $mm^3$ (28 days after implantation). Vehicle treated animals continued treatment until tumors reached a MTV (mean tumor volume) of 2211 $mm^3$. Pomalidomide treated animals were crossed over onto Compound 1 (100 μg/kg/day) at day 17 for 21 additional days. The x-axis is the time measured in days and the y-axis is the tumor volume measured in $mm^3$.

All agents were administered to mice bearing RPMI-8226 tumors on day 0 and dosed PO. Pomalidomide was dosed at 3000 μg/kg for 17 days and was formulated in PEG400 (30% v/v)+70% v/v HPMC (1% w/v) in citrate buffer (pH 5). Vehicle treated animals were treated for 28 days until tumors reached a MTV of 2211 $mm^3$. Pomalidomide treated animals were crossed over onto Compound 1 (100 μg/kg/day) starting on day 18 and dosed for 21 additional days. Data are expressed as MTV±SEM. As shown in FIG. 9, the tumor volume began to decrease when mice were crossed over from pomalidomide to Compound 1.

For the RPMI-8226 MM model, the female CB17 SCID mice were inoculated subcutaneously in the right flank with $10\times10^6$ RPMI-8226 cells in 0.2 mL of PBS supplemented with matrigel (PBS:matrigel=1:1). Tumor volume was measured twice weekly in two dimensions using calipers, and volume was calculated using the formula: $(w2\times l)/2=mm^3$, assuming 1 mg is equivalent to 1 $mm^3$ of tumor volume. Once the tumors reached a volume range of 109-158 $mm^3$ (28 days after implantation), the animals were divided randomly into groups of 6, stratified to result in about equal average tumor sizes in each treatment group. Treatment began on Day 0 with established subcutaneous RPMI-8226 tumors with a mean tumor volume (MTV) of 130 $mm^3$.

All agents were administered to mice bearing RPMI-8226 tumors on day 0 and dosed PO daily for 31 days. Compound 1 was dosed at 3, 10, 30, or 100 μg/kg and was formulated in PEG400 (30% v/v)+70% v/v IPMC (1% w/v) in citrate buffer (pH 5). Body weight and MTV was measured on a 2× weekly schedule and the study end point was a MTV of 2211 $mm^3$ in the vehicle control group on Day 31. Statistical analysis was performed using two-way analysis of variance (ANOVA). Data are expressed as MTV±SEM. The data from this experiment is presented in FIG. 35.

In another experiment each mouse was inoculated subcutaneously at the right flank with RPMI-8226 tumor cells ($10\times10^6$) in 0.2 mL of PBS supplemented with Matrigel (PBS:Matrigel=1:1) for tumor development. Tumor growth was monitored throughout the study. Tumor volume was measured in two dimensions using calipers and volume was calculated using the formula: (w2×l)/2=mm3, assuming 1 mg is equivalent to 1 mm3 of tumor volume. Measurements were twice weekly. The health of the mice was monitored, and noteworthy clinical observations were recorded. Acceptable toxicity was defined as a group's mean BW loss of less than 20% during the study and not more than one treatment related death among ten treated animals, or 10%.

Once the tumors reached a volume range of 108-158 $mm^3$ (28 days after implantation), the animals were randomized into groups of 6. Treatment began on Day 0 with established subcutaneous RPMI-8226 tumors with an MTV of 130 $mm^3$. Animals were weighed on a twice weekly schedule. Mice were administered Compound (100 μg/kg/day) or pomalidomide (3000 μg/kg/day) on a daily PO regimen. Both compounds were formulated in PEG400 (30% v/v)+70% v/v HPMC (1% w/v) in citrate buffer (pH 5). After 17 days of pomalidomide dosing, a single day of drug washout was performed and mice in this group were administered Compound 1 (100 μg/kg/day) starting on day 18). Body weight and mean tumor volume (MTV) were measured on a 2× weekly schedule, and the study end point was when the vehicle control reached a MTV of 2211 $mm^3$. Data from this experiment is presented in FIG. 40.

Example 16. Compound 1 in Lymphoma Cell Lines

Figure 10:
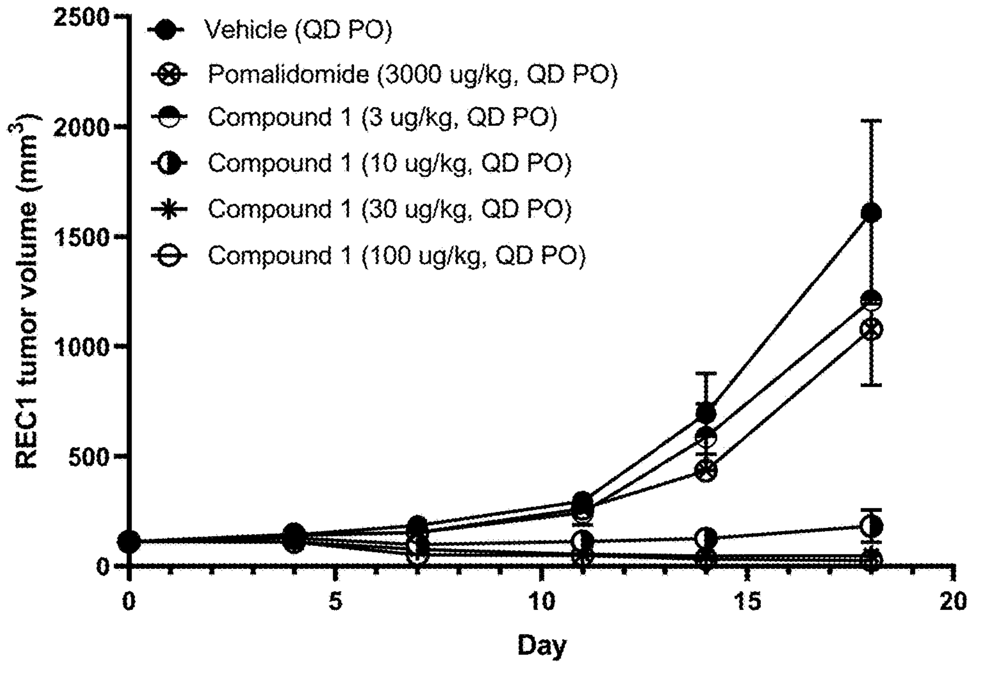
FIG. 10 is a graph of the tumor volume of mice injected with lymphoma REC1 mantle cells and administered Compound 1 or pomalidomide as described in Example 16. Compound 1 was administered at four different concentrations (3 μg/kg, 10 μg/kg, 30 μg/kg, or 100 μg/kg) and pomalidomide was administered at a dose of 3000 μg/kg.

Compound 1 was tested in both a mantle cell xenograft model (REC1) and a DLBLC tumor xenograft model (TMD8). The results are shown in FIG. 10 (REC1) and FIG. 11 (TMD8). Table 7 describes the statistical significance of the experiment in each model for each dose.

TABLE 7

Statistical Significance of Compound 1 Compared to Vehicle

| Treatment | Dose Level (μg/kg) | Statistical Significance Compared to Vehicle |
|---|---|---|
| RECI Mantle Cell Xenograft Model | | |
| Pomalidomide | 3000 | NS |
| Compound 1 | 3 | NS |
| Compound 1 | 10 | NS |
| Compound 1 | 30 | 0.04 |
| Compound 1 | 100 | 0.04 |
| TMD8 DLBCL Xenograft Model | | |
| Pomalidomide | 3000 | NS |
| Compound 1 | 100 | <0.0001 |

A xenograft study was conducted in female balb/c nude mice bearing REC1 mantle cell lymphoma tumors. Female nude mice were inoculated subcutaneously in the right flank with $5\times10^6$ tumors cells in 0.2 mL of PBS supplemented with matrigel (PBS:matrigel=1:1). Tumor volume was measured twice weekly in two dimensions using calipers, and volume was calculated using the formula: $(w2\times l)/2=mm^3$, assuming 1 mg is equivalent to 1 $mm^3$ of tumor volume. Once the tumors reached a volume range of 102-121 $mm^3$ (10 days after implantation), the animals were divided randomly into groups of 6, stratified to result in about equal average tumor sizes in each treatment group. Treatment began on Day 0 with established subcutaneous REC1 tumors with a mean tumor volume (MTV) of 112 $mm^3$.

All agents were administered to mice bearing REC1 tumors on day 0 and dosed PO daily for 18 days. Compound 1 was dosed at 3, 10, 30, or 100 μg/kg and was formulated in PEG400 (30% v/v)+70% v/v HPMC (1% w/v) in citrate buffer (pH 5). Pomalidomide was dosed at 3000 μg/kg and used the same formulation as Compound 1. Body weight and MTV were measured on a 2× weekly schedule, and the study end point was a MTV of 1608 $mm^3$ in the vehicle control group on Day 18. Statistical analysis was performed using two-way analysis of variance (ANOVA). Data are expressed as MTV±SEM. As shown in FIG. 10, tumor volume decreased in mice administered 10, 30, or 100 μg/kg of Compound 1, but increased in mice administered pomalidomide.

A xenograft study was also conducted in female NOD SCID mice bearing TMD8 DLBCL tumors. Female SCID mice were inoculated subcutaneously in the right flank with $1\times10^7$ tumors cells in 0.1 mL of PBS supplemented with matrigel (PBS:matrigel=1:1). Tumor volume was measured twice weekly in two dimensions using calipers, and volume was calculated using the formula: $(w2\times l)/2=mm^3$, assuming 1 mg is equivalent to 1 $mm^3$ of tumor volume. Once the tumors reached a volume range of 94-238 $mm^3$ (12 days after implantation), the animals were divided randomly into groups of 8, stratified to result in about equal average tumor sizes in each treatment group. Treatment began on Day 0 with established subcutaneous TMD8 tumors with a mean tumor volume (MTV) of 187 $mm^3$.

All agents were administered to mice bearing TMD8 tumors on day 0 and dosed PO daily for 18 days. Compound 1 was dosed at 100 μg/kg and Pomalidomide was dosed at 3000 μg/kg. Both compounds were formulated in PEG400 (30% v/v)+70% v/v HPMC (1% w/v) in citrate buffer (pH 5). Body weight and MTV were measured on a 2× weekly schedule and the study end point was a MTV of 2120 $mm^3$ in the vehicle control group on Day 18. Statistical analysis was performed using two-way analysis of variance (ANOVA). Data are expressed as MTV±SEM. As shown in FIG. 11, tumor volume decreased in mice administered Compound 1, but increased in mice administered pomalidomide.

Example 17. Compound 1 Induces Deep and Durable Loss of IZKF1 and IRF4 in KI-JK ALCL Tumors A xenograft study was conducted in female NOD SCID mice bearing KI-JK ALCL tumors. Female SCID mice were inoculated subcutaneously in the right flank with $10\times10^6$ tumors cells in 0.2 mL of PBS supplemented with matrigel (PBS:matrigel=1:1). Tumor volume was measured twice weekly in two dimensions using calipers, and volume was calculated using the formula: $(w2\times l)/2=mm^3$, assuming 1 mg is equivalent to 1 $mm^3$ of tumor volume. Once the tumors reached a volume range of 117-272 $mm^3$ (27 days after implantation), the animals were divided randomly into groups of 3, stratified to result in about equal average tumor sizes in each treatment group. Treatment began on Day 0 with established subcutaneous KI-JK tumors with a mean tumor volume (MTV) of 195-196 $mm^3$.

All agents were administered to mice bearing KI-JK tumors on day 0 and dosed PO daily for 21 days. Compound 1 was dosed at 30 or 100 μg/kg and was formulated in PEG400 (30% v/v)+70% v/v HPMC (1% w/v) in citrate buffer (pH 5). Pomalidomide was dosed at 3000 μg/kg and used the same formulation as Compound 1. Body weight and MTV was measured on a 2× weekly schedule and the study end point was a MTV of 1339 $mm^3$ in the vehicle control group on Day 21. Data are expressed as MTV±SEM. FIG. 12 is a graph of the tumor volume in mice administered Compound 1 or pomalidomide over the 21-day period. As shown in FIG. 12, the tumor volume decreased in mice administered Compound 1.

A pharmacodynamic study was also conducted in female NOD SCID mice bearing KI-JK ALCL tumors. Female SCID mice were inoculated subcutaneously in the right flank with $10\times10^6$ tumors cells in 0.2 mL of PBS supplemented with matrigel (PBS:matrigel=1:1). Tumor volume was measured twice weekly in two dimensions using calipers, and volume was calculated using the formula: $(w2\times l)/2=mm^3$, assuming 1 mg is equivalent to 1 $mm^3$ of tumor volume. Once tumors reached a volume of 450 $mm^3$ they were stratified into 3 treatment groups, consisting of 4 mice each.

A single dose of Vehicle, Pomalidomide (3000 μg/kg), or Compound 1 (30 or 100 μg/kg) was given to mice bearing KI-JK tumors. All compounds were formulated in PEG400

(30% v/v)+70% v/v HPMC (1% w/v) in citrate buffer (pH 5). Mice were sacrificed and tumors harvested at 6 and 24 hours post single dose. Tumors were mechanically homogenized, and protein extracted using RIPA buffer (Sigma Aldrich). Protein concentration was quantified using a Pierce™ BCA Protein Assay Kit, samples were reduced, and equal protein amounts were then loaded onto a western blot gel for analysis. Samples were analyzed for IKZF1 (Invitrogen, PA5-23728) and IRF-4 (CST, 15106) expression. IKZF1 expression is shown in FIG. 13A and IRF-4 expression is shown in FIG. 13B. Data is expressed as percentage of IKZF1 or IRF-4 in comparison to the vehicle control and normalized to GAPDH levels to control for protein loading. Error bars represent ±SEM values. As shown in FIGS. 13A and 13B, the percentage of IKZF1 and IRF-4 was smaller in mice administered Compound 1 compared to mice administered pomalidomide at both the 6-hour and 24-hour timepoint.

Example 18. Compound 1 Induces Deep and Durable Loss of IZKF1 and IRF4 in DL-40 ALCL Tumors A xenograft study was conducted in female NOD SCID mice bearing DL-40 ALCL tumors. Female SCID mice were inoculated subcutaneously in the right flank with $10\times10^6$ tumors cells in 0.2 mL of PBS supplemented with matrigel (PBS:matrigel=1:1). Tumor volume was measured twice weekly in two dimensions using calipers, and volume was calculated using the formula: $(w2\times l)/2=mm^3$, assuming 1 mg is equivalent to 1 $mm^3$ of tumor volume. Once the tumors reached a volume range of 187-335 $mm^3$ (31 days after implantation), the animals were divided randomly into groups of 3, stratified to result in about equal average tumor sizes in each treatment group. Treatment began on Day 0 with established subcutaneous DL-40 tumors with a mean tumor volume (MTV) of 241-247 $mm^3$.

All agents were administered to mice bearing DL-40 tumors on day 0 and dosed PO daily for 21 days. Compound 1 was dosed at 3, 10, 30, 100, or 300 μg/kg and was formulated in PEG400 (30% v/v)+70% v/v HPMC (1% w/v) in citrate buffer (pH 5). Pomalidomide was dosed at 3000 μg/kg and used the same formulation as Compound 1. Body weight and MTV was measured on a 2× weekly schedule and the study end point was a MTV of 1110 $mm^3$ in the vehicle control group on Day 21. Data are expressed as MTV±SEM. FIG. 14 is a graph of the tumor volume in mice over the 21-day period and as shown in FIG. 14, Compound 1 was more successful at decreasing tumor volume than pomalidomide.

A pharmacodynamic study was conducted in female NOD SCID mice bearing DL-40 ALCL tumors. Female SCID mice were inoculated subcutaneously in the right flank with $10\times10^6$ tumors cells in 0.2 mL of PBS supplemented with matrigel (PBS:matrigel=1:1). Tumor volume was measured twice weekly in two dimensions using calipers, and volume was calculated using the formula: $(w2\times l)/2=mm^3$, assuming 1 mg is equivalent to 1 $mm^3$ of tumor volume. Once tumors reached a volume of 324 $mm^3$ they were stratified into 3 treatment groups.

A single dose of Vehicle, Pomalidomide (3000 μg/kg), or Compound 1 (30 or 100 μg/kg) was given to mice bearing DL-40 tumors. All compounds were formulated in PEG400 (30% v/v)+70% v/v HPMC (1% w/v) in citrate buffer (pH 5). For the vehicle control group, 3 mice were sacrificed, and tumors harvested 24 hours post dose. Mice dosed with Pomalidomide were sacrificed at 1, 4, and 24 hours post dose, with two mice sampled per timepoint. Mice in the Compound 1 groups were sampled at 1, 4, 24, and 48 hours post dose with four tumors collected per timepoint. Tumors were then mechanically homogenized, and protein extracted using RIPA buffer (Sigma Aldrich). Protein concentration was quantified using a Pierce™ BCA Protein Assay Kit, samples were reduced, and equal protein amounts were then loaded onto a western blot gel for analysis as shown in FIG. 15B. Samples were analyzed for IKZF1 (Invitrogen, PA5-23728) expression as shown in FIG. 15A. Data is expressed as percentage of IKZF1 in comparison to the vehicle control and normalized to GAPDH levels to control for protein loading. Error bars represent ±SEM values.

Example 19. Compound 1 Efficacy in Mice with DL-40 Tumors

A xenograft study was conducted in female NOD SCID mice bearing DL-40 ALCL tumors. Female SCID mice were inoculated subcutaneously in the right flank with $10\times10^6$ tumors cells in 0.2 mL of PBS supplemented with matrigel (PBS:matrigel=1:1). Tumor volume was measured twice weekly in two dimensions using calipers, and volume was calculated using the formula: $(w2\times l)/2=mm^3$, assuming 1 mg is equivalent to 1 $mm^3$ of tumor volume. Once the tumors reached a volume range of 135-372 $mm^3$ (32 days after implantation), the animals were divided randomly into groups of 6, stratified to result in about equal average tumor sizes in each treatment group. Treatment began on Day 0 with established subcutaneous DL-40 tumors with a mean tumor volume (MTV) of 238-240 $mm^3$. Table 8 describes the statistical significance of each dose of Compound 1 compared to vehicle.

TABLE 8

Statistical Significance of Compound 1 Compared to Vehicle

| Treatment | Dose Level (μg/kg) | Statistical Significance Compared to Vehicle |
|---|---|---|
| Pomalidomide | 3000 | NS |
| Compound 1 | 3 | 0.0111 |
| Compound 1 | 10 | 0.0006 |
| Compound 1 | 30 | 0.0004 |
| Compound 1 | 100 | 0.0004 |
| Compound 1 | 300 | 0.0004 |

All agents were administered to mice bearing DL-40 tumors on day 0 and dosed PO daily for 21 days. Compound 1 was dosed at 3, 10, 30, 100, or 300 μg/kg and was formulated in PEG400 (30% v/v)+70% v/v HPMC (1% w/v) in citrate buffer (pH 5). Pomalidomide was dosed at 3000 μg/kg and used the same formulation as Compound 1. Body weight and MTV was measured on a 2× weekly schedule, and the study end point was a MTV of 2007 $mm^3$ in the vehicle control group on Day 21. Statistical analysis was performed using two-way analysis of variance (ANOVA). Data are expressed as MTV±SEM. FIG. 16 is a graph of the tumor volume of mice administered with Compound 1 or pomalidomide over the course of 21 days, and shown, Compound 1 at 30, 100, and 300 μg/kg was able to reduce tumor volume. FIG. 17 is a graph of the body weight changes of the mice over the 21-day study period.

Example 20. Compound 1 Promotes Robust Loss of IRF4 and Rise in Caspase 3 (MoA) and IRF-1 (BmX) in ALCL Model A xenograft study was conducted in female NOD SCID mice bearing KI-JK ALCL tumors. Female SCID mice were inoculated subcutaneously in the right flank with $10\times10^6$ tumors cells in 0.2 mL of PBS supplemented with matrigel (PBS:matrigel=1:1). Tumor volume was measured twice weekly in two dimensions using calipers, and volume was calculated using the formula: $(w2\times l)/2=mm^3$, assuming 1 mg is equivalent to 1 $mm^3$ of tumor volume. Once the tumors reached a volume range of 147-365 $mm^3$ (39 days after implantation), the animals were divided randomly into groups of 5, stratified to result in about equal average tumor sizes in each treatment group. Treatment began on Day 0 with established subcutaneous KI-JK tumors with a mean tumor volume (MTV) of 257-269 $mm^3$.

Compound 1 (100 μg/kg) and the vehicle control were administered to mice bearing KI-JK tumors on day 0 and dosed PO daily for 21 days. Compound 1 was formulated in PEG400 (30% v/v)+70% v/v HPMC (1% w/v) in citrate buffer (pH 5), which was also used as the vehicle control. Body weight and MTV was measured on a 2× weekly schedule and the study end point was a MTV of 1885 $mm^3$ in the vehicle control group on Day 24. Data are expressed as MTV±SEM. FIG. 18 is a graph of the tumor volume of the course of the study, and as shown, Compound 1 reduced tumor volume.

A second xenograft study was conducted in female NOD SCID mice bearing KI-JK ALCL tumors. Female SCID mice were inoculated subcutaneously in the right flank with $10\times10^6$ tumors cells in 0.2 mL of PBS supplemented with matrigel (PBS:matrigel=1:1). Tumor volume was measured twice weekly in two dimensions using calipers, and volume was calculated using the formula: $(w2\times l)/2=mm^3$, assuming 1 mg is equivalent to 1 $mm^3$ of tumor volume. Once tumors reached a mean tumor volume (MTV) of 450 $mm^3$ they were stratified into two groups.

Compound 1 (100 μg/kg) or the vehicle control were dosed PO to mice bearing KI-JK tumors. Compound 1 was formulated in PEG400 (30% v/v)+70% v/v HPMC (1% w/v) in citrate buffer (pH 5). For the vehicle control group, 2 mice were sacrificed, and tumors harvested 24 hours post a single dose. Mice in the Compound 1 group were sampled at 4- and 24-hours post dose a single dose, with two tumors collected per time point. Additional mice were dosed daily for 5 or 7 days with tumor collections 24 hours post last dose, with 2 mice sampled per time point. Tumors were then mechanically homogenized, and protein extracted using RIPA buffer (Sigma Aldrich). Protein concentration was quantified using a Pierce™ BCA Protein Assay Kit, samples were reduced, and equal protein amounts were then loaded onto a western blot gel for analysis. Tumors were analyzed for IKZF1 (Invitrogen, PA5-23728), IKZF3 (CST, 15103), IRF-1 (CST, 8478), IFR-4 (CST, 15106), and Caspase-3 (CST, 9662) expression. As shown in FIG. 19, the percentage of IKZF1, IKZF3, and IRF-4 decreased and the concentration of caspase-3 and IRF-1 increased. Data is expressed as percentage of each target in comparison to the target level measured in the vehicle control and normalized to GAPDH levels to control for protein loading. Error bars represent ±SEM values.

Example 21. The Combination of Compound 1 and Ibrutinib

A xenograft study was conducted in female CB17 SCID mice bearing TMD8 DLBCL tumors. Female SCID mice were inoculated subcutaneously in the right flank with $5\times10^6$ tumors cells in 0.2 mL of PBS supplemented with matrigel (PBS:matrigel=1:1). Tumor volume was measured twice weekly in two dimensions using calipers, and volume was calculated using the formula: $(w2\times l)/2=mm^3$, assuming 1 mg is equivalent to 1 $mm^3$ of tumor volume. Once the tumors reached a volume range of 82-130 $mm^3$ (13 days after implantation), the animals were divided randomly into groups of 6, stratified to result in about equal average tumor sizes in each treatment group. Treatment began on Day 0 with established subcutaneous TMD8 tumors with a mean tumor volume (MTV) of 107-108 $mm^3$.

All agents were administered to mice bearing TMD8 tumors on day 0 and dosed PO daily until individual tumor volumes reached or exceeded 1500 $mm^3$, at which point dosing stopped and the individual mouse was removed from the study. Compound 1 was dosed at 50 μg/kg and was formulated in PEG400 (30% v/v)+70% v/v HPMC (1% w/v) in citrate buffer (pH 5). Ibrutinib was dosed at 12.5 mg/kg and formulated in 0.5% MC+0.4% cremophor EL+0.1% sodium lauryl sulfate. Compound 1 was also dosed in combination with Ibrutinib at their respective single agent doses. Body weight and MTV was measured on a 2× weekly schedule and the study end point was when all mice were removed from the study on day 54. Statistical analysis was performed using survival analysis and the Logrank test (Mantel-Cox test). Data are expressed as MTV±SEM. FIG. 20 is a graph of the tumor volume of mice administered with vehicle, Compound 1, Ibrutinib, or the combination of Compound 1 and Ibrutinib, and as shown, the combination was the most effective in reducing tumor volume. FIG. 21 is a graph describing the percent survival of mice over the course of the study. The highest percentage of surviving mice was observed with the combination. Table 9 describes the statistical significance of the agent compared to vehicle and Table 10 describes the statistical significance of the combination compared to Ibrutinib and Compound 1.

TABLE 9

Statistical Significance of Compound 1, Ibrutinib, and the Combination Compared to Vehicle

| Treatment | Dose Level (μg/kg) | Median Survival | Statistical Significance Compared to Vehicle |
|---|---|---|---|
| Vehicle | NA | 25 | NA |
| Compound 1 | 50 | 30 | 0.02 |
| Ibrutinib | 12500 | 28 | NS |
| Combination | 50 μg/kg Compound 1 and 12500 μg/kg Ibrutinib | 52 | 0.0009 |

TABLE 10

Statistical Significance of the Combination Compared to Compound 1 and Ibrutinib

| Treatment | Median Survival | Statistical Significance Compared to Ibrutinib | Statistical Significance Compared to Compound 1 |
|---|---|---|---|
| Combination | 52 | 0.0009 | 0.0005 |

Example 22. The Combination of Compound 1 and Dexamethasone

A xenograft study was conducted in female CB17 SCID mice bearing RPMI-8226 multiple myeloma tumors. Female SCID mice were inoculated subcutaneously in the right flank with $10\times10^6$ tumors cells in 0.2 mL of PBS supplemented with matrigel (PBS:matrigel=1:1). Tumor volume was measured twice weekly in two dimensions using calipers, and volume was calculated using the formula: (w2×l)/2=$mm^3$, assuming 1 mg is equivalent to 1 $mm^3$ of tumor volume. Once the tumors reached a volume range of 108-158 $mm^3$ (28 days after implantation), the animals were divided randomly into groups of 6, stratified to result in about equal average tumor sizes in each treatment group. Treatment began on Day 0 with established subcutaneous RPMI-8226 tumors with a mean tumor volume (MTV) of 130 $mm^3$.

All agents were administered to mice bearing RPMI-8226 tumors on day 0 and dosed until an individual moue tumor volume reached or exceeded 1000 $mm^3$, at which point the mouse was removed from the study and dosing stopped. Compound 1 was dosed PO daily at 10 μg/kg and formulated in PEG400 (30% v/v)+70% v/v IPMC (1% w/v) in citrate buffer (pH 5). Dexamethasone was dosed IV once a week at 5000 μg/kg and formulated in saline. Compound 1 was also dosed in combination with Dexamethasone at their respective dose levels and schedules. Body weight and MTV were measured on a 2× weekly schedule. The study end point was reaching a TV greater than 1000 $mm^3$, at which point any mouse with a TV reaching this cut off TV was removed from the study. The last mouse was removed from the study on day 52. The survival analysis used was Logrank (Mantel-Cox test). Data are expressed as MTV±SEM. FIG. 22 is a graph of the tumor volume of mice administered with vehicle, Compound 1, Dexamethasone, or the combination of Compound 1 and Dexamethasone, and as shown, the combination was most effective in reducing tumor volume. The highest percentage of surviving mice was observed with the combination (FIG. 23). Table 11 describes the statistical significance of the agent compared to vehicle and Table 12 describes the statistical significance of the combination compared to Ibrutinib and Compound 1. This data is also presented in FIG. 41 and FIG. 42.

TABLE 11

Statistical Significance of Compound 1, Dexamethasone, and the Combination Compared to Vehicle

| Treatment | Dose Level (μg/kg) | Median Survival | Statistical Significance Compared to Vehicle |
|---|---|---|---|
| Vehicle | NA | 24 | NA |
| Compound 1 | 10 | 33 | 0.007 |
| Dexamethasone | 5000 | 30 | NS |
| Combination | 10 μg/kg Compound 1 and 5000 μg/kg Dexamethasone | 44 | 0.0007 |

TABLE 12

Statistical Significance of the Combination Compared to Compound 1 and Dexamethasone

| Treatment | Median Survival | Statistical Significance Compared to Dexamethasone | Statistical Significance Compared to Compound 1 |
|---|---|---|---|
| Combination (50 μg/kg Compound 1 and 5000 μg/kg Dexamethasone) | 44 | 0.001 | 0.03 |

Example 23. Concentration of IKZF1 and IKZF3 in Monkey Administered Compound 1

One fasted male cynomolgus monkey was administered Compound 1 formulated in 1% carboxymethylcellulose sodium+20% PEG400 in citrate buffer at 30 μg/kg by oral gavage. At indicated timepoints, blood was collected from a peripheral vessel from a restrained, non sedated monkey. 50 uL of whole blood was added to a flow tube with 1 ml PBS, centrifuged for 5 minutes at 400×g and supernatant discarded. Blood was lysed in 1 mL of lysis buffer for 10-15 minutes at room temperature, centrifuged for 5 minutes at 400× and supernatant discarded. PBS (1 mL) was added to each tube, centrifuged for 5 minutes at 400×g and supernatant discarded. PBS (1 mL) was added together with 1 ul of Zombie NIR dye to the white blood cells and incubated for 20 minutes at room temperature. The cells were centrifuged for 5 minutes at 400×g and supernatant discarded. Fixation buffer (1 mL) was added and incubated for 20 minutes at room temperature. Cells were washed with permeabilization buffer (1 mL) and centrifuged for 5 minutes at 400×g and supernatant discarded. Permeabilization buffer (1 mL) was added, incubated for 20 min at room temperature, cells were centrifuged for 5 minutes at 400×g and supernatant removed. Fc block (1 mL) was added, incubated for 15 minutes at room temperature. IKZF1-AF488 and IKZF3-AF647, or the IgG control, was added and incubated for 60 min at room temperature with shaking (200 rpm). Cells were washed twice with PBS (1 mL), resuspended in PBS and analyzed analyzed on a BD LSR Fortessa Flow Cytometer. FIG. 24 is a graph of the percent mean fluorescence intensity of IKZF1 and IZKF3 at 4 h and 24 hr post dose compared to the pre-dose sample. At both the 4-hour and 24-hour timepoint, the levels of IKZF1 and IKZF3 were smaller than the concentration at the pre-dose.

Example 24. Compound 1 Interconversion in Rats and Monkeys

Compound 1 was administered to a rat at a concentration of 30 mg/kg PO and monkeys at a concentration of either 60 μg/kg or 100 μg/kg PO. At the indicated timepoints shown in FIG. 25A and FIG. 25B, plasma samples were collected and the $C_{max}$, half-life, and $AUC_{0\text{-}inf}$ were determined for both Compound 1 and a metabolite of Compound 1, Compound 14. The percent of Compound 14 was also determined (Table 13). PK values dose normalized to 1 mg/kg. FIG. 25A is a graph measuring the concentration of Compound 1 or Compound 14 over the course of 24 hours in monkeys administered 100 μg/kg or 60 μg/kg of Compound 1. FIG. 25B is a graph measuring the concentration of Compound 1 or Compound 14 over the course of 24 hours in a rat administered 30 mg/kg of Compound 1.

(Compound 14)

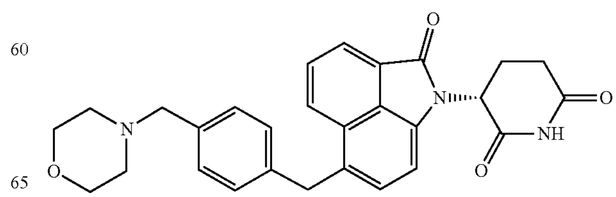

TABLE 13

| PK Values of Rat and Monkey Administered Compound 1 | | |
|---|---|---|
| | Compound 1 | Compound 14 |
| $C_{max}$ (ng/mL) Rat/Monkey | 110/83 | 6/5 |
| T ½ (H) Rat/Monkey | 2.3/9 | 2.7/ND |
| $AUC_{0-inf}$ (ng · h/mL) Rat/Monkey | 784/1278 | 47/ND |
| Percent of Compound 14 Formed | $C_{max}$: rat 5%; monkey 6% AUC: rat 6%; monkey ND | |

Example 25. Efficacy of Select Compounds Against Multiple Myeloma

A xenograft study was conducted in female NOD SCID mice bearing NCI-H929 multiple myeloma tumors. Female SCID mice were inoculated subcutaneously in the right flank with $5\times10^6$ tumors cells in 0.2 mL of PBS supplemented with matrigel (PBS:matrigel=1:1). Tumor volume was measured twice weekly in two dimensions using calipers, and volume was calculated using the formula: (w2×l)/2=$mm^3$, assuming 1 mg is equivalent to 1 $mm^3$ of tumor volume. Once the tumors reached a volume range of 112-194 $mm^3$ (14 days after implantation), the animals were divided randomly into groups of 2, stratified to result in about equal average tumor sizes in each treatment group. Treatment began on Day 0 with established subcutaneous NCI-H929 tumors with a mean tumor volume (MTV) of 146-154 $mm^3$.

Compound 1 though Compound 11 and Compound 13 were administered to mice bearing NCI-H929 tumors on day 0 and dosed PO daily for 5 days. The compounds were dosed at 100 μg/kg and formulated in PEG400 (30% v/v)+70% v/v HPMC (1% w/v) in citrate buffer (pH 5). Body weight and MTV were measured on a 2× weekly schedule and the study end point was after 5 days of dosing. FIGS. 26A-FIG. 26K and FIG. 26M are graphs measuring the tumor volumes of the mice over the course of the study. Data are expressed as MTV±SEM.

A second xenograft study was conducted in female NOD SCID mice bearing DL-40 ALCL tumors. Female SCID mice were inoculated subcutaneously in the right flank with $10\times10^6$ tumors cells in 0.2 mL of PBS supplemented with matrigel (PBS:matrigel=1:1). Tumor volume was measured twice weekly in two dimensions using calipers, and volume was calculated using the formula: (w2×l)/2=$mm^3$, assuming 1 mg is equivalent to 1 $mm^3$ of tumor volume. Once the tumors reached a volume range of 187-335 $mm^3$ (31 days after implantation), the animals were divided randomly into groups of 2, stratified to result in about equal average tumor sizes in each treatment group. Treatment began on Day 0 with established subcutaneous DL-40 tumors with a mean tumor volume (MTV) of 242-244 $mm^3$.

Compound 12 and the vehicle control were administered to mice bearing DL-40 tumors on day 0 and dosed PO for 5 days. Compound 12 was formulated in PEG400 (30% v/v)+70% v/v HPMC (1% w/v) in citrate buffer (pH 5). Body weight and MTV were measured on a 2× weekly schedule and the study end point was after 7 days of dosing. FIG. 26L is a graph measuring the tumor volumes of the mice over the course of the 5-day study. Data are expressed as MTV±SEM.

Example 26 Fluorescent Polarization

Compounds were dispensed from serially diluted DMSO stock in low dead volume plates into black 384-well compatible FP plates using acoustic technology to 1% of total reaction volume. Compounds were arranged vertically in rows A through P. Concentrations series were horizontal: columns 1-11, and then duplicates in columns 12-22. Columns 23 and 24 are reserved for 0% (5 nM probe) and 100% controls (protein at high concentration with 5 nM probe), respectively. A 20 μL mixture containing 10 nM cereblon-DDB1 and 5 nM probe dye in 50 mM HEPES, pH 7.4, 200 mM NaCl, 1 mM TCEP, 0.1% BSA and 0.05% Pluronic Acid F-127 was added to wells containing compound and incubated at room temperature for 1.5 hours. Controls wells with 100% bound probe contained 100 nM of cereblon. Matching control plates excluding cereblon-DDB1 were used to correct for background fluorescence. Plates were read on an Envision plate reader with appropriate FP filter sets. The results from testing Compound 1 and Pomalidomide in this assay are shown in FIG. 27.

Example 27 In-Cell Cereblon Competition

The cell permeability and binding affinity of Compound 1 and pomalidomide to cellular cereblon (CRBN) was determined by competitive displacement of a NanoBRET™ tracer reversibly bound to a cereblon-NanoLuc® fusion protein in 293T cells. 293T cells were modified by lentiviral transfection to express a fusion of cereblon and NanoLuc® luciferase. The modified cereblon-NanoLuc 293T cell line was co-treated with varying concentrations of test compound and a probe conjugated with NanoBRET fluorescent tracer at its predetermined $K_D$ concentration (300 nM) and incubated for 2 hours at 37° C. to reach equilibrium. Affinity of test compound was determined by displacement of NanoBRET tracer signal following the addition of NanoBRET reagents (Promega). 40 uL cereblon-NanoLuc 293T cells suspended in OptiMEM media at $2\times10^5$ cells/mL (8000 cells/well) were dispensed using a Multidrop Combi Reagent Dispenser (Thermo Fisher) to each well of 384-well white TC-treated microplates (Corning 3570). 10 mM DMSO test compound stock solution was serially diluted (half log) in DMSO to generate 11-point dose series in an acoustic ready 384-well low dead volume microplate (Labcyte). Using Echo 550 Acoustic Liquid Handler (Labcyte), 40 nL of serially diluted compound solutions were dispensed in duplicate to each 384-well white TC-treated microplate containing cereblon-NanoLuc 293T cells. 40 nL DMSO was transferred to all control wells. 40 nL NanoBRET tracer was dispensed to all wells in column 1-23 at its pre-determined $K_D$ concentration (300 nM). 40 nL additional DMSO was dispensed to column 24. Final concentration of DMSO was 0.2% for all samples. Plates were spun briefly and cells were incubated at 37° C.; 5% $CO_2$ for 2 hr. 20 uL NanoBRET TE Assay reagents were added to each well and NanoBRET signal was acquired on an EnVision Multilabel Reader (PerkinElmer). Donor emission from cereblon-NanoLuc was detected at 450 nm with a NanoLuc 460/50 filter and Acceptor fluorescence of NanoBRET-pomalidomide tracer (618 nm) was detected with a 600 nm long pass NanoBRET filter. Ratio of Acceptor signal/Donor signal was calculated for each well. Column 24 (cells without NanoBRET-pomalidomide tracer addition) was used as positive control (P). Percent response of compound-treated samples (T) were calculated by normalizing the Acceptor/Donor ratio for each well to the DMSO treated negative (N) controls on the same microtiter plate after background (i.e. positive control) signal subtraction: Response %=100×(Signal (T)−Average (P))/(Average (N)−

Average (P)). The results from testing Compound 1 and pomalidomide in this assay are shown in FIG. 28.

Example 28 IKZF1/IKZF3 Degradation

Western blot was used to assess Aiolos (IKZF3) and Ikaros (IKZF1) degradation characteristics of Compound 1. NCI-H929 cells (ATCC, CRL-9068) were seeded in 6-well plates pre-spotted with Compound 1 or pomalidomide in dose response (5-point, 0.01-100 nM). After a 4-hour incubation period with compounds, the pellets were washed with PBS and frozen at −80° C. Cell pellets were lysed in lysis buffer [RIPA (Thermo, Ref 89901), lx Halt Protease and Phosphatase inhibitor cocktail (Thermo, Pro #1361281), benzonase (Sigma, E1014-5JU)] for 10 minutes on ice. Insoluble proteins were cleared form the lysates by centrifugation (21.2× g, 10 minutes).

Protein concentrations were measured using the BCA Protein Assay Kit (Thermo, 23228). Protein standard curve, prepared with BSA, and samples protein concentrations were read using the Envision Multilabel Reader (PerkinElmer). Lysate concentrations were normalized with lysis buffer and Laemmli 6X, SDS-Sample Buffer, Reducing (Boston BioProducts, Inc. Part #BP-111R-50 ml). Normalized samples and Chameleon® Duo Pre-stained Protein Ladder (LI-COR, 928-60000) were loaded onto 4-15% Criterion™ Tris-HCl Protein Gel (Bio-Rad, #3450028). Gels ran at 120 V for 1.5 hours. Protein transfer was completed with the Trans-Blot Turbo Transfer System (Bio-Rad, 1704150EDU) at 25 V for 7 minutes using the Trans-Blot Turbo RTA Midi 0.2 μm Nitrocellulose Transfer Kit (Bio-Rad, catalog #1704271) following manufacturer recommendations.

Membranes were blocked while rocking for one hour in Intercept® Blocking Buffer (TBS) (LI-COR, catalog #927-50000). Primary antibodies were diluted in Intercept® T20 (TBS) Protein-Free Antibody Diluent (LI-COR, catalog #927-85001) and incubated while rocking at 4° C. overnight.

| | Antibody (species) | Vendor/Catalogue #/Lot | Dilution |
|---|---|---|---|
| Primary | Ikaros (Rabbit) | Cell Signaling/14859S/1 | 1:1000 |
| | Aiolos (Rabbit) | Cell Signaling/15103S/1 | 1:1000 |
| | β-actin (Mouse) | Cell Signaling/3700S/3 | 1:3000 |
| Secondary | IR Dye 800 CW goat anti-rabbit | LiCor/926-32211/C91030-13 | 1:5000 |
| | IR Dye 680 RD goat anti-mouse | LiCor/926-68072/C90910-21 | 1:5000 |

Membranes were washed 3 times for 5 minutes in TBS-T while rocking. Secondary antibodies were diluted in Intercept® T20 (TBS) Protein-Free Antibody Diluent (LI-COR, catalog #927-85001) and incubated on membranes for 1 hour while rocking at room temperature. Membranes were washed as previously described and imaged on the Odyssey CLx. Data are expressed as percentage of Aiolos or Ikaros in comparison to the vehicle control and normalized to 3-actin control for sample loading. The resulting western blot is shown in FIG. 30.

Example 29 Apoptosis Induction Assay

Apoptosis induction in NCIH929 multiple myeloma cells was determined by measuring Caspase 3/7 activity following 72 hour treatment with Compound 1 using Caspase 3/7 Assay System (Promega, G8091). Briefly, test compound was added to white 384-well TC-treated plates at a top concentration of 100 nM for Compound 1 and 10 μM for pomalidomide with 10 points, half log titration in duplicates. 30 μL NCIH929 cells were seeded into the 384-well plates in RPMI medium containing 10% FBS and 0.05 mM 2-mercaptoethanol at a cell density of 1000 cells per well. Cells treated in the absence of the test compound were the negative control. Following compound treatment, cells were incubated at 37° C. with 5% $CO_2$ for 72 hr. 30 μL reconstituted Caspase 3/7 Assay detection reagent was added to each well and luminescence was acquired on EnVision™ Multilabel Reader (PerkinElmer, Santa Clara, CA, USA). Maximum caspase 3/7 activity of >2-fold was observed following 72 hours with an EC50=0.58 nM for Compound 1 and 407 nM for pomalidomide. Data from this method is presented in FIG. 31.

Example 30 Anti-Proliferation Activity Assay

Growth of 8 multiple myeloma cell lines was determined after 96 hour treatment with Compound 1 or pomalidomide based on quantification of ATP using CellTiter-Glo® 2.0 luminescent Assay kit, which signals the presence of metabolically active cells. Briefly, test compound was added to 384-well plates at a top concentration of 100 nM for Compound 1 and 10 μM for pomalidomide with 10 points, half log titration in duplicates. 50 uL cells suspended in growth media at cell densities indicated for each cell line in Table 14 were dispensed using a Multidrop Combi Reagent Dispenser (Thermo Fisher) to 384-well black TC-treated microplates containing duplicate concentration range of test compounds and DMSO controls. Cells treated in the absence of the test compound were the negative control and cells treated in the absence of CellTiter-Glo® 2.0 were the positive control. Cells were incubated at 37° C. with 5% $CO_2$ for 96 hr. CellTiter-Glo reagent was then added to the cells and luminescence was acquired on EnVision™ Multilabel Reader (PerkinElmer, Santa Clara, CA, USA). % Viability was determined by normalizing the signal with positive and DMSO treated negative controls on the same microtiter plate. Compound 1 inhibited growth for all eight multiple myeloma cell lines with maximal inhibition greater than 50% and IC50s less than 1 nM and was 1000-fold more potent that pomalidomide. The resulting data is shown in FIG. 32.

TABLE 14

Multiple myeloma cell lines: source vendor, description of cancer cell type, growth medium conditions and experimental seeding density.

| Cell Line | Vendor | Complete Medium | Seeding Density (Cells/Well) |
|---|---|---|---|
| KMM-1 | JCRB | RPMI 1640 + 10% FBS | 2500 |
| KMS-26 | JCRB | RPMI 1640 + 10% FBS | 2500 |
| LP-1 | DSMZ | IMDM + 20% FBS | 2500 |
| MM.1R | ATCC | RPMI 1640 + 10% FBS | 4000 |
| MM.1S | ATCC | RPMI1640 + 10% FBS | 5000 |
| NCI-H929 | ATCC | RPMI-1640 + 10% FBS + 0.05 mM 2-mercaptoethanol | 5000 |
| OPM-2 | DSMZ | RPMI 1640 + 10% FBS | 2500 |
| RPMI 8226 | ATCC | RPMI1640 + 10% FBS | 2500 |

Example 31. Compound 1 Efficacy in Multiple Myeloma

Figure 7:
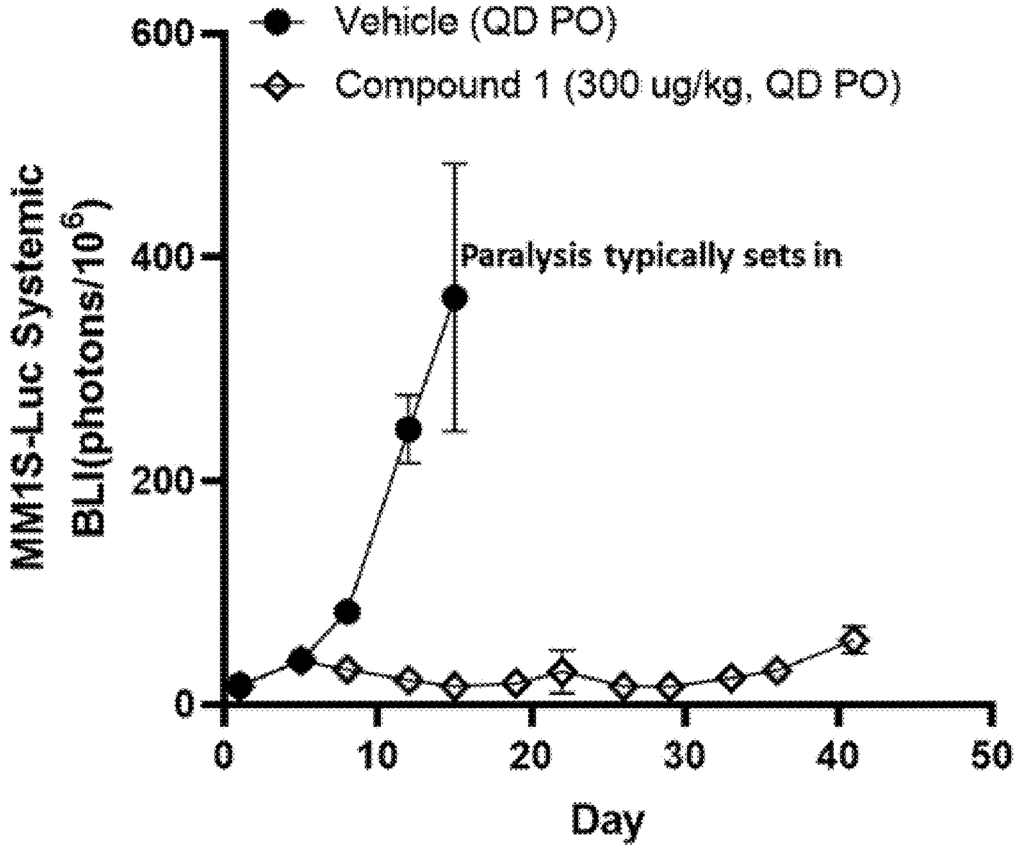
FIG. 7 is a graph of the bioluminescence signal of mice administered Compound 1 orally (PO) every day (QD) or vehicle and imaged using IVIS Lumina II as described in Example 14. The x-axis is time measured in days and the y-axis is the MM1S-Luc systemic BLI (total bioluminescence signal) measured in photons/$10^6$.

Compound 1 efficacy in a multiple myeloma cell line (NCI-H929) was evaluated at four different concentrations:

3 μg/kg, 10 μg/kg, 30 μg/kg, and 100 μg/kg. Compound 1 was administered QD (every day) orally (PO). The efficacy of Compound 1 was compared to pomalidomide (administered at 3000 μg/kg). The results in the NCI-H929 are shown in FIG. 7. Table 15 describes the statistical significance of the experiment for each dose. Treatment with Compound 1 at all 10, 30 and 100 μg/kg resulted in a reduced tumor volume more than pomalidomide administered at 3000 μg/kg.

TABLE 15

Statistical Significance of Compound 1 Compared to Vehicle

| Treatment | Dose Level (mg/kg) NCI-H929 Cells | Statistical Significance Compared to Vehicle |
|---|---|---|
| Vehicle | N/A | N/A |
| Compound 1 | 3 | NS |
| Compound 1 | 10 | <0.0001 |
| Compound 1 | 30 | <0.0001 |
| Compound 1 | 100 | <0.0001 |
| Pomalidomide | 3000 | NS |

For the NCI-H929 cells, the xenograft study was conducted in female NOD SCID mice bearing NCI-H929 multiple myeloma tumors. Female SCID mice were inoculated subcutaneously in the right flank with $5\times10^6$ tumors cells in 0.2 mL of PBS supplemented with matrigel (PBS: matrigel=1:1). Tumor volume was measured twice weekly in two dimensions using calipers, and volume was calculated using the formula: (w2×l)/2=$mm^3$, assuming 1 mg is equivalent to 1 $mm^3$ of tumor volume. Once the tumors reached a volume range of 84-267 $mm^3$ (18 days after implantation), the animals were divided randomly into groups of 6, stratified to result in about equal average tumor sizes in each treatment group. Treatment began on Day 0 with established subcutaneous NCI-H929 tumors with a mean tumor volume (MTV) of 149-150 $mm^3$.

All agents were administered to mice bearing NCI-H929 tumors on day 0 and dosed PO daily for 21 days, except for the vehicle group which was dosed for 18 days. After the dosing period, tumor growth was monitored for 45 days. Compound 1 was dosed at 3, 10, 30, or 100 μg/kg and was formulated in PEG400 (30% v/v)+70% v/v HPMC (1% w/v) in citrate buffer (pH 5). Pomalidomide was dosed at 3000 μg/kg and used the same formulation as Compound 1. Body weight and MTV were measured on a 2× weekly schedule. After the initial 21 days of dosing, all Compound 1 groups were monitored for tumor growth. The 10 μg/kg group was removed from study on 39. The 30 μg/kg group tumors began to regrow, and PO daily dosing resumed starting on day 40 for an additional 23 days. Statistical analysis was performed using two-way analysis of variance (ANOVA). Data are expressed as MTV±SEM. The resulting data is shown in FIG. 33.

Example 32 Dose Dependent IKZF3 Degradation

A xenograft study was conducted in female CB17 SCID mice bearing RPMI-8226 multiple myeloma tumors. Female SCID mice were inoculated subcutaneously in the right flank with $10\times10^6$ tumors cells in 0.2 mL of PBS supplemented with matrigel (PBS:matrigel=1:1). Tumor volume was measured twice weekly in two dimensions using calipers, and volume was calculated using the formula: (w2×l)/2=$mm^3$, assuming 1 mg is equivalent to 1 $mm^3$ of tumor volume. Once the tumors reached an average volume of 265 $mm^3$ for the multi dose study or 380 $mm^3$ for the single dose study were randomized into groups of 3.

Compound 1 (100 μg/kg) and the vehicle control were administered to mice bearing RPMI-8226 tumors on day 0 and dosed PO daily for 5 days. Compound 1 was formulated in PEG400 (30% v/v)+70% v/v HPMC (1% w/v) in citrate buffer (pH 5), which was also used as the vehicle control. Body weight and MTV was measured on a 2× weekly schedule. For the vehicle control group, 3 mice were sacrificed, and tumors harvested 24 hours post a single dose. Mice in the Compound 1 group were sampled at 4- and 24-hours post dose a single dose, with 3 tumors collected per time point. Additional mice were dosed daily for 3 or 5 days with tumor collections 24 hours post last dose, with 3 mice sampled per time point. Tumors were then mechanically homogenized, and protein extracted using RIPA buffer (Sigma Aldrich). Protein concentration was quantified using a Pierce™ BCA Protein Assay Kit, samples were reduced, and equal protein amounts were then loaded onto a western blot gel for analysis. Tumors were analyzed for IKZF1 (Invitrogen, PA5-23728), IKZF3 (CST, 15103), or IRF-4 (CST, 15106) expression. The intensity of individual bands was measured for data analysis using Image Studio NIR software. Protein expression was quantitated in relation to the reference protein, GAPDH, to control for total protein concentration. The data was then normalized to the amount of target in the Compound 1 treated samples in comparison to the vehicle control samples. Data is represented as percent of target present in the vehicle control and normalized for total protein. Error bars represent ±SEM values. This study was used to produce the data in FIG. 36 and FIG. 37.

Example 33 Reduction in Cereblon Expression with Chronic IMiD Dosing

Cells were cultured in 10 uM lenalidomide for two months. A portion of the cells were then passaged into 1 uM pomalidomide or continued to be cultured in lenalidomide in parallel for an additional two months. Cells were lysed in RIPA with protease inhibitors and 30 ug of protein were loaded into each well of a 4-12% T TGX gel and run for 90 minutes at 120 volts. Protein was transferred to a nitrocellulose membrane and blotted for indicated protein (cereblon: Sigma catalog #HPA045910; IKZF1 CST catalog #14859; IKZF3 CST catalog #15103; vinculin EMD catalog #MAB3574) for 1 hour at room temperature. Membranes were thrice washed and incubated with anti-rabbit 800 or anti-mouse 700 (LiCor) and imaged on a Odyssey CLx. This experiment produced the data in FIG. 38.

Example 34 Compound 1 Retains Activity in IMiD-Resistant H929 MM Cells

NCIH929 human multiple myeloma cell line was continuously cultured in media containing 10 μM lenalidomide for 8 weeks followed by 1 μM pomalidomide for 4 weeks to develop resistance to IMiDs. Growth of IMiD-resistant NCIH929 cells was determined after 96 hours treatment with Compound 1 or pomalidomide based on quantification of ATP using CellTiter-Glo 2.0 luminescent Assay kit, which is proportional to the number of metabolically active cells. Briefly, test compound was added to 384-well plates at a top concentration of 10 μM with 14 points, half log titration in duplicates. NCIH929 cells were seeded into the 384-well plates in RPMI medium containing 10% FBS and 0.05 mM 2-mercaptoethanol at a cell density of 750 cells per well. Cells treated in the absence of the test compound were the negative control and cells treated in the absence of CellTiter-Glo® 2.0 were the positive control. Cells treated with the test compounds were incubated at 37° C. with 5% $CO_2$ for 96 hr. CellTiter-Glo reagent was then added to the cells and luminescence was acquired on EnVision™ Multilabel Reader (PerkinElmer, Santa Clara, CA, USA). % Viability was determined by normalizing the signal with positive and DMSO treated negative controls on the same microtiter plate. Compound 1 inhibited the proliferation of IMiD-resistant NCIH929 cells with an $IC_{50}$ of 2.3 nM and maximal inhibition of 70% while pomalidomide induced less than 50% growth inhibition at concentrations up to 10 μM. This experiment produced the data in FIG. 39.

Example 35 Compound 1 is Active in REC1 Cells

Compound 1 (30 μg/kg) and the vehicle control were administered to mice bearing REC1 tumors on day 0 and dosed PO daily for 3 days. Compound 1 was formulated in PEG400 (30% v/v)+70% v/v HPMC (1% w/v) in citrate buffer (pH 5), which was also used as the vehicle control. Body weight and MTV was measured on a 2× weekly schedule. For the vehicle control group, 3 mice were sacrificed, and tumors harvested 24 hours post a single dose. Mice in the Compound 1 group were sampled at 4- and 24-hours post dose a single dose, with 3 tumors collected per time point. Additional mice were dosed daily for 3 days with tumor collections 24 hours post last dose and 3 mice sampled per time point. Tumors were then mechanically homogenized, and protein extracted using RIPA buffer (Sigma Aldrich). Protein concentration was quantified using a Pierce™ BCA Protein Assay Kit, samples were reduced, and equal protein amounts were then loaded onto a western blot gel for analysis. Tumors were analyzed for IKZF1 (Invitrogen, PA5-23728), IKZF3 (CST, 15103), IRF-4 (CST, 15106), Cyclin D1 (CST, 2922), and E2F1 (CST, 3742) expression. The intensity of individual bands was measured for data analysis using Image Studio NIR software. Protein expression was quantitated in relation to the reference protein, GAPDH, to control for total protein concentration. The data was then normalized to the amount of target in the Compound 1 treated samples in comparison to the vehicle control samples. Data is represented as percent of target present in the vehicle control and normalized for total protein. Error bars represent ±SEM values. This assay was used to produce the data shown in FIGS. 43 and 44.

Example 36. Cell Viability Assay

Materials

RPMI 1640 medium, fetal bovine serum (FBS) and 2-mercaptoethanol were purchased from Gibco (Grand Island, NY, USA). CellTiter-Glo® 2.0 Assay was purchased from Promega (Madison, WI, USA). NCIH929.1 cell line was purchased from ATCC (Manassas, VA, USA). Cell culture flasks and 384-well microplates were acquired from VWR (Radnor, PA, USA).

Cell Viability Analysis

NCIH929.1 cell viability was determined based on quantification of ATP using CellTiter-Glo® 2.0 luminescent Assay kit, which signals the presence of metabolically-active cells. Briefly, the test compound was added to 384-well plates at a top concentration of 1 μM with 10 points, half log titration in duplicates. NCIH929.1 cells were seeded into the 384-well plates in RPMI medium containing 10% FBS and 0.05 mM 2-mercaptoethanol at a cell density of 750 cells per well. Cells treated in the absence of the test compound were the negative control and cells treated in the absence of CellTiter-Glo® 2.0 were the positive control. At the same day of compound treatment, CellTiter-Glo® 2.0 was added to a plate with cells treated in the absence of the test compound to establish Cytostatic control value (CTO). Cells treated with the test compound were incubated at 37° C. with 5% CO2 for 96 hr. CellTiter-Glo reagent was then added to the cells and luminescence was acquired on EnVision™ Multilabel Reader (PerkinElmer, Santa Clara, CA, USA).

Using the above assay $GI_{50}$ data was determined for representative compounds in Table 16 below.

TABLE 16

| # | Structure | $GI_{50}$ (nM) |
|---|---|---|
| 1 | 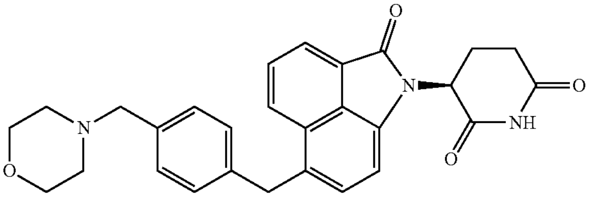 [SMILES: O=C1CC[C@H](N2C(=O)c3cccc4c(Cc5ccc(CN6CCOCC6)cc5)ccc2c34)C(=O)N1]<br>(S)-3-(6-(4-(morpholinomethyl)benzyl)-2-oxobenzo[cd]indol-1(2H)-yl)piperidine-2,6-dione | 0.0743 |
| 2 | 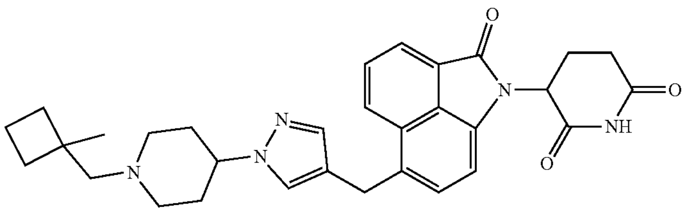 [SMILES: CC1(CN2CCC(n3cc(Cc4ccc5c6c(cccc46)C(=O)N5C4CCC(=O)NC4=O)cn3)CC2)CCC1]<br>3-(6-((1-(1-((1-methylcyclobutyl)methyl)piperidin-4-yl)-1H-pyrazol-4-yl)methyl)-2-oxobenzo[cd]indol-1(2H)-yl)piperidine-2,6-dione | 0.00933 |

TABLE 16-continued

| # | Structure | $GI_{50}$ (nM) |
|---|---|---|
| 3 | 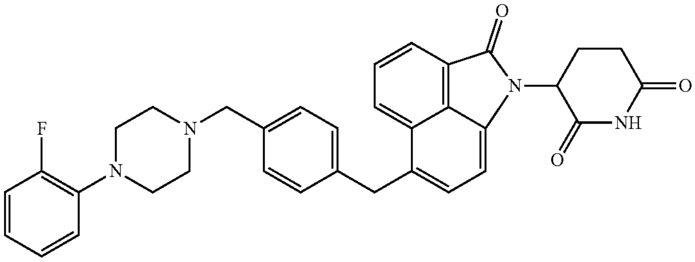 [SMILES: O=C1CCC(N2C(=O)c3cccc4c(Cc5ccc(CN6CCN(c7ccccc7F)CC6)cc5)ccc2c34)C(=O)N1] 3-(6-(4-((4-(2-fluorophenyl)piperazin-1-yl)methyl)benzyl)-2-oxobenzo[cd]indol-1(2H)-yl)piperidine-2,6-dione | 0.0409 |
| 4 | 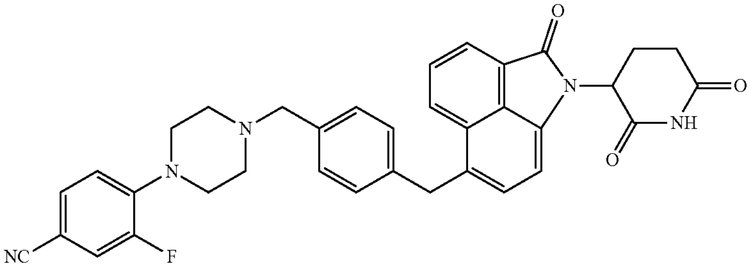 [SMILES: N#Cc1ccc(N2CCN(Cc3ccc(Cc4ccc5c6c(cccc46)C(=O)N5C4CCC(=O)NC4=O)cc3)CC2)c(F)c1] 4-(4-(4-((1-(2,6-dioxopiperidin-3-yl)-2-oxo-1,2-dihydrobenzo[cd]indol-6-yl)methyl)benzyl)piperazin-1-yl)-3-fluorobenzonitrile | 0.0201 |
| 5 | 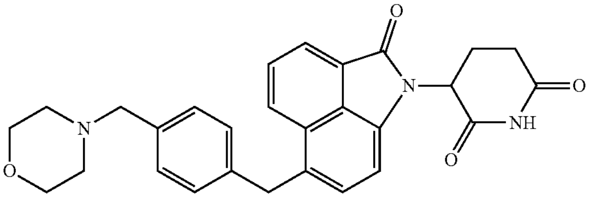 [SMILES: O=C1CCC(N2C(=O)c3cccc4c(Cc5ccc(CN6CCOCC6)cc5)ccc2c34)C(=O)N1] 3-(6-(4-(morpholinomethyl)benzyl)-2-oxobenzo[cd]indol-1(2H)-yl)piperidine-2,6-dione | 0.0498 |
| 6 | 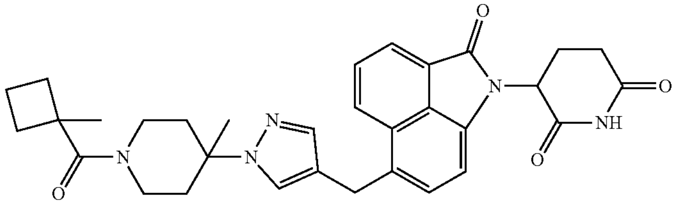 [SMILES: CC1(C(=O)N2CCC(C)(n3cc(Cc4ccc5c6c(cccc46)C(=O)N5C4CCC(=O)NC4=O)cn3)CC2)CCC1] 3-(6-((1-(4-methyl-1-(1-methylcyclobutane-1-carbonyl)piperidin-4-yl)-1H-pyrazol-4-yl)methyl)-2-oxobenzo[cd]indol-1(2H)-yl)piperidine-2,6-dione | 0.0146+ |
| 7 | 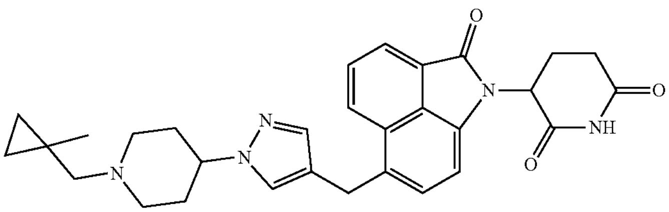 [SMILES: CC1(CN2CCC(n3cc(Cc4ccc5c6c(cccc46)C(=O)N5C4CCC(=O)NC4=O)cn3)CC2)CC1] 3-(6-((1-(1-((1-methylcyclopropyl)methyl)piperidin-4-yl)-1H-pyrazol-4-yl)methyl)-2-oxobenzo[cd]indol-1(2H)-yl)piperidine-2,6-dione | 0.0159 |

TABLE 16-continued

| # | Structure | $GI_{50}$ (nM) |
|---|---|---|
| 8 | 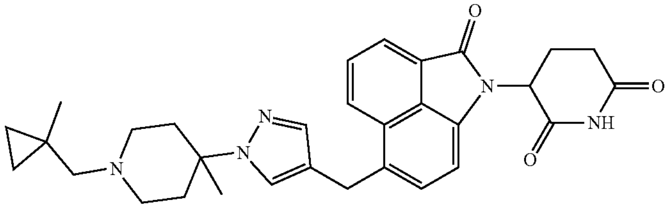 [SMILES: CC1(CN2CCC(C)(n3cc(Cc4ccc5c6c(cccc46)C(=O)N5C4CCC(=O)NC4=O)cn3)CC2)CC1]<br>3-(6-((1-(4-methyl-1-((1-methylcyclopropyl)methyl)piperidin-4-yl)-1H-pyrazol-4-yl)methyl)-2-oxobenzo[cd]indol-1(2H)-yl)piperidine-2,6-dione | 0.138 |
| 9 | 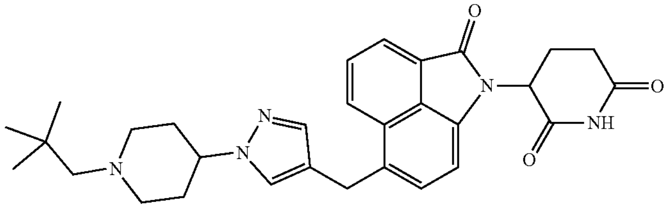 [SMILES: CC(C)(C)CN1CCC(n2cc(Cc3ccc4c5c(cccc35)C(=O)N4C3CCC(=O)NC3=O)cn2)CC1]<br>3-(6-((1-(1-neopentylpiperidin-4-yl)-1H-pyrazol-4-yl)methyl)-2-oxobenzo[cd]indol-1(2H)-yl)piperidine-2,6-dione | 0.0297 |
| 10 | 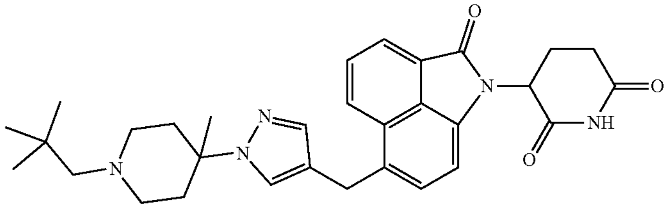 [SMILES: CC(C)(C)CN1CCC(C)(n2cc(Cc3ccc4c5c(cccc35)C(=O)N4C3CCC(=O)NC3=O)cn2)CC1]<br>3-(6-((1-(4-methyl-1-neopentylpiperidin-4-yl)-1H-pyrazol-4-yl)methyl)-2-oxobenzo[cd]indol-1(2H)-yl)piperidine-2,6-dione | 0.0621 |
| 11 | 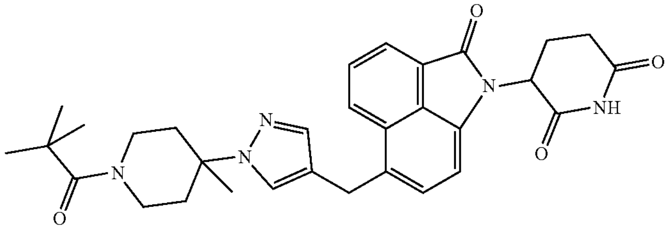 [SMILES: CC(C)(C)C(=O)N1CCC(C)(n2cc(Cc3ccc4c5c(cccc35)C(=O)N4C3CCC(=O)NC3=O)cn2)CC1]<br>3-(6-((1-(4-methyl-1-pivaloylpiperidin-4-yl)-1H-pyrazol-4-yl)methyl)-2-oxobenzo[cd]indol-1(2H)-yl)piperidine-2,6-dione | 0.0272 |
| 12 | 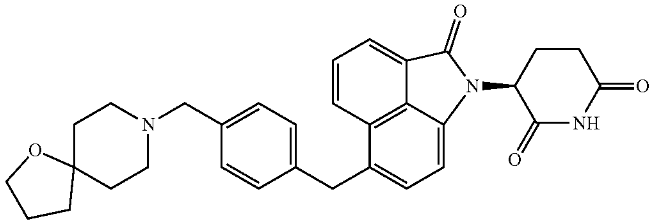 [SMILES: O=C1CC[C@H](N2C(=O)c3cccc4c(Cc5ccc(CN6CCC7(CCCO7)CC6)cc5)ccc2c34)C(=O)N1]<br>(S)-3-(6-(4-((1-oxa-8-azaspiro[4.5]decan-8-yl)methyl)benzyl)-2-oxobenzo[cd]indol-1(2H)-yl)piperidine-2,6-dione | 0.0107 |

TABLE 16-continued

| # | Structure | $GI_{50}$ (nM) |
|---|---|---|
| 13 | 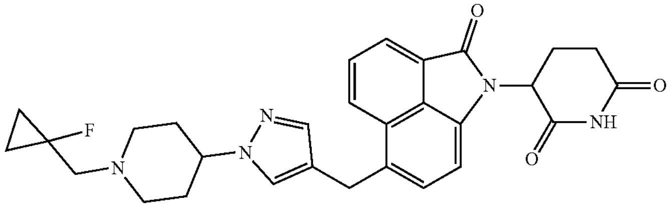 [SMILES: O=C1CCC(N2C(=O)c3cccc4c(Cc5cnn(C6CCN(CC7(F)CC7)CC6)c5)ccc2c34)C(=O)N1] 3-(6-((1-(1-((1-fluorocyclopropyl)methyl)piperidin-4-yl)-1H-pyrazol-4-yl)methyl)-2-oxobenzo[cd]indol-1(2H)-yl)piperidine-2,6-dione | 0.155 |

Example 37. NHL Cell Line Growth Inhibition Assay

Growth of NHL cell lines was determined after 96 hr treatment with Compound 1, pomalidomide or CC-92480 based on quantification of ATP using CellTiter-Glo® 2.0 luminescent Assay kit, which signals the presence of metabolically active cells. Test compound was added to 384-well plates at a top concentration of 100 nM or 10 μM for Compound 1 and 10 μM for pomalidomide and CC-92480 with 10 points, half log titration in duplicates. 50 uL cells suspended in growth media at cell densities indicated for each cell line in Table 17 were dispensed using a Multidrop Combi Reagent Dispenser (Thermo Fisher) to 384-well black TC-treated microplates containing duplicate concentration range of test compounds and DMSO controls. Cells treated in the absence of the test compound were the negative control and cells treated in the absence of CellTiter-Glo® 2.0 were the positive control. Cells were incubated at 37° C. with 5% $CO_2$ for 96 hr. CellTiter-Glo reagent was then added to the cells and luminescence was acquired on EnVision™ Multilabel Reader (PerkinElmer, Santa Clara, CA, USA). % Viability was determined by normalizing the signal with positive and DMSO treated negative controls on the same microtiter plate. The resulting data is shown in FIG. 45A, FIG. 45B, and FIG. 45C.

TABLE 17

Lymphoma cell lines: source vendor, description of cancer cell type, growth medium conditions and experimental seeding density.

| Cell Line | Vendor | Description | Complete Medium | Seeding Density (Cells/Well) |
|---|---|---|---|---|
| DB | ATCC | GCB-DLBCL | RPMI1640 + 10% FBS | 2000 |
| DOHH-2 | DSMZ | GCB-DLBCL | RPMI 1640 + 10% FBS | 4000 |
| Farage | ATCC | GCB-DLBCL | RPMI 1640 + 10% FBS | 2500 |
| GRANTA-519 | DSMZ | MCL | DMEM + 10% FBS | 5000 |
| HH | ATCC | CTCL | RPMI-1640 + 10% FBS | 4000 |
| HT | ATCC | GCB-DLBCL | RPMI-1640 + 10% FBS | 2500 |
| HuT 102 | ATCC | CTCL | RPMI-1640 + 10% FBS + 100 U/ml IL-2 | 2500 |
| JeKo-1 | ATCC | MCL | RPMI 1640 + 20% FBS | 5000 |
| Maver-1 | ATCC | MCL | RPMI 1640 + 10% FBS | 2500 |
| Mino | ATCC | MCL | RPMI-1640 + 15% FBS | 2500 |
| MJ | ATCC | CTCL | IMDM + 20% FBS | 3000 |
| DL40 | JCRB | ALCL | RPMI 1640 + 20% FBS | 2000 |
| KIJK | DSMZ | ALCL | RPMI 1640 + 20% FBS | 2000 |
| L82 | DSMZ | ALCL | RPMI 1640 + 10% FBS | 2000 |
| SR | ATCC | ALCL | RPMI 1640 + 10% FBS | 2000 |
| SU-DHL-1 | ATCC | ALCL | RPMI 1640 + 10% FBS | 2000 |
| SUPM2 | DSMZ | ALCL | RPMI 1640 + 20% FBS | 2000 |
| OCI-LY-19 | DSMZ | ABC-DLBCL | alpha-MEM + 10% FBS | 5000 |
| Pfeiffer | ATCC | GCB-DLBCL | RPMI-1640 + 10% FBS | 7000 |
| REC-1 | ATCC | MCL | RPMI-1640 + 10% FBS | 2000 |
| RL | ATCC | GCB-DLBCL | RPMI1640 + 10% FBS | 2500 |
| SU-DHL-2 | ATCC | ABC-DLBCL | RPMI1640 + 10% FBS | 2500 |
| SU-DHL-4 | DSMZ | GCB-DLBCL | RPMI 1640 + 10% FBS | 2500 |
| SU-DHL-5 | ATCC | GCB-DLBCL | RPMI 1640 + 10% FBS | 5000 |
| SU-DHL-6 | ATCC | GCB-DLBCL | RPMI-1640 + 10% FBS | 2500 |
| Toledo | ATCC | GCB-DLBCL | RPMI-1640 + 10% FBS | 2500 |
| WSU-DLCL2 | DSMZ | GCB-DLBCL | RPMI 1640 + 10% FBS | 2000 |
| Z-138 | ATCC | MCL | IMDM + 10% Horse Serum | 2500 |
| OCI-LY10 | DSMZ | ABC-DLBCL | IMDM + 20% FBS | 6000 |

TABLE 17-continued

Lymphoma cell lines: source vendor, description of cancer cell type, growth medium conditions and experimental seeding density.

| Cell Line | Vendor | Description | Complete Medium | Seeding Density (Cells/Well) |
|---|---|---|---|---|
| OCI-LY3 | DSMZ | ABC-DLBCL | IMDM + 20% FBS | 6000 |
| U-2932 | DSMZ | ABC-DLBCL | IMDM + 20% FBS | 6000 |
| KARPAS-422 | DSMZ | GCB-DLBCL | RPMI1640 + 20% FBS | 6000 |
| TMD-8 | Tokyo Medical and Dental University | ABC-DLBCL | IMDM + 20% FBS | 6000 |

Example 38. KI-JK ALCL Xenograft Study

A xenograft study was conducted in female CB17 SCID mice bearing KI-JK ALCL tumors. Female SCID mice were inoculated subcutaneously in the right flank with $10\times10^6$ tumors cells in 0.2 mL of PBS supplemented with matrigel (PBS:matrigel=1:1). Tumor volume was measured twice weekly in two dimensions using calipers, and volume was calculated using the formula: $(w2\times l)/2=mm^3$, assuming 1 mg is equivalent to 1 $mm^3$ of tumor volume. Once the tumors reached an average volume of 313 $mm^3$ mice randomized into groups of 4.

Compound 1 (100 μg/kg) and the vehicle control were administered to mice bearing KI-JK tumors on day 0 and dosed PO daily for 5 days. Compound 1 was formulated in PEG400 (30% v/v)+70% v/v HPMC (1% w/v) in citrate buffer (pH 5), which was also used as the vehicle control. Body weight and MTV was measured on a 2× weekly schedule. For the vehicle control group, 3 mice were sacrificed, and tumors harvested 24 hours post a single dose. Mice in the Compound 1 group were sampled at 4- and 24-hours post dose a single dose, with 3 tumors collected per time point. Additional mice were dosed daily for 5 days with tumor collections 24 hours post last dose, with 3 mice sampled per time point. Tumors were then mechanically homogenized, and protein extracted using RIPA buffer (Sigma Aldrich). Protein concentration was quantified using a Pierce™ BCA Protein Assay Kit, samples were reduced, and equal protein amounts were then loaded onto a western blot gel for analysis. Tumors were analyzed for IKZF3 (CST, 15103), or IRF-4 (CST, 15106) expression. The intensity of individual bands was measured for data analysis using Image Studio NIR software. Protein expression was quantitated in relation to the reference protein, GAPDH, to control for total protein concentration. The data was then normalized to the amount of target in the Compound 1 treated samples in comparison to the vehicle control samples. Data is represented as percent of target present in the vehicle control and normalized for total protein. Error bars represent ±SEM values. The resulting data is shown in FIG. 46.

Example 39. Mino Xenograft Study

A xenograft study was conducted in female CB17 SCID mice bearing the Mino mantle cell lymphoma tumors. Female SCID mice were inoculated subcutaneously in the right flank with $10\times10^6$ tumors cells in 0.2 mL of PBS supplemented with matrigel (PBS:matrigel=1:1). Tumor volume was measured twice weekly in two dimensions using calipers, and volume was calculated using the formula: $(w2\times l)/2=mm^3$, assuming 1 mg is equivalent to 1 $mm^3$ of tumor volume. Once the tumors reached an average tumor volume of 129 $mm^3$ (21 days after implantation), the animals were divided randomly into groups of 4, stratified to result in about equal average tumor sizes in each treatment group. Treatment began on Day 0 with established subcutaneous Mino tumors with a mean tumor volume (MTV) of 134 $mm^3$.

All agents were administered to mice bearing Mino tumors on day 0 and dosed for 34 days. Compound 1 was dosed PO daily at 30 ug/kg and formulated in PEG400 (30% v/v)+70% v/v IPMC (1% w/v) in citrate buffer (pH 5). Rituximab was dosed IV once a week at 10 mg/kg and formulated in saline. Compound 1 was also dosed in combination with Rituximab at their respective dose levels and schedules. Body weight and MTV were measured on a 2× weekly schedule. The study end point was day 35 when the vehicle control reached a MTV of 2320 $mm^3$. Statistical analysis was performed using paired t test analysis. Data are expressed as MTV±SEM. The resulting data is shown in FIG. 47.

Example 40. NCI-H929 Xenograft Study

A xenograft study was conducted in female NOD SCID mice bearing NCI-H929 MM tumors. Female SCID mice were inoculated subcutaneously in the right flank with $10\times10^6$ tumors cells in 0.2 mL of PBS supplemented with matrigel (PBS:matrigel=1:1). Tumor volume was measured twice weekly in two dimensions using calipers, and volume was calculated using the formula: $(w2\times l)/2=mm^3$, assuming 1 mg is equivalent to 1 $mm^3$ of tumor volume. For the efficacy portion of this study, once the tumors reached an average volume of 419 $mm^3$ mice randomized into 4 groups with 4 mice each. For the pharmacodynamic and pharmacokinetic portion of the study, once tumors reached an average tumor volume of 620 $mm^3$ mice were randomized into groups of 4 with 12 mice per group.

For the efficacy portion of the study Compound 1 (100 μg/kg), CC-92480 (1000 μg/kg), pomalidomide (3000 μg/kg) and the vehicle control were administered to mice bearing NCI-H929 tumors on day 0 and dosed PO daily for 18 days. Compound 1, CC-92480, and pomalidomide, were formulated in PEG400 (30% v/v)+70% v/v HPMC (1% w/v) in citrate buffer (pH 5), which was also used as the vehicle control. Body weight and MTV was measured on a 2× weekly schedule. The study end point was day 18 when the vehicle control reached a MTV of 2460 $mm^3$. Data are expressed as MTV±SEM.

For the pharmacodynamic and pharmacokinetic portion of this study 3 mice were sacrificed per time point with tumors and plasma harvested, with mice in the vehicle control group being sacrificed 24 post single dose. Mice in the study Compound 1 (100 μg/kg), CC-92480 (1000 μg/kg), and pomalidomide (3000 μg/kg) groups were sampled at 1, 4, 24, and 48 hours post a single dose with 3 mice sampled per time point. Tumors were then mechanically homogenized, and protein extracted using RIPA buffer (Sigma Aldrich). Protein concentration was quantified using a Pierce™ BCA Protein Assay Kit, samples were reduced, and equal protein amounts were then loaded onto a western blot gel for analysis. Tumors were analyzed for IKZF3 (CST, 15103) expression. The intensity of individual bands was measured for data analysis using Image Studio NIR software. Protein expression was quantitated in relation to the reference protein, GAPDH, to control for total protein concentration. The data was then normalized to the amount of target in the Compound 1 treated samples in comparison to the vehicle control samples. Data is represented as percent of target present in the vehicle control and normalized for total protein. For pharmacokinetic analysis of plasma and tumor samples, tumor samples were mechanically homogenized using homogenizing solution (MeOH/I5 mM PBS (1:2, v:v)) and for plasma protein precipitation performed. Samples were quenched and compared to a standard curve by LC-MS/MS analysis. Error bars represent ±SEM values. The resulting data is shown in FIG. 48, FIG. 49, and FIG. 50.

Example 41. Apoptosis Induction in TMD8 Cells

Apoptosis induction in TMD8 cells was determined by measuring Caspase 3/7 activity following 48 hr treatment with Compound 1 or pomalidomide using Caspase 3/7 Assay System (Promega, G8091). Test compound was added to white 384-well TC-treated plates at a top concentration of 10 μM for Compound 1 and pomalidomide with 10-14 points, half log titration in duplicates. 30 μL TMD8 cells were seeded into the 384-well plates in RPMI medium containing 10% FBS at a cell density of 2000 cells per well. Cells treated in the absence of the test compound were the negative control. Following compound treatment, cells were incubated at 37° C. with 5% $CO_2$ for 48 hr. 30 μL reconstituted Caspase 3/7 Assay detection reagent was added to each well and luminescence was acquired on EnVision™ Multilabel Reader (PerkinElmer, Santa Clara, CA, USA). Maximum caspase 3/7 activity of >8-fold was observed following 48 hr with an EC50=2.7 nM for Compound 1 and 1.2 μM for pomalidomide. % Caspase 3/7 Activity was determined by normalizing the signal with DMSO treated controls on the same microtiter plate. The resulting data is shown in FIG. 51.

Example 42. Cell Viability in TMD8 Cells

TMD8 cell viability was determined based on quantification of ATP using CellTiter-Glo® 2.0 luminescent Assay kit, which signals the presence of metabolically-active cells. Test compound was added to 384-well plates at a top concentration of 100 nM for Compound 1 or 10 μM for pomalidomide with 11 points, half log titration in duplicates. TMD8 cells were seeded into the 384-well plates in RPMI medium containing 10% FBS at a cell density of 6000 cells per well. Cells treated in the absence of the test compound were the negative control, normalized to 100% viability, and cells treated in the absence of CellTiter-Glo® 2.0 were the positive control, normalized to 0% viability. Cells were incubated at 37° C. with 5% $CO_2$ for 96 hr. CellTiter-Glo reagent was then added to the cells and Luminescence was acquired on EnVision™ Multilabel Reader (PerkinElmer, Santa Clara, CA, USA). The resulting data is shown in FIG. 52.

Example 43. Geneontology Study

DL-40 ALCL xenograft tumors were isolated from mice 48 hours after oral administration of 100 μg/kg Compound 1 or vehicle and quantitative global proteomics was performed as described in Example 10. Gene ontology analysis was done by using BINGO, a Java-based tool that is implemented as a plugin for Cytoscape. Default settings were used to assess the overexpression of GO categories and the interactions among altered proteins were determined using the STRING database, with a cutoff score of 700. Interferon (IFN) signaling was the most prominent network impacted by Compound 1. Genes with major changes in expression are summarized in Table 18. The study shows that the primary actions of Compound 1 are on Interferon-response genes.

TABLE 18

Gene Expression Modulation by Compound 1

| Gene Symbol | Number of Peptides | Log2 Compound 1 0.1 nM for 48 hr vs Vehicle | P-Value Compound 1 0.1 nM for 48 hr vs Vehicle |
|---|---|---|---|
| AAAS | 27 | 0.043 | 7.80E−01 |
| ABCE1 | 110 | −0.112 | 2.80E−03 |
| ADAR | 174 | 0.065 | 3.00E−04 |
| ARIHI | 26 | 0.023 | 3.00E−01 |
| B2M | 50 | −0.048 | 8.20E−02 |
| BST2 | 8 | 0.241 | 2.20E−02 |
| CAMK2A | 2 | −0.697 | 5.50E−01 |
| CAMK2B | 18 | 0.054 | 5.30E−01 |
| CAMK2D | 19 | 0.038 | 7.20E−01 |
| CAMK2G | 17 | −0.054 | 3.00E−02 |
| CD44 | 28 | −0.377 | 4.70E−06 |
| CIITA | 8 | −0.076 | 1.50E−01 |
| DDX58 | 7 | 0.455 | 3.20E−02 |
| EIF2AK2 | 52 | 0.527 | 1.60E−14 |
| EIF4A1 | 83 | 0.13 | 8.90E−03 |
| EIF4A2 | 128 | 0.08 | 5.00E−02 |
| EIF4A3 | 164 | 0.079 | 2.90E−03 |
| EIF4E2 | 27 | 0.179 | 1.30E−02 |
| EIF4E3 | 3 | 0.208 | 2.30E−02 |
| EIF4G1 | 182 | −0.048 | 1.60E−03 |
| EIF4G2 | 93 | −0.071 | 3.70E−02 |
| EIF4G3 | 40 | −0.108 | 3.00E−02 |
| FLNA | 802 | 1.179 | 1.60E−14 |
| FLNB | 203 | 0.234 | 1.60E−14 |
| GBP1 | 35 | 0.343 | 2.90E−08 |
| GBP2 | 4 | −0.269 | 1.20E−01 |
| GBP4 | 23 | 0.388 | 3.60E−06 |
| HERC5 | 8 | −0.149 | 2.30E−01 |
| HLA-A | 137 | −0.128 | 2.10E−04 |
| HLA-B | 145 | 0.066 | 3.90E−01 |
| HLA-C | 121 | −0.065 | 3.00E−02 |
| HLA-DPA1 | 34 | −0.139 | 1.20E−02 |
| HLA-DPB1 | 73 | −0.023 | 3.70E−01 |
| HLA-DQA2 | 49 | −0.144 | 4.30E−05 |
| HLA-DQB1 | 41 | 0.055 | 2.30E−01 |
| HLA-DRA | 189 | −0.133 | 1.10E−09 |
| HLA-DRB1 | 74 | −0.1 | 1.80E−01 |
| HLA-E | 17 | −0.167 | 9.80E−05 |
| HLA-F | 19 | 0.408 | 9.90E−12 |
| ICAM1 | 28 | 0.31 | 1.60E−07 |
| IFI30 | 11 | 0.217 | 2.30E−01 |
| IFI35 | 40 | 0.153 | 1.60E−03 |
| IFIT2 | 3 | −0.186 | 3.80E−02 |
| IFIT3 | 7 | 0.736 | 6.20E−03 |
| IRF1 | 4 | 0.147 | 3.00E−01 |
| IRF2 | 16 | −0.265 | 1.40E−03 |
| IRF3 | 24 | 0.114 | 6.90E−01 |
| IRF4 | 59 | −0.452 | 1.60E−14 |

TABLE 18-continued

Gene Expression Modulation by Compound 1

| Gene Symbol | Number of Peptides | Log2 Compound 1 0.1 nM for 48 hr vs Vehicle | P-Value Compound 1 0.1 nM for 48 hr vs Vehicle |
|---|---|---|---|
| IRF5 | 21 | 0.192 | 2.10E−04 |
| IRF7 | 1 | 0.264 | 4.70E−02 |
| IR.F9 | 12 | 0.535 | 1.20E−06 |
| ISG15 | 26 | 0.241 | 8.00E−05 |
| ISG20 | 22 | −0.168 | 7.40E−01 |
| J A KI | 28 | 0.036 | 7.80E−01 |
| KPNA1 | 57 | 0.045 | 7.70E−01 |
| KPNA2 | 72 | 0.058 | 1.40E−02 |
| KPNA3 | 39 | 0 | 5.20E−01 |
| KPNA4 | 47 | 0.075 | 1.30E−02 |
| KPNB1 | 435 | 0.038 | 1.00E−01 |
| MAPK3 | 42 | −0.042 | 7.00E−01 |
| MT2A | 5 | −0.297 | 3.40E−01 |
| MX1 | 49 | 1.715 | 1.60E−14 |
| MX2 | 65 | 0.83 | 1.60E−14 |
| NCAM1 | 8 | −0.127 | 6.70E−01 |
| NDC1 | 33 | −0.063 | 3.30E−01 |
| NEDD4 | 18 | 0.375 | 6.40E−08 |
| NUP107 | 55 | 0.033 | 4.50E−04 |
| NUP133 | 88 | −0.019 | 2.40E−01 |
| NUP153 | 177 | −0.013 | 1.40E−01 |
| NUP155 | 89 | 0.001 | 2.40E−01 |
| NUP160 | 85 | 0.026 | 1.20E−01 |
| NUP188 | 88 | 0.029 | 6.90E−01 |
| NUP205 | 106 | −0.001 | 4.00E−01 |
| NUP210 | 155 | 0.045 | 2.40E−01 |
| NUP214 | 91 | −0.08 | 1.50E−01 |
| NUP35 | 34 | −0.023 | 9.60E−01 |
| NUP37 | 22 | −0.009 | 3.50E−01 |
| NUP43 | 20 | −0.042 | 3.10E−01 |
| NUP50 | 84 | −0.009 | 6.40E−01 |
| NUP54 | 50 | 0.014 | 8.30E−01 |
| NUP62 | 38 | −0.019 | 9.00E−01 |
| NUP85 | 49 | −0.05 | 6.10E−03 |
| NUP88 | 36 | 0.031 | 5.30E−01 |
| NUP93 | 97 | 0.029 | 1.60E−02 |
| NUPL2 | 18 | 0.073 | 3.70E−01 |
| 0AS1 | 5 | 1.414 | 3.60E−07 |
| OAS2 | 35 | 0.478 | 9.20E−14 |
| OAS3 | 46 | 0.884 | 1.60E−14 |
| OASL | 26 | 0.111 | 8.50E−01 |
| PDE12 | 38 | 0.013 | 3.80E−01 |
| PIAS1 | 12 | −0.114 | 5.50E−01 |
| PINI | 33 | 0.05 | 1.10E−01 |
| PLCG1 | 41 | 0.052 | 1.70E−01 |
| PML | 64 | 0.176 | 1.50E−04 |
| P0M121 | 43 | −0.05 | 4.40E−01 |
| P0M121C | 7 | −0.039 | 4.90E−01 |
| PPM1B | 41 | −0.001 | 6.30E−01 |
| PRKCD | 44 | 0.506 | 1.60E−14 |
| PSMB8 | 98 | 0.021 | 2.60E−01 |
| PTPN1 | 44 | 0.009 | 5.40E−01 |
| PTPN11 | 43 | 0.001 | 8.60E−01 |
| PTPN6 | 51 | 0.402 | 1.60E−14 |
| RAE1 | 60 | −0.034 | 1.90E−01 |
| RANBP2 | 355 | −0.044 | 8.30E−03 |
| RNASEL | 24 | −0.218 | 2.50E−04 |
| RPS27A | 285 | −0.054 | 3.40E−02 |
| SAMHD1 | 68 | 0.128 | 3.50E−03 |
| SP100 | 52 | −0.028 | 1.50E−01 |
| STAT1 | 175 | 0.218 | 1.60E−14 |
| STAT2 | 26 | 0.271 | 2.80E−03 |
| TPR | 274 | −0.053 | 3.90E−02 |
| TRIM14 | 15 | 0.183 | 8.60E−02 |
| TRIM21 | 15 | 0.175 | 1.00E−02 |
| TRIM22 | 5 | 0.331 | 5.10E−03 |
| TRIM25 | 59 | 0.161 | 1.50E−04 |
| TRIM26 | 27 | 0.019 | 3.20E−01 |
| TRIM35 | 1 | 0.144 | 8.10E−01 |
| TRIM38 | 9 | 0.119 | 1.60E−01 |
| TRIM5 | 11 | 0.107 | 1.90E−01 |
| TYK2 | 64 | −0.039 | 6.20E−01 |
| UBA7 | 10 | 0.366 | 1.10E−02 |
| UBE2E1 | 5 | −0.218 | 3.60E−01 |
| UBE2L6 | 54 | 0.13 | 2.60E−01 |
| UBE2N | 43 | 0.02 | 1.70E−01 |
| VCAM1 | 91 | −0.744 | 1.60E−14 |

Example 44 CB17 SCID Mino Mantle Cell Lymphoma Xenograft Study

A xenograft study was conducted in female CB17 SCID mice bearing Mino multiple mantle cell lymphoma tumors. Female SCID mice were inoculated subcutaneously in the right flank with $10\times10^6$ tumors cells in 0.2 mL of PBS supplemented with matrigel (PBS:matrigel=1:1). Tumor volume was measured twice weekly in two dimensions using calipers, and volume was calculated using the formula: $(w2\times l)/2=mm^3$, assuming 1 mg is equivalent to 1 $mm^3$ of tumor volume. Once the tumors reached an average tumor volume of 129 $mm^3$ (21 days after implantation), the animals were divided randomly into groups of 5, stratified to result in about equal average tumor sizes in each treatment group. Treatment began on Day 0 with established subcutaneous Mino tumors with a mean tumor volume (MTV) of 134 $mm^3$.

All agents were administered to mice bearing Mino tumors on day 0 and dosed for 34 days. Compound 1 was dosed PO daily at 30 ug/kg and formulated in PEG400 (30% v/v)+70% v/v HPMC (1% w/v) in citrate buffer (pH 5). Ibrutinib was dosed PO daily at 25 mg/kg and formulated in 0.5% MC+0.4% EL+0.1% SDS. Compound 1 was also dosed in combination with Ibrutinib at their respective dose levels and schedules. Body weight and MTV were measured on a 2× weekly schedule. The study end point was day 35 when the vehicle control reached a MTV of 2320 $mm^3$. Statistical analysis was performed using paired t test analysis. Data are expressed as MTV±SEM.

The resulting data is shown in FIG. 53.

Example 45 CB17 SCID RPMI-8226 Xenograft Study

A xenograft study was conducted in female CB17 SCID mice bearing RPMI-8226 multiple myeloma tumors. Female SCID mice were inoculated subcutaneously in the right flank with $10\times10^6$ tumors cells in 0.2 mL of PBS supplemented with matrigel (PBS:matrigel=1:1). Tumor volume was measured twice weekly in two dimensions using calipers, and volume was calculated using the formula: $(w2\times l)/2=mm^3$, assuming 1 mg is equivalent to 1 $mm^3$ of tumor volume. Once the tumors reached an average volume of 101 $mm^3$ for the efficacy study or 342 $mm^3$ for the multi dose pharmacodynamic study the mice were randomized into groups of 4 or 3 respectively.

For the efficacy portion of the study Compound 1 (100 μg/kg), pomalidomide (3000 μg/kg), CC-92480 (1000 μg/kg) and the vehicle control were administered to mice bearing RPMI-8226 tumors on day 0 and dosed PO daily for 19 days. Compounds were formulated in PEG400 (30% v/v)+70% v/v HPMC (1% w/v) in citrate buffer (pH 5), which was also used as the vehicle control. Body weight and MTV was measured on a 2× weekly schedule. The study end point was day 19 when the vehicle control reached a MTV of 1789 $mm^3$. Statistical analysis was performed using paired t test analysis. Data are expressed as MTV±SEM.

For the pharmacodynamic portion of the study, mice were dosed daily. Compound 1 (100 μg/kg), pomalidomide (3000 μg/kg), CC-92480 (1000 μg/kg) and the vehicle control were administered to mice bearing RPMI-8226 tumors starting on day 0. Mice were dosed orally for 7 days with tumor collections 4 and 24 hours post a single dose or 24 hours post 3, 5, or 7 daily doses. Tumors were then mechanically homogenized, and protein extracted using RIPA buffer (Sigma Aldrich). Protein concentration was quantified using a Pierce™ BCA Protein Assay Kit, samples were reduced, and equal protein amounts were then loaded onto a western blot gel for analysis. Tumors were analyzed for IKZF3 (CST, 15103) expression. The intensity of individual bands was measured for data analysis using Image Studio NIR software. Protein expression was quantitated in relation to the reference protein, GAPDH, to control for total protein concentration. The data was then normalized to the amount of target in the Compound 1 treated samples in comparison to the vehicle control samples. Data is represented as percent of target present in the vehicle control and normalized for total protein. Error bars represent ±SEM values.

The resulting data is shown in FIG. 54 and FIG. 55.

Example 46 Cytokine Profiling $CD4^+/CD8^+$ human T-cells were isolated from a Leukopak using a magnetic negative selection enrichment kit (StemCell T-cell enrichment catalog #17851). T-cells were plated in anti-CD3 coated cells (OKT3 clone; 10 ug/mL) at 500,000 cells/mL in RPMI1640+10% fetal-bovine serum and treated with a seven-point dilution series of Pomalidomide, CC-92480, Compound 1, Compound 15, or Compound 2 in duplicate. After six days, supernatants were collected, centrifuged to clear debris, and snap frozen until analysis. To determine cytokine concentration, a 45-plex Procarta panel was performed using manufacturer's protocol (Thermo cat #EPX450-12171-901). Briefly, antibody-coated beads were incubated with supernatants, washed, and a biotinylated detection antibody was added that is detected with the addition of streptavidin-RPE. Absolute values of each cytokine were extrapolated from standard curves via nonlinear regression. Cytokine levels were normalized and levels of fold-change were determined relative to DMSO treated controls.

Compound 15 is

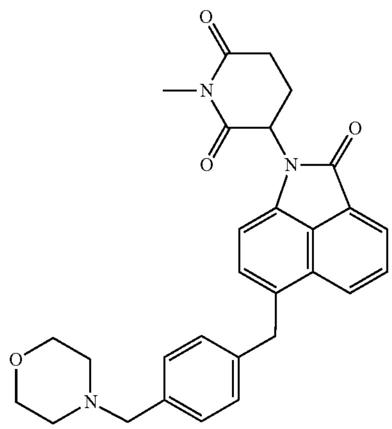 [SMILES: CN1C(=O)CCC(N2C(=O)c3cccc4c(Cc5ccc(CN6CCOCC6)cc5)ccc2c34)C1=O]

The results are graphically summarized in FIGS. 58-64 and Table 19.

| Cytokine | Up-Fold Change | Down-Fold Change |
|---|---|---|
| IL21 | 100 | |
| IL6 | 60 | |
| IL2 | 40 | |
| IL9 | 10 | |
| IL13 | 6 | |
| MCP-1 (CCL2) | 6 | |
| TNF-alpha | 5 | |
| ILIA | 4 | |
| Eotaxin | 4 | |
| IP10 | 4 | |
| IL IB | 3 | |
| IL4 | 2.5 | |
| IFNg | 2 | |
| GMCSF | 2 | |
| IL22 | 2 | |
| IL10 | 2 | |
| IL18 | 2 | |
| IL1RA | 2 | |
| PIGF1 | 2 | |
| IL5 | 1.5 | 2 |
| TNF-beta | 1.4 | |
| IL17A | | 2.5 |
| LIF | | 2 |

Table 19 summarizes the effect of Compound 1, Compound 2, Compound 15, CC-92480, or Pomalidomide on cytokine levels secreted from anti-CD3 stimulated T-cells after a six-day incubation. Values are fold-change relative to DMSO treated control wells.

All publications and patent applications cited in this specification are herein incorporated by reference as if each individual publication or patent application were specifically and individually indicated to be incorporated by reference.

Although the foregoing invention has been described in some detail by way of illustration and example for the purposes of clarity of understanding, it will be readily apparent to one of ordinary skill in the art in light of the teaching of this invention that certain changes and modification may be made thereto without departing from the spirit or scope of the invention as defined in the claims.

We claim:

1. A method of treating a hematological malignancy in a human patient comprising administering a dose between 1 microgram and 500 micrograms (μg) of a compound of Formula:

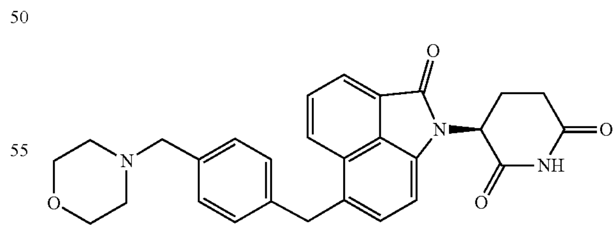

or a pharmaceutically acceptable salt thereof, wherein the hematological malignancy is a lymphoma or multiple myeloma.

2. The method of claim 1, wherein the compound is administered once a day or twice a day.

3. The method of claim 1, wherein the compound is administered for multiple days with a drug holiday in between subsequent treatment cycles.

4. The method of claim 1, wherein the dose is less than or equal to 400 μg.

5. The method of claim 1, wherein the dose is less than or equal to 300 μg.

6. The method of claim 1, wherein the dose is less than or equal to 200 μg.

7. The method of claim 1, wherein the dose is less than or equal to 100 μg.

8. The method of claim 1, wherein the dose is less than or equal to 50 μg.

9. The method of claim 1, wherein the dose is less than or equal to 25 μg.

10. The method of claim 1, wherein the dose is less than or equal to 10 μg.

11. The method of claim 1, wherein the dose is less than or equal to 5 μg.

12. The method of claim 1, wherein the hematological malignancy is non-Hodgkin's lymphoma.

13. The method of claim 1, wherein the hematological malignancy is multiple myeloma.

14. The method of claim 1, wherein the hematological malignancy is a diffuse large B-cell lymphoma.

15. The method of claim 14, wherein the diffuse large B-cell lymphoma is activated B-cell lymphoma or germinal center B-cell lymphoma.

16. The method of claim 1, wherein the hematological malignancy is anaplastic large cell lymphoma or cutaneous T-cell lymphoma.

17. The method of claim 1, wherein the hematological malignancy is peripheral T-cell lymphoma.

18. The method of claim 1, wherein the hematological malignancy is mantle cell lymphoma.

19. The method of claim 1, wherein the hematological malignancy is resistant to treatment with thalidomide, pomalidomide, lenalidomide, or iberdomide.

* * * * *